(12) United States Patent
Shimada et al.

(10) Patent No.: US 7,947,738 B2
(45) Date of Patent: May 24, 2011

(54) BICYCLIC γ-AMINO ACID DERIVATIVE

(75) Inventors: Kousei Shimada, Kanagawa (JP); Asuka Kawamura, Tokyo (JP); Naohisa Arakawa, Kanagawa (JP); Yuki Domon, Saitama (JP)

(73) Assignee: Daiichi Sankyo Company, Ltd., Tokyo (JP)

( * ) Notice: Subject to any disclaimer, the term of this patent is extended or adjusted under 35 U.S.C. 154(b) by 1 day.

(21) Appl. No.: 12/714,267

(22) Filed: Feb. 26, 2010

(65) Prior Publication Data

US 2010/0249229 A1 Sep. 30, 2010

Related U.S. Application Data

(63) Continuation of application No. PCT/JP2008/067223, filed on Sep. 25, 2008.

(30) Foreign Application Priority Data

Sep. 28, 2007 (JP) ................................. 2007-255430

(51) Int. Cl.
*A01N 37/12* (2006.01)
*A01N 37/00* (2006.01)
*A61K 31/21* (2006.01)

(52) U.S. Cl. ........................................ 514/561; 514/510

(58) Field of Classification Search ........................ None
See application file for complete search history.

(56) References Cited

U.S. PATENT DOCUMENTS

| 2003/0078300 | A1 | 4/2003 | Blakemore et al. |
| 2004/0116525 | A1 | 6/2004 | Derrick |
| 2010/0104575 | A1 | 4/2010 | Sooknanan et al. |

FOREIGN PATENT DOCUMENTS

| WO | WO-99/21824 | 5/1999 |
| WO | WO-01/28978 | 4/2001 |
| WO | WO-02/085839 | 10/2002 |
| WO | WO-2004/006836 | 1/2004 |

OTHER PUBLICATIONS

Bryans, , "Identification of Novel Ligands for the Gabapentin Binding Site on the α₂ δ Subunit of a Calcium Channel and Their Evaluation as Anticonvulsant Agents", *J. Med. Chem.* (41) 1998, 1838-1845.

Frampton, James E. et al., "Pregabalin: In the Treatment of Painful Diabetic Peripheral Neuropathy", *Drugs*, vol. 64, No. 24 2004, 2813-2820.

Gee, Nicolas S. et al., "The Novel Anticonvulsant Drug, Gabapentin (Neurontin), Binds to the α₂ δ Subunit of a Calcium Channel", *Journal of Biological Chemistry*, vol. 271, No. 10 Mar. 8, 1996, 5768-5776.

Mann, Andre et al., "Synthesis and Biochemical Evaluation of Baclofen Analogs Locked in the Baclofen Solid-State Conformation", *Journal of Medicinal Chemistry*, vol. 34, No. 4 1991, 1307-1313.

Nicholson, B. , "Gabapentin use in neuropathic pain syndromes", *Acta Neurol Scand*, vol. 101 2000, 359-371.

Cott, Jerry, "Pharmacology Reviews," *Pharmacology/Toxicology Review and Evaluation*, Food and Drug Administration, Center for Drug Evaluation and Research, NDA No. 21-446, May 24, 2004, pp. 1-136.

*Primary Examiner* — Daniel M Sullivan
*Assistant Examiner* — Jennifer C Sawyer
(74) *Attorney, Agent, or Firm* — Dorsey & Whitney LLP

(57) ABSTRACT

It is intended to provide a bicyclic γ-amino acid derivative having excellent activity as an α₂δ ligand. The present invention provides a compound represented by the general formula (I):

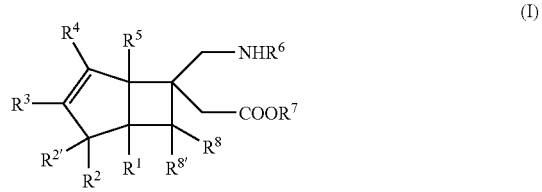

wherein $R^1$, $R^2$, $R^{2'}$, $R^4$, $R^5$, $R^6$, $R^7$, $R^8$, and $R^{8'}$ are a hydrogen atom or the like; and $R^3$ is a hydrogen atom, a halogen atom, a C1-C6 alkyl group, or the like.

20 Claims, No Drawings

```
                         SEQUENCE LISTING

<160> NUMBER OF SEQ ID NOS: 7

<210> SEQ ID NO 1
<211> LENGTH: 42
<212> TYPE: DNA
<213> ORGANISM: Artificial
<220> FEATURE:
<223> OTHER INFORMATION: PCR sense primer for human Cacna2d1 front

<400> SEQUENCE: 1
agctgcggcc gctagcgcca ccatggctgg ctgcctgctg gc                    42

<210> SEQ ID NO 2
<211> LENGTH: 27
<212> TYPE: DNA
<213> ORGANISM: Artificial
<220> FEATURE:
<223> OTHER INFORMATION: PCR antisense primer for human Cacna2d1 front

<400> SEQUENCE: 2
attaggatcg attgcaaagt aataccc                                     27

<210> SEQ ID NO 3
<211> LENGTH: 26
<212> TYPE: DNA
<213> ORGANISM: Artificial
<220> FEATURE:
<223> OTHER INFORMATION: PCR sense primer for human Cacna2d1 rear

<400> SEQUENCE: 3
aatgggtatt actttgcaat cgatcc                                      26

<210> SEQ ID NO 4
<211> LENGTH: 32
<212> TYPE: DNA
<213> ORGANISM: Artificial
<220> FEATURE:
<223> OTHER INFORMATION: PCR antisense primer for human Cacna2d1 rear

<400> SEQUENCE: 4
agtcggatcc tcataacagc cggtgtgtgc tg                               32
```

<210> SEQ ID NO 5
<211> LENGTH: 98
<212> TYPE: DNA
<213> ORGANISM: Artificial
<220> FEATURE:
<223> OTHER INFORMATION: multi cloning site of vector pBluescript 2

<400> SEQUENCE: 5

```
ccaccgcggt ggcggccgct ctagaactag tggatccccc gggctgcagg aattcgatat      60
caagcttatc gataccgtcg acctcgaggg ggggcccg                              98
```

<210> SEQ ID NO 6
<211> LENGTH: 1573
<212> TYPE: DNA
<213> ORGANISM: Homo sapiens

<400> SEQUENCE: 6

```
ggcggccgct agcgccacca tggctgctgg ctgcctgctg gccttgactc tgacactttt      60
ccaatctttg ctcatcggcc cctcgtcgga ggagccgttc ccttcggccg tcactatcaa     120
atcatgggtg gataagatgc aagaagacct tgtcacactg gcaaaaacag caagtggagt     180
caatcagctt gttgatattt atgagaaata tcaagatttg tatactgtgg aaccaaataa     240
tgcacgccag ctggtagaaa ttgcagccag ggatattgag aaacttctga gcaacagatc     300
taaagccctg gtgcgcctgg cattggaagc ggagaaagtt caagcagctc accagtggag     360
agaagatttt gcaagcaatg aagttgtcta ctacaatgca aaggatgatc tcgatcctga     420
gaaaaatgac agtgagccag gcagccagag gataaaacct gttttcattg aagatgctaa     480
ttttggacga caaatatctt atcagcacgc agcagtccat attcctactg acatctatga     540
gggctcaaca attgtgttaa atgaactcaa ctggacaagt gccttagatg aagttttcaa     600
aaagaatcgc gaggaagacc cttcattatt gtggcaggtt tttggcagtg ccactgcct      660 agctcgatat tatccagctt caccatgggt tgataatagt agaactccaa ataagattga     720 ccttttatgat gtacgcagaa gaccatggta catccaagga gctgcatctc taaagacat     780 gcttattctg gtggatgtga gtggaagtgt tagtggattg acacttaaac tgatccgaac     840
atctgtctcc gaaatgttag aaaccctctc agatgatgat tcgtgaatg tagcttcatt     900 taacagcaat gctcaggatg taagctgtttt tcagcacctt gtccaagcaa atgtaagaaa     960
taaaaaagtg ttgaaagacg cggtgaataa tatcacagcc aaaggaatta cagattataa    1020
gaagggcttt agttttgctt ttgaacagct gcttaattat aatgttttcca gagcaaactg    1080 caataagatt attatgctat tcacggatgg aggagaagag agagcccagg agatatttaa    1140 caatacaat aaagataaaa aagtacgtgt attcacgttt tcagttggtc aacacaatta    1200
tgacagagga cctattcagt ggatggcctg tgaaaacaaa ggttattatt atgaaattcc    1260
ttccattggt gcaataagaa tcaatactca ggaatatttg gatgtttttgg gaagaccaat    1320 ggttttagca ggagacaaag ctaagcaagt ccaatggaca aatgtgtacc tggatgcatt    1380
ggaactggga cttgtcatta ctggaactct tccggtcttc aacataaccg gccaatttga    1440
aaataagaca aacttaaaga accagctgat tcttggtgtg atgggagtag atgtgtcttt    1500
ggaagatatt aaaagactga caccacgttt tacactgtgc cccaatgggt attactttgc    1560
aatcgatcct aat                                                       1573
```

<210> SEQ ID NO 7
<211> LENGTH: 3301
<212> TYPE: DNA

<213> ORGANISM: Homo sapiens

<400> SEQUENCE: 7

```
ggcggccgct agcgccacca tggctgctgg ctgcctgctg gccttgactc tgacactttt      60
ccaatctttg ctcatcggcc cctcgtcgga ggagccgttc ccttcggccg tcactatcaa     120
atcatgggtg ataagatgc aagaagacct tgtcacactg caaaaacag caagtggagt      180
caatcagctt gttgatattt atgagaaata tcaagatttg tatactgtgg aaccaaataa     240
tgcacgccag ctggtagaaa ttgcagccag ggatattgag aaacttctga gcaacagatc     300
taaagccctg gtgcgcctgg cattggaagc ggagaaagtt caagcagctc accagtggag     360
agaagatttt gcaagcaatg aagttgtcta ctacaatgca aggatgatc tcgatcctga     420
gaaaaatgac agtgagccag gcagccagag gataaaacct gttttcattg aagatgctaa     480
ttttggacga caaatatctt atcagcacgc agcagtccat attcctactg acatctatga     540
gggctcaaca attgtgttaa atgaactcaa ctggacaagt gccttagatg aagttttcaa     600
aaagaatcgc gaggaagacc cttcattatt gtggcaggtt tttggcagtg ccactggcct     660
agctcgatat tatccagctt caccatgggt tgataatagt agaactccaa ataagattga     720
cctttatgat gtacgcagaa gaccatggta catccaagga gctgcatctc ctaaagacat     780
gcttattctg gtggatgtga gtggaagtgt tagtggattg acacttaaac tgatccgaac     840
atctgtctcc gaaatgttag aaaccctctc agatgatgat ttcgtgaatg tagcttcatt     900
taacagcaat gctcaggatg taagctgttt tcagcacctt gtccaagcaa atgtaagaaa     960
taaaaaagtg ttgaaagacg cggtgaataa tatcacagcc aaaggaatta cagattataa    1020
gaagggcttt agttttgctt ttgaacagct gcttaattat aatgtttcca gagcaaactg    1080
caataagatt attatgctat tcacggatgg aggagaagag agagcccagg agatatttaa    1140
caaatacaat aaagataaaa aagtacgtgt attcacgttt tcagttggtc aacacaatta    1200
tgacagagga cctattcagt ggatggcctg tgaaaacaaa ggttattatt atgaaattcc    1260
ttccattggt gcaataagaa tcaatactca ggaatatttg gatgttttgg gaagaccaat    1320
ggttttagca ggagacaaag ctaagcaagt ccaatggaca aatgtgtacc tggatgcatt    1380
ggaactggga cttgtcatta ctggaactct tccggtcttc aacataaccg gccaatttga    1440
aaataagaca aacttaaaga accagctgat tcttggtgtg atgggagtag atgtgtcttt    1500
ggaagatatt aaaagactga caccacgttt tacactgtgc cccaatgggt attactttgc    1560
aatcgatcct aatggttatg ttttattaca tccaaatctt cagccaaaga ccccaaatc     1620
tcaggagcca gtaacattgg atttccttga tgcagagtta gagaatgata ttaaagtgga    1680
gattcgaaat aagatgattg atggggaaag tggagaaaaa acattcagaa ctctggttaa    1740
atctcaagat gagagatata ttgacaaagg aaacaggaca tacacatgga cacctgtcaa    1800
tggcacagat tacagtttgg ccttggtatt accaacctac agttttttact atataaaagc    1860
caaactagaa gagacaataa ctcaggccag atcaaaaaag ggcaaaatga aggattcgga    1920
aaccctgaag ccagataatt ttgaagaatc tggctataca ttcatagcac caagagatta    1980
ctgcaatgac ctgaaaatat cggataataa cactgaattt ctttaaatt tcaacgagtt    2040
tattgataga aaaactccaa acaacccatc atgtaacgcg gatttgatta atagagtctt    2100
gcttgatgca ggctttacaa atgaacttgt ccaaaattac tggagtaagc agaaaaatat    2160
caagggagtg aaagcacgat tgttgtgac tgatggtggg attaccagag tttatcccaa    2220
agaggctgga gaaaattggc aagaaaaccc agagacatat gaggacagct tctataaaag    2280
```

```
gagcctagat aatgataact atgttttcac tgctccctac tttaacaaaa gtggacctgg    2340
tgcctatgaa tcgggcatta tggtaagcaa agctgtagaa atatatattc aagggaaact    2400
tcttaaacct gcagttgttg gaattaaaat tgatgtaaat tcctggatag agaatttcac    2460
caaaacctca atcagagatc cgtgtgctgg tccagtttgt gactgcaaaa gaaacagtga    2520
cgtaatggat tgtgtgattc tggatgatgg tgggtttctt ctgatggcaa atcatgatga    2580
ttatactaat cagattggaa gattttttgg agagattgat cccagcttga tgagacacct    2640
ggttaatata tcagtttatg cttttaacaa atcttatgat tatcagtcag tatgtgagcc    2700
cggtgctgca ccaaaacaag gagcaggaca tcgctcagca tatgtgccat cagtagcaga    2760
catattacaa attggctggt gggccactgc tgctgcctgg tctattctac agcagtttct    2820
cttgagtttg acctttccac gactccttga ggcagttgag atggaggatg atgacttcac    2880
ggcctccctg tccaagcaga gctgcattac tgaacaaacc cagtatttct tcgataacga    2940
cagtaaatca ttcagtggtg tattagactg tggaaactgt tccagaatct ttcatggaga    3000
aaagcttatg aacaccaact taatattcat aatggttgag agcaaaggga catgtccatg    3060
tgacacacga ctgctcatac aagcggagca gacttctgac ggtccaaatc cttgtgacat    3120
ggttaagcaa cccagatacc gaaaagggcc tgatgtctgc tttgataaca atgtcttgga    3180
ggattatact gactgtggtg gtgtttctgg attaaatccc tccctgtggt atatcattgg    3240
aatccagttt ctactacttt ggctggtatc tggcagcaca caccggctgt tatgaggatc    3300
c                                                                   3301
```

BICYCLIC γ-AMINO ACID DERIVATIVE

This application is a continuation of PCT Application No. PCT/JP2008/067223, filed Sep. 25, 2008, which claims priority to Japanese Application No. 2007-255430, filed Sep. 28, 2007, the contents of all of which are hereby incorporated herein by reference in their entirety.

TECHNICAL FIELD

The present invention relates to a bicyclic γ-amino acid derivative or a pharmacologically acceptable salt thereof. Particularly, the present invention relates to a compound having activity as an $\alpha_2\delta$ ligand and affinity for voltage-dependent calcium channel subunit $\alpha_2\delta$, or a pharmacologically acceptable salt thereof. The present invention further relates to a pharmaceutical composition comprising the compound or the pharmacologically acceptable salt thereof as an active ingredient.

BACKGROUND ART

Compounds that exhibit high-affinity binding to a voltage-dependent calcium channel subunit $\alpha_2\delta$ have been shown to be effective for treating, for example, neuropathic pain (see e.g., Non-Patent Documents 1 and 2). In this context, neuropathic pain refers to chronic pain caused by nervous tissue injury or the like and is a disease that significantly impairs quality of life to the extent that patients suffer from depression due to severe pain attacks.

Several types of $\alpha_2\delta$ ligands are currently known as therapeutic drugs for such neuropathic pain. Examples of $\alpha_2\delta$ ligands include gabapentine and pregabalin. $\alpha_2\delta$ ligands such as these compounds are useful for treating epilepsy and neuropathic pain or the like (e.g., Patent Document 1).

However, it has been reported that, for example, for gabapentine, its efficacy in the treatment of postherpetic neuralgia is approximately 60% according to patients' own evaluations (see e.g., Non-Patent Document 3) and that for pregabalin, its efficacy in the treatment of painful diabetic neuropathy is approximately 50% according to patients' own evaluations (see e.g., Non-Patent Document 4).

Other compounds are disclosed in, for example, Patent Documents 2, 3, and 4. However, the compounds disclosed in these Patent Documents are, principally, bicyclic saturated hydrocarbon compounds, which evidently differ from the compounds of the present invention.

Patent Document 1: Pamphlet of WO 04/006836
Patent Document 2: Pamphlet of WO 99/21824
Patent Document 3: Pamphlet of WO 01/28978
Patent Document 4: Pamphlet of WO 02/085839
Non-Patent Document 1: J. Biol. Chem. 271 (10): 5768-5776, 1996
Non-Patent Document 2: J. Med. Chem. 41: 1838-1845, 1998
Non-Patent Document 3: Acta Neurol. Scand. 101:359-371, 2000
Non-Patent Document 4: Drugs 64 (24): 2813-2820, 2004

DISCLOSURE OF THE INVENTION

Problems to be Solved by the Invention

Of great significance in treatment will be to provide a compound having a greater therapeutic effect than that of compounds having activity as an $\alpha_2\delta$ ligand conventionally used in the treatment.

Thus, an object of the present invention is to provide a bicyclic γ-amino acid derivative having excellent activity as an $\alpha_2\delta$ ligand, or a pharmacologically acceptable salt thereof, a pharmaceutical composition having an excellent therapeutic and/or preventive effect on pain or disorders such as those involving the central nervous system, and an intermediate for producing the same.

Means for Solving the Problems

The present invention provides:
(1) a compound represented by the general formula (I) or a pharmacologically acceptable salt thereof:

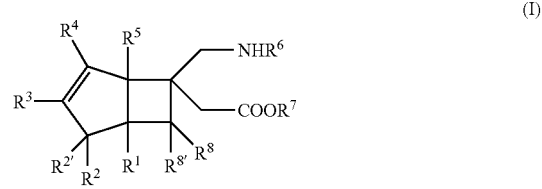

wherein
$R^1$, $R^2$, $R^{2'}$, $R^4$, $R^5$, $R^6$, $R^7$, $R^8$, and $R^{8'}$ are each independently a hydrogen atom, a halogen atom, or a C1-C6 alkyl group, or $R^2$ and $R^{2'}$ together with the carbon atom to which they are bound form a C3-C7 cycloalkyl group; and
$R^3$ is a hydrogen atom, a halogen atom, a C1-C6 alkyl group, a C1-C6 alkyl halide group, a hydroxy-C1-C6 alkyl group, a sulfanyl-C1-C6 alkyl group, a C1-C6 alkoxy-C1-C6 alkyl group, a C2-C6 alkenyl group, a C2-C6 alkynyl group, a C1-C6 alkoxy group, a C1-C6 alkylsulfanyl group, a C1-C6 alkylsulfanyl-C1-C6 alkyl group, a C2-C7 acylthio-C1-C6 alkyl group, a C2-C7 acyloxy-C1-C6 alkyl group, or a C3-C7 cycloalkyl group.

According to a preferred aspect, the present invention provides:
(2) the compound according to (1) or a pharmacologically acceptable salt thereof, wherein $R^1$ is a hydrogen atom;
(3) the compound according to (1) or (2) or a pharmacologically acceptable salt thereof, wherein both $R^2$ and $R^{2'}$ are hydrogen atoms;
(4) the compound according to any one of (1) to (3) or a pharmacologically acceptable salt thereof, wherein $R^3$ is a hydrogen atom or a C1-C6 alkyl group;
(5) the compound according to (4) or a pharmacologically acceptable salt thereof, wherein $R^3$ is a hydrogen atom, a methyl group, an ethyl group, a propyl group, or a butyl group;
(6) the compound according to (5) or a pharmacologically acceptable salt thereof, wherein $R^3$ is a hydrogen atom or an ethyl group;
(7) the compound according to any one of (1) to (6) or a pharmacologically acceptable salt thereof, wherein $R^4$ is a hydrogen atom;
(8) the compound according to any one of (1) to (7) or a pharmacologically acceptable salt thereof, wherein $R^5$ is a hydrogen atom;
(9) the compound according to any one of (1) to (8) or a pharmacologically acceptable salt thereof, wherein $R^6$ is a hydrogen atom;
(10) the compound according to any one of (1) to (9) or a pharmacologically acceptable salt thereof, wherein $R^7$ is a hydrogen atom;
(11) the compound according to any one of (1) to (10) or a pharmacologically acceptable salt thereof, wherein both $R^8$ and $R^{8'}$ are hydrogen atoms;

(12) a pharmacologically acceptable salt of a compound according to any one of (1) to (11), wherein the pharmacologically acceptable salt is hydrochloride, benzenesulfonate, or p-toluenesulfonate;

(13) a compound represented by the general formula (Ia) or a pharmacologically acceptable salt thereof:

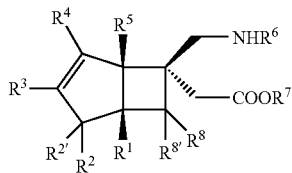

(Ia)

wherein $R^1$, $R^2$, $R^{2'}$, $R^4$, $R^5$, $R^6$, $R^7$, $R^8$, and $R^{8'}$ are each independently a hydrogen atom, a halogen atom, or a C1-C6 alkyl group, or $R^2$ and $R^{2'}$ together with the carbon atom to which they are bound form a C3-C7 cycloalkyl group; and $R^3$ is a hydrogen atom, a halogen atom, a C1-C6 alkyl group, a C1-C6 alkyl halide group, a hydroxy-C1-C6 alkyl group, a sulfanyl-C1-C6 alkyl group, a C1-C6 alkoxy-C1-C6 alkyl group, a C2-C6 alkenyl group, a C2-C6 alkynyl group, a C1-C6 alkoxy group, a C1-C6 alkylsulfanyl group, a C1-C6 alkylsulfanyl-C1-C6 alkyl group, a C2-C7 acylthio-C1-C6 alkyl group, a C2-C7 acyloxy-C1-C6 alkyl group, or a C3-C7 cycloalkyl group;

(14) a compound represented by the general formula (Ib) or a pharmacologically acceptable salt thereof:

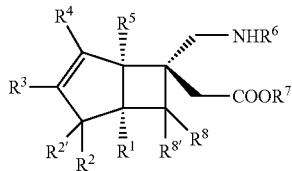

(Ib)

wherein $R^1$, $R^2$, $R^{2'}$, $R^4$, $R^5$, $R^6$, $R^7$, $R^8$, and $R^{8'}$ are each independently a hydrogen atom, a halogen atom, or a C1-C6 alkyl group, or $R^2$ and $R^{2'}$ together with the carbon atom to which they are bound form a C3-C7 cycloalkyl group; and $R^3$ is a hydrogen atom, a halogen atom, a C1-C6 alkyl group, a C1-C6 alkyl halide group, a hydroxy-C1-C6 alkyl group, a sulfanyl-C1-C6 alkyl group, a C1-C6 alkoxy-C1-C6 alkyl group, a C2-C6 alkenyl group, a C2-C6 alkynyl group, a C1-C6 alkoxy group, a C1-C6 alkylsulfanyl group, a C1-C6 alkylsulfanyl-C1-C6 alkyl group, a C2-C7 acylthio-C1-C6 alkyl group, a C2-C7 acyloxy-C1-C6 alkyl group, or a C3-C7 cycloalkyl group;

(15) a compound represented by the general formula (II) or a pharmacologically acceptable salt thereof:

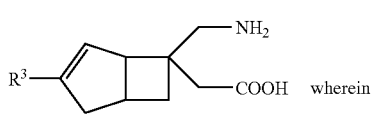

(II)

wherein $R^3$ is a hydrogen atom, a halogen atom, a C1-C6 alkyl group, a C1-C6 alkyl halide group, a hydroxy-C1-C6 alkyl group, a sulfanyl-C1-C6 alkyl group, a C1-C6 alkoxy-C1-C6 alkyl group, a C2-C6 alkenyl group, a C2-C6 alkynyl group, a C1-C6 alkoxy group, a C1-C6 alkylsulfanyl group, a C1-C6 alkylsulfanyl-C1-C6 alkyl group, a C2-C7 acylthio-C1-C6 alkyl group, a C2-C7 acyloxy-C1-C6 alkyl group, or a C3-C7 cycloalkyl group;

(16) a compound selected from the group consisting of the following:
(±)-[(1S,5R,6R)-6-(aminomethyl)bicyclo[3.2.0]hept-3-en-6-yl]acetic acid;
(±)-[(1S,5R,6R)-6-aminomethyl-3-methylbicyclo[3.2.0]hept-3-en-6-yl]acetic acid;
(±)-[(1S,5R,6R)-6-aminomethyl-3-ethylbicyclo[3.2.0]hept-3-en-6-yl]acetic acid;
(±)-[(1S,5R,6R)-6-aminomethyl-3-propylbicyclo[3.2.0]hept-3-en-6-yl]acetic acid;
(±)-[(1S,5R,6R)-6-aminomethyl-3-butylbicyclo[3.2.0]hept-3-en-6-yl]acetic acid;
[(1R,5S,6S)-6-(aminomethyl)bicyclo[3.2.0]hept-3-en-6-yl]acetic acid;
[(1S,5R,6R)-6-(aminomethyl)bicyclo[3.2.0]hept-3-en-6-yl]acetic acid;
[(1S,5R,6R)-6-(aminomethyl)bicyclo[3.2.0]hept-3-en-6-yl]acetic acid hydrochloride;
[(1S,5R,6R)-6-(aminomethyl)bicyclo[3.2.0]hept-3-en-6-yl]acetic acid benzenesulfonate;
[(1R,5S,6S)-6-aminomethyl-3-ethylbicyclo[3.2.0]hept-3-en-6-yl]acetic acid;
[(1R,5S,6S)-6-aminomethyl-3-ethylbicyclo[3.2.0]hept-3-en-6-yl]acetic acid p-toluenesulfonate;
[(1R,5S,6S)-6-(aminomethyl)-3-ethylbicyclo[3.2.0]hept-3-en-6-yl]acetic acid benzenesulfonate; and
[(1S,5R,6R)-6-aminomethyl-3-ethylbicyclo[3.2.0]hept-3-en-6-yl]acetic acid;

(17) a pharmaceutical composition comprising a compound or a pharmacologically acceptable salt thereof according to any one of (1) to (16) as an active ingredient;

(18) the pharmaceutical composition according to (17), for treating and/or preventing pain;

(19) the pharmaceutical composition according to (17), for treating and/or preventing a disease selected from the group consisting of acute pain, chronic pain, pain caused by soft tissue or peripheral injury, postherpetic neuralgia, occipital neuralgia, trigeminal neuralgia, myelomere or intercostal neuralgia, central pain, neuropathic pain, migraine, pain associated with osteoarthritis or articular rheumatism, pain associated with contusion, sprain, or trauma, spondylalgia, pain caused by spinal cord or brain stem injury, pain in the lower back, sciatic neuralgia, toothache, myofascial pain syndrome, episiotomy pain, gouty pain, pain caused by burn, cardiac pain, muscular pain, ocular pain, inflammatory pain, orofacial pain, abdominal pain, pain associated with dysmenorrhea, labor pain, or endometriosis, somatalgia, pain associated with nerve or radicular injury, pain associated with amputation, tic douloureux, neuroma, or angiitis, pain caused by diabetic neuropathy (or diabetic peripheral neuropathic pain), pain caused by chemotherapy-induced neuropathy, atypical facial neuralgia, neuropathic pain in the lower back, neuralgia associated with HIV, neuralgia associated with AIDS, hyperalgesia, burning pain, sudden pain, pain caused by chemotherapy, occipital neuralgia, psychogenic pain, pain associated with gallstone, neuropathic or non-neuropathic pain associated with cancer, phantom limb pain, functional abdominal pain, headache, acute or chronic tension headache, sinus headache, cluster headache, temporomandibular joint pain, maxillary sinus pain, pain caused by ankylosing spondylarthritis, postoperative pain, scar pain, chronic non-neuropathic pain, fibromyalgia, amyotrophic lateral sclerosis, epilepsy (particularly, partial epilepsy, adult partial seizure, and partial seizure in epilepsy patients), generalized anxiety disorder, and restless legs syndrome;

(20) the pharmaceutical composition according to (17), for treating and/or preventing pain caused by diabetic neuropathy;

(21) use of a compound or a pharmacologically acceptable salt thereof according to any one of (1) to (16) for producing a pharmaceutical composition;

(22) the use according to (21), wherein the pharmaceutical composition is a composition for treating and/or preventing pain;

(23) the use according to (21), wherein the pharmaceutical composition is a composition for treating and/or preventing pain caused by diabetic neuropathy;

(24) a method for treating and/or preventing pain, comprising administering a pharmacologically effective amount of a compound or a pharmacologically acceptable salt thereof according to any one of (1) to (16) to a mammal;

(25) the method according to (24), wherein the pain is pain caused by diabetic neuropathy;

(26) the method according to (24) or (25), wherein the mammal is a human; and

(27) a compound represented by the general formula (III):

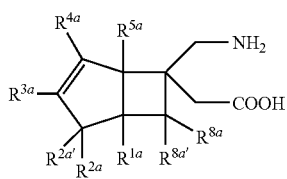

(III)

wherein $R^{1a}$, $R^{2a}$, $R^{2a'}$, $R^{4a}$, $R^{5a}$, $R^{8a}$ and $R^{8a'}$ are each independently a hydrogen atom, a halogen atom, or a C1-C6 alkyl group, or $R^{2a}$ and $R^{2a'}$ together with the carbon atom to which they are bound form a C3-C7 cycloalkyl group; and $R^{3a}$ is a hydrogen atom, a halogen atom, a C1-C6 alkyl group, a C1-C6 alkyl halide group, a hydroxy-C1-C6 alkyl group, a sulfanyl-C1-C6 alkyl group, a C1-C6 alkoxy-C1-C6 alkyl group, a C2-C6 alkenyl group, a C2-C6 alkynyl group, a C1-C6 alkoxy group, a C1-C6 alkylsulfanyl group, a C1-C6 alkylsulfanyl-C1-C6 alkyl group, a C2-C7 acylthio-C1-C6 alkyl group, a C2-C7 acyloxy-C1-C6 alkyl group, or a C3-C7 cycloalkyl group.

Advantages of the Invention

The present invention can provide a bicyclic γ-amino acid derivative having excellent activity as an $\alpha_2\delta$ ligand, or a pharmacologically acceptable salt thereof, a pharmaceutical composition having an excellent therapeutic and/or preventive effect on pain or disorders such as those involving the central nervous system, and an intermediate for producing the same.

BEST MODE FOR CARRYING OUT THE INVENTION

In the present specification, a "halogen atom" refers to a fluorine, chlorine, bromine, or iodine atom.

In the present specification, a "C1-C6 alkyl group" refers to a linear or branched alkyl group having 1 to 6 carbon atoms and includes methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups.

In the present specification, a "C1-C6 alkyl halide group" refers to the "C1-C6 alkyl group" substituted by the "halogen atom" and includes trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, and 6-iodohexyl groups.

In the present specification, a "hydroxy-C1-C6 alkyl group" refers to the "C1-C6 alkyl group" substituted by a hydroxyl group and includes hydroxymethyl, 2-hydroxyethyl, 3-hydroxypropyl, 4-hydroxybutyl, 5-hydroxypentyl, 6-hydroxyhexyl, 1-hydroxyethyl, and 1-hydroxypropyl groups.

In the present specification, a "sulfanyl-C1-C6 alkyl group" refers to the "C1-C6 alkyl group" substituted by a sulfanyl group and includes mercaptomethyl, mercaptoethyl, 2-mercaptoethyl, mercaptopropyl, 2-mercaptopropyl, and 3-mercaptopropyl groups.

In the present specification, a "C2-C6 alkenyl group" refers to a linear or branched alkenyl group having 2 to 6 carbon atoms and includes vinyl, allyl, 1-propenyl, isopropenyl, 1-butenyl, 2-butenyl, 3-butenyl, 2-methyl-1-propenyl, 2-methylallyl, 1-methyl-1-propenyl, 1-methylallyl, 1-pentenyl, 2-pentenyl, 3-pentenyl, 4-pentenyl, 3-methyl-1-butenyl, 3-methyl-2-butenyl, 3-methyl-3-butenyl, 2-methyl-1-butenyl, 2-methyl-2-butenyl, 2-methyl-3-butenyl, 1-methyl-1-butenyl, 1-methyl-2-butenyl, 1-methyl-3-butenyl, 1,1-dimethylallyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1,1-dimethyl-1-butenyl, 1,1-dimethyl-2-butenyl, 1,1-dimethyl-3-butenyl, 3,3-dimethyl-1-butenyl, 1-methyl-1-pentenyl, 1-methyl-2-pentenyl, 1-methyl-3-pentenyl, 1-methyl-4-pentenyl, 4-methyl-1-pentenyl, 4-methyl-2-pentenyl, and 4-methyl-3-pentenyl groups.

In the present specification, a "C2-C6 alkynyl group" refers to a linear or branched alkynyl group having 2 to 6 carbon atoms and includes ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 2-methyl-3-butynyl, 1-methyl-2-butynyl, 1-methyl-3-butynyl, 1,1-dimethyl-2-propynyl, 1-hexynyl, 2-hexynyl, 3-hexynyl, 4-hexynyl, and 5-hexynyl groups.

In the present specification, a "C1-C6 alkoxy group" refers to the "C1-C6 alkyl group" bound to an oxygen atom and includes methoxy, ethoxy, propoxy, isopropoxy, butoxy, isobutoxy, s-butoxy, tert-butoxy, pentoxy, isopentoxy, 2-methylbutoxy, neopentoxy, hexyloxy, 4-methylpentoxy, 3-methylpentoxy, and 2-methylpentoxy groups.

In the present specification, a "C1-C6 alkylsulfanyl group" refers to the "C1-C6 alkyl group" bound to a sulfur atom and includes methylsulfanyl, ethylsulfanyl, propylsulfanyl, isopropylsulfanyl, butylsulfanyl, isobutylsulfanyl, sec-butylsulfanyl, tert-butylsulfanyl, pentylsulfanyl, isopentylsulfanyl, 2-methylbutylsulfanyl, neopentylsulfanyl, 1-ethylpropylsulfanyl, hexylsulfanyl, isohexylsulfanyl, 4-methylpentylsulfanyl, 3-methylpentylsulfanyl, 2-methylpentylsulfanyl, 1-methylpentylsulfanyl, 3,3-dimethylbutylsulfanyl, 2,2-dimethylbutylsulfanyl, 1,1-dimethylbutylsulfanyl, 1,2-dimethylbutylsulfanyl, 1,3-dimethylbutylsulfanyl, 2,3-dimethylbutylsulfanyl, and 2-ethylbutylsulfanyl groups.

In the present specification, a "C1-C6 alkoxy-C1-C6 alkyl group" refers to the "C1-C6 alkyl group" substituted by the "C1-C6 alkoxy group" and includes methoxymethyl, ethoxymethyl, propoxymethyl, butoxymethyl, 3-methoxypropyl, 3-ethoxypropyl, 4-methoxybutyl, 5-methoxypentyl, and 6-methoxyhexyl groups.

In the present specification, a "C1-C6 alkylsulfanyl-C1-C6 alkyl group" refers to the "C1-C6 alkyl group" substituted by the "C1-C6 alkylsulfanyl group" and includes methylsulfanylmethyl, ethylsulfanylmethyl, propylsulfanylmethyl, isopropylsulfanylmethyl, butylsulfanylmethyl, isobutylsulfanylmethyl, sec-butylsulfanylmethyl, tert-butylsulfanylmethyl, pentylsulfanylmethyl, isopentylsulfanylethyl, 2-methylbutylsulfanylethyl, neopentylsulfanylethyl, 1-ethylpropylsulfanylethyl, hexylsulfanylethyl, isohexylsulfanylethyl, 4-methylpentylsulfanylethyl, 3-methylpentylsulfanylethyl, 2-methylpentylsulfanylpropyl, 1-methylpentylsulfanylpropyl, 3,3-dimethylbutylsulfanylpropyl, 2,2-dimethylbutylsulfanylpropyl, 1,1-dimethylbutylsulfanylpropyl, 1,2-dimethylbutylsulfanylpropyl, 1,3-dimethylbutylsulfanylpropyl, 2,3-dimethylbutylsulfanylpropyl, and 2-ethylbutylsulfanylpropyl groups.

In the present specification, a "C2-C7 acylthio-C1-C6 alkyl group" refers to the "C1-C6 alkyl group" substituted by a "C2-C7 acylthio group". The "C2-C7 acylthio group" refers to a "C2-C7 acyl group" bound to a sulfur atom. The "C2-C7 acyl group" refers to the "C1-C6 alkyl group" bound to a carbonyl group.

The "C2-C7 acyl group" includes acetyl, propionyl, butyryl, isobutyryl, sec-butyryl, tert-butyryl, pentanoyl, isopentanoyl, 2-methylbutyryl, neopentanoyl, 1-ethylpropionyl, hexanoyl, 4-methylpentanoyl, 3-methylpentanoyl, 2-methylpentanoyl, and 1-methylpentanoyl groups.

The "C2-C7 acylthio group" includes acetylthio, propionylthio, butyrylthio, isobutyrylthio, sec-butyrylthio, tert-butyrylthio, pentanoylthio, isopentanoylthio, 2-methylbutyrylthio, neopentanoylthio, 1-ethylpropionylthio, hexanoylthio, 4-methylpentanoylthio, 3-methylpentanoylthio, 2-methylpentanoylthio, and 1-methylpentanoylthio groups.

The "C2-C7 acylthio-C1-C6 alkyl group" includes acetylthiomethyl, 2-acetylthioethyl, 3-acetylthiopropyl, 4-acetylthiobutyl, propionylthiomethyl, 2-propionylthioethyl, and butyrylthiomethyl groups.

In the present specification, a "C2-C7 acyloxy-C1-C6 alkyl group" refers to the "C1-C6 alkyl group" substituted by a "C2-C7 acyloxy group". The "C2-C7 acyloxy group" refers to the "C2-C7 acyl group" bound to an oxygen atom.

The "C2-C7 acyloxy group" includes acetyloxy, propionyloxy, butyryloxy, isobutyryloxy, sec-butyryloxy, tert-butyryloxy, pentanoyloxy, isopentanoyloxy, 2-methylbutyryloxy, neopentanoyloxy, 1-ethylpropionyloxy, hexanoyloxy, 4-methylpentanoyloxy, 3-methylpentanoyloxy, 2-methylpentanoyloxy, and 1-methylpentanoyloxy groups.

The "C2-C7 acyloxy-C1-C6 alkyl group" includes acetyloxymethyl, 2-acetyloxyethyl, 3-acetyloxypropyl, 4-acetyloxybutyl, propionyloxymethyl, 2-propionyloxyethyl, and butyryloxymethyl groups.

In the present specification, a "C3-C7 cycloalkyl group" refers to a saturated cyclic hydrocarbon group having 3 to 7 carbon atoms and includes cyclopropyl, cyclobutyl, cyclopentyl, cyclohexyl, and cycloheptyl groups.

Since a compound represented by the general formula (I), when having amino and/or carboxyl groups in the structure, forms a salt through reaction with an acid or a base, a "pharmacologically acceptable salt" refers to this salt.

Salts based on an amino group include: hydrohalides such as hydrofluoride, hydrochloride, hydrobromide, and hydroiodide; inorganic acid salts such as hydrochloride, nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, ascorbate, tartrate, oxalate, and maleate; and amino acid salts such as glycine salt, lysine salt, arginine salt, ornithine salt, glutamate, and aspartate. Inorganic acid salts or arylsulfonates are preferable, and hydrochloride, benzenesulfonate, or p-toluenesulfonate is more preferable.

Salts based on a carboxyl group include: alkali metal salts such as sodium salt, potassium salt, and lithium salt; alkaline-earth metal salts such as calcium salt and magnesium salt; metal salts such as aluminum salt and iron salt; inorganic salts such as ammonium salt; amine salts, for example, organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris(hydroxymethyl)aminomethane salt; and amino acid salts such as glycine salt, lysine salt, arginine salt, ornithine salt, glutamate, and aspartate.

A compound represented by the general formula (I), (Ia), (Ib), or (II), when left in the air or recrystallized, may associate with adsorbed water through water absorption to form a hydrate. Such hydrates are also encompassed by the salt of the present invention.

The compound represented by the general formula (I) or (II) has an asymmetric carbon atom in its molecule and therefore includes optical isomers. All these isomers and mixtures of these isomers are represented by a single formula, i.e., the general formula (I) or (II). Thus, the compound represented by the general formula (I) or (II) also encompasses all such optical isomers and mixtures of these optical isomers at appropriate ratios.

The compound represented by the general formula (I) is preferably a compound represented by the general formula (Ia) or (Ib), more preferably, a compound represented by the general formula (Ib).

In the general formula (I), (Ia), or (Ib), $R^1$ is preferably a hydrogen atom.

In the general formula (I), (Ia), or (Ib), $R^2$ is preferably a hydrogen atom.

In the general formula (I), (Ia), or (Ib), $R^{2'}$ is preferably a hydrogen atom.

In the general formula (I), (Ia), (Ib), or (II), $R^3$ is preferably a hydrogen atom or a C1-C6 alkyl group, more preferably a hydrogen atom, a methyl group, an ethyl group, a propyl group, or a butyl group, even more preferably a hydrogen atom or an ethyl group.

In the general formula (I), (Ia), or (Ib), $R^4$ is preferably a hydrogen atom.

In the general formula (I), (Ia), or (Ib), $R^5$ is preferably a hydrogen atom.

In the general formula (I), (Ia), or (Ib), $R^6$ is preferably a hydrogen atom.

In the general formula (I), (Ia), or (Ib), $R^7$ is preferably a hydrogen atom.

In the general formula (I), (Ia), or (Ib), $R^8$ is preferably a hydrogen atom.

In the general formula (I), (Ia), or (Ib), $R^{8'}$ is preferably a hydrogen atom.

In the general formula (III), $R^{1a}$ is preferably a hydrogen atom.

In the general formula (III), $R^{2a}$ is preferably a hydrogen atom.

In the general formula (III), $R^{2a'}$ is preferably a hydrogen atom.

In the general formula (III), $R^{3a}$ is preferably a hydrogen atom or a C1-C6 alkyl group, more preferably a hydrogen atom, a methyl group, an ethyl group, a propyl group, or a butyl group, even more preferably a hydrogen atom or an ethyl group.

In the general formula (III), $R^{4a}$ is preferably a hydrogen atom. In the general formula (III), $R^{5a}$ is preferably a hydrogen atom. In the general formula (III), $R^{8a}$ is preferably a hydrogen atom. In the general formula (III), $R^{8a'}$ is preferably a hydrogen atom.

The compound represented by the general formula (I) is specifically exemplified by compounds described in, for example, Table 1 below. However the present invention is not limited to these.

In the examples below, n-Pr represents an n-propyl group and i-Pr represents an isopropyl group.

TABLE 1

(I)

| No | $R^1$ | $R^2$ | $R^{2'}$ | $R^3$ | $R^4$ | $R^5$ | $R^6$ | $R^7$ | $R^8$ | $R^{8'}$ |
|---|---|---|---|---|---|---|---|---|---|---|
| 1 | —H | —H | —H | —H | —H | —H | —H | —H | —H | —H |
| 2 | —CH$_3$ | —H | —H | —H | —H | —H | —H | —H | —H | —H |
| 3 | —H | —CH$_3$ | —H | —H | —H | —H | —H | —H | —H | —H |
| 4 | —H | —H | —H | —CH$_3$ | —H | —H | —H | —H | —H | —H |
| 5 | —H | —H | —H | —H | —CH$_3$ | —H | —H | —H | —H | —H |
| 6 | —H | —H | —H | —H | —H | —CH$_3$ | —H | —H | —H | —H |
| 7 | —H | —H | —H | —H | —H | —H | —H | —H | —CH$_3$ | —H |
| 8 | —H | —H | —H | —CH$_2$CH$_3$ | —H | —H | —H | —H | —H | —H |
| 9 | —H | —H | —H | —CH$_2$CH$_2$CH$_3$ | —H | —H | —H | —H | —H | —H |
| 10 | —H | —H | —H | —CH$_2$CH$_2$CH$_2$CH$_3$ | —H | —H | —H | —H | —H | —H |
| 11 | —H | —H | —H | —CH(CH$_3$)$_2$ | —H | —H | —H | —H | —H | —H |
| 12 | —H | —H | —H | —CH(CH$_3$)CH$_2$CH$_3$ | —H | —H | —H | —H | —H | —H |
| 13 | —H | —H | —H | —CH$_2$CH(CH$_3$)$_2$ | —H | —H | —H | —H | —H | —H |
| 14 | —H | —H | —H | —CH$_2$CH=CH$_2$ | —H | —H | —H | —H | —H | —H |
| 15 | —H | —H | —H | -cyclopentyl | —H | —H | —H | —H | —H | —H |
| 16 | —H | —H | —H | —CH$_2$OC(O)CH$_3$ | —H | —H | —H | —H | —H | —H |
| 17 | —H | —H | —H | —CH$_2$OCH$_3$ | —H | —H | —H | —H | —H | —H |
| 18 | —H | —H | —H | —CH$_2$SCH$_3$ | —H | —H | —H | —H | —H | —H |
| 19 | —H | —H | —H | —CH$_3$ | —CH$_3$ | —H | —H | —H | —H | —H |
| 20 | —H | —H | —H | —CH$_2$CH$_3$ | —H | —H | —H | —C(CH$_3$)$_3$ | —H | —H |
| 21 | —H | —H | —H | —H | —H | —H | —CH$_3$ | —H | —H | —H |
| 22 | —H | —H | —H | —H | —H | —H | —CH$_2$CH$_3$ | —H | —H | —H |
| 23 | —H | —H | —H | —H | —H | —H | -n-Pr | —H | —H | —H |
| 24 | —H | —H | —H | —H | —H | —H | -i-Pr | —H | —H | —H |
| 25 | —H | —H | —H | —H | —H | —H | —H | —CH$_3$ | —H | —H |
| 26 | —H | —H | —H | —H | —H | —H | —H | —CH$_2$CH$_3$ | —H | —H |
| 27 | —H | —H | —H | —H | —H | —H | —H | -n-Pr | —H | —H |
| 28 | —H | —H | —H | —H | —H | —H | —H | -i-Pr | —H | —H |
| 29 | —H | —H | —H | —H | —H | —H | —H | —H | —CH$_3$ | —CH$_3$ |
| 30 | —H | —H | —H | —CH$_2$CH$_2$F | —H | —H | —H | —H | —H | —H |
| 31 | —H | —H | —H | —CH$_2$CHF$_2$ | —H | —H | —H | —H | —H | —H |
| 32 | —H | —H | —H | —CH$_2$CF$_3$ | —H | —H | —H | —H | —H | —H |
| 33 | —H | —H | —H | —F | —H | —H | —H | —H | —H | —H |
| 34 | —H | —H | —H | —H | —CH$_2$CH$_3$ | —H | —H | —H | —H | —H |
| 35 | —H | —H | —H | —CH$_2$CCH | —H | —H | —H | —H | —H | —H |
| 36 | —H | —H | —H | —CH$_2$SC(O)CH$_3$ | —H | —H | —H | —H | —H | —H |
| 37 | —H | —H | —H | —CH$_2$SC(O)CH$_2$CH$_3$ | —H | —H | —H | —H | —H | —H |
| 38 | —H | Cyclopropane formed by these moieties together with the carbon atom bound thereto | | —H | —H | —H | —H | —H | —H | —H |
| 39 | —H | Cyclobutane formed by these moieties together with the carbon atom bound thereto | | —H | —H | —H | —H | —H | —H | —H |

TABLE 1-continued

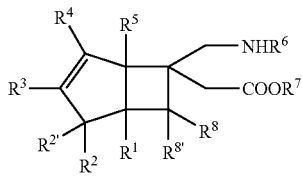

(I)

| No | R¹ | R² | R²' | R³ | R⁴ | R⁵ | R⁶ | R⁷ | R⁸ | R⁸' |
|---|---|---|---|---|---|---|---|---|---|---|
| 40 | —F | —H | —H | —H | —H | —H | —H | —H | —H | —H |
| 41 | —H | —F | —H | —H | —H | —H | —H | —H | —H | —H |
| 42 | —H | —H | —H | —H | —F | —H | —H | —H | —H | —H |
| 43 | —H | —H | —H | —H | —H | —F | —H | —H | —H | —H |
| 44 | —H | —H | —H | —CH₂CH₃ | —H | —H | —CH₃ | —H | —H | —H |
| 45 | —H | —H | —H | —CH₂CH₃ | —H | —H | —CH₂CH₃ | —H | —H | —H |
| 46 | —H | —H | —H | —CH₂CH₃ | —H | —H | -n-Pr | —H | —H | —H |
| 47 | —H | —H | —H | —CH₂CH₃ | —H | —H | -i-Pr | —H | —H | —H |
| 48 | —H | —H | —H | —CH₂CH₃ | —H | —H | —H | —CH₃ | —H | —H |
| 49 | —H | —H | —H | —CH₂CH₃ | —H | —H | —H | —CH₂CH₃ | —H | —H |
| 50 | —H | —H | —H | —CH₂CH₃ | —H | —H | —H | -n-Pr | —H | —H |
| 51 | —H | —H | —H | —CH₂CH₃ | —H | —H | —H | -i-Pr | —H | —H |
| 52 | —H | —H | —H | —H | —H | —H | —H | —H | —F | —H |

Among the exemplary compounds, the compounds 1, 4, 8, 9, and 10 are preferred.

Of the compounds represented by the general formula (I), a compound wherein both $R^6$ and $R^7$ are hydrogen atoms is produced by, for example, a process A (step A-1, step A-2, step A-3, optional step A-4, and step A-5) or a process D (step A-1, step D-1, step D-2, optional step A-4, and step A-5).

On the other hand, of the compounds represented by the general formula (I), a compound wherein both $R^6$ and $R^7$ are moieties other than a hydrogen atom is produced through, for example, a step A-6, a step A-7, an optional step A-8, and a step A-9 in this order following the step A-5.

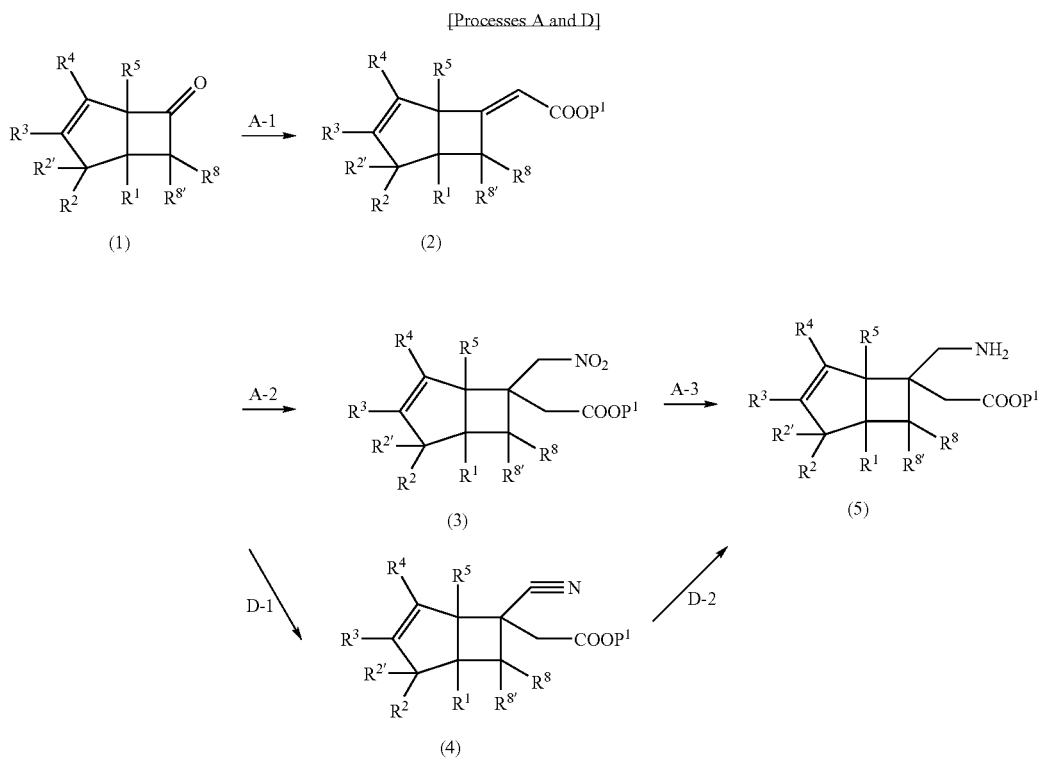

[Processes A and D]

-continued

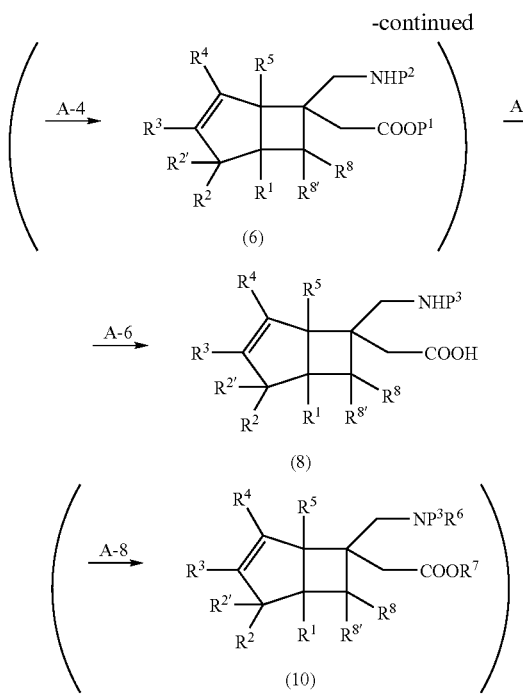

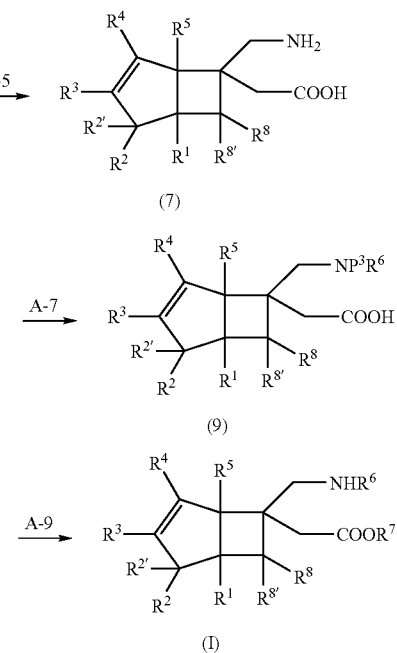

wherein $R^1$, $R^2$, $R^{2'}$, $R^3$, $R^4$, $R^5$, $R^6$, $R^7$, $R^8$, and $R^{8'}$ are as defined above; $P^1$ represents a protective group for a carboxyl group; and $P^2$ and $P^3$ represent a protective group for an amino group.

$P^1$ is not particularly limited as long as it is generally used as a protective group for carboxyl groups. Examples thereof include methyl, ethyl, propyl, isopropyl, butyl, isobutyl, sec-butyl, tert-butyl, hexyl, bromo-tert-butyl, trichloroethyl, benzyl, p-nitrobenzyl, o-nitrobenzyl, p-methoxybenzyl, p-tert-butylbenzyl, acetoxymethyl, propionyloxymethyl, butyryloxymethyl, isobutyryloxymethyl, valeryloxymethyl, pivaloyloxymethyl, acetoxyethyl, acetoxypropyl, acetoxybutyl, propionyloxyethyl, propionyloxypropyl, butyryloxyethyl, isobutyryloxyethyl, pivaloyloxyethyl, hexanoyloxyethyl, ethylbutyryloxymethyl, dimethylbutyryloxymethyl, pentanoyloxyethyl, methoxycarbonyloxymethyl, ethoxycarbonyloxymethyl, propoxycarbonyloxymethyl, tert-butoxycarbonyloxymethyl, methoxycarbonyloxyethyl, ethoxycarbonyloxyethyl, isopropoxycarbonyloxyethyl, tert-butyldimethylsilyl, trimethylsilyl, methoxymethyl, ethoxymethyl, propoxymethyl, isopropoxymethyl, (2-methylthio)-ethyl, 3-methyl-2-butenyl, 5-indanyl, and 3-phthalidyl groups.

$P^2$ and $P^3$ are not particularly limited as long as they are generally used as protective groups for amino groups. Examples thereof include formyl, phenylcarbonyl, methoxycarbonyl, ethoxycarbonyl, phenyloxycarbonyl, 9-fluorenylmethyloxycarbonyl, adamantyloxycarbonyl, benzyloxycarbonyl, benzylcarbonyl, benzyl, benzhydryl, trityl, and phthaloyl groups.

Of the various conditions for the production processes of the compound represented by the general formula (I), the reaction time in each step differs depending on the types of starting compounds, secondary materials, catalysts, reagents, solvents, etc., used in the step and is usually 1 to 48 hours, preferably 1 to 24 hours. On the other hand, other conditions are described below in detail for each step.

[Step A-1]

The step A-1 is a step of producing a compound (2) through alkenylation reaction from a compound (1).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, and sulfoxide solvents. Ether solvents are preferable, and tetrahydrofuran is more preferable.

Secondary materials used include: Horner-Emmons reagents; alkyl dialkylphosphonoacetates such as ethyl diethylphosphonoacetate; phosphorus ylide reagents; and phosphonium ylides such as ethoxycarbonylmethylene triphenylphosphorane.

Reagents used are inorganic bases, alkali metal alkoxides, organic bases, organic metal bases, and the like. Inorganic bases are preferable, and sodium hydride is more preferable.

The reaction temperature differs depending on the types of the starting compound, the solvents, the secondary materials, the reagents, etc., and is usually 0 to 100° C., preferably 0° C. to room temperature.

After completion of the reaction, the compound of interest of the present reaction is collected from the reaction mixture according to a standard method. For example, according to need, excess reagents are degraded, and the reaction is terminated. The reaction mixture is appropriately neutralized. Moreover, insoluble matter, if any, is removed by filtration. To the residue, water and a water-immiscible organic solvent such as ethyl acetate are then added, and the organic layer containing the compound of interest is separated, then washed with water or the like, and then dried over anhydrous magnesium sulfate, anhydrous sodium sulfate, anhydrous sodium bicarbonate, or the like. Then, the solvent is distilled off to obtain the compound of interest. The obtained compound of interest is separated and purified by appropriately combining standard methods according to need, for example, usual methods routinely used in the separation and purification of organic compounds, such as recrystallization and reprecipitation, followed by elution with an appropriate eluent by use of chromatography.

Moreover, in the subsequent procedures, the compound of interest of each reaction is usually collected from the reaction mixture after completion of the reaction in each step in the same way as in the aftertreatment of the step A-1.

[Step A-2]

The step A-2 is a step of producing a compound (3) from the compound (2).

Solvents used are the same as those in the step A-1. Ether solvents or nitrile solvents are preferable, and tetrahydrofuran or acetonitrile is more preferable.

Secondary materials used include nitromethane.

Reagents used include the same as those in the step A-1. Organic bases or organic metal bases are preferable, and diazabicycloundecene or tetraalkyl ammonium halide is more preferable.

The reaction temperature differs depending on the types of the starting compound, the solvents, the secondary materials, the reagents, etc., and is usually 0 to 100° C., preferably 0 to 60° C.

[Step A-3]

The step A-3 is a step of reducing the compound (3) to produce a compound (5).

Solvents used are not particularly limited as long as they are solvents that do not inhibit the reaction and can dissolve the starting material to some extent. The solvents include alcohol solvents, ester solvents, ether solvents, and aqueous solvents. Alcohol solvents and aqueous solvents are preferable, and ethanol or water is more preferable.

Reagents used include palladium-carbon, palladium hydroxide-carbon, nickel chloride, tin chloride, sodium borohydride, iron powder, tin, zinc, and hydrogen. Iron powder or tin is preferable.

The reaction temperature differs depending on the types of the starting compound, the solvents, the reagents, etc., and is usually 0 to 100° C., preferably 60 to 80° C.

[Step D-1]

The step D-1 is a step of producing a compound (4) from the compound (2).

Solvents used include the same as those in the step A-1, alcohol solvents, and aqueous solvents. Amide solvents are preferable, and N,N-dimethylformamide is more preferable.

Reagents used include: cyanating agents; and metal cyanide reagents such as aluminum cyanide. Cyanating agents are preferable, and sodium cyanide or potassium cyanide is more preferable.

The reaction temperature differs depending on the types of the starting compound, the solvents, the reagents, etc., and is usually 0 to 100° C., preferably 60 to 80° C.

[Step D-2]

The step D-2 is a step of reducing the compound (4) to produce the compound (5).

Solvents used include the same as those in the step D-1. Alcohol solvents or ether solvents are preferable, and methanol or tetrahydrofuran is more preferable.

Catalysts used include transition metal catalysts. Nickel chloride or cobalt chloride is preferable.

Reagents used include boron reagents. Sodium borohydride is preferable.

The reaction temperature differs depending on the types of the starting compound, the solvents, the catalysts, the reagents, etc., and is usually 0 to 100° C., preferably 0° C. to room temperature.

[Step A-4]

A step of protecting the amino group of the compound (5) (step A-4) may optionally be performed to prepare a compound (6).

Solvents used include the same as those in the step A-3. Alcohol solvents or aqueous solvents are preferable, and ethanol or water is more preferable.

Reagents used include di-tert-butyl dicarbonate, chloroformate, acid halide, acid anhydride, sulfonyl chloride, inorganic bases, alkali metal alkoxides, organic bases, and organic metal bases. Di-tert-butyl dicarbonate, inorganic bases, or organic bases are preferable, and di-tert-butyl dicarbonate, sodium hydroxide, or triethylamine is more preferable.

The reaction temperature differs depending on the types of the starting compound, the solvents, the reagents, etc., and is usually 0 to 100° C., preferably 0° C. to room temperature.

[Step A-5]

The step A-5 is a step of producing a compound (7) from the compound (5) or (6) through deprotection of the protective group.

Solvents used include the same as those in the step A-3. Ether solvents or ester solvents are preferable, and dioxane or ethyl acetate is more preferable.

Reagents used are inorganic acids, inorganic bases, or organic acids. Hydrochloric acid, acetic acid, or trifluoroacetic acid is more preferable.

The reaction temperature differs depending on the types of the starting compound, the solvents, the secondary materials, the reagents, etc., and is usually 0 to 100° C., preferably 0° C. to room temperature.

[Step A-6]

The step A-6 is a step of protecting the amino group of the compound (7) to produce a compound (8).

Solvents used include the same as those in the step A-3. Alcohol solvents or aqueous solvents are preferable, and ethanol or water is more preferable.

Reagents used include the same as those in the step A-4. Di-tert-butyl dicarbonate, inorganic bases, or organic bases are preferable, and di-tert-butyl dicarbonate, sodium hydroxide, or triethylamine is more preferable.

The reaction temperature differs depending on the types of the starting compound, the solvents, the reagents, etc., and is usually 0 to 100° C., preferably 0° C. to room temperature.

[Step A-7]

The step A-7 is a step of alkylating the compound (8) to produce a compound (9).

Solvents used include the same as those in the step A-1. Ether solvents are preferable.

Secondary materials used include alkyl halide.

Reagents used include the same as those in the step A-1. Sodium hydride is preferable.

The reaction temperature differs depending on the types of the starting compound, the solvents, the secondary materials, the reagents, etc., and is usually −78° C. to room temperature, preferably 0° C. to room temperature.

[Step A-8]

After the step A-7, the step A-8 may optionally be performed. The step A-8 is a step of alkylating the compound (9) to produce a compound (10).

Solvents used include the same as those in the step A-1. Ether solvents or amide solvents are preferable.

Secondary materials used include alkyl halide.

Reagents used include the same as those in the step A-1. Sodium carbonate or potassium carbonate is preferable.

The reaction temperature differs depending on the types of the starting compound, the solvents, the secondary materials, the reagents, etc., and is usually −78° C. to room temperature, preferably 0° C. to room temperature.

[Step A-9]

The step A-9 is a step of producing the compound represented by the general formula (I) from the compound (9) through deprotection of the protective group.

Solvents used include the same as those in the step A-3. Ether solvents or ester solvents are preferable, and dioxane or ethyl acetate is more preferable.

Reagents used include the same as those in the step A-4. Hydrochloric acid, acetic acid, or trifluoroacetic acid is preferable.

The reaction temperature differs depending on the types of the starting compound, the solvents, the secondary materials, the reagents, etc., and is usually 0 to 100° C., preferably 0° C. to room temperature.

The compound (1) obtained by the production processes can also be produced by, for example, a process B, C, or E shown below. The process B consists of steps B-1, B-2, B-3, and B-4. The process C consists of steps C-1, B-3, and B-4.

hol solvents, or mixed solvents thereof are preferable, and tetrahydrofuran-methanol is more preferable.

Reagents used include borohydride reagents. Sodium borohydride is preferable.

The reaction temperature differs depending on the types of the starting compound, the solvents, the reagents, etc., and is usually 0 to 100° C., preferably 0° C. to room temperature.

[Step C-1]

The step C-1 is a step of producing the compound (13) from a compound (15) through coupling reaction.

Solvents used include the same as those in the step A-1 and boric acid derivatives. Ether solvents or boric acid derivatives are preferable, and tetrahydrofuran, dimethyl ether, or trimethyl borate is more preferable.

Secondary materials used include alkyl α-halogenoacetate. Alkyl bromoacetate is preferable, and methyl bromoacetate, ethyl bromoacetate, or tert-butyl bromoacetate is more preferable.

Reagents used include zinc.

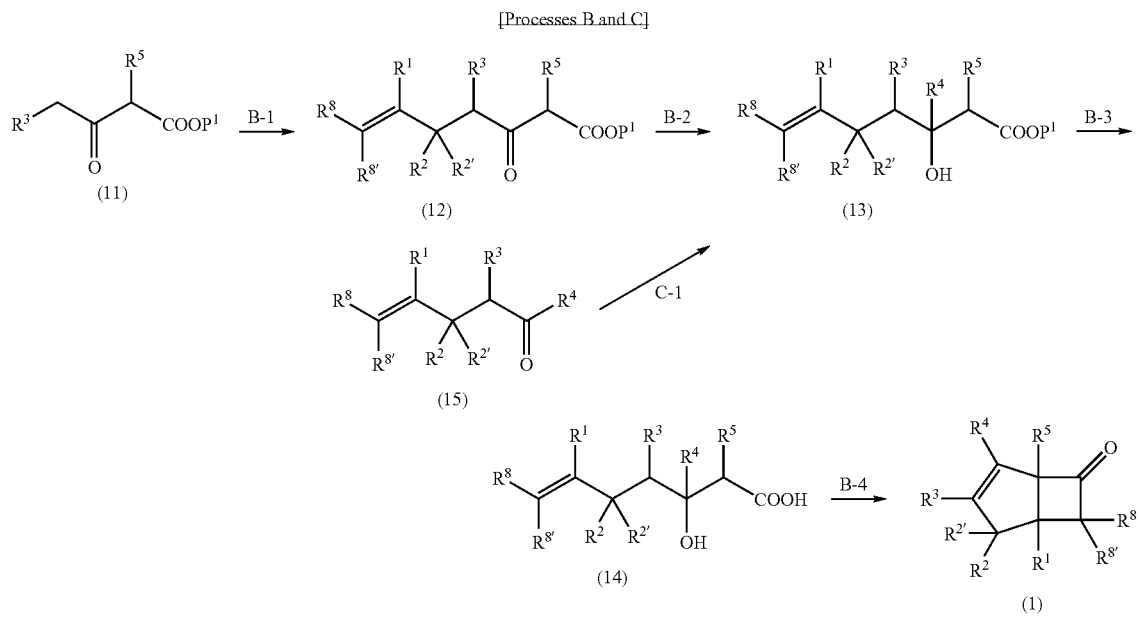

[Processes B and C]

wherein $R^1$, $R^2$, $R^{2'}$, $R^3$, $R^4$, $R^5$, $R^6$, $R^7$, $R^8$, $R^{8'}$, and $P^1$ are as defined above.

[Step B-1]

The step B-1 is a step of producing a compound (12) from a compound (11) through substitution reaction.

Solvents used include the same as those in the step A-1. Ether solvents are preferable.

Secondary materials used include allyl halide and crotyl halide. Allyl bromide or crotyl chloride is preferable.

Reagents used include the same as those in the step A-1. Sodium hydride or butyllithium is preferable.

The reaction temperature differs depending on the types of the starting compound, the solvents, the secondary materials, the reagents, etc., and is usually −78° C. to room temperature, preferably 0° C. to room temperature.

[Step B-2]

The step B-2 is a step of producing a compound (13) from the compound (12) through reduction reaction.

Solvents used include the same as those in the step A-1, alcohol solvents, and aqueous solvents. Ether solvents, alco- The reaction temperature differs depending on the types of the starting compound, the solvents, the secondary materials, the reagents, etc., and is usually 0 to 100° C., preferably 60 to 80° C.

[Step B-3]

The step B-3 is a step of hydrolyzing the compound (13) to produce a compound (14).

Solvents used are not particularly limited as long as they are solvents that do not inhibit the reaction and can dissolve the starting material to some extent. The solvents include aromatic solvents, ether solvents, halogenated hydrocarbon solvents, nitrile solvents, amide solvents, sulfoxide solvents, alcohol solvents, and aqueous solvents. Alcohol solvents, aqueous solvents, or mixed solvents thereof are preferable, and methanol-water is more preferable.

Reagents used include inorganic bases. Potassium hydroxide, sodium hydroxide, or lithium hydroxide is preferable.

The reaction temperature differs depending on the types of the starting compound, the solvents, the reagents, etc., and is usually 0 to 100° C., preferably 0° C. to room temperature.

19

[Step B-4]

The step B-4 is a step of cyclizing the compound (14) through alkali treatment to produce the compound (1).

Solvents used are not particularly limited as long as they are solvents that do not inhibit the reaction and can dissolve the starting material to some extent. The solvents include aromatic solvents, ether solvents, halogenated hydrocarbon solvents, nitrile solvents, acids, and acid anhydrides. Acids or acid anhydrides are preferable, and acetic acid or acetic anhydride is more preferable.

Reagents used include alkali metal salts. Potassium acetate is preferable.

The reaction temperature differs depending on the types of the starting compound, the solvents, the reagents, etc., and is usually 0 to 150° C., preferably room temperature to 140° C.

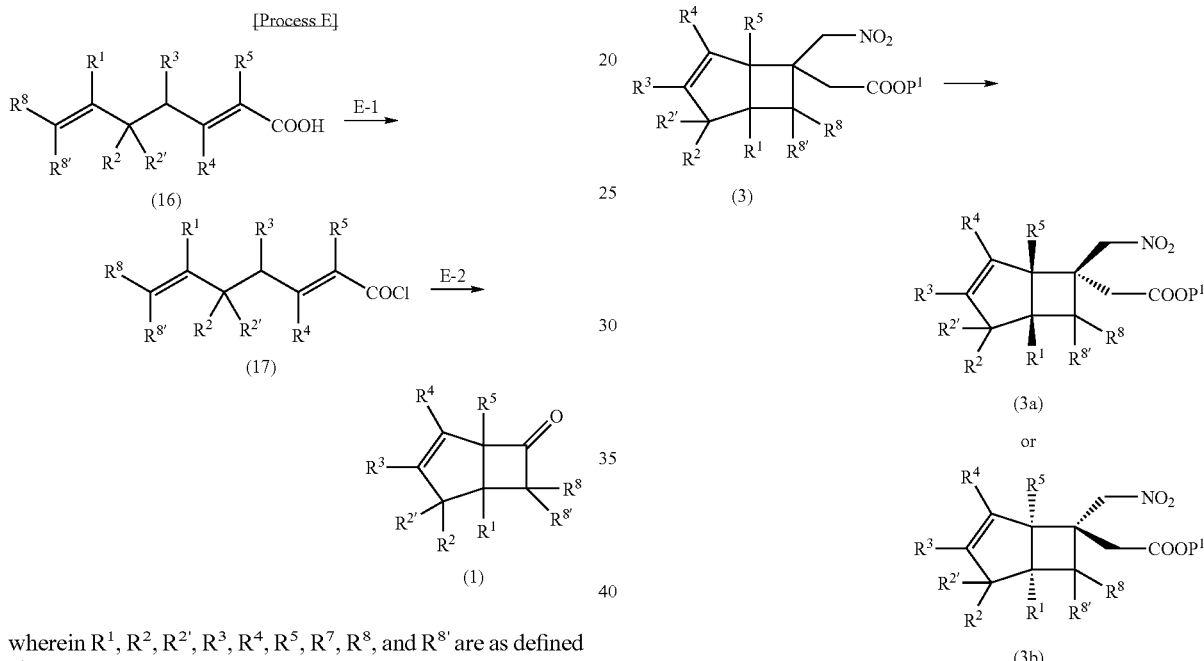

wherein $R^1$, $R^2$, $R^{2'}$, $R^3$, $R^4$, $R^5$, $R^7$, $R^8$, and $R^{8'}$ are as defined above.

[Step E-1]

The step E-1 is a step of producing a compound (17) from a compound (16).

Solvents used include the same as those in the step A-1 and hydrocarbon solvents. Aromatic solvents, halogenated hydrocarbon solvents, or hydrocarbon solvents are preferable, and toluene is more preferable.

Reagents used include oxalyl chloride and thionyl chloride. Oxalyl chloride is preferable.

The reaction temperature differs depending on the types of the starting compound, the solvents, the reagents, etc., and is usually 0 to 150° C., preferably room temperature to 120° C.

[Step E-2]

The step E-2 is a step of producing the compound (1) from the compound (17).

Solvents used include the same as those in the step E-1. Aromatic solvents, halogenated hydrocarbon solvents, or hydrocarbon solvents are preferable, and toluene is more preferable.

Reagents used include organic bases. Triethylamine is preferable.

The reaction temperature differs depending on the types of the starting compound, the solvents, the reagents, etc., and is usually 0 to 150° C., preferably room temperature to 120° C.

20

The compound represented by the general formula (II) can be produced in the same way as in the compound represented by the general formula (I).

The compound represented by the general formula (Ia) or (Ib) is an optical isomer of the compound represented by the general formula (I) and is produced by the process A plus, for example, a process F, G, or H shown below.

[Process F]

The process F is a process of performing, after the step A-2 in the process A, optical resolution to produce optical isomers (3a) and (3b) of the compound (3). From the optical isomer (3a) or (3b), the compound represented by the general formula (Ia) or (Ib) is produced through the steps A-3 to A-5 or the steps A-3 to A-9.

wherein $R^1$, $R^2$, $R^{2'}$, $R^3$, $R^4$, $R^5$, $R^6$, $R^7$, $R^8$, $R^{8'}$, and $P^1$ are as defined above.

Solvents used include the same as those in the step A-1, hydrocarbon solvents, alcohol solvents, and mixed solvents of hydrocarbon solvents and alcohol solvents. Hexane-isopropanol or hexane-ethanol is preferable.

The column used in the optical resolution is not particularly limited as long as it is a chiral column that permits optical resolution. The column is preferably CHIRALPAK (registered trademark) AD-H or CHIRALPAK (registered trademark) IC manufactured by Daicel Chemical Industries, Ltd.

The temperature used is usually 0 to 40° C., preferably 20 to 40° C.

After completion of the reaction, the eluent (solvent) is distilled off to obtain the compound of interest of the present reaction.

The compound represented by the general formula (Ia) or (Ib) is produced by subjecting the compound (1) to optical resolution as shown below and then performing the same steps as those in the process A.

The process G is a process of performing, before the step A-1 in the process A, optical resolution to produce optical isomers (Ia) and (Ib) of the compound (1). From the optical isomer (Ia) or (Ib), the compound represented by the general formula (Ia) or (Ib) is produced through the steps A-1 to A-5 or the steps A-1 to A-9.

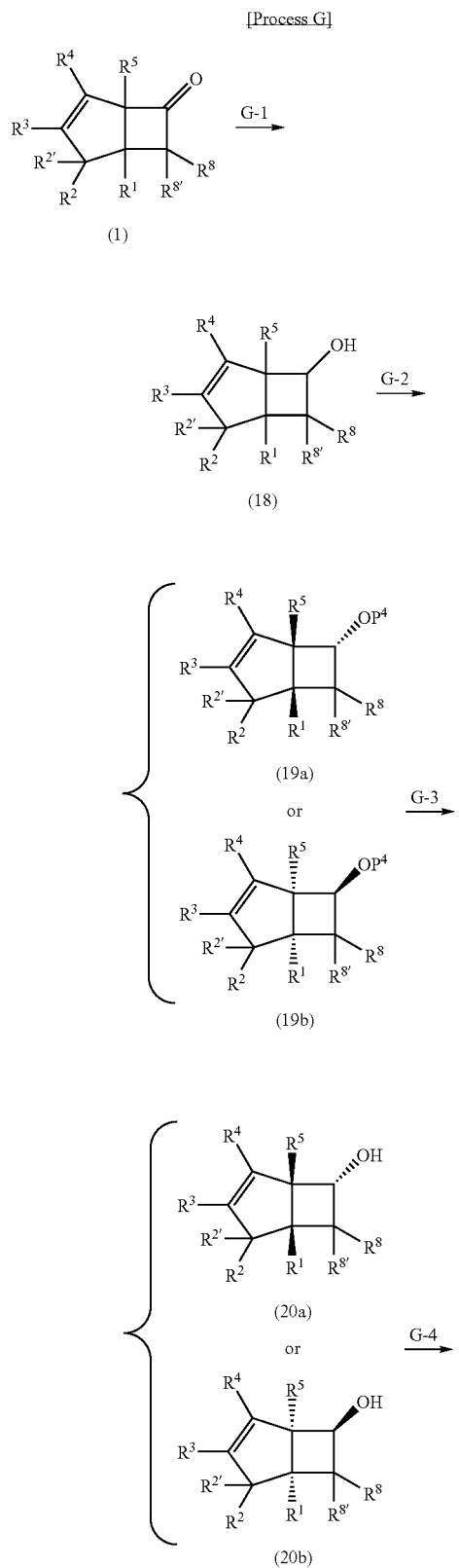

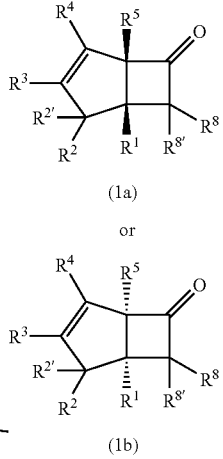

wherein $R^1$, $R^2$, $R^{2'}$, $R^3$, $R^4$, $R^5$, $R^6$, $R^7$, $R^8$, and $R^{8'}$ are as defined above; and $P^4$ represents a protective group for a hydroxyl group.

$P^4$ is not particularly limited as long as it is generally used as a protective group for hydroxyl groups. Examples thereof include trimethylsilyl, tert-butyldimethylsilyl, methoxymethyl, 2-methoxyethoxymethyl, tetrahydropyranyl, benzyl, p-methoxybenzyl, 2,4-dimethoxybenzyl, o-nitrobenzyl, p-nitrobenzyl, trityl, formyl, acetyl, tert-butoxycarbonyl, 2-iodoethoxycarbonyl, 2,2,2-trichloroethoxycarbonyl, 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl, cinnamyloxycarbonyl, benzyloxycarbonyl, p-methoxybenzyloxycarbonyl, o-nitrobenzyloxycarbonyl, and p-nitrobenzyloxycarbonyl groups.

[Step G-1]

The step G-1 is a step of reducing the compound (1) to produce a compound (18).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, sulfoxide solvents, and hydrocarbon solvents. Aromatic solvents, halogenated hydrocarbon solvents, or hydrocarbon solvents are preferable, and tetrahydrofuran is more preferable.

Reagents used include boron reagents and aluminum reagents. Trimethoxy aluminum hydride is preferable.

The reaction temperature differs depending on the types of the starting compound, the solvents, the reagents, etc., and is usually −78° C. to room temperature, preferably −78 to 0° C.

[Step G-2]

The step G-2 is a process of performing optical resolution of the compound (18) using an enzyme such as lipase to obtain a compound (19a) or (19b).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, sulfoxide solvents, and hydrocarbon solvents. Aromatic solvents, halogenated hydrocarbon solvents, or hydrocarbon solvents are preferable, and hexane is more preferable.

Reagents used include ester reagents. Vinyl esters are preferable, and vinyl acetate is more preferable.

The enzyme used includes *Candida antarctica* lipase, *Pseudomonas fluorescens* lipase, Pseudomonas cepacia lipase, porcine pancreatic lipase, porcine liver esterase, and *Candida rugosa* lipase.

The reaction temperature differs depending on the types of the starting compound, the solvents, the reagents, the enzyme, etc., and is usually 0 to 150° C., preferably room temperature to 40° C.

Moreover, in the step G-2, the compound (18) can also be converted, using an appropriate chiral auxiliary, to diastereomers, which are then subjected to resolution by an appropriate method such as recrystallization, distillation, and column chromatography. The resolution can be performed by a method described in, for example, Experimental Chemistry 18, Reaction of Organic Compound—(II)—, first volume (Nov. 25, 1957, published by Maruzen Co. Ltd., ed. by the Chemical Society of Japan), p. 503-556. More specifically, the compound (18) is reacted with a carboxylic acid reagent such as phthalic anhydride, and from the resulting mixture of carboxylic acid derivatives (19a) and (19b), resolution can be performed by recrystallization or the like using phenethylamine, quinine, cinchonidine, methylbenzylamine, naphthylethylamine, or the like.

[Step G-3]

The step G-3 is a process of hydrolyzing the compound (19a) or (19b) to synthesize a compound (20a) or (20b).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, sulfoxide solvents, hydrocarbon solvents, alcohol solvents, aqueous solvents, and mixed solvents thereof. Ether solvents, alcohol solvents, aqueous solvents, or mixed solvents thereof are preferable, and methanol, ethanol, or water is more preferable.

Reagents used include inorganic bases. Potassium carbonate, sodium hydroxide, or potassium hydroxide is preferable.

The reaction temperature differs depending on the types of the starting compound, the solvents, the reagents, etc., and is usually 0 to 60° C., preferably 0° C. to room temperature.

[Step G-4]

The step G-4 is a process of oxidizing the compound (20a) or (20b) to synthesize the compound (1a) or (1b).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, sulfoxide solvents, and hydrocarbon solvents. Halogenated hydrocarbon solvents are preferable, and dichloromethane is more preferable.

Reagents used include acid chloride. Oxalyl chloride is preferable.

The reaction temperature differs depending on the types of the starting compound, the solvents, the reagents, etc., and is usually −78° C. to room temperature, preferably −78 to 0° C.

[Process H]

The process H is a process of performing, before the step A-1 in the process A, optical resolution to produce the compound (1a) or (1b) as an optical isomer of the compound (1). From the compound (1a) or (1b), the compound represented by the general formula (Ia) or (Ib) is produced through the steps A-1 to A-5 or the steps A-1 to A-9.

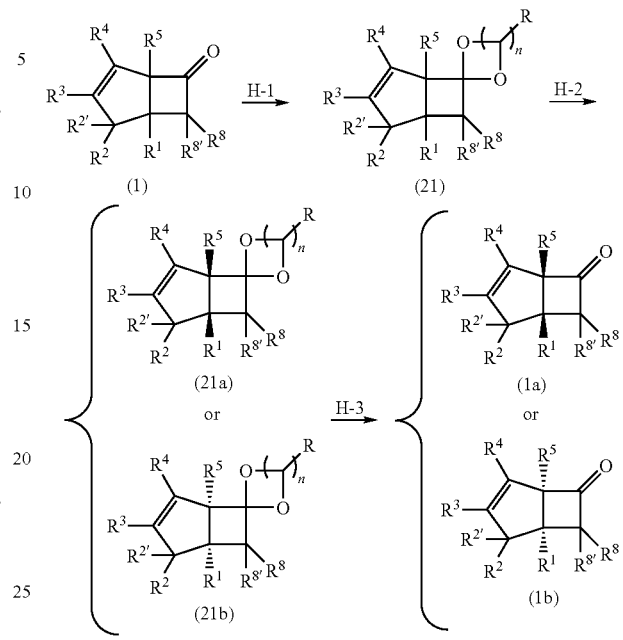

[Step H-1]

The step H-1 is a step of producing a compound (21) from the compound (1).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, sulfoxide solvents, and hydrocarbon solvents. Aromatic solvents, halogenated hydrocarbon solvents, or hydrocarbon solvents are preferable, and benzene or toluene is more preferable.

Reagents used include ethanediol and propanediol. Hydrobenzoin is preferable.

The reaction temperature differs depending on the types of the starting compound, the solvents, the reagents, etc., and is usually −78° C. to reflux conditions, preferably 60° C. to reflux conditions.

[Step H-2]

The step H-2 is a step of subjecting the compound (21) to optical resolution to produce a compound (21a) or (21b).

Solvents used include the same as those in the step A-1, hydrocarbon solvents, alcohol solvents, and mixed solvents of hydrocarbon solvents and alcohol solvents. Hexane-isopropanol or hexane-ethanol is preferable.

The column used in the optical resolution includes the same as those in the process F.

The temperature used is usually 0 to 40° C., preferably 20 to 40° C.

After completion of the reaction, the eluent (solvent) is distilled off to obtain the compound of interest of the present reaction.

[Step H-3]

The step H-3 is a step of synthesizing the compound (1a) or (1b) from the compound (21a) or (21b).

Solvents used are not particularly limited as long as they are solvents that do not inhibit the reaction and can dissolve the starting material to some extent. The solvents include aromatic solvents, ether solvents, ester solvents, halogenated hydrocarbon solvents, nitrile solvents, amide solvents, sulfoxide solvents, hydrocarbon solvents, ketone solvents, and aqueous solvents. Ketone solvents or aqueous solvents are preferable, and acetone or water is more preferable.

Reagents used include acid catalysts, for example, inorganic or organic acids such as hydrochloric acid, acetic acid, sulfuric acid, toluenesulfonic acid, and camphorsulfonic acid.

The reaction temperature differs depending on the types of the starting compound, the solvents, the reagents, etc., and is usually 0 to 100° C., preferably 60 to 100° C.

The compound represented by the general formula (I), (Ia), (Ib), or (II), obtained by the processes, or the pharmacologically acceptable salt thereof exhibits activity as an $\alpha_2\delta$ ligand and affinity for voltage-dependent calcium channel subunit $\alpha_2\delta$ and is useful as an active ingredient in a pharmaceutical composition used for treating and/or preventing pain, disorders involving the central nervous system, and other disorders.

Examples of pain include acute pain, chronic pain, pain caused by soft tissue or peripheral injury, postherpetic neuralgia, occipital neuralgia, trigeminal neuralgia, myelomere or intercostal neuralgia, central pain, neuropathic pain, migraine, pain associated with osteoarthritis or articular rheumatism, pain associated with contusion, sprain, or trauma, spondylalgia, pain caused by spinal cord or brain stem injury, pain in the lower back, sciatic neuralgia, toothache, myofascial pain syndrome, episiotomy pain, gouty pain, pain caused by burn, cardiac pain, muscular pain, ocular pain, inflammatory pain, orofacial pain, abdominal pain, pain associated with dysmenorrhea, labor pain, or endometriosis, somatalgia, pain associated with nerve or radicular injury, pain associated with amputation, tic douloureux, neuroma, or angiitis, pain caused by diabetic neuropathy (or diabetic peripheral neuropathic pain), pain caused by chemotherapy-induced neuropathy, atypical facial neuralgia, neuropathic pain in the lower back, neuralgia associated with HIV, neuralgia associated with AIDS, hyperalgesia, burning pain, sudden pain, pain caused by chemotherapy, occipital neuralgia, psychogenic pain, pain associated with gallstone, neuropathic or non-neuropathic pain associated with cancer, phantom limb pain, functional abdominal pain, headache, acute or chronic tension headache, sinus headache, cluster headache, temporomandibular joint pain, maxillary sinus pain, pain caused by ankylosing spondylarthritis, postoperative pain, scar pain, chronic non-neuropathic pain, pain attributed to hyperlipidemia, fibromuscular pain, and fibromyalgia.

Examples of disorders involving the central nervous system include fainting episode, epilepsy (particularly, partial epilepsy, adult partial seizure, and partial seizure in epilepsy patients), asphyxia, general anoxia, hypoxia, spinal cord injury, traumatic brain injury, head injury, cerebral ischemia, seizure, cerebral angiopathy, neurocardiogenic syncope, neurogenic syncope, hypersensitive carotid sinus, neurovascular syndrome, arrhythmia, mood disorder (e.g., depression), treatment-resistant depression, seasonal affective disorder, child depression, premenstrual syndrome, premenstrual dysphoric disorder, hot flash, bipolar disorder, manic depression, conduct disorder, disruptive behavior disorder, stress-related physical disorder, anxiety disorders, borderline personality disorder, schizophrenia, schizoaffective disorder, delusional disorder, brief psychotic disorder, shared psychotic disorder, substance-induced psychotic disorder, anxiety associated with psychosis, psychotic mood disorder, mood disorder associated with schizophrenia, behavior disorder associated with mental retardation, insomnia (e.g., primary insomnia, secondary insomnia, and transient insomnia), noctambulism, sleep deprivation, REM sleep disorder, sleep apnea, hypersomnia, parasomnia, sleep-wake cycle disorder, jet lag, narcolepsy, and generalized anxiety disorder.

Examples of other disorders include chronic obstructive airway disease, bronchopneumonia, chronic bronchitis, cystic fibrosis, adult respiratory distress syndrome, bronchospasm, cough, pertussis, allergy, contact dermatitis, atopic dermatitis, urticaria, pruritus, pruritus associated with hemodialysis, inflammatory bowel disease, psoriasis, osteoarthritis, cartilage injury, articular rheumatism, psoriatic arthritis, asthma, sunburn, hypersensitivity, Parkinson's disease, Huntington's disease, Alzheimer's disease, delirium, dementia, forgetfulness, autism, attention deficit hyperactivity disorder, Reiter's syndrome, Down's syndrome, Sjogren's syndrome, hypertension, hematopoiesis, postoperative neuroma, benign prostatic hypertrophy, periodontal disease, hemorrhoids, fissure-in-ano, infertility, reflex sympathetic dystrophy, hepatitis, vasodilation, fibrosing disease, collagen disease, angina pectoris, migraine, Raynaud's disease, dry eye syndrome, conjunctivitis, vernal conjunctivitis, proliferative vitreoretinopathy, multiple sclerosis, amyotrophic lateral sclerosis, pervasive development disorder, human immunodeficiency virus infection, HIV encephalopathy, dissociative disorder, eating disorder, ulcerative colitis, Crohn's disease, irritable bowel syndrome, chronic pancreatitis, chronic fatigue syndrome, sudden infant death syndrome, overactive bladder, chronic cystitis, chemotherapy-induced cystitis, primary motor disorder, akinesia, dyskinesia, cramp, Tourette's syndrome, Scott syndrome, paralysis, extrapyramidal motor disorder, restless legs syndrome, mastalgia syndrome, motion sickness, lupus erythematosus, immunodeficiency, inflammatory gastrointestinal disorder, gastritis, proctitis, gastroduodenal ulcer, peptic ulcer, dyspepsia, emesis, breast cancer, gastric cancer, gastric lymphoma, ganglioneuroblastoma, and small-cell cancer.

A pharmaceutical composition comprising the compound represented by the general formula (I), (Ia), (Ib), or (II) or the pharmacologically acceptable salt thereof, when administered to mammals (e.g., humans, horses, cow, or pigs, preferably humans), is administered systemically or locally through an oral or parenteral route.

The pharmaceutical composition of the present invention can be prepared in an appropriate form selected according to the administration method, by preparation methods of various preparations usually used.

The form of the pharmaceutical composition for oral administration includes tablets, pills, powders, granules, capsules, solutions, suspensions, emulsions, syrups, and elixirs. The pharmaceutical composition in such a form is prepared according to a standard method by appropriately selecting, according to need, additives from among excipients, binders, disintegrants, lubricants, swelling agents, swelling aids, coating agents, plasticizers, stabilizers, antiseptics, antioxidants, coloring agents, solubilizers, suspending agents, emulsifiers, sweeteners, preservatives, buffers, diluents, wetting agents, etc. usually used.

The form of the pharmaceutical composition for parenteral administration includes injections, ointments, gels, creams, poultices, patches, aerosols, sprays, eye drops, nasal drops, suppositories, and inhalants. The pharmaceutical composition in such a form is prepared according to a standard method by appropriately selecting, according to need, additives from among stabilizers, antiseptics, solubilizers, humectants, preservatives, antioxidants, flavors, gelling agents, neutralizing agents, buffers, tonicity agents, surfactants, coloring agents, buffering agents, thickeners, wetting agents, fillers, absorption promoters, suspending agents, binders, etc. usually used.

The dose of the compound represented by the general formula (I), (Ia), or (Ib) or the pharmacologically acceptable salt thereof differs depending on symptoms, age, body weight, etc., and is, for oral administration, 1 to 2000 mg, preferably 10 to 600 mg (in terms of the amount of the compound) per dose which is administered once to several times a day to an adult (body weight: approximately 60 Kg) and, for parenteral administration, 0.1 to 1000 mg, preferably 1 to 300 mg (in terms of the amount of the compound) per dose which is administered once to several times a day to an adult.

EXAMPLES

Example 1

(±)-[(1S,5R,6R)-6-(aminomethyl)bicyclo[3.2.0]hept-3-en-6-yl]acetic acid (Exemplary Compound No: 1)

(1-a) (2E)-hepta-2,6-dienoic acid

4-Pentenal (4.45 g, 51.4 mmol) and malonic acid (6.41 g, 61.6 mmol) were dissolved in pyridine (9.9 mL). To the solution, piperidine (1.9 mL) was added, and the mixture was then stirred at 90° C. for 5 hours. The mixture was allowed to cool and then made acidic by the addition of 2 N hydrochloric acid, followed by extraction with diethyl ether. The organic layer was washed with saturated saline and dried over anhydrous magnesium sulfate, and the filtrate was then concentrated under reduced pressure. The residue was distilled under reduced pressure to obtain the compound of interest as a colorless oil substance (3 mmHg, 110-116° C., 3.27 g, 50%).

(1-b) Tert-butyl(±)-(1S,5R)bicyclo[3.2.0]hept-3-en-6-ylideneacetate

Oxalyl chloride (10 mL) was added dropwise to a toluene solution (60 mL) of (2E)-hepta-2,6-dienoic acid (3.27 g, 25.9 mmol) under ice cooling. The mixture was stirred for 20 minutes, then removed from the ice water bath, and gradually heated to room temperature. After stirring for 50 minutes, the reaction solution was stirred for 1 hour under heating to reflux. The solution was allowed to cool, and the solvent was then distilled off under reduced pressure. To the residue, toluene was further added, and the solvent was then distilled off again under reduced pressure. The residue was dissolved in toluene (20 mL), and this solution was added dropwise over 1 hour to a toluene solution (20 mL) of triethylamine (9.19 g, 91 mmol) heated in advance to 90° C. After completion of the dropwise addition, the mixture was further heated with stirring for 2 hours. The reaction solution was cooled, then diluted with saturated saline and water, and filtered through Celite. The filtrate was separated into organic and aqueous layers. The organic layer was then washed with 1 N hydrochloric acid, then dried over magnesium sulfate, and filtered. This filtrate was added to a reaction solution prepared in advance from a dimethoxyethane solution (20 mL) of tert-butyl dimethoxyphosphorylacetate (5.98 g, 25.9 mmol) and sodium hydride (>65% oil, 986.7 mg, 25.9 mmol), and the mixture was stirred for 1.5 hours. To the reaction solution, a saturated aqueous solution of ammonium chloride, saturated saline, and water were added in this order, and the reaction solution was subjected to extraction with ethyl acetate. The organic layer was dried over anhydrous magnesium sulfate and then filtered. The solvent was distilled off under reduced pressure, and the residue was purified by silica gel column chromatography to obtain the compound of interest as a pale yellow oil substance (1.73 g, 32%, E/Z mixture).

(1-c) Tert-butyl(±)-[(1S,5R,6R)-6-(nitromethyl)bicyclo[3.2.0]hept-3-en-6-yl]acetate Tert-butyl(±)-(1S,5R)bicyclo[3.2.0]hept-3-en-6-ylideneacetate (1.73 g, 8.39 mmol) was dissolved in nitromethane (10 mL). To the solution, 1,8-diazabicyclo[5.4.0]undec-7-ene (1.3 mL, 8.4 mmol) was added, and the mixture was stirred at room temperature for 1 hour and then heated with stirring at 50 to 60° C. for 5 hours. The mixture was allowed to cool and then diluted with 1 N hydrochloric acid and saturated saline, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.98 g, 89%).

(1-d) Tert-butyl(±)-[(1S,5R,6R)-6-(aminomethyl)bicyclo[3.2.0]hept-3-en-6-yl]acetate Tert-butyl(±)-[(1S,5R,6R)-6-(nitromethyl)bicyclo[3.2.0]hept-3-en-6-yl]acetate (1.98 g, 7.41 mmol) was dissolved in ethanol (20 mL) and water (10 mL). To the solution, iron powder (2.07 g, 37.0 mmol) and ammonium chloride (392.7 mg, 7.41 mmol) were added, and the mixture was stirred for 4.5 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate. Then, the solvent was distilled off under reduced pressure to obtain the compound of interest as a pale yellow solid (1.99 g, this compound was used directly in the next reaction without being purified).

(1-e) (±)-[(1S,5R,6R)-6-(aminomethyl)bicyclo[3.2.0]hept-3-en-6-yl]acetic acid

A 4 N hydrochloric acid-ethyl acetate solution (10 mL) was added to tert-butyl(±)-[(1S,5R,6R)-6-(aminomethyl)bicyclo[3.2.0]hept-3-en-6-yl]acetate (0.99 g, 4.17 mmol), and the mixture was stirred at room temperature for 1 hour. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane and then dried under reduced pressure to obtain the compound of interest as a white powder (211.6 mg, 35%).

Example 2

[(1R,5S,6S)-6-(aminomethyl)bicyclo[3.2.0]hept-3-en-6-yl]acetic acid (exemplary compound No: 1, optically active form)

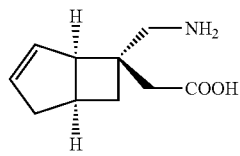

(2-a) Resolution of tert-butyl(±)-[(1S,5R,6R)-6-(nitromethyl)bicyclo[3.2.0]hept-3-en-6-yl]acetate Tert-butyl(±)-[(1S,5R,6R)-6-(nitromethyl)bicyclo[3.2.0]hept-3-en-6-yl]acetate (154 g, 576 mmol) was resolved using Chiralpak AD-H (n-hex:EtOH=95:5, 1.0 mL/min, 40° C.) manufactured by Daicel Chemical Industries, Ltd. to respectively obtain 65.5 g of a peak 1 (retention time: 5.1 min) and 64.8 g of a peak 2 (retention time: 6.5 min).

(2-b) Tert-butyl[(1R,5S,6S)-6-(aminomethyl)bicyclo[3.2.0]hept-3-en-6-yl]acetate

Tert-butyl[(1R,5S,6S)-6-(nitromethyl)bicyclo[3.2.0]hept-3-en-6-yl]acetate (peak 2, 20.7 g, 77.4 mmol) was dissolved in ethanol (200 mL) and water (100 mL). To the solution, iron powder (34.69 g, 619.5 mmol) and ammonium chloride (2.09 g, 38.72 mmol) were added, and the mixture was stirred for 6.5 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate. Then, the solvent was distilled off under reduced pressure to obtain a mixture of the compound of interest and the starting material at almost 1:1 ratio (20.18 g, estimated by $^1$H-NMR). This mixture was dissolved again in ethanol (200 mL) and water (100 mL). To the solution, iron powder (40.36 g, 720.7 mmol) and ammonium chloride (4.18 g, 78.1 mmol) were added, and the mixture was stirred for 9 hours under heating to reflux while iron powder (32.73 g, 584.5 mmol) was further added thereto in three portions. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate. Then, the solvent was distilled off under reduced pressure to obtain the compound of interest as a pale yellow oil substance (17.53 g, 95%).

(2-c) (−)-[(1R,5S,6S)-6-(aminomethyl)bicyclo[3.2.0]hept-3-en-6-yl]acetic acid

A 4 N hydrochloric acid-ethyl acetate solution (200 mL) was added to tert-butyl[(1R,5S,6S)-6-(aminomethyl)bicyclo[3.2.0]hept-3-en-6-yl]acetate (17.53 g, 7.4 mmol), and the mixture was stirred at room temperature for 1.5 hours. Then, the solvent was distilled off under reduced pressure. The residue was suspended in dichloromethane. To the suspension, triethylamine was added dropwise, and the resulting powder was collected by filtration, then washed with dichloromethane, and then dried to obtain a white powder A (6.85 g). From the filtrate, the solvent was distilled off under reduced pressure. To the residue, a 4 N hydrochloric acid-ethyl acetate solution (200 mL) was then added again, and the mixture was stirred at room temperature for 2 hours. The solvent was distilled off under reduced pressure, and the residue was suspended in dichloromethane. To the residue, triethylamine was added dropwise, and the resulting powder was collected by filtration, then washed with dichloromethane, and then dried to obtain a white powder B (2.48 g). This white powder B was combined with the above-obtained white powder A and washed with ethanol and ethyl acetate to obtain the compound of interest as a white powder (7.39 g, 55%).

Example 3

[(1R,5S,6S)-6-(aminomethyl)bicyclo[3.2.0]hept-3-en-6-yl]acetic acid (exemplary compound No: 1, optically active form differing in production process from that of Example 2)

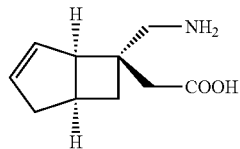

(3-a) Tert-butyl[(1R,5S,6S)-6-(tert-butoxycarbonylaminomethyl)bicyclo[3.2.0]hept-3-en-6-yl]acetate Tert-butyl[(1R,5S,6S)-6-(nitromethyl)bicyclo[3.2.0]hept-3-en-6-yl]acetate (peak 2, 30 g, 0.11 mol) was dissolved in ethanol (300 mL) and water (100 mL). To the solution, iron powder (18.8 g, 0.34 mol) and ammonium chloride (3.6 g, 67.3 mmol) were added, and the mixture was stirred for 4 hours in an oil bath at 80° C. Since the nitro form of the starting material remained, iron powder (18.8 g, 0.34 mol) was added thereto, and the mixture was stirred in an oil bath at 80° C. After 3 hours, iron powder (18.8 g, 0.34 mol) was added thereto, and the mixture was further stirred for 4 hours in an oil bath at 80° C. and then left overnight. Iron powder (18.8 g, 0.34 mol) was added thereto, and the mixture was stirred for 2 hours in an oil bath at 80° C. Although further iron powder (18.8 g, 0.34 mol) was added thereto, the mixture became difficult to stir. Therefore, the reaction was terminated. The mixture was allowed to cool and then filtered to remove insoluble matter. To the filtrate, (Boc)$_2$O (36.7 g, 0.17 mol) and triethylamine (46.9 mL, 0.34 mol) were added, and the mixture was stirred at room temperature for 2 hours. The organic solvent was distilled off under reduced pressure, followed by extraction with ethyl acetate from the remaining aqueous layer. The organic layer was washed with an aqueous citric acid solution, water, saturated aqueous sodium bicarbonate, and saturated saline and dried over anhydrous magnesium sulfate. Then, the solvent was distilled off under reduced pressure. The residue was purified by silica gel column chromatography to obtain the compound of interest as a colorless oil (30.8 g).

(3-b) (−)-[(1R,5S,6S)-6-(aminomethyl)bicyclo[3.2.0]hept-3-en-6-yl]acetic acid

A 4 N hydrochloric acid-ethyl acetate solution (500 mL) was added to an ethyl acetate (150 mL) solution of tert-butyl [(1R,5S,6S)-6-(tert-butoxycarbonylaminomethyl)bicyclo [3.2.0]hept-3-en-6-yl]acetate (76.9 g, 0.23 mol), and the mixture was stirred at room temperature for 5 hours. Then, the deposited powder was collected by filtration and dried. Since the partial tert-butyl ester was not eliminated, the obtained powder was suspended again in a 4 N hydrochloric acid-ethyl acetate solution (300 mL), and the suspension was stirred at room temperature for 4 hours and then left overnight. The deposited powder was collected by filtration and dried to obtain the hydrochloride of the compound of interest as a white powder (43.2 g). To a methylene chloride (800 mL) suspension of the obtained hydrochloride, triethylamine (27.7 mL, 0.198 mol) was added dropwise at room temperature, and the mixture was stirred for 2 hours and then left standing overnight. Again, the resulting powder was collected by filtration and washed with an methanol-ethyl acetate mixed solvent to obtain the compound of interest as a white powder (25.6 g).

Example 4

[(1S,5R,6R)-6-(aminomethyl)bicyclo[3.2.0]hept-3-en-6-yl]acetic acid (exemplary compound No: 1, optically active form differing in configuration from that of Example 2)

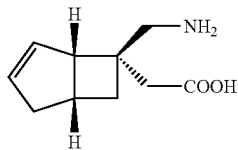

(4-a) Tert-butyl[(1S,5R,6R)-6-(aminomethyl)bicyclo[3.2.0]hept-3-en-6-yl]acetate

Tert-butyl[(1S,5R,6R)-6-(nitromethyl)bicyclo[3.2.0]hept-3-en-6-yl]acetate (peak 1, 21.6 g, 80.8 mmol) was dissolved in ethanol (200 mL) and water (100 mL). To the solution, iron powder (45.1 g, 80.8 mmol) and ammonium chloride (2.59 g, 48.5 mmol) were added, and the mixture was stirred for 5.5 hours under heating to reflux. To the reaction solution, iron powder (9.0 g, 161 mmol) was then further added, and the mixture was further stirred for 2 hours under heating to reflux. The mixture was allowed to cool, then diluted with a saturated aqueous solution of sodium bicarbonate and ethyl acetate, and filtered to remove insoluble matter. From the filtrate, the organic solvent was distilled off under reduced pressure, followed by extraction with ethyl acetate from the aqueous layer. The organic layer was washed with saturated saline and dried over anhydrous magnesium sulfate. Then, the solvent was distilled off under reduced pressure, and the residue was purified by amino column chromatography to obtain the compound of interest as a pale yellow oil (5.5 g).

(4-b) [(1S,5R,6R)-6-(aminomethyl)bicyclo[3.2.0]hept-3-en-6-yl]acetic acid

A 4 N hydrochloric acid-ethyl acetate solution (200 mL) was added to tert-butyl [(1S,5R,6R)-6-(aminomethyl)bicyclo[3.2.0]hept-3-en-6-yl]acetate (17.4 g, 73.3 mmol), and the mixture was stirred at room temperature for 4 hours. Then, the deposited powder was collected by filtration to obtain the hydrochloride of the compound of interest as a white powder (15.6 g). To a methylene chloride (300 mL) suspension of the obtained hydrochloride, triethylamine (10.2 mL, 72.8 mol) was added dropwise at room temperature, and the mixture was stirred for 2 hours. Then, again, the resulting powder was collected by filtration. The obtained powder was washed with an ethanol-ethyl acetate mixed solvent to obtain the compound of interest as a white powder (8.43 g).

Example 5

[(1R,5S,6S)-6-(aminomethyl)bicyclo[3.2.0]hept-3-en-6-yl]acetic acid hydrochloride (Exemplary Compound No: 1, hydrochloride of the compound of Example 2)

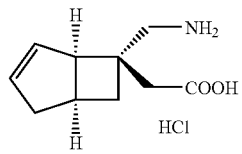

(5-a) [(1R,5S,6S)-6-(aminomethyl)bicyclo[3.2.0]hept-3-en-6-yl]acetic acid hydrochloride Water (5 mL) and a 4 N hydrochloric acid-1,4-dioxane solution (22 mL) were added to (1R,5S,6S)-6-(aminomethyl)bicyclo[3.2.0]hept-3-en-6-yl]acetic acid (320.2 mg, 1.77 mmol), and the mixture was stirred at room temperature for 5 minutes. The solvent was distilled off under reduced pressure. To the residue, 1,4-dioxane was added, and the mixture was heated and then allowed to cool to room temperature. The resulting powder was collected by filtration. The obtained powder was washed with 1,4-dioxane and then dried to obtain the compound of interest as a white powder (350.0 mg, 92%).

Example 6

[(1R,5S,6S)-6-(aminomethyl)bicyclo[3.2.0]hept-3-en-6-yl]acetic acid benzenesulfonate (Exemplary Compound No: 1, benzenesulfonate of the compound of Example 2)

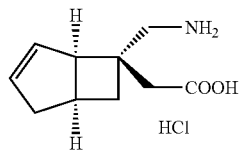

(1R,5S,6S)-6-(aminomethyl)bicyclo[3.2.0]hept-3-en-6-yl]acetic acid (152.2 g, 391 mmol) was dissolved in 2-propanol (7.5 mL) and water (2.6 mL). To the solution, benzenesulfonic acid monohydrate (305.2 mg, 1.73 mmol) was then added, and the mixture was stirred at room temperature for 5 minutes. The solvent was distilled off under reduced pressure, followed by further azeotropic dehydration with 2-propanol. Then, the residue was washed with 2-propanol to obtain the compound of interest as a white powder (260.4 mg, 55%).

Example 7

(±)-[(1S,5R,6R)-6-aminomethyl-3-methylbicyclo[3.2.0]hept-3-en-6-yl]acetic acid (Exemplary Compound No: 4)

(7-a) Methyl 4-methyl-3-hydroxyhept-6-enoate

Sodium hydride (>63% oil, 1.64 g, 43.1 mmol) was added to a tetrahydrofuran solution (50 mL) of methyl 3-oxopentanoate (5.10 g, 39.2 mmol) under ice cooling, and the mixture was stirred in this state for 10 minutes. To the reaction solution, n-butyllithium (1.66 M hexane solution, 25.9 mL, 43.1 mmol) was added dropwise, and the mixture was further stirred for 10 minutes under ice cooling. Then, allyl bromide (5.18 g, 43.1 mmol) was added thereto, and the mixture was stirred in this state for 30 minutes and then further stirred overnight at room temperature. To the reaction solution, 1 N hydrochloric acid and saturated saline were added, followed by extraction with diethyl ether. The organic layer was washed with saturated saline and dried over anhydrous magnesium sulfate, and the solvent was distilled off under reduced pressure. The obtained residue was dissolved in methanol (100 mL). To the solution, sodium borohydride (1.89 g, 50 mmol) was added under ice cooling, and the mixture was stirred in this state for 1.5 hours. 2 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (5.72 g, 85%, mixture of diastereomers).

(7-b) 4-Methyl-3-hydroxyhept-6-enoic acid

Methyl 4-methyl-3-hydroxyhept-6-enoate (5.72 g, 33.2 mmol) was dissolved in a 2 N potassium hydroxide-methanol solution (50 mL), and the solution was stirred overnight at room temperature. From the reaction solution, the solvent was distilled off under reduced pressure. To the residue, a 1 N aqueous sodium hydroxide solution was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a yellow oil substance (2.21 g, 42%, mixture of diastereomers).

(7-c) Tert-butyl(±)-(1S,5R)-3-methylbicyclo[3.2.0] hept-3-en-6-ylideneacetate

4-Methyl-3-hydroxyhept-6-enoic acid (2.21 g, 13.9 mmol) was dissolved in acetic anhydride (14 mL). To the solution, potassium acetate (3.29 g, 33.4 mmol) was added, and the mixture was stirred at room temperature for 2 hours. The reaction solution was heated to 110 to 120° C. and stirred for 3.5 hours. To the reaction solution, ice water and toluene were then added, and this mixture was stirred at room temperature for 1 hour. The mixture was separated into aqueous and organic layers by the addition of saturated saline and toluene. Then, the organic layer was washed with a 1 N aqueous sodium hydroxide solution and saturated saline in this order, then dried over anhydrous magnesium sulfate, and then filtered. This filtrate was added to a reaction solution prepared by adding sodium hydride (>63% oil, 533.3 mg, 14.0 mmol) to a tetrahydrofuran solution (20 mL) of tert-butyl dimethoxyphosphorylacetate (3.24 g, 14.5 mmol) under ice cooling, and the mixture was further stirred for 1.5 hours. The reaction solution was separated into aqueous and organic layers by the addition of a saturated aqueous solution of ammonium chloride and saturated saline. The aqueous layer was subjected to extraction with ethyl acetate. These organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.21 g, 40%, E/Z mixture).

(7-d) Tert-butyl(±)-[(1S,5R,6R)-3-methyl-6-(nitromethyl)bicyclo[3.2.0]hept-3-en-6-yl]acetate Tert-butyl(±)-(1S,5R)-3-methylbicyclo[3.2.0]hept-3-en-6-ylideneacetate (1.21 g, 5.50 mmol) was dissolved in nitromethane (7 mL). To the solution, 1,8-diazabicyclo[5.4.0]undec-7-ene (0.91 mL, 6.0 mmol) was added, and the mixture was heated with stirring at 50 to 60° C. for 6 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.14 g, 74%).

(7-e) Tert-butyl(±)-[(1S,5R,6R)-6-aminomethyl-3-methylbicyclo[3.2.0]hept-3-en-6-yl]acetate Tert-butyl(±)-[(1S,5R,6R)-3-methyl-6-(nitromethyl)bicyclo[3.2.0]hept-3-en-6-yl]acetate (1.12 g, 3.99 mmol) was dissolved in ethanol (20 mL) and water (10 mL). To the solution, iron powder (892.8 mg, 15.9 mmol) and ammonium chloride (211.5 mg, 3.99 mmol) were added, and the mixture was stirred for 4 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline, then dried over anhydrous magnesium sulfate, and the solvent was then distilled off under reduced pressure. To the residue, a 4 N hydrochloric acid-ethyl acetate solution (5 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (105.8 mg, 28%).

Example 8

(±)-[(1S,5R,6R)-6-aminomethyl-3-ethylbicyclo [3.2.0]hept-3-en-6-yl]acetic acid (Exemplary Compound No: 8)

(8-a) Ethyl 4-ethyl-3-hydroxyhept-6-enoate

Sodium hydride (>63% oil, 2.09 g, 55 mmol) was added to a tetrahydrofuran solution (50 mL) of ethyl 3-oxohexanoate (7.91 g, 50 mmol) under ice cooling, and the mixture was stirred in this state for 10 minutes. To the reaction solution, n-butyllithium (1.58 M hexane solution, 34.8 mL, 55 mmol) was added dropwise, and the mixture was further stirred for 10 minutes under ice cooling. Then, allyl bromide (4.7 mL, 55 mmol) was added thereto, and the mixture was stirred in this state for 1 hour and then further stirred at room temperature for 4 hours. To the reaction solution, 1 N hydrochloric acid and a saturated aqueous solution of ammonium chloride were added, followed by extraction with n-pentane. The organic layer was washed with saturated saline and dried over anhydrous magnesium sulfate, and the solvent was distilled off under reduced pressure. The obtained residue was dissolved in ethanol (80 mL). To the solution, sodium borohydride (1.51 g, 40 mmol) was added under ice cooling, and the mixture was stirred in this state for 2 hours. 1 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (3.64 g, 37%, mixture of diastereomers).

(8-b) 4-Ethyl-3-hydroxyhept-6-enoic acid

Ethyl 4-ethyl-3-hydroxyhept-6-enoate (3.64 g, 18.2 mmol) was dissolved in a 2 N potassium hydroxide-methanol solution (120 mL), and the solution was stirred overnight at room temperature. From the reaction solution, the solvent was distilled off under reduced pressure. To the residue, a 1 N aqueous sodium hydroxide solution (200 mL) was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a pale yellow oil substance (3.14 g, <100%, mixture of diastereomers).

(8-c) Tert-butyl(±)-(1S,5R)-3-ethylbicyclo[3.2.0]hept-3-en-6-ylideneacetate

4-Ethyl-3-hydroxyhept-6-enoic acid (3.13 g, 18.2 mmol) was dissolved in acetic anhydride (15 mL). To the solution, potassium acetate (4.27 g, 43.6 mmol) was added, and the mixture was stirred at room temperature for 100 minutes. The reaction solution was heated to reflux and stirred for 3.5 hours. To the reaction solution, ice water and toluene were then added, and this mixture was stirred overnight at room temperature. The mixture was separated into aqueous and organic layers by the addition of saturated saline (50 mL) and toluene (20 mL). Then, the organic layer was washed with a 1 N aqueous sodium hydroxide solution and saturated saline in this order, then dried over anhydrous magnesium sulfate, and then filtered. This filtrate was added to a reaction solution prepared by adding sodium hydride (>65% oil, 761.9 mg, 20 mmol) to a tetrahydrofuran solution (50 mL) of tert-butyl dimethoxyphosphorylacetate (4.48 g, 20 mmol) under ice cooling, and the mixture was further stirred for 1 hour. The reaction solution was separated into aqueous and organic layers by the addition of a saturated aqueous solution of ammonium chloride and saturated saline. The aqueous layer was subjected to extraction with ethyl acetate. These organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.32 g, 31%, E/Z mixture).

(8-d) Tert-butyl((±)-[(1S,5R,6R)-3-ethyl-6-(nitromethyl)bicyclo[3.2.0]hept-3-en-6-yl]acetate Tert-butyl(±)-[(1S,5R)-3-ethylbicyclo[3.2.0]hept-3-en-6-ylideneacetate (1.32 g, 5.63 mmol) was dissolved in nitromethane (7 mL). To the solution, 1,8-diazabicyclo[5.4.0]undec-7-ene (1.2 mL, 7.3 mmol) was added, and the mixture was heated with stirring at 50 to 60° C. for 7 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.39 g, 84%).

(8-e) (±)-[(1S,5R,6R)-6-aminomethyl-3-ethylbicyclo[3.2.0]hept-3-en-6-yl]acetic acid Tert-butyl(±)-[(1S,5R,6R)-3-ethyl-6-(nitromethyl)bicyclo[3.2.0]hept-3-en-6-yl]acetate (1.09 g, 4.71 mmol) was dissolved in ethanol (10 mL) and water (5 mL). To the solution, iron powder (1.32 g, 23.5 mmol) and ammonium chloride (249.6 mg, 4.71 mmol) were added, and the mixture was stirred for 2 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N hydrochloric acid-ethyl acetate solution (20 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (425.1 mg, 43%).

Example 9

(±)-[(1S,5R,6R)-6-aminomethyl-3-propylbicyclo[3.2.0]hept-3-en-6-yl]acetic acid (Exemplary Compound No: 9)

(9-a) Methyl 4-propyl-3-hydroxyhept-6-enoate

Sodium hydride (>63% oil, 2.09 g, 55 mmol) was added to a tetrahydrofuran solution (50 mL) of methyl 3-oxoheptanoate (7.91 g, 50 mmol) under ice cooling, and the mixture was stirred in this state for 25 minutes. To the reaction solution, n-butyllithium (1.58 M hexane solution, 34.8 mL, 55 mmol) was added dropwise, and the mixture was further stirred for 1 hour under ice cooling. Then, allyl bromide (4.7 mL, 55 mmol) was added thereto, and the mixture was stirred in this state for 1 hour and then further stirred overnight at room temperature. To the reaction solution, 1 N hydrochloric acid and a saturated aqueous solution of ammonium chloride were added, followed by extraction with ethyl acetate. The organic layer was washed with saturated saline and dried over anhydrous magnesium sulfate, and the solvent was distilled off under reduced pressure. The obtained residue was dissolved in methanol (35 mL). To the solution, sodium borohydride (0.61 g, 16.1 mmol) was added under ice cooling, and the mixture was stirred in this state for 1 hour. 1 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (3.24 g, 33%, mixture of diastereomers).

(9-b) 4-Propyl-3-hydroxyhept-6-enoic acid

Methyl 4-propyl-3-hydroxyhept-6-enoate (3.24 g, 16.2 mmol) was dissolved in a 2 N potassium hydroxide-methanol solution (16 mL), and the solution was stirred overnight at room temperature. From the reaction solution, the solvent was distilled off under reduced pressure. To the residue, a 1 N aqueous sodium hydroxide solution (150 mL) was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a pale yellow oil substance (2.79 g, 92%, mixture of diastereomers).

(9-c) Tert-butyl(±)-(1S,5R)-3-propyl-bicyclo[3.2.0]hept-3-en-6-ylideneacetate

4-Propyl-3-hydroxyhept-6-enoic acid (2.79 g, 15.0 mmol) was dissolved in acetic anhydride (13 mL). To the solution, potassium acetate (3.52 g, 36.0 mmol) was added, and the mixture was stirred at room temperature for 2 hours. The reaction solution was heated to 120° C. and stirred for 3 hours. To the reaction solution, ice water and n-pentane were then added, and this mixture was stirred overnight at room temperature. Saturated saline was added thereto, and the mixture was separated into aqueous and organic layers by the addition of n-pentane. Then, the organic layer was washed with a 1 N aqueous sodium hydroxide solution and saturated saline in this order and dried over anhydrous magnesium sulfate, and the solvent was then distilled off under reduced pressure. The residue was dissolved in tetrahydrofuran (50 mL). The solution was added to a reaction solution prepared in advance by adding sodium hydride (>65% oil, 761.9 mg, 20 mmol) to a tetrahydrofuran solution (50 mL) of tert-butyl dimethoxyphosphorylacetate (4.48 g, 20 mmol) under ice cooling, and the mixture was further stirred for 1 hour. The reaction solution was separated into aqueous and organic layers by the addition of a saturated aqueous solution of ammonium chloride and saturated saline. The aqueous layer was subjected to extraction with ethyl acetate. These organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.81 g, 49%, E/Z mixture).

(9-d) Tert-butyl(±)-[(1S,5R,6R)-3-propyl-6-(nitromethyl)bicyclo[3.2.0]hept-3-en-6-yl]acetate Tert-butyl(±)-(1S,5R)-3-propyl-bicyclo[3.2.0]hept-3-en-6-ylideneacetate (1.81 g, 7.29 mmol) was dissolved in nitromethane (7 mL). To the solution, 1,8-diazabicyclo[5.4.0]undec-7-ene (1.5 mL, 10.2 mmol) was added, and the mixture was heated with stirring at 50 to 60° C. for 8 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (2.22 g, 95%).

(9-e) (±)-[(1S,5R,6R)-6-aminomethyl-3-propylbicyclo[3.2.0]hept-3-en-6-yl]acetic acid Tert-butyl(±)-[(1S,5R,6R)-3-propyl-6-(nitromethyl)bicyclo[3.2.0]hept-3-en-6-yl]acetate (1.09 g, 4.71 mmol) was dissolved in ethanol (10 mL) and water (5 mL). To the solution, iron powder (1.32 g, 23.5 mmol) and ammonium chloride (249.6 mg, 4.71 mmol) were added, and the mixture was stirred for 2 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N hydrochloric acid-ethyl acetate solution (20 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (425.1 mg, 43%).

Example 10

(±)-[(1S,5R,6R)-6-aminomethyl-3-butylbicyclo[3.2.0]hept-3-en-6-yl]acetic acid (Exemplary Compound No: 10)

(10-a) Methyl 4-allyl-3-hydroxyoctanoate

2-Allylhexanal (J. Org. Chem. 46, 1980, 5250) (5 g, 33.7 mmol), methyl bromoacetate (3.7 mL, 40 mmol), and zinc (2.6 g, 40 mmol) were added to tetrahydrofuran (30 mL) and trimethyl borate (15 mL), and the mixture was vigorously stirred. Then, the reaction vessel was placed in an oil bath and heated to 70° C., and the mixture was stirred for 2 hours. The mixture was allowed to cool, and glycerin (20 mL) and a saturated aqueous solution of ammonium chloride (100 mL) were then added thereto, followed by extraction with ethyl acetate. The organic layer was washed with water and saturated saline and dried over anhydrous magnesium sulfate. Then, the solvent was distilled off under reduced pressure, and the residue was purified by silica gel column chromatography to obtain the compound of interest (diastereomeric mixture) as a colorless oil substance (6.8 g, 94%).

(10-b) 4-Allyl-3-hydroxyoctanoic acid

Methyl 4-allyl-3-hydroxyoctanoate (6.8 g, 31.7 mmol) was dissolved in a 2 N potassium hydroxide-methanol solution (20 mL), and the solution was stirred overnight at room temperature. The reaction solution was concentrated, then diluted with water, and washed with ether. The aqueous solution was made acidic using hydrochloric acid, followed by extraction with ethyl acetate. The organic layer was washed with water and saturated saline and dried over anhydrous magnesium sulfate. Then, the solvent was distilled off under reduced pressure to obtain the compound of interest as an oil substance (6.0 g, 30 mmol). This compound was used in the next reaction without being purified.

(10-c) Tert-butyl(±)-[(1S,5R)-3-butylbicyclo[3.2.0] hept-3-en-6-ylidene]acetate

A mixed solution of 4-allyl-3-hydroxyoctanoic acid (6.0 g, 30 mmol), potassium acetate (9.4 g, 96 mmol), and acetic anhydride (30 mL) was stirred at room temperature for 2 hours and then stirred for 4 hours under reflux. The reaction solution was placed on ice and stirred overnight, and this reaction solution was subjected to extraction with ether. The ether layer was washed with a saturated aqueous solution of sodium bicarbonate and saturated saline and dried over anhydrous magnesium sulfate. This ether solution was added to a reaction solution prepared in advance from a dimethoxyethane solution (30 mL) of methyl tert-butyl-p,p-dimethylphosphonoacetate (7.8 g, 35 mmol) and sodium hydride (>63% oil, 1500 mg, >35 mmol), and the mixture was stirred for 1.5 hours. To the reaction solution, a saturated aqueous solution of ammonium chloride, saturated saline, and water were added in this order, and the reaction solution was subjected to extraction with ethyl acetate. The organic layer was dried over anhydrous magnesium sulfate and then filtered. The solvent was distilled off under reduced pressure, and the residue was purified by silica gel column chromatography to obtain the compound of interest as a pale yellow oil substance (4.3 g, 51%, E/Z mixture).

(10-d) Tert-butyl(±)-[(1S,5R,6R)-3-butyl-6-nitromethylbicyclo[3.2.0]hept-3-en-6-yl]acetate The title compound (4.8 g, 14.8 mmol) was obtained as an oil substance in the same way as in paragraph (1-c) using tert-butyl(±)-[(1S,5R)-3-butylbicyclo[3.2.0]hept-3-en-6-ylidene]acetate (4.3 g, 16.4 mmol).

(10-e) Tert-butyl(±)-[(1S,5R,6R)-6-(tert-butoxycarbonylamino)methyl-3-butylbicyclo[3.2.0]hept-3-en-6-yl]acetate The title compound (3.63 g, 63%) was obtained as an oil substance in the same way as in paragraph (3-a) using tert-butyl(±)-[(1S,5R,6R)-3-butyl-6-nitromethylbicyclo[3.2.0] hept-3-en-6-yl]acetate (4.8 g, 14.8 mmol).

(10-f) (±)-[(1S,5R,6R)-6-aminomethyl-3-butylbicyclo[3.2.0]hept-3-en-6-yl]acetic acid The title compound (1.5 g, 70%) was obtained as a white powder in the same way as in paragraph (3-b) using tert-butyl (±)-[(1S,5R,6R)-6-(tert-butoxycarbonylamino)methyl-3-butylbicyclo[3.2.0]hept-3-en-6-yl]acetate (3.63 g, 9.1 mmol).

Example 11

(±)-[(1S,5R,6R)-6-aminomethyl-3-isopropylbicyclo [3.2.0]hept-3-en-6-yl]acetic acid (Exemplary Compound No: 11)

(11-a) 2-Isopropylpent-4-enal
Dimethyl sulfoxide (18.70 mL, 263.3 mmol) was added dropwise over 15 minutes to a dichloromethane (290 mL) solution of oxalic acid chloride (17.30 g, 136.3 mmol) cooled to −78° C., and the mixture was then stirred at −78° C. for 15 minutes. Subsequently, a dichloromethane (75 mL) solution of 2-isopropylpent-4-en-1-ol (11.30 g, 88.1 mmol) was added dropwise thereto over 30 minutes, and the mixture was stirred at −78° C. for 1 hour. Triethylamine (62.40 g, 616.7 mmol) was added dropwise thereto over 5 minutes, and the mixture was then stirred at room temperature for 2 hours. The mixture was neutralized with 2 N hydrochloric acid (320 mL). The organic layer was dried over anhydrous magnesium sulfate. Then, the solvent was distilled off under reduced pressure to obtain a yellow oil substance as a mixture containing the compound of interest. This compound was used in the next reaction without being further purified.

(11-b) Methyl 3-hydroxy-4-isopropylhept-6-enoate

The 2-isopropylpent-4-enal obtained in paragraph (11-a) and methyl bromoacetate (16.18 g, 105.8 mmol) were prepared into a tetrahydrofuran (25 mL) solution. An aliquot of approximately ⅕ of the amount was added to a trimethyl borate (25 mL) suspension of zinc powder (6.92 g, 105.8 mmol). The mixture was heated to 80° C. Then, the remaining solution was added thereto over 30 minutes, and the mixture was then stirred at 80° C. for 2.5 hours. The mixture was allowed to cool, and glycerin (25 mL), a saturated aqueous solution of ammonium chloride (25 mL), and diethyl ether were then added thereto. The obtained organic layer was dried over anhydrous magnesium sulfate. The solvent was distilled off under reduced pressure, and the residue was purified by silica gel column chromatography to obtain the compound of interest as a yellow oil substance (12.30 g, 70%).

(11-c) 3-Hydroxy-4-isopropylhept-6-enoic acid

A 2 N potassium hydroxide-methanol solution (200 mL) was added to a methanol (132 mL) solution of methyl 3-hydroxy-4-isopropylhept-6-enoate (12.30 g, 61.5 mmol), and the mixture was stirred at room temperature for 13 hours. The solvent was distilled off under reduced pressure. To the residue, water and diethyl ether were then added, and the aqueous layer was neutralized with 2 N hydrochloric acid. Diethyl ether was added thereto, and the organic layer was dried over anhydrous magnesium sulfate. Then, the solvent was distilled off under reduced pressure to obtain the compound of interest as a brown oil substance (11.10 g, 97%).

(11-d) (±)-(1S,5R)-3-isopropylbicyclo[3.2.0]hept-3-en-6-one

Potassium acetate (14.00 g, 142.7 mmol) was added to an acetic anhydride (67 mL) solution of 3-hydroxy-4-isopropylhept-6-enoic acid (11.10 g, 59.6 mmol), and the mixture was stirred at room temperature for 1 hour and then stirred at 120° C. for 3.5 hours. The mixture was treated with ice water, followed by extraction with diethyl ether. The organic layer was washed with a saturated aqueous solution of sodium bicarbonate. The organic layer was dried over anhydrous magnesium sulfate. Then, the solvent was distilled off under reduced pressure, and the residue was purified by silica gel column chromatography to obtain the compound of interest as a yellow oil substance (6.6 g, 74%).

(11-e) Tert-butyl(±)-[(1S,5R)-3-isopropylbicyclo [3.2.0]hept-3-en-6-ylidene]acetate (E/Z mixture)

A tetrahydrofuran (15 mL) solution of tert-butyl dimethylphosphonoacetate (3.70 g, 16.5 mmol) was added dropwise at 0° C. over 20 minutes to a tetrahydrofuran (15 mL) suspension of sodium hydride (0.68 g, 63%, 18.0 mmol), and the mixture was stirred at 0° C. for 20 minutes. To this solution, a tetrahydrofuran (15 mL) solution of (±)-(1S,5R)-3-isopropylbicyclo[3.2.0]hept-3-en-6-one (2.25 g, 15.0 mmol) was added dropwise at 0° C. over 15 minutes, and the mixture was stirred at room temperature for 2 hours. The mixture was treated with water, followed by extraction with diethyl ether. The organic layer was dried over anhydrous magnesium sulfate. Then, the solvent was distilled off under reduced pressure, and the residue was purified by silica gel column chromatography to obtain the compound of interest as a yellow oil substance (3.00 g, 81%).

(11-f) Tert-butyl(±)-[(1S,5R,6R)-6-(nitromethyl)-3-isopropylbicyclo[3.2.0]hept-3-en-6-yl]acetate Tert-butyl(±)-[(1S,5R)-3-isopropylbicyclo[3.2.0]hept-3-en-6-ylidene]acetate (3.00 g, 12.1 mmol) was dissolved in nitromethane (30 mL). To the solution, 1,8-diazabicyclo[5.4.0]undec-7-ene (2.20 g, 14.5 mmol) was added, and the mixture was stirred at 60° C. for 5 hours. The mixture was allowed to cool, and a saturated aqueous solution of potassium dihydrogen phosphate was then added thereto, followed by extraction with dichloromethane. The organic layer was dried over anhydrous magnesium sulfate. The solvent was distilled off under reduced pressure, and the residue was purified by silica gel chromatography to obtain the compound of interest as a yellow oil substance (3.00 g, 80%).

(11-g) Tert-butyl(±)-[(1S,5R,6R)-6-aminomethyl-3-isopropylbicyclo[3.2.0]hept-3-en-6-yl]acetate Tert-butyl(±)-[(1S,5R,6R)-6-(nitromethyl)-3-isopropylbicyclo[3.2.0]hept-3-en-6-yl]acetate (3.00 g, 9.70 mmol) was dissolved in ethanol (60 mL). To the solution, iron powder (4.47 g, 80.05 mmol) and then an aqueous ammonium chloride (0.54 g, 10.00 mmol) solution (20 mL) were added, and the mixture was stirred for 4.5 hours under heating to reflux. The mixture was allowed to cool and then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain the compound of interest as a colorless oil substance (2.50 g, 92%).

(11-h) (±)-[(1S,5R,6R)-6-aminomethyl-3-isopropylbicyclo[3.2.0]hept-3-en-6-yl]acetic acid Tert-butyl(±)-[(1S,5R,6R)-6-aminomethyl-3-isopropylbicyclo[3.2.0]hept-3-en-6-yl]acetate (2.50 g, 9.0 mmol) was dissolved in a 4 N hydrochloric acid-ethyl acetate solution (25 mL), and the solution was stirred at room temperature for 2 hours. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane to obtain the compound of interest as a white powder (1.01 g, 51%).

Example 12

(±)-[(1S,5R,6R)-6-aminomethyl-3-isobutylbicyclo[3.2.0]hept-3-en-6-yl]acetic acid (Exemplary Compound No: 13)

(12-a) 2-Isobutylpent-4-en-1-ol 2-isobutyl-4-pentenoic acid (J. Am. Chem. Soc. 115, 1993, 8669) (13 g, 83 mmol) was dissolved in tetrahydrofuran (80 mL), and the solution was added dropwise to a tetrahydrofuran (80 mL) mixed solution of lithium aluminum hydride (3.4 g, 90 mmol) under ice cooling. The mixture was stirred at this temperature for 1 hour. Then, water (3.4 mL), a 15% aqueous sodium hydroxide solution (3.4 mL), and water (10.2 mL) were added thereto in this order, and the mixture was stirred overnight. After removal of insoluble matter, the filtrate was concentrated to obtain the compound of interest as an oil substance (4.9 g, 42%).

(12-b) 2-Isobutyl-4-pentenal

Oxalyl chloride (5.45 g, 43 mmol) was dissolved in methylene chloride (50 mL), and the solution was cooled to −78° C. Then, dimethyl sulfoxide (6.1 mL) was added dropwise thereto. To the mixture, a methylene chloride (40 mL) solution of 2-isobutylpent-4-en-1-ol (4.9 g, 34 mmol) was subsequently added dropwise, and the mixture was stirred at this temperature for 1 hour. Triethylamine (24 mL) was added thereto, and the mixture was brought to room temperature. A saturated aqueous solution of ammonium chloride was added thereto. The organic layer was separated, washed with water and saturated saline, then dried, and then concentrated to obtain the compound of interest as an oil substance. This compound was used in the next reaction without being purified.

(12-c) Methyl 3-hydroxy-2-isobutyl-6-heptenoate

The compound of interest (4.5 g, 61%) was obtained as an oil substance (diastereomeric mixture) in the same way as in paragraph (10-a) using 2-isobutyl-4-pentenal.

(12-d) 3-Hydroxy-2-isobutyl-6-heptenoic acid

The compound of interest (4.3 g) was obtained as an oil substance in the same way as in paragraph (10-b) using methyl 3-hydroxy-2-isobutyl-6-heptenoate (4.5 g, 21 mmol). This compound was used in the next reaction without being purified.

(12-e) Tert-butyl(±)-(1S,5R)-[3-isobutylbicyclo[3.2.0]hept-3-en-6-ylidene]acetate The compound of interest (3.7 g, 67%) was obtained as an oil substance (E/Z mixture) in the same way as in paragraph (10-c) using 3-hydroxy-2-isobutyl-6-heptenoic acid (4.3 g).

(12-f) Tert-butyl(±)-[(1S,5R,6R)-3-isobutyl-6-nitromethylbicyclo[3.2.0]hept-3-en-6-yl]acetate The compound of interest (3.8 g, 84%) was obtained as an oil substance in the same way as in paragraph (10-c) using tert-butyl(±)-(1S,5R)-[3-isobutylbicyclo[3.2.0]hept-3-en-6-ylidene]acetate (3.7 g, 14 mmol).

(12-g) Tert-butyl(±)-[(1S,5R,6R)-6-(tert-butoxycarbonylamino)methyl-3-isobutylbicyclo[3.2.0]hept-3-en-6-yl]acetate The compound of interest (2.7 g, 54%) was obtained as an oil substance in the same way as in paragraph (3-a) using tert-butyl(±)-[(1S,5R,6R)-3-isobutyl-6-nitromethylbicyclo[3.2.0]hept-3-en-6-yl]acetate (3.8 g, 12 mmol).

(12-h) (±)-[(1S,5R,6R)-6-aminomethyl-3-isobutylbicyclo[3.2.0]hept-3-en-6-yl]acetic acid The title compound (1.0 g, 62%) was obtained as a white powder in the same way as in paragraph (3-b) using tert-butyl (±)-[(1S,5R,6R)-6-(tert-butoxycarbonylamino)methyl-3-isobutylbicyclo[3.2.0]hept-3-en-6-yl]acetate (2.7 g, 6.8 mmol).

Example 13

(±)-[(1S,5R,6R)-6-aminomethyl-3-sec-bicyclo[3.2.0]hept-3-en-6-yl]acetic acid (Exemplary Compound No: 12)

(13-a) Ethyl 2-sec-butylpent-4-enoate

Lithium chloride (9.67 g, 228.1 mmol) and water (2.05 mL, 113.9 mmol) were added to a dimethyl sulfoxide (60 mL) solution of diethyl allyl(sec-butyl)malonate (30.90 g, 120.5 mmol), and the mixture was stirred at 185° C. for 6 hours. The mixture was treated with water, followed by extraction with diethyl ether. The organic layer was dried over anhydrous magnesium sulfate. Then, the solvent was distilled off under reduced pressure to obtain the compound of interest as a brown oil substance. This compound was used in the next reaction without being purified.

(13-b) 2-Sec-butylpent-4-en-1-ol

A tetrahydrofuran (50 mL) solution of ethyl 2-sec-butylpent-4-enoate was added dropwise over 30 minutes to a tetrahydrofuran (120 mL) solution of lithium aluminum hydride (4.79 g, 126.3 mmol) cooled to 0° C., and the mixture was then stirred at 0° C. for 1 hour and then stirred at room temperature for 2 hours. The mixture was cooled again to 0° C. Ethyl acetate (55.4 mL), water (44.7 mL), tetrahydrofuran (83.1 mL), and sodium fluoride (53.0 g) were added thereto, and the mixture was stirred for 1.5 hours. The mixture was filtered through Celite to remove insoluble matter. Then, the solution was concentrated, and the residue was purified by silica gel column chromatography to obtain the compound of interest as a colorless oil substance (12.20 g, 69%).

(13-c) 2-Sec-butylpent-4-enal

Dimethyl sulfoxide (18.20 mL, 256.4 mmol) was added dropwise over 15 minutes to a dichloromethane (280 mL) solution of oxalic acid chloride (16.90 g, 133.1 mmol) cooled to −78° C., and the mixture was then stirred at −78° C. for 25 minutes. Subsequently, a dichloromethane (75 mL) solution of 2-sec-butylpent-4-en-1-ol (12.20 g, 85.8 mmol) was added dropwise thereto over 30 minutes, and the mixture was stirred at −78° C. for 1 hour. Triethylamine (60.80 g, 600.8 mmol) was added dropwise thereto over 5 minutes, and the mixture was then stirred at room temperature for 2 hours. The mixture was neutralized with 2 N hydrochloric acid (310 mL). The organic layer was dried over anhydrous magnesium sulfate. Then, the solvent was distilled off under reduced pressure to obtain a yellow oil substance as a mixture containing the compound of interest. This compound was used in the next reaction without being further purified.

(13-d) Methyl 3-hydroxy-4-sec-butylhept-6-enoate

2-Sec-butylpent-4-enal and methyl bromoacetate (15.74 g, 102.9 mmol) were prepared into a tetrahydrofuran (25 mL) solution. An aliquot of approximately ⅓ of the amount was added to a trimethyl borate (25 mL) suspension of zinc powder (6.73 g, 102.9 mmol). The mixture was heated to 80° C. Then, the remaining solution was added thereto over 30 minutes, and the mixture was then stirred at 80° C. for 2.5 hours. The mixture was allowed to cool, and glycerin (25 mL), a saturated aqueous solution of ammonium chloride (25 mL), and diethyl ether were then added thereto. The obtained organic layer was dried over anhydrous magnesium sulfate. The solvent was distilled off under reduced pressure, and the residue was purified by silica gel column chromatography to obtain the compound of interest as a yellow oil substance (14.40 g, 78%).

(13-e) 3-Hydroxy-4-sec-butylhept-6-enoic acid

Methyl 3-hydroxy-4-sec-butylhept-6-enoate (14.40 g, 67.2 mmol) was dissolved in a 2 N potassium hydroxide-methanol solution (200 mL), and the solution was stirred at room temperature for 13.5 hours. The solvent was distilled off under reduced pressure. To the residue, water and diethyl ether were then added, and the aqueous layer was neutralized with 2 N hydrochloric acid. Diethyl ether was added thereto, and the organic layer was dried over anhydrous magnesium sulfate. Then, the solvent was distilled off under reduced pressure to obtain the compound of interest as a yellow oil substance (12.70 g, 94%).

(13-f) (±)-(1S,5R)-3-sec-butylbicyclo[3.2.0]hept-3-en-6-one

Potassium acetate (14.90 g, 151.8 mmol) was added to an acetic anhydride (71 mL) solution of 3-hydroxy-4-sec-butylhept-6-enoic acid (12.70 g, 63.5 mmol), and the mixture was stirred at room temperature for 1 hour and then stirred at 120° C. for 3.5 hours. The mixture was treated with ice water, followed by extraction with diethyl ether. The organic layer was washed with a saturated aqueous solution of sodium bicarbonate. The organic layer was dried over anhydrous magnesium sulfate. Then, the solvent was distilled off under reduced pressure, and the residue was purified by silica gel column chromatography to obtain the compound of interest as a yellow oil substance (6.70 g, 64%).

(13-g) Tert-butyl(±)-[(1S,5R)-3-sec-butylbicyclo[3.2.0]hept-3-en-6-ylidene]acetate (E/Z mixture)

A tetrahydrofuran (15 mL) solution of tert-butyl dimethylphosphonoacetate (3.70 g, 16.5 mmol) was added dropwise at 0° C. over 20 minutes to a tetrahydrofuran (15 mL) suspension of sodium hydride (0.68 g, 63%, 18.0 mmol), and the mixture was stirred at 0° C. for 20 minutes. To this solution, a tetrahydrofuran (15 mL) solution of (±)-(1S,5R)-3-sec-butylbicyclo[3.2.0]hept-3-en-6-one (2.48 g, 15.1 mmol) was added dropwise at 0° C. over 15 minutes, and the mixture was stirred at room temperature for 2 hours. The mixture was treated with water, followed by extraction with diethyl ether. The organic layer was dried over anhydrous magnesium sulfate. Then, the solvent was distilled off under reduced pressure, and the residue was purified by silica gel column chromatography to obtain the compound of interest as a yellow oil substance (3.10 g, 78%).

(13-h) Tert-butyl(±)-[(1S,5R,6R)-6-(nitromethyl)-3-sec-butylbicyclo[3.2.0]hept-3-en-6-yl]acetate Tert-butyl(±)-[(1S,5R)-3-sec-butylbicyclo[3.2.0]hept-3-en-6-ylidene]acetate (3.10 g, 11.8 mmol) was dissolved in nitromethane (30 mL). To the solution, 1,8-diazabicyclo[5.4.0]undec-7-ene (2.20 g, 14.5 mmol) was added, and the mixture was stirred at 60° C. for 5 hours. The mixture was allowed to cool, and a saturated aqueous solution of potassium dihydrogen phosphate was then added thereto, followed by extraction with dichloromethane. The organic layer was dried over anhydrous magnesium sulfate. The solvent was distilled off under reduced pressure, and the residue was purified by silica gel chromatography to obtain the compound of interest as a yellow oil substance (3.28 g, 86%).

(13-i) Tert-butyl(±)-[(1S,5R,6R)-6-aminomethyl-3-sec-butylbicyclo[3.2.0]hept-3-en-6-yl]acetate Tert-butyl(±)-[(1S,5R,6R)-6-(nitromethyl)-3-sec-butylbicyclo[3.2.0]hept-3-en-6-yl]acetate (3.28 g, 10.2 mmol) was dissolved in ethanol (60 mL). To the solution, iron powder (4.47 g, 80.0 mmol) and then an aqueous ammonium chloride (0.54 g, 10.0 mmol) solution (20 mL) were added, and the mixture was stirred for 4.5 hours under heating to reflux. The mixture was allowed to cool and then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain the compound of interest as a colorless oil substance (2.26 g, 75%).

(13-j) (±)-[(1S,5R,6R)-6-aminomethyl-3-sec-butylbicyclo[3.2.0]hept-3-en-6-yl]acetic acid Tert-butyl(±)-[(1S,5R,6R)-6-aminomethyl-3-sec-butylbicyclo[3.2.0]hept-3-en-6-yl]acetate (2.26 g, 7.7 mmol) was dissolved in a 4 N hydrochloric acid-ethyl acetate solution (30 mL), and the solution was stirred at room temperature for 2 hours. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane to obtain the compound of interest as a white powder (0.98 g, 54%).

Example 14

(±)-[(1S,5R,6R)-6-aminomethyl-3-cyclopentylbicyclo[3.2.0]hept-3-en-6-yl]acetic acid (Exemplary Compound No: 15)

(14-a) Ethyl 2-cyclopentylpent-4-enoate

Lithium chloride (3.60 g, 84.9 mmol) and water (0.76 mL, 41.9 mmol) were added to a dimethyl sulfoxide (20 mL) solution of diethyl allyl(cyclopentyl)malonate (10.10 g, 37.7 mmol), and the mixture was stirred at 185° C. for 6 hours. The mixture was treated with water, followed by extraction with diethyl ether. The organic layer was dried over anhydrous magnesium sulfate. Then, the solvent was distilled off under reduced pressure to obtain the compound of interest as a brown oil substance (6.10 g, 84%).

(14-b) 2-Cyclopentylpent-4-en-1-ol

A tetrahydrofuran (15 mL) solution of ethyl 2-cyclopentylpent-4-enoate (6.10 g, 31.6 mmol) was added dropwise over 20 minutes to a tetrahydrofuran (40 mL) solution of lithium aluminum hydride (1.21 g, 31.9 mmol) cooled to 0° C., and the mixture was then stirred at 0° C. for 1 hour and then stirred at room temperature for 2 hours. The mixture was cooled again to 0° C. Ethyl acetate (14.0 mL), water (11.3 mL), tetrahydrofuran (21.0 mL), and sodium fluoride (13.4 g) were added thereto, and the mixture was stirred for 1 hour. The mixture was filtered through Celite to remove insoluble matter. Then, the solution was concentrated, and the residue was purified by silica gel column chromatography to obtain the compound of interest as a colorless oil substance (3.50 g, 56%).

(14-c) 2-Cyclopentylpent-4-enal

Dimethyl sulfoxide (4.82 mL, 67.9 mmol) was added dropwise over 15 minutes to a dichloromethane (75 mL) solution of oxalic acid chloride (4.47 g, 35.2 mmol) cooled to −78° C., and the mixture was then stirred at −78° C. for 30 minutes. Subsequently, a dichloromethane (20 mL) solution of 2-cyclopentylpent-4-en-1-ol (3.50 g, 22.7 mmol) was added dropwise thereto over 15 minutes, and the mixture was stirred at −78° C. for 45 minutes. Triethylamine (16.11 g, 159.3 mmol) was added dropwise thereto over 5 minutes, and the mixture was then stirred at room temperature for 2 hours. The mixture was neutralized with 1 N hydrochloric acid (160 mL). The organic layer was dried over anhydrous magnesium sulfate. Then, the solvent was distilled off under reduced pressure to obtain a yellow oil substance as a mixture containing the compound of interest. This compound was used in the next reaction without being further purified.

(14-d) Methyl 3-hydroxy-4-cyclopentylhept-6-enoate

The 2-cyclopentylpent-4-enal obtained in the preceding paragraph and methyl bromoacetate (4.22 g, 27.6 mmol) were prepared into a tetrahydrofuran (12 mL) solution. An aliquot of approximately ⅓ of the amount was added to a trimethyl borate (12 mL) suspension of zinc powder (1.81 g, 27.6 mmol). The mixture was heated to 80° C. Then, the remaining solution was added thereto over 30 minutes, and the mixture was then stirred at 80° C. for 2.5 hours. The mixture was allowed to cool, and glycerin (6 mL), a saturated aqueous solution of ammonium chloride (6 mL), and diethyl ether were then added thereto. The obtained organic layer was dried over anhydrous magnesium sulfate. The solvent was distilled off under reduced pressure, and the residue was purified by silica gel column chromatography to obtain the compound of interest as a yellow oil substance (4.00 g, 77%).

(14-e) 3-Hydroxy-4-cyclopentylhept-6-enoic acid

Methyl 3-hydroxy-4-cyclopentylhept-6-enoate (4.00 g, 17.7 mmol) was dissolved in a 2 N potassium hydroxide-methanol solution (53 mL), and the solution was stirred at room temperature for 1.5 hours. The solvent was distilled off under reduced pressure. To the residue, water and diethyl ether were then added, and the aqueous layer was neutralized with 2 N hydrochloric acid. Diethyl ether was added thereto. The organic layer was dried over anhydrous magnesium sulfate. Then, the solvent was distilled off under reduced pressure to obtain the compound of interest as a yellow oil substance (4.00 g (including the residual solvent)).

(14-f) 3-Cyclopentylbicyclo[3.2.0]hept-3-en-6-one

Potassium acetate (4.16 g, 42.4 mmol) was added to an acetic anhydride (20 mL) solution of 3-hydroxy-4-cyclopentylhept-6-enoic acid (4.00 g, 17.7 mmol at the maximum), and the mixture was stirred at room temperature for 1 hour and then stirred at 120° C. for 3.5 hours. The mixture was treated with ice water, followed by extraction with diethyl ether. The organic layer was washed with a saturated aqueous solution of sodium bicarbonate. The organic layer was dried over anhydrous magnesium sulfate. Then, the solvent was distilled off under reduced pressure, and the residue was purified by silica gel column chromatography to obtain the compound of interest as a yellow oil substance (2.30 g, 74%).

(14-g) Tert-butyl(±)-[(1S,5R)-3-cyclopentylbicyclo [3.2.0]hept-3-en-6-ylidene]acetate (E/Z mixture)

A tetrahydrofuran (15 mL) solution of tert-butyl dimethylphosphonoacetate (3.21 g, 14.4 mmol) was added dropwise at 0° C. over 15 minutes to a tetrahydrofuran (15 mL) suspension of sodium hydride (0.59 g, 63%, 15.7 mmol), and the mixture was stirred at 0° C. for 25 minutes. To this solution, a tetrahydrofuran (15 mL) solution of 3-cyclopentylbicyclo [3.2.0]hept-3-en-6-one (2.30 g, 13.1 mmol) was added dropwise at 0° C. over 10 minutes, and the mixture was stirred at room temperature for 16 hours. The mixture was treated with water, followed by extraction with diethyl ether. The organic layer was dried over anhydrous magnesium sulfate. Then, the solvent was distilled off under reduced pressure, and the residue was purified by silica gel column chromatography to obtain the compound of interest as a yellow oil substance (3.30 g, 92%).

(14-h) Tert-butyl(±)-[(1S,5R,6R)-6-(nitromethyl)-3-cyclopentylbicyclo[3.2.0]hept-3-en-6-yl]acetate Tert-butyl(±)-[(1S,5R)-3-cyclopentylbicyclo[3.2.0]hept-3-en-6-ylidene]acetate (3.30 g, 12.0 mmol) was dissolved in nitromethane (30 mL). To the solution, 1,8-diazabicyclo [5.4.0]undec-7-ene (2.20 g, 14.5 mmol) was added, and the mixture was stirred at 60° C. for 5 hours. The mixture was allowed to cool, and a saturated aqueous solution of potassium dihydrogen phosphate was then added thereto, followed by extraction with dichloromethane. The organic layer was dried over anhydrous magnesium sulfate. The solvent was distilled off under reduced pressure, and the residue was purified by silica gel chromatography to obtain the compound of interest as a yellow oil substance (3.50 g, 87%).

(14-i) Tert-butyl(±)-[(1S,5R,6R)-6-aminomethyl-3-cyclopentylbicyclo[3.2.0]hept-3-en-6-yl]acetate Tert-butyl(±)-[(1S,5R,6R)-6-(nitromethyl)-3-cyclopentylbicyclo[3.2.0]hept-3-en-6-yl]acetate (3.30 g, 9.8 mmol) was dissolved in ethanol (60 mL). To the solution, iron powder (4.47 g, 80.0 mmol) and then an aqueous ammonium chloride (0.54 g, 10.0 mmol) solution (20 mL) were added, and the mixture was stirred for 4.5 hours under heating to reflux. The mixture was allowed to cool and then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain the compound of interest as a colorless oil substance (2.00 g, 67%).

(14-j) (±)-[(1S,5R,6R)-6-aminomethyl-3-cyclopentylbicyclo[3.2.0]hept-3-en-6-yl]acetic acid Tert-butyl(±)-[(1S,5R,6R)-6-aminomethyl-3-cyclopentylbicyclo[3.2.0]hept-3-en-6-yl]acetate (2.00 g, 6.5 mmol) was dissolved in a 4 N hydrochloric acid-ethyl acetate solution (30 mL), and the solution was stirred at room temperature for 2 hours. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane to obtain the compound of interest as a white powder (0.70 g, 43%).

Example 15

(±)-[(1S,5R,6R)-6-aminomethyl-3-allylbicyclo [3.2.0]hept-3-en-6-yl]acetic acid (Exemplary Compound No: 14)

(15-a) 4-Allylhepta-2,6-dienoic acid

Lithium aluminum hydride (0.74 g, 20 mmol) was added to a tetrahydrofuran solution (30 mL) of ethyl 2-allylpent-4-ene-acetate (2.20 g, 13.1 mmol) under ice cooling, and the mixture was stirred in this state for 1 hour. To the reaction solution, a 1 N aqueous sodium hydroxide solution (10 mL) was added, and the mixture was stirred at room temperature for 1 hour and then filtered through Celite. The filtrate was diluted with saturated saline and ethyl acetate and separated into aqueous and organic layers. The organic layer was washed with saturated saline and dried over anhydrous magnesium sulfate, and the solvent was distilled off under reduced pressure. A dichloromethane solution (20 mL) of oxalyl chloride (1.6 mL, 13.1 mmol) was added dropwise to a dichloromethane solution (10 mL) of dimethyl sulfoxide (2.7 mL, 19.5 mmol) under cooling to −78° C. To the reaction solution, a dichloromethane (10 mL) solution of the above-obtained residue was added, and this mixture was stirred at −78° C. for 1 hour. To the reaction solution, triethylamine (7.1 mL, 52.4 mmol) was added, and the mixture was stirred at room temperature for 1 hour. 1 N hydrochloric acid and saturated saline were added thereto, followed by extraction with ethyl acetate. The organic layer was washed with saturated saline and then dried over anhydrous magnesium sulfate, and the solvent was distilled off under reduced pressure. The obtained residue was dissolved in pyridine (2.3 mL). To the solution, malonic acid (1.55 g, 14.95 mmol) and pyrrolidine (0.43 mL) were added, and the mixture was stirred overnight at room temperature and further stirred for 6 hours under heating to reflux. The mixture was allowed to cool, then diluted with a 2 N aqueous sodium hydroxide solution, and then washed with dimethyl ether. The aqueous layer was made acidic using concentrated hydrochloric acid under ice cooling, followed by extraction with diethyl ether. The organic layer was washed with saturated saline and dried over anhydrous magnesium sulfate. The solvent was distilled off under reduced pressure to obtain the compound of interest as a pale yellow oil substance (1.49 g, 78%).

(15-b) Tert-butyl(±)-(1S,5R)-3-allylbicyclo[3.2.0]hept-3-en-6-ylideneacetate

4-Allylhepta-2,6-dienoic acid (2.00 g, 12.0 mmol) was dissolved in benzene (5 mL). To the solution, oxalyl chloride (7.01 g, 55.2 mmol) was added under ice cooling, and the mixture was stirred in this state for 1 hour. The mixture was further stirred at room temperature for 30 minutes, then heated to 80° C., and stirred for 1 hour. Then, the solvent was distilled off under reduced pressure. To the residue, toluene was added, and the solvent was distilled off again under reduced pressure. The residue was dissolved in toluene (20 mL). This solution was added dropwise to a toluene solution (30 mL) of triethylamine (4.41 g, 43.68 mmol) heated in advance to reflux, and the mixture was further stirred for 2.5 hours. The reaction solution was allowed to cool, then diluted with saturated saline and ethyl acetate, and filtered through Xelite. The filtrate was separated into aqueous and organic layers. Then, the organic layer was washed with 1 N hydrochloric acid and saturated saline in this order, then dried over anhydrous magnesium sulfate, and then filtered. This filtrate was added to a reaction solution prepared in advance by adding sodium hydride (>65% oil, 457.1 mg, 12 mmol) to a tetrahydrofuran solution (20 mL) of tert-butyl dimethoxyphosphorylacetate (3.03 g, 12 mmol) under ice cooling, and the mixture was stirred for 1 hour. The solvent was distilled off under reduced pressure to obtain the compound of interest as a pale yellow oil substance (0.63 g, 16%, E/Z mixture).

(15-c) Tert-butyl(±)-[(1S,5R,6R)-3-allyl-6-(nitromethyl)bicyclo[3.2.0]hept-3-en-6-yl]acetate Tert-butyl(±)-(1S,5R)-3-allylbicyclo[3.2.0]hept-3-en-6-ylideneacetate (0.63 g, 2 mmol) was dissolved in nitromethane (5 mL). To the solution, 1,8-diazabicyclo[5.4.0]undec-7-ene (0.45 mL, 3 mmol) was added, and the mixture was heated with stirring at 50 to 60° C. for 7 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (367.0 mg, 60%).

(15-d) (±)-[(1S,5R,6R)-3-allyl-6-(aminomethyl)bicyclo[3.2.0]hept-3-en-6-yl]acetic acid Tert-butyl(±)-[(1S,5R,6R)-3-allyl-6-(nitromethyl)bicyclo[3.2.0]hept-3-en-6-yl]acetate (335.2 mg, 1.09 mmol) was dissolved in ethanol (10 mL) and water (5 mL). To the solution, iron powder (611.0 mg, 10.9 mmol) and ammonium chloride (57.8 mg, 1.09 mmol) were added, and the mixture was stirred for 2 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N hydrochloric acid-ethyl acetate solution (10 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (68.5 mg, 28%).

Example 16

(±)-[(1S,5R,6S)-6-aminomethyl-5-methylbicyclo[3.2.0]hept-3-en-6-yl]acetic acid (Exemplary Compound No: 6)

(16-a) Ethyl 2-methyl-3-oxohept-6-enoate

Ethyl 2-methyl-3-oxobutanoate (10 mL, 70.7 mmol) was added dropwise to an anhydrous tetrahydrofuran suspension of sodium hydride (2.83 g, 74.2 mmol) with stirring under ice cooling. The mixture was stirred for 15 minutes in this bath. Then, n-butyllithium (1.59 M hexane solution, 45.3 mL, 72.1 mmol) was added dropwise thereto, and the mixture was further stirred for 30 minutes. Then, allyl bromide (6.73 mL, 77.7 mmol) was added dropwise thereto. After removal of the ice bath, the mixture was stirred for 2 hours, and the reaction was then terminated by pouring dilute hydrochloric acid to the reaction solution. The reaction solution was subjected to extraction with ethyl acetate. The organic layer was washed with water, saturated aqueous sodium bicarbonate, and saturated saline and dried over anhydrous magnesium sulfate, and the solvent was then distilled off under reduced pressure. The obtained residue was purified by silica gel column chromatography to obtain the compound of interest as a pale yellow oil (7.67 g).

(16-b) Ethyl 3-hydroxy-2-methylhept-6-enoate

Sodium borohydride (2.48 g, 65.7 mmol) was added to a methanol (200 mL) solution of ethyl 2-methyl-3-oxohept-6-enoate (12.1 g, 65.7 mmol) with stirring under ice cooling. The mixture was stirred for 30 minutes in this bath, further stirred at room temperature for 2 hours, and then concentrated under reduced pressure to remove the solvent. The residue was diluted with dilute hydrochloric acid, followed by extraction with ethyl acetate. The organic layer was washed with water, saturated aqueous sodium bicarbonate, and saturated saline, then dried over anhydrous magnesium sulfate, and then concentrated under reduced pressure. The obtained residue was purified by silica gel column chromatography to obtain the compound of interest as a colorless oil (6.11 g).

(16-c) 3-Hydroxy-2-methylhept-6-enoic acid

Ethyl 3-hydroxy-2-methylhept-6-enoate (6.11 g, 32.8 mmol) was dissolved in a 2 N potassium hydroxide-methanol solution (100 mL), and the mixture was stirred at room temperature for 2 hours and then left overnight. The methanol was distilled off under reduced pressure, and the residue was diluted with water, then washed with methylene chloride, and then neutralized with dilute hydrochloric acid. The aqueous layer was subjected to extraction with ethyl acetate, and the extract was washed with water and saturated saline and dried over anhydrous magnesium sulfate. Then, the solvent was distilled off under reduced pressure to obtain the compound of interest as a pale yellow oil (5.46 g).

(16-d) (±)-(1S,5R)-5-methylbicyclo[3.2.0]hept-3-en-6-one

A mixed solution of 3-hydroxy-2-methylhept-6-enoic acid (5.45 g, 34.5 mmol), potassium acetate (7.0 g, 71.3 mmol), and acetic anhydride (30 mL) was stirred at room temperature for 1.5 hours and then stirred for 3 hours under conditions of heating to reflux. The reaction solution was left overnight, then diluted with ethyl acetate, washed with water, saturated aqueous sodium bicarbonate, and saturated saline, and then dried over anhydrous magnesium sulfate. The solvent was distilled off under reduced pressure, and the obtained residue was purified by silica gel column chromatography to obtain the compound of interest as a pale yellow oil (810 mg).

(16-e) Tert-butyl(±)-[(1S,5R)-5-methyl-bicyclo[3.2.0]hept-3-en-6-ylidene]acetate An anhydrous tetrahydrofuran solution (2 mL) of (±)-(1S,5R)-5-methylbicyclo[3.2.0]hept-3-en-6-one (800 mg, 6.55 mmol) was added dropwise with stirring under ice cooling to a reaction solution prepared in advance from an anhydrous tetrahydrofuran solution (10 mL) of tert-butyl dimethylphosphorylacetate (1.28 g, 6.55 mmol) and sodium hydride (>63% oil, 245 mg, 6.55 mmol), and the mixture was then stirred for 1 hour in this bath and further stirred at room temperature for 2 hours. The reaction solution was diluted with an aqueous citric acid solution, followed by extraction with ethyl acetate. The organic layer was washed with water, saturated aqueous sodium bicarbonate, and saturated saline and dried over anhydrous magnesium sulfate. Then, the solvent was distilled off under reduced pressure, and the obtained residue was purified by silica gel column chromatography to obtain the compound of interest as a colorless oil substance (389 mg).

(16-f) Tert-butyl(±)-[(1S,5R,6S)-6-cyano-5-methyl-bicyclo[3.2.0]hept-3-en-6-yl]acetate Tert-butyl(±)-[(1S,5R)-5-methyl-bicyclo[3.2.0]hept-3-en-6-ylidene]acetate (300 mg, 1.36 mmol) and potassium cyanide (89 mg, 1.36 mmol) were mixed at room temperature in anhydrous dimethyl sulfoxide (2 mL), and the mixture was stirred for 2 hours and then left overnight. The mixture was further stirred for 10 hours in an oil bath at 100° C. and then left overnight. The reaction solution was diluted with ethyl acetate, then washed with water and saturated saline, and dried over anhydrous magnesium sulfate. Then, the solvent was distilled off under reduced pressure, and the obtained residue was purified by silica gel column chromatography to obtain the compound of interest as a colorless oil (128 mg). In this procedure, a by-product tert-butyl(±)-[(1S,5R,6R)-6-cyano-5-methyl-bicyclo[3.2.0]hept-3-en-6-yl]acetate was obtained as a colorless oil (45 mg).

(16-g) Tert-butyl(±)-[(1S,5R,6S)-6-(tert-butoxycarbonylaminomethyl)-5-methylbicyclo[3.2.0]hept-3-en-6-yl]acetate Sodium borohydride (134 mg, 3.54 mmol) was added in small portions to a methanol (5 mL) solution of tert-butyl(±)-[(1S,5R,6S)-6-cyano-5-methyl-bicyclo[3.2.0]hept-3-en-6-yl]acetate (125 mg, 0.51 mmol), nickel (II) chloride hexahydrate (12 mg, 0.05 mmol), and (Boc)$_2$O (221 mg, 1.01 mmol) with stirring at room temperature, and the mixture was then stirred at room temperature for 2 hours. The reaction solution was diluted with ethyl acetate and saturated aqueous sodium bicarbonate and filtered to remove insoluble matter. Then, the organic layer was washed with saturated saline and dried over anhydrous sodium sulfate. The solvent was distilled off under reduced pressure, and the residue was purified by silica gel column chromatography to obtain the compound of interest as a colorless oil substance (123 mg).

(16-h) (±)-[(1S,5R,6S)-6-aminomethyl-5-methyl-bicyclo[3.2.0]hept-3-en-6-yl]acetic acid Tert-butyl(±)-[(1S,5R,6S)-6-(tert-butoxycarbonylaminomethyl)-5-methylbicyclo[3.2.0]hept-3-en-6-yl]acetate (120 mg, 0.34 mmol) was dissolved in a 4 N hydrochloric acid-ethyl acetate solution (2 mL), and the solution was stirred at room temperature for 3 hours and then concentrated under reduced pressure. The residue was dissolved in methylene chloride (2 mL). To the solution, triethylamine (0.048 mL, 0.34 mmol) was added dropwise at room temperature, and the mixture was stirred for 2 hours. The resulting powder was collected by filtration and dried to obtain the compound of interest as a white solid (22 mg).

Example 17

(±)-[(1S,5R,6R)-6-aminomethyl-2-methylbicyclo[3.2.0]hept-3-en-6-yl]acetic acid (Exemplary Compound No: 3)

(17-a) Methyl 5-methyl-3-hydroxy-6-heptenoate

The title compound was obtained as an oil substance (3.4 g, 33%) in the same way as in paragraph (10-a) using 3-methyl-4-pentenal (5 g, 59 mmol).

(17-b) 5-Methyl-3-hydroxy-6-heptenoic acid

The title compound was obtained as an oil substance (2.23 g, 74%) in the same way as in paragraph (10-b) using methyl 5-methyl-3-hydroxy-6-heptenoate (3.4 g, 19 mmol). This compound was used in the next reaction without being purified.

(17-c) Tert-butyl(±)-(1S,5R)-[2-methylbicyclo[3.2.0]hept-3-en-6-ylidene]acetate The title compound (major:minor=3:1, E/Z mixture) was obtained as an oil substance (1.9 g, 61%) in the same way as in paragraph (10-c) using 5-methyl-3-hydroxy-6-heptenoic acid (2.23 g, 14 mmol).

(17-d) Tert-butyl(±)-[(1S,5R,6R)-2-methyl-6-nitromethylbicyclo[3.2.0]hept-3-en-6-yl]acetate The title compound (1.9 g, 80 mmol) was obtained as an oil substance in the same way as in paragraph (1-c) using tert-butyl(±)-(1S,5R)-[2-methylbicyclo[3.2.0]hept-3-en-6-ylidene]acetate (1.9 g, 14 mmol).

(17-e) Tert-butyl(±)-[(1S,5R,6R)-6-(tert-butoxycarbonylamino)methyl-2-methylbicyclo[3.2.0]hept-3-en-6-yl]acetate The title compound (2.3 g, 99%) was obtained as an oil substance in the same way as in paragraph (3-a) using tert-butyl(±)-[(1S,5R,6R)-2-methyl-6-nitromethylbicyclo[3.2.0]hept-3-en-6-yl]acetate (1.9 g, 6.75 mmol).

(17-f) (±)-[(1S,5R,6R)-6-aminomethyl-2-methylbicyclo[3.2.0]hept-3-en-6-yl]acetic acid The title compound (major:minor=3:1, 0.68 g, 52%) was obtained as a white powder in the same way as in paragraph (3-b) using tert-butyl(±)-[(1S,5R,6R)-6-(tert-butoxycarbonylamino)methyl-2-methylbicyclo[3.2.0]hept-3-en-6-yl]acetate (2.3 g, 6.7 mmol).

Example 18

(±)-[(1R,5R,6R)-3-(acetoxymethyl)-6-(aminomethyl)bicyclo[3.2.0]hept-3-en-6-yl]acetic acid (Exemplary Compound No: 16)

(18-a) Ethyl 3-hydroxy-4-{[(4-methoxybenzyl)oxy]methyl}hept-6-enoate

A methylene chloride solution (10 mL) of titanium tetrachloride (0.97 mL, 8.88 mmol) and [(1-ethoxyvinyl)oxy](trimethyl)silane (J. Am. Chem. Soc. 2003, 125, 5644) was added to a methylene chloride solution (80 mL) of 2-{[(4-methoxybenzyl)oxy]methyl}pent-4-enal (Tetrahedron: Asymmetry 2001, 12, 3223) (1.98 g, 8.46 mmol) with stirring at −78° C., and the mixture was stirred at this temperature for 1.5 hours. The reaction was terminated by the addition of a saturated aqueous solution of sodium bicarbonate (100 mL) and water (100 mL), followed by extraction with methylene chloride. The organic layer was washed with a saturated aqueous solution of sodium bicarbonate, water, and saturated saline and dried over anhydrous sodium sulfate. The residue was filtered and concentrated under reduced pressure. Then, the obtained crude product was purified by silica gel column chromatography to obtain the compound of interest as an oil substance (1.31 g, 48%).

(18-b) 3-Hydroxy-4-{[(4-methoxybenzyl)oxy]methyl}hept-6-enoic acid

The compound of interest was obtained as an oil substance (1.20 g, >99%) in the same way as in paragraph (7-b) from ethyl 3-hydroxy-4-{[(4-methoxybenzyl)oxy]methyl}hept-6-enoate (1.31 g, 4.06 mmol).

(18-c) Tert-butyl(±)-[(1R,5R)-3-{[(4-methoxybenzyl)oxy]methyl}bicyclo[3.2.0]hept-3-en-6-ylidene]acetate The compound of interest was obtained as an oil substance (1.00 g, 69%) in the same way as in paragraph (7-c) from 3-hydroxy-4-{[(4-methoxybenzyl)oxy]methyl}hept-6-enoic acid (1.20 g, 4.06 mmol).

(18-d) Tert-butyl(±)-[(1R,5R,6R)-3-{[(4-methoxybenzyl)oxy]methyl}-6-(nitromethyl)bicyclo[3.2.0]hept-3-en-6-yl]acetate The compound of interest was obtained as an oil substance (1.02 g, 87%) in the same way as in paragraph (1-c) from tert-butyl(±)-[(1R,5R)-3-{[(4-methoxybenzyl)oxy]methyl}bicyclo[3.2.0]hept-3-en-6-ylidene]acetate (1.00 g, 2.80 mmol).

(18-e) Tert-butyl(±)-[(1R,5R,6R)-6-{[(tert-butoxycarbonyl)amino]methyl}-3-{[(4-methoxybenzyl)oxy]methyl}bicyclo[3.2.0]hept-3-en-6-yl]acetate The compound of interest was obtained as an oil substance (1.19 g, >99%) in the same way as in paragraph (3-a) from tert-butyl(±)-[(1R,5R,6R)-3-{[(4-methoxybenzypoxy]methyl}-6-(nitromethyl)bicyclo[3.2.0]hept-3-en-6-yl]acetate (1.02 g, 2.44 mmol).

(18-f) Tert-butyl(±)-[(1R,5R,6R)-6-{[(tert-butoxycarbonyl)amino]methyl}-3-(hydroxymethyl)bicyclo[3.2.0]hept-3-en-6-yl]acetate Water (1.4 mL) and 2,3-dichloro-5,6-dicyano-1,4-benzoquinone (831 mg, 3.66 mmol) were added to a methylene chloride solution (25 mL) of tert-butyl(±)-[(1R,5R,6R)-6-{[(tert-butoxycarbonyl)amino]methyl}-3-{[(4-methoxybenzyl)oxy]methyl}bicyclo[3.2.0]hept-3-en-6-yl]acetate (1.19 g, 2.44 mmol) with stirring at 0° C. The mixture was stirred at this temperature 0° C. for 1 hour and further stirred at room temperature for 1 hour. Then, the reaction was terminated by the addition of a saturated aqueous solution of sodium bicarbonate, followed by extraction with methylene chloride. The organic layer was washed with water, a saturated aqueous solution of sodium bicarbonate, and saturated saline and dried over anhydrous sodium sulfate. The residue was filtered and concentrated under reduced pressure. Then, the obtained crude product was purified by silica gel column chromatography to obtain the compound of interest as an oil substance (571 mg, 64%).

(18-g) (±)-[(1R,5R,6R)-3-(acetoxymethyl)-6-(aminomethyl)bicyclo[3.2.0]hept-3-en-6-yl]acetic acid The compound of interest was obtained as a white solid (85.2 mg, 45%) in the same way as in paragraph (3-b) from tert-butyl(±)-[(1R,5R,6R)-6-{[(tert-butoxycarbonyl)amino]methyl}-3-(hydroxymethyl)bicyclo[3.2.0]hept-3-en-6-yl]acetate (275 mg, 0.75 mmol).

Example 19

(±)-[(1R,5R,6R)-6-aminomethyl-3-(methoxymethyl)bicyclo[3.2.0]hept-3-en-6-yl]acetic acid (Exemplary Compound No: 17)

(19-a) Methyl (2E)-4-({[tert-butyl(dimethyl)silyl]oxy}methyl)hepta-2,6-dienoate Dimethyl sulfoxide (4.71 mL, 66.3 mmol) was added to a methylene chloride solution (70 mL) of oxalyl chloride (2.84 mL, 33.2 mmol) with stirring at −78° C., and the mixture was stirred at this temperature for 5 minutes. Then, a methylene chloride solution (30 mL) of 2-({[tert-butyl(dimethyl)silyl]oxy}methyl)pent-4-en-1-ol (J. Chem. Soc., Perkin Trans. 1 1991, 2073) (5.10 g, 22.1 mmol) was added thereto. The mixture was stirred at this temperature for 15 minutes. Then, triethylamine (12.3 mL, 88.4 mmol) was added thereto, and the mixture was heated to room temperature and stirred. The mixture was separated into aqueous and organic layers by the addition of 0.1 M hydrochloric acid. The organic layer was washed with 0.1 M hydrochloric acid, water, and saturated saline and then dried over anhydrous magnesium sulfate. The residue was filtered and concentrated under reduced pressure, and the obtained residue was dissolved in toluene (50 mL). To the solution, (methoxycarbonylmethylene)triphenylphosphorane (11.1 g, 33.2 mmol) was added, and the mixture was stirred at room temperature for 4 hours and further stirred at 60° C. for 2 hours. The reaction solution was concentrated under reduced pressure, then filtered through Celite, and concentrated again under reduced pressure. Then, the obtained crude product was purified by silica gel column chromatography to obtain the compound of interest as an oil substance (5.69 g, 91%).

(19-b) (2E)-4-({[tert-butyl(dimethyl)silyl]oxy}methyl)hepta-2,6-dienoic acid

Lithium hydroxide monohydrate (2.52 g, 60.0 mmol) was added to a tetrahydrofuran:methanol:water (3:1:1, 100 mL) mixed solution of methyl (2E)-4-({[tert-butyl(dimethyl)silyl]oxy}methyl)hepta-2,6-dienoate (5.69 g, 20.0 mmol), and the mixture was stirred at room temperature for 6 hours. The reaction solution was concentrated under reduced pressure. To the residue, water was then added, followed by extraction with methylene chloride. The aqueous layer was made acidic by the addition of 10% hydrochloric acid, followed by extraction with methylene chloride again. Then, the combined organic layers were dried over anhydrous sodium sulfate. The residue was filtered and concentrated under reduced pressure. Then, the obtained crude product was purified by silica gel column chromatography to obtain the compound of interest as an oil substance (3.11 g, 57%).

(19-c) Tert-butyl(±)-[(1R,5R)-3-({[tert-butyl(dimethyl)silyl]oxy}methyl)bicyclo[3.2.0]hept-3-en-6-ylidene]acetate The compound of interest was obtained as an oil substance (2.03 g, 50%) in the same way as in paragraph (1-b) from (2E)-4-({[tert-butyl(dimethyl)silyl]oxy}methyl)hepta-2,6-dienoic acid (3.11 g, 11.5 mmol).

(19-d) Tert-butyl(±)-[(1R,5R)-3-(hydroxymethyl)bicyclo[3.2.0]hept-3-en-6-ylidene]acetate Tetrabutyl ammonium fluoride (1.0 M tetrahydrofuran solution, 8.69 mL, 8.69 mmol) was added to a tetrahydrofuran solution (15 mL) of tert-butyl(±)-[(1R,5R)-3-({[tert-butyl(dimethyl)silyl]oxy}methyl)bicyclo[3.2.0]hept-3-en-6-ylidene]acetate (2.03 g, 5.79 mmol), and the mixture was stirred at room temperature for 2 hours. To the reaction solution, water was added, followed by extraction with ethyl acetate. Then, the organic layer was washed with water and saturated saline and dried over anhydrous sodium sulfate. The residue was filtered and concentrated under reduced pressure. Then, the obtained crude product was purified by silica gel column chromatography to obtain the compound of interest as an oil substance (1.29 g, 94%).

(19-e) Tert-butyl(±)-[(1R,5R,6R)-3-(methoxymethyl)-6-(nitromethyl)bicyclo[3.2.0]hept-3-en-6-yl]acetate Methyl iodide (2.03 mL, 32.6 mmol) and silver (I) oxide (1.62 g, 6.99 mmol) were added to a methylene chloride solution (6.0 mL) of tert-butyl(±)-[(1R,5R)-3-(hydroxymethyl)bicyclo[3.2.0]hept-3-en-6-ylidene]acetate (550 mg, 2.33 mmol), and the mixture was stirred at room temperature for 40 hours. The mixture was filtered through Celite and concentrated under reduced pressure. Then, the residue was dissolved in nitromethane (4.5 mL). To the solution, 1,8-diazabicyclo[5.4.0]undec-7-ene (0.70 mL, 4.66 mmol) was added, and the mixture was stirred at 60° C. for 7 hours. To the reaction solution, a saturated aqueous solution of potassium dihydrogen phosphate was added, followed by extraction with ethyl acetate. The organic layer was washed with a saturated aqueous solution of potassium dihydrogen phosphate and saturated saline and dried over anhydrous sodium sulfate. The residue was filtered and concentrated under reduced pressure. Then, the residue was purified by silica gel column chromatography to obtain the compound of interest as an oil substance (368 mg, 51%).

(19-f) Tert-butyl(±)-[(1R,5R,6R)-6-{[(tert-butoxycarbonyl)amino]methyl}-3-(methoxymethyl)bicyclo[3.2.0]hept-3-en-6-yl]acetate The compound of interest was obtained as an oil substance (450 mg, >99%) in the same way as in paragraph (3-a) from tert-butyl(±)-[(1R,5R,6R)-3-(methoxymethyl)-6-(nitromethyl)bicyclo[3.2.0]hept-3-en-6-yl]acetate (368 mg, 1.18 mmol).

(19-g) (±)-[(1R,5R,6R)-6-aminomethyl-3-(methoxymethyl)bicyclo[3.2.0]hept-3-en-6-yl]acetic acid The compound of interest was obtained as a white solid (143 mg, 53%) in the same way as in paragraph (1-e) from (±)-[(1R,5R,6R)-6-aminomethyl-3-(methoxymethyl)bicyclo[3.2.0]hept-3-en-6-yl]acetic acid (450 mg, 1.18 mmol).

Example 20

(±)-[(1S,5R,6R)-6-aminomethyl-3,4-dimethylbicyclo[3.2.0]hept-3-en-6-yl]acetic acid p-toluenesulfonate (p-toluenesulfonate of the Compound of Exemplary Compound No: 19)

(20-a) Methyl 3-hydroxy-3,4-dimethyl-6-heptenoate

The compound of interest (11.7 g, 60%) was obtained as an oil substance (diastereomeric mixture) in the same way as in paragraph (10-a) using 3-methyl-5-hexen-2-one (17 g, 106 mmol).

(20-b) 3-Hydroxy-3,4-dimethyl-6-heptenoic acid

The compound of interest (10.1 g) was obtained as an oil substance in the same way as in paragraph (10-b) using methyl 3-hydroxy-3,4-dimethyl-6-heptenoate (11.7 g, 63 mmol). This compound was used in the next reaction without being purified.

(20-c) Tert-butyl(±)-(1S,5R)-[3,4-dimethylbicyclo[3.2.0]hept-3-en-6-ylidene]acetate The compound of interest (4.2 g, 33%) was obtained as an oil substance (E/Z mixture) in the same way as in paragraph (10-c) using 3-hydroxy-3,4-dimethyl-6-heptenoic acid (10.1 g).

(20-d) Tert-butyl(±)-[(1S,5R,6R)-3,4-dimethyl-6-nitromethylbicyclo[3.2.0]hept-3-en-6-yl]acetate The compound of interest (4.5 g, 85%) was obtained as an oil substance in the same way as in paragraph (1-c) using tert-butyl(±)-(1S,5R)-[3,4-dimethylbicyclo[3.2.0]hept-3-en-6-ylidene]acetate (4.2 g, 18 mmol).

(20-e) Tert-butyl(±)-[(1S,5R,6R)-6-(tert-butoxycarbonylamino)methyl-3,4-dimethylbicyclo[3.2.0]hept-3-en-6-yl]acetate The compound of interest (5.6 g, 99%) was obtained as an oil substance in the same way as in paragraph (3-a) using tert-butyl(±)-[(1S,5R,6R)-3,4-dimethyl-6-nitromethylbicyclo[3.2.0]hept-3-en-6-yl]acetate (4.5 g, 15 mmol).

(20-f) (±)-[(1S,5R,6R)-6-aminomethyl-3,4-dimethylbicyclo[3.2.0]hept-3-en-6-yl]acetic acid p-toluenesulfonate Tert-butyl(±)-[(1S,5R,6R)-6-(tert-butoxycarbonylamino)methyl-3,4-dimethylbicyclo[3.2.0]hept-3-en-6-yl]acetate (4.0 g, 11 mmol) and p-toluenesulfonic acid monohydrate (2.5 g, 13 mmol) were suspended in toluene (30 mL) and thioanisole (3.8 mL), and the suspension was stirred at 80° C. for 2 hours. The reaction solution was concentrated, and the resulting oil substance was treated with ethyl acetate and hexane to obtain the title compound (2.3 g, 55%) as a white powder.

Example 21

[(1R,5S,6S)-6-aminomethyl-3-ethylbicyclo[3.2.0]hept-3-en-6-yl]acetic acid (Exemplary Compound No: 8, Optically Active Faun of the Compound of Example 8)

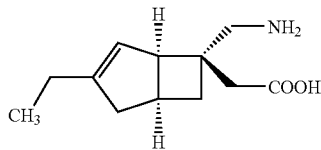

(21-a) Resolution of tert-butyl(±)-[(1R,5S,6S)-3-ethyl-6-(nitromethyl)bicyclo[3.2.0]hept-3-en-6-yl]acetate Tert-butyl(±)-[(1R,5S,6S)-3-ethyl-6-(nitromethyl)bicyclo[3.2.0]hept-3-en-6-yl]acetate (230 g, 778 mmol) was resolved using Chiralpak IC (N-Hex:EtOH=98:2, 1.0 mL/min, 40° C.) manufactured by Daicel Chemical Industries, Ltd. to respectively obtain 115 g of a peak 1 (retention time: 5.2 min) and 93.7 g of a peak 2 (retention time: 6.3 min).

(21-b) Tert-butyl([(1R,5S,6S)-6-(tert-butoxycarbonylamino)methyl-3-ethylbicyclo[3.2.0]hept-3-en-6-yl]acetate Tert-butyl[(1R,5S,6S)-3-ethyl-6-(nitromethyl)bicyclo[3.2.0]hept-3-en-6-yl]acetate (peak 1, 7.0 g, 23.7 mmol) was dissolved in ethanol (60 mL) and water (21 mL). To the solution, iron powder (13.27 g, 237 mmol) and ammonium chloride (628.1 mg, 11.9 mmol) were added, and the mixture was stirred for 5.5 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate. Then, the solvent was distilled off under reduced pressure to obtain a pale yellow oil substance (7.02 g). This substance was dissolved in dichloromethane (200 mL). To the solution, (Boc)$_2$O (5.25 g, 25 mmol) and triethylamine (5.01 g, 50 mmol) were added, and the mixture was stirred overnight at room temperature. The solvent was distilled off under reduced pressure, and the residue was then purified by silica gel chromatography to obtain the title compound of interest as a pale yellow oil substance (8.82 g, <100%).

(21-c) [(1R,5S,6S)-6-aminomethyl-3-ethylbicyclo[3.2.0]hept-3-en-6-yl]acetic acid A 4 N hydrochloric acid-ethyl acetate solution (100 mL) was added to tert-butyl (1R,5S,6S)-[6-(tert-butoxycarbonylaminomethyl)-3-ethylbicyclo[3.2.0]hept-3-en-6-yl]acetate (9.82 g, 23.7 mmol), and the mixture was stirred at room temperature for 1 hour. Then, the solvent was distilled off under reduced pressure. The residue was dissolved in dichloromethane. To the solution, triethylamine was added dropwise, and the resulting powder was collected by filtration, then washed with dichloromethane, and then dried to obtain 4.02 g of a white powder. This powder was washed with ethanol and ethyl acetate to obtain the title compound of interest as a white powder (2.14 g, 43%).

Example 22

[(1R,5S,6S)-6-aminomethyl-3-ethylbicyclo[3.2.0]hept-3-en-6-yl]acetic acid p-toluenesulfonate (Exemplary Compound No: 8, p-toluenesulfonate of the compound of Example 21)

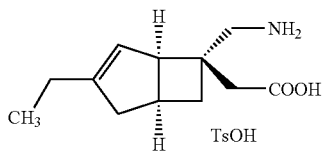

Tert-butyl[(1R,5S,6S)-6-(tert-butoxycarbonylamino)methyl-3-ethylbicyclo[3.2.0]hept-3-en-6-yl]acetate (1152.23 g, 391.6 mmol) was dissolved in benzene (1.2 L). To the solution, thioanisole (145.57 g, 1173 mmol) and p-toluenesulfonic acid monohydrate (89.39 g) were then added, and the mixture was stirred for 2 hours under reflux. The mixture was left standing overnight at room temperature, and the resulting powder was collected by filtration. The obtained powder was washed with ethyl acetate and then dried to obtain the compound of interest as a white powder (88.29 g, 59%).

Example 23

[(1S,5R,6R)-6-aminomethyl-3-ethylbicyclo[3.2.0]hept-3-en-6-yl]acetic acid (Exemplary Compound No: 8, Optical Isomer of the Compound of Example 21)

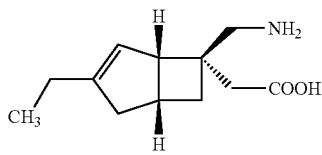

(23-a) Tert-butyl-[(1S,5R,6R)-6-(tert-butoxycarbonylamino)methyl-3-ethylbicyclo[3.2.0]hept-3-en-6-yl]acetate Tert-butyl[(1S,5R,6R)-6-(nitromethyl)-3-ethylbicyclo[3.2.0]hept-3-en-6-yl]acetate (peak 2, 6.90 g, 23.36 mmol) was dissolved in ethanol (80 mL) and water (20 mL). To the solution, iron powder (6.52 g, 116.8 mmol) and ammonium chloride (1.25 g, 23.36 mmol) were added, and the mixture was stirred for 4.5 hours under heating to reflux. The mixture was allowed to cool and then filtered through Celite to remove insoluble matter. To the filtrate, (Boc)$_2$O (15.30 g, 70.08 mmol) was added, and the filtrate was then made basic (pH>9) using a 2 N sodium hydroxide solution and stirred at room temperature for 2 hours. The solution was concentrated, and the residue was diluted with ethyl acetate. The dilution was washed with water and saturated saline and dried over anhydrous magnesium sulfate. Then, the solvent was distilled off under reduced pressure, and the residue was purified by silica gel column chromatography to obtain the compound of interest as a colorless oil substance (8.51 g, 99%).

(23-b) [(1S,5R,6R)-6-aminomethyl-3-ethylbicyclo[3.2.0]hept-3-en-6-yl]acetic acid Tert-butyl[(1S,5R,6R)-6-[(tert-butoxycarbonylamino)methyl-3-ethylbicyclo[3.2.0]hept-3-en-6-yl]acetate (8.54 g, 23.36 mmol) was dissolved in a 4 N hydrochloric acid-ethyl acetate solution (100 mL), and the solution was stirred at room temperature for 2 hours. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane and then washed with isopropanol-ethyl acetate to obtain the compound of interest as a white powder (2.7 g, 55%).

Example 24

(±)-{(1R,5R,6R)-6-aminomethyl-3-[(methylthio)methyl]bicyclo[3.2.0]hept-3-en-6-yl}acetic acid (Exemplary Compound No: 18)

(24-a) Tert-butyl(±)-[(1R,5R,6R)-3-(hydroxymethyl)-6-(nitromethyl)bicyclo[3.2.0]hept-3-en-6-yl]acetate The compound of interest was obtained as an oil substance in the same way as in paragraph (1-c) from the tert-butyl(±)-[(1R,5R)-3-(hydroxymethyl)bicyclo[3.2.0]hept-3-en-6-ylidene]acetate (726 mg, 3.07 mmol) produced in paragraph (19-d).

(24-b) Tert-butyl(±)-[(1R,5R,6R)-3-[(methylthio)methyl]-6-(nitromethyl)bicyclo[3.2.0]hept-3-en-6-yl]acetate Triphenylphosphine (1.85 g, 7.05 mmol) and carbon tetrachloride (0.78 mL, 8.14 mmol) were added to a dimethylformamide solution (8.0 mL) of tert-butyl(±)-[(1R,5R,6R)-3-(hydroxymethyl)-6-(nitromethyl)bicyclo[3.2.0]hept-3-en-6-yl]acetate (807 mg, 2.71 mmol), and the mixture was stirred at room temperature for 1 hour. To the reaction solution, water was added, followed by extraction with diethyl ether. The organic layer was washed with saturated saline and then dried over anhydrous sodium sulfate. The residue was filtered and concentrated under reduced pressure. Then, the obtained crude product of tert-butyl(±)-[(1R,5R,6R)-3-(chloromethyl)-6-(nitromethyl)bicyclo[3.2.0]hept-3-en-6-yl]acetate was dissolved in dimethylformamide (10 mL). To the solution, sodium thiomethoxide (570 mg, 8.14 mmol) was added with stirring at 0° C., and the mixture was stirred at this temperature for 4 hours. The reaction solution was diluted with ethyl acetate and separated into aqueous and organic layers. The organic layer was washed with a 1 M aqueous sodium hydroxide solution, water, and saturated saline and then dried over anhydrous sodium sulfate. The residue was filtered and concentrated under reduced pressure. Then, the obtained crude product was purified by silica gel column chromatography to obtain the compound of interest as an oil substance (632 mg, 71%).

(24-c) Tert-butyl(±)-{(1R,5R,6R)-6-{[(tert-butoxycarbonyl)amino]methyl}-3-[(methylthio)methyl]bicyclo[3.2.0]hept-3-en-6-yl}acetate The compound of interest was obtained as an oil substance (755 mg, 98%) in the same way as in to paragraph (3-a) from tert-butyl(±)-[(1R,5R,6R)-3-[(methylthio)methyl]-6-(nitromethyl)bicyclo[3.2.0]hept-3-en-6-yl]acetate (632 mg, 1.93 mmol).

(24-d) (±)-{(1R,5R,6R)-6-aminomethyl-3-[(methylthio)methyl]bicyclo[3.2.0]hept-3-en-6-yl}acetic acid The compound of interest was obtained as a white solid (342 mg, 75%) in the same way as in paragraph (1-e) from tert-butyl(±)-{(1R,5R,6R)-6-{[(tert-butoxycarbonyl)amino]methyl}-3-[(methylthio)methyl]bicyclo[3.2.0]hept-3-en-6-yl}acetate (755 mg, 1.90 mmol).

Example 25

[(1R,5S,6S)-6-aminomethyl-3-methylbicyclo[3.2.0]hept-3-en-6-yl]acetic acid (Exemplary Compound No: 4, Optically Active Form of the Compound of Example 7)

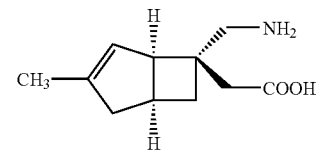

(25-a) Resolution of tert-butyl(±)-[(1R,5S,6S)-3-methyl-6-(nitromethyl)bicyclo[3.2.0]hept-3-en-6-yl]acetate Tert-butyl(±)-[(1R,5S,6S)-3-methyl-6-(nitromethyl)bicyclo[3.2.0]hept-3-en-6-yl]acetate (15 g) was resolved using Chiralpak IC (N-Hex:EtOH=98:2, 1.0 mL/min, 40° C.) manufactured by Daicel Chemical Industries, Ltd. to respectively obtain 5.5 g of a peak 1 (retention time: 6.1 min) and 5.2 g of a peak 2 (retention time: 7.7 min).

(25-b) Tert-butyl[(1R,5S,6S)-6-(tert-butoxycarbonylamino)methyl-3-methylbicyclo[3.2.0]hept-3-en-6-yl]acetate Tert-butyl[(1R,5S,6S)-3-methyl-6-(nitromethyl)bicyclo[3.2.0]hept-3-en-6-yl]acetate (peak 1, 5.5 g, 19.5 mmol) was dissolved in ethanol (40 mL). To the solution, Raney nickel (1.2 g) was added. To the mixture, hydrazine monohydrate (3.9 g, 78.2 mmol) was added with stirring, and the mixture was stirred overnight at room temperature. The catalyst was filtered off, and the filtrate was then concentrated. The residue was diluted with ethyl acetate, washed with water and saturated saline, then dried, and then concentrated. The residue was dissolved in ethanol (50 mL). To the solution, di-tert-butyl dicarbonate (8.53 g, 39.1 mmol) was added, and the mixture was stirred at room temperature for 2 hours. The reaction solution was concentrated, and the residue was washed with water and saturated saline, then dried, and then concentrated. The residue was purified by silica gel column chromatography (100 g) to obtain the compound of interest as an oil substance (6.8 g, 99%).

(25-c) [(R1R,5S,6S)-6-aminomethyl-3-methylbicyclo[3.2.0]hept-3-en-6-yl]acetic acid benzenesulfonic acid Tert-butyl[(1R,5S,6S)-6-(tert-butoxycarbonylamino)methyl-3-methylbicyclo[3.2.0]hept-3-en-6-yl]acetate (6.8 g, 13.9 mmol) and benzenesulfonic acid monohydrate (3.79 g, 21 mmol) were added to benzene (40 mL), and the mixture was heated with stirring for 2 hours. The resulting solid was collected by filtration to obtain the compound of interest as a white solid (5.6 g, 81%).

(25-d) [(1R,5S,6S)-6-aminomethyl-3-methylbicyclo[3.2.0]hept-3-en-6-yl]acetic acid

[(1R,5S,6S)-6-tert-butoxycarbonylaminomethyl-3-methylbicyclo[3.2.0]hept-3-en-6-yl]acetic acid benzenesulfonic acid (5.6 g, 15.8 mmol) was suspended in methylene chloride (50 mL). To the suspension, triethylamine (4.4 ml, 31.7 mmol) was added, and the mixture was stirred at room temperature for 1 hour. The resulting solid was collected by filtration and washed with isopropanol to obtain the compound of interest as a white solid (2.4 g, 77%).

Example 26

[(1R,5S,6S)-6-aminomethyl-3-methylbicyclo[3.2.0]hept-3-en-6-yl]acetic acid (Exemplary Compound No: 4, Optically Active Form of the Compound of Example 7 Differing in Production Process from that of Example 25)

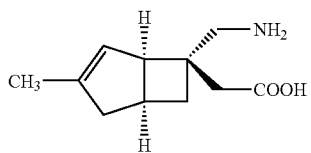

(26-a) Tert-butyl[(1S,5R,6R)-6-(tert-butoxycarbonylamino)methyl-3-methylbicyclo[3.2.0]hept-3-en-6-yl]acetate Tert-butyl[(1S,5R,6R)-3-methyl-6-(nitromethyl)bicyclo[3.2.0]hept-3-en-6-yl]acetate (peak 2, 5.2 g, 18.5 mmol) was dissolved in ethanol (40 mL). To the solution, Raney nickel (1.2 g) was added. To the mixture, hydrazine monohydrate (3.7 g, 74.1 mmol) was added with stirring, and the mixture was stirred overnight at room temperature. The catalyst was filtered off, and the filtrate was then concentrated. The residue was diluted with ethyl acetate, washed with water and saturated saline, then dried, and then concentrated. The residue was dissolved in ethanol (50 mL). To the solution, di-tert-butyl dicarbonate (7.99 g, 36.6 mmol) was added, and the mixture was stirred at room temperature for 2 hours. The reaction solution was concentrated, and the residue was washed with water and saturated saline, then dried, and then concentrated. The residue was purified by silica gel column chromatography (100 g) to obtain the compound of interest as an oil substance (6.4 g, 99%).

(26-b) [(1S,5R,6R)-6-aminomethyl-3-methylbicyclo[3.2.0]hept-3-en-6-yl]acetic acid benzenesulfonic acid Tert-butyl[(1S,5R,6R)-6-(tert-butoxycarbonylamino)methyl-3-methylbicyclo[3.2.0]hept-3-en-6-yl]acetate (6.4 g, 18.2 mmol) and benzenesulfonic acid monohydrate (3.53 g, 20 mmol) were added to benzene (40 mL), and the mixture was heated with stirring for 2 hours. The resulting solid was collected by filtration to obtain the compound of interest as a white solid (5.8 g, 90%).

(26-c) [(1S,5R,6R)-6-aminomethyl-3-methylbicyclo[3.2.0]hept-3-en-6-yl]acetic acid

[(1S,5R,6R)-6-tert-butoxycarbonylaminomethyl-3-methylbicyclo[3.2.0]hept-3-en-6-yl]acetic acid benzenesulfonic acid (5.8 g, 16.4 mmol) was suspended in methylene chloride (50 mL). To the suspension, triethylamine (4.6 ml, 32.7 mmol) was added, and the mixture was stirred at room temperature for 1 hour. The resulting solid was collected by filtration and washed with isopropanol to obtain the compound of interest as a white solid (2.0 g, 63%).

Example 27

(±)-[(1R,5S,6S)-6-aminomethyl-3,4-dimethyl-bicyclo[3.2.0]hept-3-en-6-yl]acetic acid (Exemplary Compound No: 19, Salt-Free Form of the Compound of Example 20)

(27-a) Methyl 3,4-dimethyl-3-hydroxy-6-heptenoate

3-Methyl-5-hexen-2-one (J. Chem. Soc., Chem. Comm. 19, 1991, 1399) (17 g, 106 mmol) and methyl bromoacetate (24.4 g, 159 mmol) were dissolved in tetrahydrofuran (100 mL), and the solution was added dropwise to a tetrahydrofuran (50 mL) (zinc (10.4 g, 159 mmol) and trimethyl borate (30 mL)) solution under reflux. After reflux for 3 hours, the mixture was cooled to room temperature, and glycerin (30 mL) and a saturated aqueous solution of ammonia chloride (100 mL) were added thereto, followed by two extractions with ethyl acetate. The ethyl acetate layer was washed with saturated saline, then dried, and then concentrated. The residue was purified by silica gel column chromatography (200 g) to obtain the compound of interest as an oil substance (11.7 g, 60%).

(27-b) 3,4-Dimethyl-3-hydroxy-6-heptenoic acid

Methyl 3,4-dimethyl-3-hydroxy-6-heptenoate (11.7 g, 62.8 mmol) was dissolved in a 2 N potassium hydroxide-methanol solution (44 mL), and the solution was stirred overnight at room temperature. The reaction solution was concentrated, then dissolved in water (30 mL), and washed with ether. The aqueous layer was made acidic (<pH=2) using aqueous hydrochloric acid, followed by two extractions with ethyl acetate. The ethyl acetate layer was washed with saturated saline, then dried, and then concentrated to obtain the compound of interest as an oil substance (10.1 g, 93%). This compound was used in the next reaction without being purified.

(27-c) Tert-butyl(±)-(1R,5S)-3,4-dimethyl-[3.2.0]
hept-3-en-6-ylideneacetate 3,4-Dimethyl-3-hydroxy-6-heptenoic acid (10.1 g, 54.2 mmol) and potassium acetate (12.8 g, 130 mmol) were dissolved in acetic anhydride (100 mL), and the solution was stirred at room temperature for 30 minutes and then stirred for 3 hours under heating to reflux. The reaction solution was placed in an ice bath, followed by three extractions with ether-pentane. The organic layer was washed with an aqueous sodium hydroxide solution and a saturated saline solution and then concentrated to obtain an oil substance. This oil substance was dissolved in tetrahydrofuran (70 mL), and the solution was added dropwise to a tetrahydrofuran (50 mL) (sodium hydride (2.17 g, 54.3 mmol) and tert-butyl dimethoxyphosphorylacetate (12.2 g, 54.3 mmol)) solution under ice cooling. The reaction solution was poured to a saturated aqueous solution of ammonia chloride, followed by extraction with ethyl acetate. The ethyl acetate layer was washed with saturated saline, then dried, and then concentrated. The residue was purified by silica gel column chromatography (200 g) to obtain the compound of interest as an oil substance (4.2 g, 33%).

(27-d) Tert-butyl(±)-[(1R,5S,6S)-3,4-dimethyl-6-
(nitromethyl)bicyclo[3.2.0]hept-3-en-6-yl]acetate Tert-butyl(±)-(1R,5S)-3,4-dimethyl-[3.2.0]hept-3-en-6-ylideneacetate (4.2 g, 17.9 mmol) was dissolved in nitromethane (20 mL). To the solution, 1,8-diazabicyclo[5.4.0]undec-7-ene (4.9 g, 27 mmol) was added, and the mixture was stirred overnight at room temperature. A saturated aqueous solution of potassium dihydrogen phosphate was added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (4.5 g, 85%).

(27-e) Tert-butyl[(1R,5S,6S)-6-(tert-butoxycarbonylamino)methyl-3,4-dimethylbicyclo[3.2.0]hept-3-en-6-yl]acetate The compound of interest was obtained as an oil substance (5.5 g, 99%) in the same way as in paragraph (3-a) using tert-butyl(±)-[(1R,5S,6S)-3,4-dimethyl-6-(nitromethyel)bicyclo[3.2.0]hept-3-en-6-yl]acetate (4.5 g, 15.2 mmol).

(27-f) (±)-[(1R,5S,6S)-6-aminomethyl-3,4-dimethyl-
bicyclo[3.2.0]hept-3-en-6-yl]acetic acid The compound of interest was obtained as a white solid (440 mg, 45%) in the same way as in paragraph (3-b) using tert-butyl[(1R,5S,6S)-6-(tert-butoxycarbonylamino)methyl-3,4-dimethylbicyclo[3.2.0]hept-3-en-6-yl]acetate (1.7 g, 4.65 mmol).

Example 28

(±)-[(1R,5S,6S)-6-aminomethyl-3-(2-fluoroethyl)-
bicyclo[3.2.0]hept-3-en-6-yl]acetic acid (Exemplary
Compound No: 30)

(28-a) Ethyl(E)-4-(2-hydroxyethyl)-hepta-2,6-dienoate 3-allyl-tetrahydrofuran-2-ol (18 g, 140 mmol) and ethoxycarbonyl triphenylphosphorane (35 g, 104 mmol) were stirred overnight in toluene (200 mL). The reaction solution was concentrated, and the residue was purified by silica gel column chromatography to obtain the compound of interest as an oil substance (15.8 g, 61.1%).

(28-b) Ethyl(E)-4-(2-fluoroethyl)-hepta-2,6-dienoate

Ethyl(E)-4-(2-hydroxyethyl)-hepta-2,6-dienoate (5 g, 27.1 mmol) was dissolved in tetrahydrofuran (40 mL). To the solution, DAST (4.8 g, 29.8 mmol) was added under ice cooling, and the mixture was stirred for 1 hour. The reaction solution was poured to a saturated aqueous solution of sodium bicarbonate, followed by extraction with ethyl acetate. The ethyl acetate layer was washed with saturated saline, then dried, and then concentrated. The residue was purified by silica gel column chromatography (200 g) to obtain the compound of interest as an oil substance (2.2 g, 44%).

(28-c) Tert-butyl(±)-[(1R,5S,6S)-3-(2-fluoroethyl)-6-
(nitromethyl)bicyclo[3.2.0]hept-3-en-6-yl]acetate The compound of interest was obtained (870 mg, 23%) in the same way as in paragraph (27-b), (27-c), and (27-d) using ethyl(E)-4-(2-fluoroethyl)-hepta-2,6-dienoate (2.2 g, 11.9 mmol).

(28-d) Tert-butyl[(1R,5S,6S)-6-(tert-butoxycarbonylamino)methyl-3-(2-fluoroethyl)bicyclo[3.2.0]hept-
3-en-6-yl]acetate The compound of interest was obtained as an oil substance (700 mg, 65.8%) in the same way as in paragraph (3-a) using tert-butyl(±)-[(1R,5S,6S)-3-(2-fluoroethyl)-6-(nitromethyl)bicyclo[3.2.0]hept-3-en-6-yl]acetate (870 mg, 2.77 mmol).

(28-e) (±)-[(1R,5S,6S)-6-aminomethyl-3-(2-fluoroethyl)-bicyclo[3.2.0]hept-3-en-6-yl]acetic acid The compound of interest was obtained as a white solid (330 mg, 79%) in the same way as in paragraph (3-b) using tert-butyl[(1R,5S,6S)-6-(tert-butoxycarbonylamino)methyl-3-(2-fluoroethyl)bicyclo[3.2.0]hept-3-en-6-yl]acetate (700 mg, 1.83 mmol).

Example 29

(±)-[(1S,5R,6R)-6-(aminomethyl)-4-methylbicyclo
[3.2.0]hept-3-en-6-yl]acetic acid (Exemplary Compound No: 5)

(29-a) 3-Hydroxy-3-methylhept-6-enoic acid

Trimethyl borate (15 mL), zinc powder (washed in advance with dilute hydrochloric acid and dried for use, 4.24 g), and tert-butyl bromoacetate (9.91 mL, 48.6 mmol) were added in this order to a tetrahydrofuran solution (15 mL) of hex-5-en- 2-one (5.29 g, 53.9 mmol), and the mixture was heated to 30° C. for 30 minutes using an oil bath, then brought to room temperature, and stirred for 3 hours. The mixture was separated into organic and aqueous layers by the addition of glycerol, a saturated aqueous solution of ammonium chloride, and saturated saline, and the aqueous layer was then subjected to extraction with diethyl ether. These organic layers were combined, then washed with saturated saline, and then dried over anhydrous magnesium sulfate, and the solvent was then distilled off under reduced pressure. To the residue, a 2 N potassium hydroxide-methanol solution (50 mL) was added, and the mixture was stirred at room temperature for 6 hours. The solvent was distilled off under reduced pressure. To the residue, a 1 N aqueous sodium hydroxide solution was then added, followed by washing with diethyl ether. The aqueous layer was made acidic using concentrated hydrochloric acid under ice cooling, followed by extraction with diethyl ether. The organic layer was washed with saturated saline and then dried over anhydrous magnesium sulfate. The solvent was distilled off under reduced pressure to obtain the compound of interest as a pale yellow oil substance (5.24 g, 75%).

(29-b) (±)-(1S,5R)-4-methylbicyclo[3.2.0]hept-3-en-6-one

3-Hydroxy-3-methylhept-6-enoic acid (5.24 g, 36.4 mmol) was dissolved in acetic anhydride (40 mL). To the solution, potassium acetate (12.52 g, 127 mmol) was added, and the mixture was stirred at room temperature for 2 hours. The reaction solution was heated to reflux and stirred for 4 hours. To the reaction solution, ice water and toluene were then added, and this mixture was stirred overnight at room temperature. The mixture was separated into aqueous and organic layers by the addition of diethyl ether and saturated saline. Then, the organic layer was washed with saturated saline and dried over anhydrous magnesium sulfate, and the solvent was distilled off under reduced pressure. The residue was purified by silica gel chromatography to obtain the compound of interest as a pale yellow oil substance (1.10 g, 17%, diastereomeric mixture).

(29-c) Tert-butyl(±)-(1S,5R)-4-methylbicyclo[3.2.0]hept-3-en-6-ylideneacetate (±)-(1S,5R)-4-methylbicyclo[3.2.0]hept-3-en-6-one (1.10 g, 9.0 mmol) was added to a reaction solution prepared in advance by adding sodium hydride (>65% oil, 342.8 mg, 9.0 mmol) to a tetrahydrofuran solution (10 mL) of tert-butyl dimethoxyphosphorylacetate (2.08 g, 9.3 mmol) under ice cooling, and the mixture was further stirred for 2 hours. The reaction solution was separated into aqueous and organic layers by the addition of a saturated aqueous solution of ammonium chloride and saturated saline. The aqueous layer was subjected to extraction with ethyl acetate. These organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.59 g, 80%, E/Z mixture).

(29-d) Tert-butyl(±)-[(1S,5R,6R)-6-(nitromethyl)-4-methylbicyclo[3.2.0]hept-3-en-6-yl]acetate The compound of interest was obtained as a colorless oil substance (2.02 g, <100%) in the same way as in Example (8-d) using tert-butyl(±)-[(1S,5R)-4-methylbicyclo[3.2.0]hept-3-en-6-ylideneacetate (1.59 g, 7.22 mmol).

(29-e) (±)-[(1S,5R,6R)-6-(aminomethyl)-4-methylbicyclo[3.2.0]hept-3-en-6-yl]acetic acid The compound of interest was obtained as a white powder (125.1 mg, 20%) in the same way as in Example (8-e) using tert-butyl(±)-[(1S,5R,6R)-6-(nitromethyl)-4-methylbicyclo[3.2.0]hept-3-en-6-yl]acetate (1.00 g, 3.2 mmol).

Example 30

Tert-butyl[(1R,5S,6S)-6-aminomethyl-3-ethylbicyclo[3.2.0]hept-3-en-6-yl]acetate (Exemplary Compound No: 20)

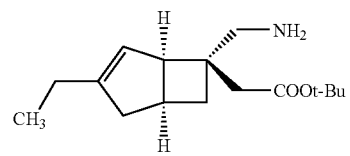

Tert-butyl[(1R,5S,6S)-3-ethyl-6-(nitromethyl)bicyclo[3.2.0]hept-3-en-6-yl]acetate (7.0 g, 23.7 mmol) was dissolved in ethanol (60 mL) and water (21 mL). To the solution, iron powder (13.27 g, 237 mmol) and ammonium chloride (628.1 mg, 11.9 mmol) were added, and the mixture was stirred for 5.5 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline. The organic layer was dried over anhydrous magnesium sulfate. Then, the solvent was distilled off under reduced pressure to obtain the compound of interest as a pale yellow oil substance (7.02 g, <100%).

Example 31

[(1R,5S,6S)-6-(aminomethyl)-3-ethylbicyclo[3.2.0]hept-3-en-6-yl]acetic acid benzenesulfonate (Exemplary Compound No: 8, optically active benzenesulfonate)

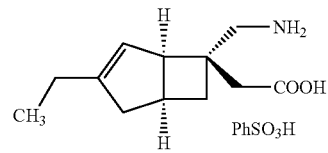

(1R,5S,6S)-6-(aminomethyl)-3-ethylbicyclo[3.2.0]hept-3-en-6-yl]acetic acid (4.50 g, 20.6 mmol) was dissolved by heating in a 1 M aqueous solution (22.7 mL) of benzenesulfonic acid monohydrate, and the solution was then allowed to cool to room temperature. The resulting solid was collected by filtration. The solid was washed with water (15 mL) and then dried using a vacuum pump to obtain the compound of interest as a colorless solid (6.45 g, 77%).

Example 32

(±)-{(1S,5R,6R)-6-(aminomethyl)-spiro[bicyclo[3.2.0]hepta-2,1'-cyclobutan]-3-en-6-yl}acetic acid
(Exemplary Compound No: 39)

(32-a) Methyl cyclobutylideneacetate

Sodium hydride (>65% oil, 3.62 g, 95 mmol) was added to a tetrahydrofuran solution (200 mL) of trimethyl phosphonoacetate (18.21 g, 100 mmol) under ice cooling, and the mixture was stirred for 1 hour. To the reaction solution, a tetrahydrofuran solution (50 mL) of cyclobutanone (5.00 g, 71.4 mmol) was added dropwise, and the mixture was then brought to room temperature and stirred for 1.5 hours. To the reaction solution, a saturated aqueous solution of ammonium chloride was added, followed by extraction with hexane. The organic layer was washed with saturated saline and dried over anhydrous magnesium sulfate. The solvent was distilled off under reduced pressure to obtain the compound of interest as a pale yellow oil substance (18.94 g, <100%).

(32-b) Cyclobutylideneethanol

Lithium aluminum hydride (1.89 g, 50 mmol) was added to a tetrahydrofuran solution (200 mL) of methyl cyclobutylideneacetate (18.92 g, <71.4 mmol) under ice cooling, and the mixture was stirred in this state for 2.5 hours. Methanol (10 mL) and a 1 N aqueous sodium hydroxide solution (5 mL) were added thereto, and the mixture was further stirred at room temperature for 1 hour and then filtered through Celite. The residue was washed with ethyl acetate and saturated saline. These filtrates were combined and separated into aqueous and organic layers. The organic layer was washed with saturated saline and then dried over anhydrous sodium sulfate. The solvent was distilled off under reduced pressure to obtain the compound of interest as a pale yellow oil substance (22.14 g, <84%).

(32-c) (1-Vinylcyclobutyl)ethanol

Cyclobutylideneethanol (22.14 g, <60 mmol) was dissolved in triethyl orthoacetate (25 mL). To the solution, phenol (1.02 g, 11.6 mmol) was added, and the mixture was stirred for 1 day under heating to reflux. The mixture was allowed to cool, and saturated saline was then added thereto, followed by extraction with ethyl acetate. The organic layer was washed with saturated saline and then dried over anhydrous sodium sulfate, and the solvent was distilled off under reduced pressure. To the residue, a 2 N potassium hydroxide-methanol solution (80 mL) was added, and the mixture was stirred overnight at room temperature. The solvent was distilled off under reduced pressure, and the residue was then dissolved in a 2 N aqueous sodium hydroxide solution and washed with diethyl ether. The aqueous layer was made acidic using concentrated hydrochloric acid under ice cooling, followed by extraction with ethyl acetate. The organic layer was washed with saturated saline and then dried over anhydrous magnesium sulfate, and the solvent was distilled off under reduced pressure. The residue was dissolved in tetrahydrofuran (70 mL). To the solution, lithium aluminum hydride (948.8 mg, 25 mmol) was then added under ice cooling. The mixture was brought to room temperature and then stirred for 7 hours under heating to reflux. Methanol (1.5 mL) and a 1 N aqueous sodium hydroxide solution (1.5 mL) were added thereto under ice cooling, and the mixture was further stirred at room temperature for 1 hour and then filtered through Celite. The residue was washed with dichloromethane and saturated saline. These filtrates were combined and separated into aqueous and organic layers. The organic layer was washed with a 1 N aqueous sodium hydroxide solution and saturated saline and then dried over anhydrous sodium sulfate. The solvent was distilled off under reduced pressure to obtain the compound of interest as a colorless oil substance (1.94 g, 25%).

(32-d) Methyl 3-hydroxy-4-(1-vinylcyclobutyl)butanoate

A dichloromethane solution (80 mL) of oxalyl chloride (1.88 mL, 22.5 mmol) was cooled to −78° C., and a dichloromethane solution (20 mL) of dimethyl sulfoxide (3.0 mL, 43.0 mmol) was added dropwise thereto. The mixture was stirred at −78° C. for 10 minutes. Then, a dichloromethane solution (20 mL) of (1-vinylcyclobutyl)ethanol (1.94 g, 15 mmol) was added dropwise thereto, and the mixture was further stirred at −78° C. for 3 hours. Triethylamine (8 mL, 60 mmol) was added thereto, and the mixture was gradually brought to room temperature and then stirred for 1 hour. 1 N hydrochloric acid and saturated saline were added thereto, followed by extraction with dichloromethane. The organic layer was washed with saturated saline and then dried over anhydrous sodium sulfate, and the solvent was distilled off under reduced pressure. The residue was dissolved in tetrahydrofuran (40 mL). To the solution, trimethylboron (6.2 mL) and zinc powder (4.46 g) were added, and methyl bromoacetate (4.2 mL, 44.1 mmol) was then added dropwise thereto. After stirring at room temperature for 30 minutes, the reaction solution was heated to 40° C. and stirred for 20 minutes. The mixture was further brought to room temperature and stirred for 1 hour, and glycerol, water, and saturated saline were then added thereto, followed by extraction with ethyl acetate. The organic layer was washed with saturated saline and then dried over anhydrous sodium sulfate, and the solvent was distilled off under reduced pressure. The residue was purified by column chromatography to obtain the compound of interest as a colorless oil substance (1.22 g, 40%).

(32-e) 3-Hydroxy-4-(1-vinylcyclobutyl)butanoic acid

The compound of interest was obtained as a colorless oil substance (1.16 g, <100%) in the same way as in Example (8-b) using methyl 3-hydroxy-4-(1-vinylcyclobutyl)butanoate (1.22 g, 6.16 mmol).

(32-f) Tert-butyl(±)-(1S,5R)-spiro[bicyclo[3.2.0]hepta-2,1'-cyclobutan]-3-en-6-ylideneacetate 3-Hydroxy-4-(1-vinylcyclobutyl)butanoic acid (1.16 g, 6.16 mmol) was dissolved in N,N-dimethylacetamide (12 mL) and acetic anhydride (1.5 mL). To the solution, potassium acetate (664.9 mg, 6.77 mmol) was added, and the mixture was stirred at 140° C. for 4 hours. To the reaction solution, ice water and saturated saline were added, and the mixture was stirred for 2 hours, followed by extraction with ethyl acetate. The organic layer was washed with a saturated aqueous solution of sodium bicarbonate and saturated saline in this order and dried over anhydrous magnesium sulfate, and the solvent was then distilled off under reduced pressure. The residue was dissolved in tetrahydrofuran (30 mL), and the solution was added to a reaction solution prepared in advance from a tetrahydrofuran solution (30 mL) of tert-butyl dimethoxyphosphorylacetate (1.82 g, 10 mmol) and sodium hydride (63% oil, 342.9 mg, 9 mmol). The mixture was stirred at room temperature for 1 hour, and the reaction solution was then separated into aqueous and organic layers by the addition of a saturated aqueous solution of ammonium chloride and saturated saline. The aqueous layer was subjected to extraction with ethyl acetate. These organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.07 g, 70%, E/Z mixture).

(32-g) Tert-butyl(±)-{(1S,5R,6R)-6-(nitromethyl) spiro[bicyclo[3.2.0]hepta-2,1'-cyclobutan]-3-en-6-yl}acetate Tert-butyl(±)-(1S,5R)-spiro[bicyclo[3.2.0]hepta-2,1'-cyclobutan]-3-en-6-ylideneacetate was dissolved in nitromethane (8 mL). To the solution, 1,8-diazabicyclo[5.4.0]undec-7-ene (0.97 mL, 6.51 mmol) was added, and the mixture was heated with stirring at 50 to 60° C. for 5.5 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a pale yellow oil substance (1.08 g, 81%).

(32-h) (±)-{(1S,5R,6R)-6-(aminomethyl)-spiro[bicyclo[3.2.0]hepta-2,1'-cyclobutan]-3-en-6-yl}acetic acid Tert-butyl(±)-{(1S,5R,6R)-6-(nitromethyl)spiro[bicyclo [3.2.0]hepta-2,1'-cyclobutan]-3-en-6-yl}acetate (1.08 g, 3.52 mmol) was dissolved in ethanol (15 mL) and water (6 mL). To the solution, iron powder (0.99 g, 17.6 mmol) and ammonium chloride (93.3 mg, 1.76 mmol) were added, and the mixture was stirred for 4 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N hydrochloric acid-ethyl acetate solution (10 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (439.2 mg, 57%).

Example 33

(±)-{(1S,5R,6R)-6-(aminomethyl)-spiro[bicyclo [3.2.0]hepta-2,1'-cyclopent]-3-en-6-yl}acetic acid (33-a) Methyl cyclopentylideneacetate The compound of interest was obtained as a pale yellow oil substance (14.31 g, <100%) in the same way as in Example (32-a) using cyclopentanone (8.42 g, 100 mmol).

(33-b) Cyclopentylideneethanol

The compound of interest was obtained as a pale yellow oil substance (8.90 g, including ethyl acetate) in the same way as in Example (32-b) using methyl cyclopentylideneacetate (7.16 g, 50 mmol).

(33-c) (1-Vinylcyclopentyl)ethanol

The compound of interest was obtained as a colorless oil substance (0.47 g, 7%) in the same way as in Example (32-c) using cyclopentylideneethanol (8.90 g, <50 mmol).

(33-d) Methyl 3-hydroxy-4-(1-vinylcyclopentyl)butanoate

The compound of interest was obtained as a colorless oil substance (417.3 mg, 48%) in the same way as in Example (32-d) using (1-vinylcyclopentyl)ethanol (0.47 g, 3.36 mmol).

(33-e) 3-Hydroxy-4-(1-vinylcyclopentyl)butanoic acid

The compound of interest was obtained as a light brown oil substance (the partial solvent remained; 504.1 mg, <100%) in the same way as in Example (32-e) using methyl 3-hydroxy-4-(1-vinylcyclopentyl)butanoate (417.3 mg, 1.97 mmol).

(33-f) Tert-butyl(±)-(1S,5R)-spiro[bicyclo[3.2.0] hepta-2,1'-cyclopent]-3-en-6-ylideneacetate The compound of interest was obtained as a pale yellow oil substance (232.3 mg, 47%, E/Z mixture) in the same way as in Example (32-f) using 3-hydroxy-4-(1-vinylcyclopentyl) butanoic acid (504.1 mg, <1.9 mmol).

(33-g) Tert-butyl(±)-{(1S,5R,6R)-6-(nitromethyl) spiro[bicyclo[3.2.0]hepta-2,1'-cyclopent]-3-en-6-yl}acetate The compound of interest was obtained as a colorless oil substance (250.2 mg, 88%) in the same way as in Example (32-g) using tert-butyl(±)-(1S,5R)-spiro[bicyclo[3.2.0] hepta-2,1'-cyclopent]-3-en-6-ylideneacetate (232.3 mg, 0.89 mmol).

(33-h) (±)-{(1S,5R,6R)-6-(aminomethyl)-spiro[bicyclo[3.2.0]hepta-2,1'-cyclopent]-3-en-6-yl}acetic acid The compound of interest was obtained as a white powder (124.4 mg, 72%) in the same way as in Example (32-h) using tert-butyl(±)-{(1S,5R,6R)-6-(nitromethyl)spiro[bicyclo [3.2.0]hepta-2,1'-cyclopent]-3-en-6-yl}acetate (249.0 mg, 0.77 mmol).

Example 34

(±)-[(1S,5R,6R)-6-(aminomethyl)-3-cyclobutylbicyclo[3.2.0]hept-3-en-6-yl]acetic acid (34-a) Ethyl(±)-2-cyclobutylpent-4-enoate A 1.9 M tetramethyldisilazane sodium-tetrahydrofuran solution (9.44 mL, 18.0 mmol) was added dropwise over 10 minutes to a tetrahydrofuran (40 mL) solution of ethyl 2-cyclobutylacetate (2.32 g, 16.3 mmol) cooled to −78° C., and the mixture was then stirred at −78° C. for 10 minutes. Subsequently, a tetrahydrofuran (10 mL) solution of allyl bromide (7.90 g, 65.3 mmol) was added dropwise thereto over 10 minutes, and the mixture was stirred at room temperature for 17 hours. The mixture was treated with water, and volatile portions were then removed under reduced pressure. To the obtained liquid, ethyl acetate and water were added, and the obtained organic layer was dried over anhydrous magnesium sulfate. Then, the solvent was distilled off under reduced pressure to obtain the compound of interest as a yellow oil substance (1.80 g, 61%).

(34-b) Ethyl(±)-4-cyclobutylpenta-2,6-dienoate

A 1 M diisobutyl aluminum hydride/toluene solution (9.88 mL, 9.9 mmol) was added dropwise over 40 minutes to a toluene (20 mL) solution of ethyl(±)-2-cyclobutylpent-4-enoate (1.80 g, 9.9 mmol) cooled to −78° C., and the mixture was then stirred at −78° C. for 2 hours. A 30% aqueous acetic acid solution (9.4 mL) was added dropwise thereto over 5 minutes. Then, the organic layer was dried over magnesium sulfate. After removal of insoluble matter by filtration, ethyl (triphenylphosphoranylidene)acetate (3.78 g, 10.9 mmol) was added to the liquid, and the mixture was stirred at room temperature for 18 hours. The solvent was distilled off under reduced pressure, and the residue was purified by column chromatography to obtain a colorless oil substance as a mixture containing the compound of interest. This compound was used in the next reaction without being further purified.

(34-c) (±)-4-Cyclobutylpenta-2,6-dienoic acid

A 5 N aqueous sodium hydroxide solution (15 mL) was added to an ethyl alcohol (20 mL) solution of the ethyl(±)-4-cyclobutylpenta-2,6-dienoate obtained in the preceding paragraph, and the mixture was stirred at room temperature for 1.5 hours and subsequently stirred at 60° C. for 2 hours. The mixture was allowed to cool, and the solvent was then distilled off under reduced pressure. The residue was dissolved in water. The aqueous layer was washed with dichloromethane and then neutralized with a 2 N aqueous hydrochloric acid solution (100 mL), followed by extraction with dichloromethane. The organic layer was dried over magnesium sulfate. The solvent was distilled off under reduced pressure to obtain a yellow oil substance as a mixture containing the compound of interest. This compound was used in the next reaction without being further purified.

(34-d) Tert-butyl(±)-[(1S,5R)-3-cyclobutylbicyclo[3.2.0]hept-3-en-6-ylidene]acetate (E/Z mixture)

Potassium acetate (1.05 g, 10.7 mmol) was added to a dimethylacetamide (20 mL) solution of the (±)-4-cyclobutylpenta-2,6-dienoic acid obtained in the preceding paragraph and acetic anhydride (1.09 g, 10.7 mmol), and the mixture was stirred at room temperature for 1 hour and then stirred at 120° C. for 2 hours. The mixture was treated with ice water and a 2 N aqueous sodium hydroxide solution, followed by extraction with hexane and diethyl ether. The organic layer was dried over anhydrous magnesium sulfate. Then, the solvent was distilled off under reduced pressure to obtain a pale yellow oil substance. The substance obtained here was added to an acetonitrile (20 mL) solution of tert-butyl dimethylphosphonoacetate (0.84 g, 3.7 mmol), lithium chloride (0.16 g, 3.7 mmol), and 1,8-diazabicyclo[5.4.0]undec-7-ene (0.59 g, 3.7 mmol) stirred in advance for 1 hour, and the mixture was further stirred for 12 hours. The mixture was treated with water, and volatile portions were then distilled off under reduced pressure, followed by extraction with ethyl acetate. The organic layer was dried over anhydrous magnesium sulfate. The solvent was distilled off under reduced pressure, and the residue was purified by silica gel column chromatography to obtain the compound of interest as a yellow oil substance (0.36 g, 24%) (yield from (34-b) ethyl 4-cyclobutylpenta-2,6-dienoate).

(34-e) Tert-butyl(±)-[(1S,5R,6R)-6-(nitromethyl)-3-cyclobutylbicyclo[3.2.0]hept-3-en-6-ylidene]acetate Tert-butyl(±)-[(1S,5R)-3-cyclobutylbicyclo[3.2.0]hept-3-en-6-ylidene]acetate (0.36 g, 1.4 mmol) was dissolved in nitromethane (20 mL). To the solution, 1,8-diazabicyclo[5.4.0]undec-7-ene (0.26 g, 1.7 mmol) was added, and the mixture was stirred at 60° C. for 3 hours. 1,8-diazabicyclo[5.4.0]undec-7-ene (0.26 g, 1.7 mmol) was further added thereto, and the mixture was stirred at 60° C. for 4.5 hours. The mixture was allowed to cool, and a saturated aqueous solution of potassium dihydrogen phosphate was then added thereto, followed by extraction with dichloromethane. The organic layer was dried over anhydrous magnesium sulfate. The solvent was distilled off under reduced pressure, and the residue was purified by silica gel chromatography to obtain the compound of interest as a pale yellow oil substance (0.40 g, 90%).

(34-f) Tert-butyl(±)-[(1S,5R,6R)-6-(aminomethyl)-3-cyclobutylbicyclo[3.2.0]hept-3-en-6-ylidene]acetate Tert-butyl(±)-[(1S,5R,6R)-6-(nitromethyl)-3-cyclobutylbicyclo[3.2.0]hept-3-en-6-ylidene]acetate (0.40 g, 1.2 mmol) was dissolved in ethanol (20 mL). To the solution, iron powder (0.56 g, 10.0 mmol) and then an aqueous ammonium chloride (0.07 g, 1.2 mmol) solution (7 mL) were added, and the mixture was stirred for 4.5 hours under heating to reflux. The mixture was allowed to cool and then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain the compound of interest as a colorless oil substance (0.30 g, 83%).

(34-g) (±)-[(1S,5R,6R)-6-(aminomethyl)-3-cyclobutylbicyclo[3.2.0]hept-3-en-6-yl]acetic acid Tert-butyl(±)-[(1S,5R,6R)-6-(aminomethyl)-3-cyclobutylbicyclo[3.2.0]hept-3-en-6-ylidene]acetate (0.30 g, 1.0 mmol) was dissolved in a 4 N hydrochloric acid-ethyl acetate solution (10 mL), and the solution was stirred at room temperature for 1.5 hours. Then, the solvent was distilled off under reduced pressure. The residue was suspended by the addition of dichloromethane. To the suspension, triethylamine was then added dropwise, and the resulting powder was collected by filtration. The obtained powder was dried under reduced pressure to obtain the compound of interest as a white powder (0.17 g, 67%).

Example 35

(±)-[(1S,5R,6R)-6-(aminomethyl)-4-ethylbicyclo[3.2.0]hept-3-en-6-yl]acetic acid (Exemplary Compound No: 34)

(35-a) Methyl 3-ethylhepta-2,6-dienoate (E/Z mixture)

A tetrahydrofuran (25 mL) solution of trimethyl phosphonoacetate (4.67 g, 25.1 mmol) was added dropwise at 0° C. over 1 hour to a tetrahydrofuran (25 mL) suspension of sodium hydride (1.04 g, 63%, 27.4 mmol). To the mixture, tetrahydrofuran (25 mL) was further added, and the mixture was then stirred at 0° C. for 1 hour. To this solution, a tetrahydrofuran (25 mL) solution of 6-hepten-3-one (2.56 g, 22.8 mmol) was added dropwise at 0° C. over 20 minutes, and the mixture was stirred at room temperature for 2.5 hours and subsequently stirred at 65° C. for 3 hours. The mixture was treated with water, and volatile portions were then distilled off under reduced pressure, followed by extraction with hexane. The organic layer was dried over anhydrous magnesium sulfate. Then, the solvent was distilled off under reduced pressure to obtain the compound of interest as a pale yellow oil substance (3.04 g, 79%).

(35-b) 3-Ethylhepta-2,6-dienoic acid (E/Z mixture)

A 5 N aqueous sodium hydroxide solution (14.5 mL) was added to an ethyl alcohol (40 mL) solution of methyl 3-ethylhepta-2,6-dienoate (3.04 g, 18.1 mmol), and the mixture was stirred at room temperature for 17 hours. The mixture was neutralized with a 5 N aqueous hydrochloric acid solution (15 mL), followed by extraction with dichloromethane. The organic layer was dried over magnesium sulfate. The solvent was distilled off under reduced pressure to obtain the compound of interest as a pale yellow oil substance (2.01 g, 71%).

(35-c) Tert-butyl(±)-[(1S,5R)-4-ethylbicyclo[3.2.0]hept-3-en-6-ylidene]acetate (E/Z mixture)

Potassium acetate (2.56 g, 26.1 mmol) was added to a dimethylacetamide (25 mL) solution of 3-ethylhepta-2,6-dienoic acid (2.01 g, 13.0 mmol) and acetic anhydride (2.66 g, 26.1 mmol), and the mixture was stirred at room temperature for 1 hour and then stirred at 120° C. for 3 hours. The mixture was treated with an ice water solution, followed by extraction with diethyl ether. The organic layer was dried over anhydrous magnesium sulfate. Then, the solvent was distilled off under reduced pressure, and the residue was applied to column chromatography to obtain a pale yellow oil substance. The substance obtained here was added to an acetonitrile (40 mL) solution of tert-butyl dimethylphosphonoacetate (2.60 g, 16.6 mmol), lithium chloride (0.70 g, 16.6 mmol), and 1,8-diazabicyclo[5.4.0]undec-7-ene (2.60 g, 16.6 mmol) stirred in advance for 1 hour, and the mixture was further stirred for 3.5 hours. The mixture was treated with water, and volatile portions were then distilled off under reduced pressure, followed by extraction with ethyl acetate. The organic layer was dried over anhydrous magnesium sulfate. The solvent was distilled off under reduced pressure, and the residue was purified by silica gel column chromatography to obtain the compound of interest as a yellow oil substance (2.20 g, 68%).

(35-d) Tert-butyl(±)-[(1S,5R,6R)-6-(nitromethyl)-4-ethylbicyclo[3.2.0]hept-3-en-6-ylidene]acetate Tert-butyl(±)-[(1S,5R)-4-ethylbicyclo[3.2.0]hept-3-en-6-ylidene]acetate (2.20 g, 9.4 mmol) was dissolved in nitromethane (30 mL). To the solution, 1,8-diazabicyclo[5.4.0]undec-7-ene (1.77 g, 11.3 mmol) was added, and the mixture was stirred at room temperature for 63 hours. A saturated aqueous solution of potassium dihydrogen phosphate was added thereto, followed by extraction with dichloromethane. The organic layer was dried over anhydrous magnesium sulfate. The solvent was distilled off under reduced pressure, and the residue was purified by silica gel chromatography to obtain the compound of interest as a mixture with the starting material (2.38 g).

(35-e) Tert-butyl(±)-[(1S,5R,6R)-6-(aminomethyl)-4-ethylbicyclo[3.2.0]hept-3-en-6-ylidene]acetate A mixture (2.38 g) of tert-butyl(±)-[(1S,5R,6R)-6-(nitromethyl)-4-ethylbicyclo[3.2.0]hept-3-en-6-ylidene]acetate and tert-butyl(±)-[(1S,5R)-4-ethylbicyclo[3.2.0]hept-3-en-6-ylidene]acetate was dissolved in ethanol (30 mL). To the solution, iron powder (2.25 g, 40.1 mmol) and then an aqueous ammonium chloride (0.43 g, 8.1 mmol) solution (10 mL) were added, and the mixture was stirred for 4.5 hours under heating to reflux. The mixture was allowed to cool and then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain the compound of interest as a colorless oil substance (1.00 g, 40%: yields in two steps).

(35-f) (±)-[(1S,5R,6R)-6-(aminomethyl)-4-ethylbicyclo[3.2.0]hept-3-en-6-yl]acetic acid Tert-butyl(±)-[(1S,5R,6R)-6-(aminomethyl)-4-ethylbicyclo[3.2.0]hept-3-en-6-ylidene]acetate (1.00 g, 3.8 mmol) was dissolved in a 4 N hydrochloric acid-ethyl acetate solution (20 mL), and the mixture was stirred at room temperature for 1 hour. Then, the resulting solid was collected by filtration. The solid was suspended by the addition of dichloromethane. To the suspension, triethylamine was then added dropwise. Again, the resulting powder was collected by filtration and dried under reduced pressure to obtain the compound of interest as a white powder (0.51 g, 65%).

Example 36

(±)-[(1S,5R,6R)-3-ethyl-6-(hydroxyaminomethyl)bicyclo[3.2.0]hept-3-en-6-yl]acetic acid hydrochloride Ammonium formate (1.10 g, 16.9 mmol) was added to an ethanol (10 mL) suspension of tert-butyl(±)-[(1S,5R,6R)-3-ethyl-6-[(hydroxyamino)methyl]bicyclo[3.2.0]hept-3-en-6-yl]acetate (0.50 g, 1.7 mmol) and barium sulfate-supported palladium (0.05 g), and the mixture was stirred at room temperature for 19 hours. Water (20 mL) was added thereto, and the mixture was then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain a colorless liquid (0.34 g). The liquid was dissolved in a 4 N hydrochloric acid-ethyl acetate solution (15 mL), and the solution was stirred at room temperature for 1 hour. Then, the

Example 37

[(1R,5S,6R)-6-(aminomethyl)-3-ethylbicyclo[3.2.0]hept-3-en-6-yl]acetic acid

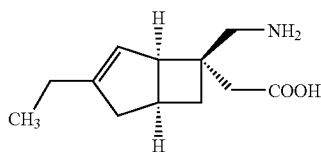

p-Toluenesulfonic acid (13.14 g, 69.1 mmol) was added to an ethanol (150 mL)/water (50 mL) suspension of tert-butyl [(1R,5S,6R)-6-{[(tert-butoxycarbonyl)amino]methyl}-3-ethylbicyclo[3.2.0]hept-3-en-6-yl]acetate (10.20 g, 34.5 mmol) and iron powder (9.64 g, 172.7 mmol), and the mixture was stirred at 80° C. for 2.5 hours. The mixture was allowed to cool and then filtered through Celite to remove insoluble matter. The solution was concentrated, and the residue was diluted with ethyl acetate. The dilution was washed with water and dried over anhydrous magnesium sulfate. Then, the solvent was distilled off under reduced pressure, and the obtained solid was washed with hexane to obtain a white solid (14.62 g). This compound was dissolved in benzene (100 mL). To the solution, p-toluenesulfonic acid (1.27 g, 6.7 mmol) was added, and the mixture was stirred at 80° C. for 2.5 hours. The mixture was allowed to cool and then filtered to remove insoluble matter. The solution was concentrated, and the obtained solid (2.32 g) was dissolved in chloroform (50 mL). To the solution, triethylamine (1.4 mL) was added, and the resulting solid was collected by filtration and suspended in ethyl acetate (25 mL). To the suspension, p-toluenesulfonic acid (0.44 g) was added. The mixture was ultrasonically irradiated for 1 hour, and the obtained solid was washed with methanol to obtain the compound of interest as a white solid (0.06 g, 1%).

Example 38

(±)-[(1S,5R,6R)-6-(aminomethyl)-1-methylbicyclo[3.2.0]hept-3-en-6-yl]acetic acid (Exemplary Compound No: 2)

(38-a) Tert-butyl(±)-[(1S,5R)-1-methylbicyclo[3.2.0]hept-3-en-6-ylidene]acetate (E/Z mixture)

A tetrahydrofuran (15 mL) solution of tert-butyl dimethylphosphonoacetate (3.29 g, 14.7 mmol) was added dropwise at 0° C. over 5 minutes to a tetrahydrofuran (15 mL) suspension of sodium hydride (0.59 g, 63%, 15.5 mmol), and the mixture was stirred at 0° C. for 15 minutes. To this solution, a tetrahydrofuran (15 mL) solution of 1-methylbicyclo[3.2.0]hept-3-en-6-one (1.60 g, 13.1 mmol) was added dropwise at 0° C. over 10 minutes, and the mixture was stirred at room temperature for 4 hours. The mixture was treated with water, followed by extraction with diethyl ether. The organic layer was dried over anhydrous magnesium sulfate. Then, the solvent was distilled off under reduced pressure, and the residue was purified by silica gel column chromatography to obtain the compound of interest as a yellow oil substance (1.80 g, 62%).

(38-b) Tert-butyl(±)-[(1S,5R,6R)-6-(nitromethyl)-1-methylbicyclo[3.2.0]hept-3-en-6-ylidene]acetate Tert-butyl(±)-[(1S,5R)-1-methylbicyclo[3.2.0]hept-3-en-6-ylidene]acetate (1.80 g, 8.2 mmol) was dissolved in nitromethane (30 mL). To the solution, 1,8-diazabicyclo[5.4.0]undec-7-ene (1.52 g, 10.0 mmol) was added, and the mixture was stirred at 60° C. for 11 hours. The mixture was allowed to cool, and a saturated aqueous solution of potassium dihydrogen phosphate was then added thereto, followed by extraction with ethyl acetate. The organic layer was dried over anhydrous magnesium sulfate. The solvent was distilled off under reduced pressure, and the residue was purified by silica gel chromatography to obtain the compound of interest as a yellow oil substance (1.80 g, 78%).

(38-c) Tert-butyl(±)-[(1S,5S,6R)-6-(aminomethyl)-1-methylbicyclo[3.2.0]hept-3-en-6-yl]acetate Tert-butyl(±)-[(1S,5R,6R)-6-(nitromethyl)-1-methylbicyclo[3.2.0]hept-3-en-6-ylidene]acetate (1.80 g, 6.4 mmol) was dissolved in ethanol (45 mL). To the solution, iron powder (6.52 g, 51.1 mmol) and then an aqueous ammonium chloride (0.34 g, 6.4 mmol) solution (15 mL) were added, and the mixture was stirred for 4.5 hours under heating to reflux. The mixture was allowed to cool and then filtered through Celite to remove insoluble matter. The solution was concentrated, and the residue was diluted with ethyl acetate. The dilution was washed with a saturated aqueous solution of sodium bicarbonate and dried over anhydrous magnesium sulfate. Then, the solvent was distilled off under reduced pressure, and the residue was purified by silica gel column chromatography to obtain the compound of interest as a colorless oil substance (0.90 g, 56%).

(38-d) (±)-[(1S,5R,6R)-6-(aminomethyl)-1-methylbicyclo[3.2.0]hept-3-en-6-yl]acetic acid Tert-butyl(±)-[(1S,5S,6R)-6-(aminomethyl)-1-methylbicyclo[3.2.0]hept-3-en-6-yl]acetate (0.90 g, 3.6 mmol) was dissolved in a 4 N hydrochloric acid-ethyl acetate solution (20 mL), and the solution was stirred at room temperature for 2 hours. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane to obtain the compound of interest as a white powder (0.33 g, 47%).

Example 39

(±) {(1R,5R)-6-(aminomethyl)-7-methylbicyclo[3.2.0]hept-3-en-6-yl}acetic acid (Exemplary Compound No: 7)

(39-a) Tert-butyl(±) {(1R,5R)-7-methylbicyclo[3.2.0]hept-3-en-6-ylidene}acetate

The compound of interest was obtained as an oil substance (5.88 g, 53%) in the same way as in Example (11-e) from (±)(1R,5R)-7-methylbicyclo[3.2.0]hept-3-en-6-one (J. Org.

Chem., 1988, 53, 5320) (6.16 g, 50.4 mmol). The compound of interest was a diastereomeric mixture mainly composed of two diastereomers.

(39-b) Tert-butyl(±) {(1R,5R)-7-methyl-6-(nitromethyl)bicyclo[3.2.0]hept-3-en-6-yl}acetate The compound of interest was obtained as an oil substance (4.07 g, 56%) in the same way as in Example (1-c) from tert-butyl(±) {(1R,5R)-7-methylbicyclo[3.2.0]hept-3-en-6-ylidene}acetate (5.74 g, 26.1 mmol). The compound of interest was a diastereomeric mixture mainly composed of three diastereomers.

(39-c) Tert-butyl(±) {(1R,5R)-6-{[(tert-butoxycarbonyl)amino]methyl}-7-methylbicyclo[3.2.0]hept-3-en-6-yl}acetate The compound of interest was obtained as an oil substance (1.11 g, 89%) in the same way as in Example (3-a) from tert-butyl(±){(1R,5R)-7-methyl-6-(nitromethyl)bicyclo[3.2.0]hept-3-en-6-yl}acetate (1.00 g, 3.55 mmol). The compound of interest was a diastereomeric mixture mainly composed of two diastereomers.

(39-d) (±){(1R,5R)-6-(aminomethyl)-7-methylbicyclo[3.2.0]hept-3-en-6-yl}acetic acid The compound of interest was obtained as a white solid (281 mg, 46%) in the same way as in Example (1-e) from tert-butyl(±) {(1R,5R)-6-{[(tert-butoxycarbonyl)amino]methyl}-7-methylbicyclo[3.2.0]hept-3-en-6-yl}acetate (1.11 g, 3.16 mmol). The compound of interest was a diastereomeric mixture mainly composed of two diastereomers.

Example 40

{(1S,5R,6R)-3-ethyl-6-[(methylamino)methyl]bicyclo[3.2.0]hept-3-en-6-yl}acetic acid hydrochloride (Exemplary Compound No: 44)

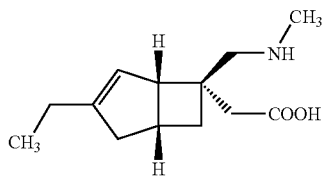

(40-a) [(1S,5R,6R)-6-{[(tert-butoxycarbonyl)amino]methyl}-3-ethylbicyclo[3.2.0]hept-3-en-6-yl]acetic acid

[(1S,5R,6R)-6-(aminomethyl)-3-ethylbicyclo[3.2.0]hept-3-en-6-yl]acetic acid p-toluenesulfonate (2.48 g, 6.50 mmol) was dissolved in a mixed solution of water (6.5 mL), a 1 M aqueous sodium hydroxide solution (10 mL), and 1,4-dioxane (13 mL). To the solution, di-tert-butyl dicarbonate (2.84 g, 13.0 mmol) was added with stirring at room temperature. The mixture was stirred overnight at this temperature, and the reaction solution was then made acidic by the addition of 1 M citric acid, followed by extraction with methylene chloride. The organic layer was washed with saturated saline and dried over anhydrous sodium sulfate. The residue was filtered and concentrated under reduced pressure to obtain the compound of interest as an oil substance (2.01 g, >99%).

(40-b) [(1S,5R,6R)-6-{[(tert-butoxycarbonyl)(methyl)amino]methyl}-3-ethylbicyclo[3.2.0]hept-3-en-6-yl]acetic acid Sodium hydride (63%, 2.48 g, 65.0 mmol) was added in small portions to a tetrahydrofuran solution (25 mL) of [(1S,5R,6R)-6-{[(tert-butoxycarbonyl)amino]methyl}-3-ethylbicyclo[3.2.0]hept-3-en-6-yl]acetic acid (2.01 g, 6.50 mmol) and methyl iodide (4.05 mL, 65.0 mmol) with stirring at room temperature. The mixture was stirred at this temperature for 6 hours, and water (50 mL) was then added thereto while the reaction solution was cooled on ice, followed by washing with diethyl ether. The aqueous layer was made acidic using 1 M citric acid, followed by extraction with ethyl acetate. The organic layer was dried over anhydrous sodium sulfate. The residue was filtered and concentrated under reduced pressure. Then, the obtained crude product was purified by silica gel column chromatography to obtain the compound of interest as an oil substance (2.00 g, 95%).

(40-c) {(1S,5R,6R)-3-ethyl-6-[(methylamino)methyl]bicyclo[3.2.0]hept-3-en-6-yl}acetic acid hydrochloride A 4 N hydrochloric acid-ethyl acetate (13 mL) was added to [(1S,5R,6R)-6-{[(tert-butoxycarbonyl)(methyl)amino]methyl}-3-ethylbicyclo[3.2.0]hept-3-en-6-yl]acetic acid (0.90 g, 2.78 mmol), and the mixture was stirred at room temperature for 1 hour. The mixture was concentrated under reduced pressure, and the obtained residue was recrystallized from hexane-isopropanol to obtain the compound of interest as a white solid (0.34 g, 47%).

Example 41

(±) [(1S,5R,6S)-6-(aminomethyl)-2-ethylbicyclo[3.2.0]hept-3-en-6-yl]acetic acid (41-a) Tert-butyl[(2-ethylbut-3-en-1-yl)oxy]dimethylsilane (Methyl)triphenylphosphonium bromide (59.1 g, 165 mmol) was suspended in tetrahydrofuran (330 mL). To the suspension, n-butyllithium (1.57 M hexane solution, 97.3 mL, 153 mmol) was gradually added with stirring at 0° C. The mixture was stirred at this temperature for 1 hour, and a tetrahydrofuran solution (110 mL) of 2-({[tert-butyl(dimethyl)silyl]oxy}methyl)butanal (Tetrahedron 2004, 60, 9307) (27.6 g, 127 mmol) was then gradually added thereto. The mixture was stirred at 0° C. for 2 hours, and the reaction was then terminated by the addition of a saturated aqueous solution of ammonium chloride and water, followed by extraction with ethyl acetate. The organic layer was washed with a saturated aqueous solution of ammonium chloride, water, and saturated saline and then dried over anhydrous sodium sulfate. The residue was filtered and concentrated under reduced pressure. Then, the obtained crude product was purified by silica gel column chromatography to obtain the compound of interest as an oil substance (19.9 g, 73%).

(41-b) Ethyl (2E)-5-ethylhepta-2,6-dienoate

Tetrabutyl ammonium fluoride (1 M tetrahydrofuran solution, 99.3 mL, 99.3 mmol) was added to a diethyl ether solution (80 mL) of tert-butyl[(2-ethylbut-3-en-1-yl)oxy]dimethylsilane (19.9 g, 93 mmol) with stirring at room temperature. The mixture was stirred overnight, and the reaction solution was then separated into aqueous and organic layers by the addition of water, followed by extraction with diethyl ether. The organic layer was washed with water and saturated saline and then dried over anhydrous sodium sulfate. The residue was filtered and concentrated under reduced pressure, and the residue was then dissolved in methylene chloride (180 mL). To the solution, triethylamine (25.7 mL, 186 mmol) and methanesulfonyl chloride (10.8 mL, 139 mmol) were added with stirring at 0° C. The mixture was stirred overnight at 0° C., and the reaction solution was then separated into aqueous and organic layers by the addition of 1 M hydrochloric acid (200 mL), followed by extraction with methylene chloride. The organic layer was washed with saturated saline and dried over anhydrous sodium sulfate. The residue was filtered and concentrated under reduced pressure, and the residue was then dissolved in dimethyl sulfoxide (240 mL) and water (12 mL). To the solution, potassium cyanide (15.1 g, 232 mmol) was added. The mixture was stirred overnight at 60° C., and water (400 mL) was then gradually added thereto while the reaction solution was cooled on ice, followed by extraction with diethyl ether. The organic layer was washed with water and saturated saline and then dried over anhydrous sodium sulfate. The residue was filtered and concentrated under reduced pressure, and the residue was then dissolved in toluene (150 mL). To the solution, diisobutyl aluminum hydride (0.99 M toluene solution, 169 mL, 167 mmol) was added dropwise with stirring at −78° C. The mixture was stirred at this temperature for 1 hour, and a 30% aqueous acetic acid solution (167 mL) was then gradually added thereto while the reaction solution was gradually heated. To this reaction solution, a saturated aqueous solution of sodium bicarbonate (130 mL) was added with stirring at 0° C., and the mixture was then separated into aqueous and organic layers, followed by extraction with toluene. The organic layer was washed with water, a saturated aqueous solution of sodium bicarbonate, and saturated saline and dried over magnesium sulfate. After filtration, ethyl(triphenylphosphoranylidene)acetate (33.9 g, 97.4 mmol) was added to the filtrate, and the mixture was stirred overnight at room temperature. The reaction solution was concentrated, and the obtained crude product was then purified by silica gel column chromatography to obtain the compound of interest as an oil substance (9.52 g, 56%).

(41-c) (2E)-5-ethylhepta-2,6-dienoic acid

Lithium hydroxide monohydrate (4.39 g, 104 mmol) was added to a tetrahydrofuran:methanol:water (3:3:1, 100 mL) mixed solution of ethyl (2E)-5-ethylhepta-2,6-dienoate (9.52 g, 52.2 mmol), and the mixture was stirred overnight at room temperature. The reaction solution was concentrated under reduced pressure. To the residue, water was then added, followed by washing with diethyl ether. The aqueous layer was made acidic by the addition of 5 M hydrochloric acid, followed by extraction with ethyl acetate. Then, the organic layer was washed with saturated saline and dried over anhydrous sodium sulfate. The residue was filtered and concentrated under reduced pressure to obtain the compound of interest as an oil substance (8.00 g, >99%).

(41-d) Tert-butyl(±) [(1S,5R)-2-ethylbicyclo[3.2.0]hept-3-en-6-ylidene]acetate

The compound of interest was obtained as an oil substance (3.00 g, 44%, Major/Minor=3/1) in the same way as in Example (7-c) from (2E)-5-ethylhepta-2,6-dienoic acid (4.50 g, 29.4 mmol).

(41-e) Tert-butyl(±) [(1S,5R,6S)-2-ethyl-6-(nitromethyl)bicyclo[3.2.0]hept-3-en-6-yl]acetate The compound of interest was obtained as an oil substance (3.52 g, 93%, Major/Minor=3/1) in the same way as in Example (1-c) from tert-butyl(±)[(1S,5R)-2-ethylbicyclo[3.2.0]hept-3-en-6-ylidene]acetate (3.00 g, 12.8 mmol).

(41-f) Tert-butyl(±) [(1S,5R,6S)-6-(aminomethyl)-2-ethylbicyclo[3.2.0]hept-3-en-6-yl]acetate The compound of interest was obtained as an oil substance (2.75 g, 87%, Major/Minor=3/1) in the same way as in Example (4-a) from tert-butyl(±) [(1S,5R,6S)-2-ethyl-6-(nitromethyl)bicyclo[3.2.0]hept-3-en-6-yl]acetate (3.52 g, 11.9 mmol).

(41-g) (±) [(1S,5R,6S)-6-(aminomethyl)-2-ethylbicyclo[3.2.0]hept-3-en-6-yl]acetic acid p-toluenesulfonate p-Toluenesulfonic acid monohydrate (2.17 g, 11.4 mmol) was added to a benzene solution (20 mL) of tert-butyl(±) [(1S,5R,6S)-6-(aminomethyl)-2-ethylbicyclo[3.2.0]hept-3-en-6-yl]acetate (2.75 g, 10.4 mmol), and the mixture was refluxed for 1 hour. The mixture was allowed to cool, and the deposited solid was then washed with methylene chloride to obtain the compound of interest as a gray solid (3.17 g, 80%, Major/Minor=3/1).

(41-h) (±) [(1S,5R,6S)-6-(aminomethyl)-2-ethylbicyclo[3.2.0]hept-3-en-6-yl]acetic acid (±) [(1S,5R,6S)-6-(aminomethyl)-2-ethylbicyclo[3.2.0]hept-3-en-6-yl]acetic acid p-toluenesulfonate (3.17 g, 8.31 mmol) was suspended in methylene chloride (35 mL). To the suspension, triethylamine (1.27 mL, 9.14 mmol) was added with stirring at room temperature. The mixture was stirred at this temperature for 3 hours, and the deposited solid was then collected by filtration and washed with methylene chloride to obtain the compound of interest as a white solid (1.58 g, 91%, Major/Minor=3/1).

Example 42

(±) [(1R,5S,6S)-6-(aminomethyl)-3-vinylbicyclo[3.2.0]hept-3-en-6-yl]acetic acid (42-a) (±)-(1R,5R)-spiro[bicyclo[3.2.0]heptane-6,2'-[1,3]dioxolan]-3-one A tetrahydrofuran solution (120 mL) of (±)-(1'R,2'R,4'S,6'R)-spiro[1,3-dioxolan-2,7'-[3]oxatricyclo[4.2.0.0$^{2,4}$]octane] (J. Chem. Soc. Perkin Trans. 1, 1980, 852) (20.0 g, 119 mmol) was gradually added dropwise to a tetrahydrofuran suspension (480 mL) of lithium aluminum hydride (6.77 g, 178 mmol) with stirring at 0° C. The mixture was stirred overnight at room temperature, and tetrahydrofuran (200 mL), water (6.8 mL), a 15% aqueous sodium hydroxide solution (6.8 mL), and water (20.4 mL) were then added thereto while the reaction solution was cooled on ice. The mixture was stirred at room temperature for 3 hours. The mixture was filtered through Celite and concentrated under reduced pressure. Then, the obtained crude product was purified by silica gel column chromatography (separation from positional isomers in regard to hydroxyl groups) to obtain (±)-(1R,3R,5R)-spiro[bicyclo[3.2.0]heptane-6,2'-[1,3]dioxolan]-3-ol as an oil substance (7.78 g, 38%). Dimethyl sulfoxide (9.11 mL, 128 mmol) was added to a methylene chloride solution (110 mL) of oxalyl chloride (5.50 mL, 64.2 mmol) with stirring at −78° C., and the mixture was stirred at this temperature for 5 minutes. Then, a methylene chloride solution (30 mL) of the above-obtained alcohol (7.28 g, 42.8 mmol) was added thereto. The mixture was stirred at this temperature for 15 minutes. Then, triethylamine (23.7 mL, 171 mmol) was added thereto, and the mixture was heated to room temperature and stirred. The mixture was separated into aqueous and organic layers by the addition of 0.1 M hydrochloric acid. The organic layer was washed with 0.1 M hydrochloric acid, water, and saturated saline and then dried over anhydrous sodium sulfate. The residue was filtered and concentrated under reduced pressure. Then, the obtained crude product was purified by silica gel column chromatography to obtain the compound of interest as an oil substance (6.61 g, 92%).

(42-b) (±)-(1R,5S)-spiro[bicyclo[3.2.0]hept-3-ene-6,2'-[1,3]dioxolan]-3-yl trifluoromethanesulfonate Potassium bis(trimethylsilyl)amide (0.5 M tetrahydrofuran solution, 96.8 mL, 48.4 mmol) was added to tetrahydrofuran (180 mL), and a tetrahydrofuran solution (85 mL) of (±)-(1R,5R)-spiro[b]cyclo[3.2.0]heptane-6,2'-[1,3]dioxolan]-3-one (6.11 g, 36.3 mmol) was gradually added dropwise thereto with stirring at −78° C. The mixture was stirred at this temperature for 2 hours, and a tetrahydrofuran solution (95 mL) of N-phenylbis(trifluoromethanesulfonimide) (17.3 g, 48.4 mmol) was then gradually added dropwise thereto. The mixture was heated to room temperature and stirred overnight. Then, the reaction was terminated by the addition of a saturated aqueous solution of ammonium chloride and water, and the mixture was separated into aqueous and organic layers, followed by extraction with diethyl ether. The organic layer was washed with saturated saline and dried over anhydrous sodium sulfate. The residue was filtered and concentrated under reduced pressure. Then, the obtained crude product was purified by silica gel column chromatography (separation from positional isomers in regard to olefin) to obtain the compound of interest as an oil substance (4.74 g, 43%).

(42-c) (±)-(1R,5S)-3-vinylspiro[bicyclo[3.2.0]hept-3-ene-6,2'-[1,3]dioxolane]

Lithium chloride (1.97 g, 46.4 mmol), tetrakis(triphenylphosphine)palladium (0) (0.36 g, 0.31 mmol), and tributyl(vinyl)tin (2.47 mL, 8.50 mmol) were added to a tetrahydrofuran solution (60 mL) of (±)-(1R,5S)-spiro[bicyclo[3.2.0]hept-3-ene-6,2'-[1,3]dioxolan]-3-yl trifluoromethanesulfonate (2.32 g, 7.73 mmol). The mixture was heated to reflux for 2 hours, and water was then added to the reaction solution, followed by extraction with diethyl ether. The organic layer was washed with saturated saline and dried over anhydrous sodium sulfate. The residue was filtered and concentrated under reduced pressure. Then, the obtained crude product was purified by silica gel column chromatography to obtain the compound of interest as an oil substance (990 mg, 72%).

(42-d) Tert-butyl(±)[(1R,5S)-3-vinylbicyclo[3.2.0]hept-3-en-6-ylidene]acetate (±)-(1R,5S)-3-vinylspiro[bicyclo[3.2.0]hept-3-ene-6,2'-[1,3]dioxolane] (990 mg, 5.55 mmol) was dissolved in a mixed solvent of acetonitrile (16 mL) and water (7 mL). To the solution, 2 M sulfuric acid (2.60 mL) was added with stirring at room temperature. The mixture was stirred at room temperature for 7 hours, and the reaction solution was then neutralized by the addition of a saturated aqueous solution of sodium bicarbonate, followed by extraction with ethyl acetate. The organic layer was washed with saturated saline and dried over anhydrous sodium sulfate. The residue was filtered and concentrated under reduced pressure. Then, the compound of interest was obtained as an oil substance (710 mg, 55%, Major/Minor=2/1) in the same way as in Example (11-e) from the obtained (1R,5S)-3-vinylbicyclo[3.2.0]hept-3-en-6-one.

(42-e) Tert-butyl(±) [(1R,5S,6S)-6-(nitromethyl)-3-vinylbicyclo[3.2.0]hept-3-en-6-yl]acetate The compound of interest was obtained as an oil substance (670 mg, 75%) in the same way as in Example (1-c) from tert-butyl(±) [(1R,5S)-3-vinylbicyclo[3.2.0]hept-3-en-6-ylidene]acetate (710 mg, 3.06 mmol).

(42-f) Tert-butyl(±) [(1R,5S,6S)-6-(aminomethyl)-3-vinylbicyclo[3.2.0]hept-3-en-6-yl]acetate The compound of interest was obtained as an oil substance (527 mg, 88%) in the same way as in Example (4-a) from tert-butyl(±)[(1R,5S,6S)-6-(nitromethyl)-3-vinylbicyclo[3.2.0]hept-3-en-6-yl]acetate (670 mg, 2.28 mmol).

(42-g) (±) [(1R,5S,6S)-6-(aminomethyl)-3-vinylbicyclo[3.2.0]hept-3-en-6-yl]acetic acid p-toluenesulfonate The compound of interest was obtained as a light gray solid (590 mg, 78%) in the same way as in Example (41-g) from tert-butyl(±)[(1R,5S,6S)-6-(aminomethyl)-3-vinylbicyclo[3.2.0]hept-3-en-6-yl]acetate (527 mg, 2.00 mmol).

(42-h) (±) [(1R,5S,6S)-6-(aminomethyl)-3-vinylbicyclo[3.2.0]hept-3-en-6-yl]acetic acid The compound of interest was obtained as a light brown solid (286 mg, 89%) in the same way as in Example (41-h) from (±) [(1R,5S,6S)-6-(aminomethyl)-3-vinylbicyclo[3.2.0]hept-3-en-6-yl]acetic acid p-toluenesulfonate (590 mg, 1.55 mmol).

Example 43

(±) [(1R,5S,6S)-6-(aminomethyl)-3-ethynylbicyclo[3.2.0]hept-3-en-6-yl]acetic acid (43-a) (±)-Trimethyl[(1R,5S)-spiro[bicyclo[3.2.0]hept-3-ene-6,2'-[1,3]dioxolan]-3-ylethynyl]silane Bis(triphenylphosphine)palladium (II) chloride (98%, 0.29 g, 0.40 mmol), 2,6-lutidine (1.41 mL, 12.1 mmol), trimethylsilylacetylene (1.45 mL, 10.5 mmol), and copper (I) iodide (0.15 g, 0.81 mmol) were added to a dimethylformamide solution (5 mL) of the (±)-(1R,5S)-spiro[b]cyclo[3.2.0]hept-3-ene-6,2'-[1,3]dioxolan]-3-yltrifluoromethanesulfonate (2.42 g, 8.06 mmol) obtained in Example (42-b). The mixture was heated with stirring at 50° C. for 2 hours, and a saturated aqueous solution of ammonium chloride was then added to the reaction solution, followed by extraction with diethyl ether. The organic layer was washed with saturated saline and dried over anhydrous sodium sulfate. The residue was filtered and concentrated under reduced pressure. Then, the obtained crude product was purified by silica gel column chromatography to obtain the compound of interest as an oil substance (1.78 g, 89%).

(43-b) Tert-butyl(±)-{(1S,5S)-3-[(trimethylsilyl)ethynyl]bicyclo[3.2.0]hept-3-en-6-ylidene}acetate The compound of interest was obtained as an oil substance (1.50 g, 69%, Major/Minor=2/1) in the same way as in Example (42-d) from (±)-trimethyl[(1R,5S)-spiro[b]cyclo[3.2.0]hept-3-ene-6,2'-[1,3]dioxolan]-3-ylethynyl]silane (1.78 g, 7.17 mmol).

(43-c) Tert-butyl(±)-[(1R,5S,6S)-3-ethynyl-6-(nitromethyl)bicyclo[3.2.0]hept-3-en-6-yl]acetate The compound of interest was obtained as an oil substance (870 mg, 60%) in the same way as in Example (1-c) from tert-butyl(±)-{(1S,5S)-3-[(trimethylsilyl)ethynyl]bicyclo[3.2.0]hept-3-en-6-ylidene}acetate (1.50 g, 4.98 mmol).

(43-d) Tert-butyl(±)-[(1R,5S,6S)-6-(aminomethyl)-3-ethynylbicyclo[3.2.0]hept-3-en-6-yl]acetate The compound of interest was obtained as an oil substance (630 mg, 81%) in the same way as in Example (4-a) from tert-butyl(±)-[(1R,5S,6S)-3-ethynyl-6-(nitromethyl)bicyclo[3.2.0]hept-3-en-6-yl]acetate (870 mg, 2.99 mmol).

(43-e) (±)[(1R,5S,6S)-6-(aminomethyl)-3-ethynylbicyclo[3.2.0]hept-3-en-6-yl]acetic acid p-toluenesulfonate The compound of interest was obtained as a pale yellow solid (821 mg, 90%) in the same way as in Example (41-g) from tert-butyl(±)-[(1R,5S,6S)-6-(aminomethyl)-3-ethynylbicyclo[3.2.0]hept-3-en-6-yl]acetate (630 mg, 2.41 mmol).

(43-f) (±)[(1R,5S,6S)-6-(aminomethyl)-3-ethynylbicyclo[3.2.0]hept-3-en-6-yl]acetic acid The compound of interest was obtained as a light brown solid (371 mg, 83%) in the same way as in Example (41-h) from (±)[(1R,5S,6S)-6-(aminomethyl)-3-ethynylbicyclo[3.2.0]hept-3-en-6-yl]acetic acid p-toluenesulfonate (821 mg, 2.17 mmol).

The physical analysis data of the compounds described in the Examples is shown below.

TABLE 2

| Example No. | Analysis data |
|---|---|
| 1(1-a) | 1H-NMR(400 MHz, CDCl3): d ppm: 2.21-2.26(2H, m), 2.32-2.37(2H, m), 5.01-5.08(2H, m), 5.75-6.87(2H, m), 7.03-7.11(1H, m). |
| 1(1-b) | 1H-NMR(400 MHz, CDCl3): d ppm: <br> Major isomer 1.45 (9H, S), 2.29-2.35 (1H, m), 2.62-2.71 (2H, m), 2.89-2.98(1H, m), 3.27-3.35(1H, m), 3.92 (1H, broad), 5.47-5.49 (1H, m), 5.80-5.87 (2H, m). <br> Minor isomer 1.49 (9H, s), 2.42-2.48 (1H, m), 2.62-2.71 (2H, m), 2.89-2.98 (2H, m), 4.34-4.36 (1H, m), 5.37-5.38 (1H, m), 5.61-5.64 (2H, m). |
| 1(1-c) | MS (FAB): m/z: 268 (M + H)+, 290 (M + Na)+ <br> 1H-NMR(400 MHz, CDCl3): d ppm: 1.45(9H, s), 1.53(1H, dd, J = 7.5, 12.9 Hz), 2.17(1H, d, J = 15.2 Hz), 2.31(1H, ddd, J = 2.4, 8.6, 12.1 Hz), 2.47 (2H, s), 2.52-2.58(1H, m), 2.87(1H, quint, J = 7.5 Hz), 3.25-2.66(1H, m), 4.78(1H, d, J = 11.4 Hz), 4.87(1H, d, J = 11.4 Hz), 5.65-5.67(1H, m), 5.95(1H, dd, J = 1.6, 5.9 Hz). |
| 1(1-d) | 1H-NMR(400 MHz, CDCl3): d ppm: 1.39-1.49(1H, m), 1.44(9H, s), 1.97(1H, ddd, J = 2.8, 9.0, 11.7 Hz), 2.14(1H, dd, J = 2.3, 16.8 Hz), 2.25(1H, d, J = 13.7 Hz), 2.32(1H, d, J = 13.7 Hz), 2.47-2.55(1H, m), 2.75(1H, quint, J = 7.4 Hz), 2.88(2H, s), 2.98-2.99(1H, m), 5.77-5.79(1H, m), 5.87-5.89(1H, m). |
| 1(1-e) | Mp: 176-178°. <br> 1H-NMR(400 MHz, CDCl3): d ppm: 1.49(1H, dd, J = 7.6, 12.5 Hz), 2.06(1H, ddd, J = 2.6, 7.6, 12.5 Hz), 2.17(1H, dd, J = 2.6, 16.8 Hz), 2.49(2H, s), 2.48-2.56(1H, m), 2.86(1H, quint, J = 7.6 Hz), 3.15-3.16(1H, m), 3.18(1H, d, J = 12.7 Hz), 3.22(1H, d, J = 12.7 Hz), 5.75-5.78(1H, m), 5.91-5.93(1H, m). <br> IR (KBr): cm − 1: 2953, 2896, 2840, 1635, 1573, 1504, 1395, 1174, 724. <br> MS (EI): m/z: 181 (M)+. <br> Anal. calcd for C10H15NO2: C, 66.27; H, 8.34; N, 7.73; Found C, 65.13; H, 8.31; N, 7.64. |
| 2(2-b) | 1H-NMR(400 MHz, CDCl3): d ppm: 1.39-1.49(1H, m), 1.44(9H, s), 1.97(1H, ddd, J = 2.8, 9.0, 11.7 Hz), 2.14(1H, dd, J = 2.3, 16.8 Hz), 2.25(1H, d, J = 13.7 Hz), 2.32(1H, d, J = 13.7 Hz), 2.47-2.55(1H, m), 2.75(1H, quint, J = 7.4 Hz), 2.88(2H, s), 2.98-2.99(1H, m), 5.77-5.79(1H, m), 5.87-5.89(1H, m). |
| 2(2-c) | Mp. 190-191°. <br> [a]25D −159.3° (c = 1.06, H2O). <br> 1H-NMR(400 MHz, CD3OD): d ppm: 1.49(1H, dd, J = 7.6, 12.5 Hz), 2.06(1H, ddd, J = 2.6, 7.6, 12.5 Hz), 2.17(1H, dd, J = 2.6, 16.8 Hz), 2.49(2H, s), 2.48-2.56(1H, m), 2.86(1H, quint, J = 7.6 Hz), 3.15-3.17(1H, m), 3.18(1H, d, J = 12.7 Hz), 3.22(1H, d, J = 12.7 Hz), 5.75-5.78(1H, m), 5.91-5.93(1H, m). <br> IR (KBr): cm − 1: 2953, 2896, 2840, 1635, 1573, 1504, 1395, 1174, 724. <br> MS (EI): m/z: 181 (M)+. <br> Anal. calcd for C10H15NO2: C, 66.27; H, 8.34; N, 7.73; Found C, 63.81; H, 8.31; N, 7.75. |

TABLE 2-continued

| Example No. | Analysis data |
|---|---|
| 3(3-a) | 1H-NMR(400 MHz, CDCl3): d ppm: 1.38-1.49(1H, m), 1.44(18H, s), 2.04(1H, ddd, J = 2.7, 8.6, 11.3 Hz), 2.08-2.12, 2.12-2.16(total 1H, dd, each s), 2.21(1H, d, J = 14.0 Hz), 2.28(1H, d, J = 14.5 Hz), 2.46-2.55(1H, m), 2.80-2.91(1H, m), 3.02-3.08(1H, m), 3.36(1H, dd, J = 6.2, 14.1 Hz), 3.45(1H, dd, J = 6.6, 14.0 Hz), 5.72-5.76(1H, m), 5.85-5.89(1H, m). |
| 3(3-b) | 1H-NMR(400 MHz, CD3OD): d ppm: 1.49(1H, dd, J = 7.6, 12.5 Hz), 2.06(1H, ddd, J = 2.6, 7.6, 12.5 Hz), 2.17(1H, dd, J = 2.6, 16.8 Hz), 2.49(2H, s), 2.48-2.56(1H, m), 2.86(1H, dt, J = 16.8, 7.6 Hz), 3.16(1H, broad), 3.18(1H, d, J = 12.7 Hz), 3.22(1H, d, J = 12.7 Hz), 5.75-5.78(1H, m), 5.91-5.93(1H, m).<br>IR (KBr): cm − 1: 2900, 1572, 1523, 1383<br>MS (EI): m/z: 181 (M)+.<br>Anal. calcd for C10H15NO2: C, 66.27; H, 8.34; N, 7.73; Found C, 66.15; H, 8.33; N, 7.75.<br>[a]D: −155° (H2O, c = 1.0)<br>Mp. 192-193°. |
| 4(4-a) | 1H-NMR(400 MHz, CDCl3): d ppm: 1.39-1.49(1H, m), 1.44(9H, s), 1.97(1H, ddd, J = 2.8, 9.0, 11.7 Hz), 2.14(1H, dd, J = 2.3, 16.8 Hz), 2.25(1H, d, J = 13.7 Hz), 2.32(1H, d, J = 13.7 Hz), 2.47-2.55(1H, m), 2.75(1H, dt, J = 7.4, 16.8 Hz), 2.88(2H, s), 2.99(1H, broad), 5.77-5.79(1H, m), 5.87-5.89(1H, m). |

TABLE 3

| | |
|---|---|
| 4(4-b) | 1H-NMR(400 MHz, CD3OD): δ ppm: 1.49(1H, dd, J = 7.6, 12.5 Hz), 2.06(1H, ddd, J = 2.6, 7.6, 12.5 Hz), 2.17(1H, dd, J = 2.6, 16.8 Hz), 2.49(2H, s), 2.48-2.56(1H, m), 2.86(1H, dt, J = 7.6, 16.8 Hz), 3.16(1H, broad), 3.18(1H, d, J = 12.7 Hz), 3.22(1H, d, J = 12.7 Hz), 5.75-5.78(1H, m), 5.91-5.93(1H, m).<br>IR (KBr): cm − 1: 2901, 1571, 1524, 1383<br>MS (EI): m/z: 181 (M)+.<br>Anal. calcd for C10H15NO2: C, 66.27; H, 8.34; N, 7.73; Found C, 65.34; H, 8.43; N, 7.75.<br>[α]D: +156° (H2O, c = 1.0)<br>Mp 198-199° C. |
| 5(5-a) | Mp: 185-186° C.<br>1H-NMR(400 MHz, CD3OD): δ ppm: 1.51(1H, dd, J = 7.6, 12.7 Hz), 2.16(1H, ddd, J = 2.8, 7.6, 15.6 Hz), 2.19(1H, dd, J = 2.2, 16.8 Hz), 2.51(2H, s), 2.53-2.59(1H, m), 2.89(1H, quint, J = 7.6 Hz), 3.18-3.19(1H, m), 3.33(1H, d, J = 13.3 Hz), 3.37(1H, d, J = 13.3 Hz), 5.70-5.73(1H, m), 5.97-6.00(1H, m).<br>IR (KBr): cm − 1: 3128, 2914, 1702, 1498, 1236.<br>MS (FAB): m/z: 182 (free + H)+.<br>Anal. calcd for C10H16NO2Cl: C, 55.17; H, 7.41; N, 6.43; Cl, 16.29; Found C, 54.71; H, 7.43; N, 6.38, Cl: 18.10. |
| 6 | Mp: 161-162° C.<br>1H-NMR(400 MHz, CD3OD): δ ppm: 1.51(1H, dd, J = 7.4, 12.7 Hz), 2.12-2.21 (2H, m), 2.51(2H, s), 2.51-2.59(1H, m), 2.89(1H, quint, J = 7.4 Hz), 3.17-3.18(1H, m), 3.32(1H, d, J = 13.3 Hz), 3.36(1H, d, J = 13.3 Hz), 5.69-5.71(1H, m), 5.97-6.00(1H, m), 7.40-7.46(3H, m), 7.80-7.84(2H, m).<br>IR (KBr): cm − 1: 3094, 3053, 1704, 1514, 1445, 1236, 1163, 1034, 730.<br>MS (FAB+): m/z: 181 (free + H)+.<br>Anal. calcd for C16H21NO5S: C, 55.16; H, 6.36; N, 4.02; S, 9.20; Found C, 56.42; H, 6.21; N, 4.04; S, 9.51. |
| 7(7-a) | 1H-NMR(400 MHz, CDCl3): δ ppm: 0.89-0.94 (3H, m), 1.58-1.75 (1H, m), 1.91-2.03 (1H, m), 2.21-2.33 (1H, m), 2.43-2.56 (2H, m), 3.72 (3H, s), 3.84-4.00 (1H, m), 5.01-5.07 (2H, m), 5.74-5.84 (1H, m).<br>MS (FAB): m/z: 173 (M + H)+. |
| 7(7-b) | 1H-NMR(400 MHz, CDCl3): δ ppm: 0.90-0.94 (3H, m), 1.64-1.74 (1H, m), 1.93-2.00 (1H, m), 2.24-2.32 (1H, m), 2.45-2.61 (2H, m), 3.87-4.03 (1H, m), 5.03-5.08 (2H, m), 5.75-5.83 (1H, m).<br>MS (FAB): m/z: 159 (M + H)+, 181 (M + Na)+. |
| 7(7-c) | 1H-NMR(400 MHz, CDCl3): δ ppm:<br>Major isomer 1.45 (9H, s), 2.11-2.22 (4H, m), 2.59-2.71 (2H, m), 2.87-2.97 (1H, m), 3.26-3.34 (1H, m), 3.87 (1H, broad), 5.22-5.23 (1H, m), 5.45-5.47 (1H, m).<br>Minor isomer 1.49 (9H, s), 2.11-2.21 (4H, m), 2.43-2.46 (1H, m), 2.59-2.70 (1H, m), 2.75-2.83 (1H, m), 2.87-2.97 (1H, m), 4.29 (1H, broad), 5.36 (1H, s), 5.59 (1H, s).<br>MS (EI): m/z: 220 (M)+. |
| 7(7-d) | 1H-NMR(400 MHz, CDCl3): δ ppm: 1.45 (9H, s), 1.53 (1H, dd, J = 7.6, 12.9 Hz), 1.80(3H, s), 2.04 (1H, d, J = 16.4 Hz), 2.29 (1H, ddd, J = 2.8, 7.6, 12.9 Hz), 2.47(2H, s), 2.49(1H, dd, H = 7.6, 16.4 Hz), 2.86 (1H, quint, J = 7.6 Hz), 3.21-3.22 (1H, m), 4.74 (1H, d, J = 11.7 Hz), 4.84 (1H, J = 11.7 Hz), 5.25 (1H, s). |
| 7(7-e) | Mp: 188-190° C.<br>1H-NMR(400 MHz, CD3OD): δ ppm: 1.40 (1H, dd, J = 7.6, 12.3 Hz), 1.79 (3H, s), 2.02-2.08(2H, m), 2.43-2.50 (1H, m), 2.45 (1H, d, J = 16.2 Hz), 2.51 (1H, d, J = 16.2 Hz), 2.85 (1H, quint, J = 7.6 Hz), 3.05-3.12 (1H, m), 3.13 (1H, d, J = 13.0 Hz), 3.17 (1H, d, J = 13.0 Hz), 5.36 (1H, t, J = 1.6 Hz).<br>IR (KBr): cm − 1: 2946, 2927, 2905, 2832, 1564, 1525, 1396, 1384.<br>MS (FAB): m/z: 196 (M + H)+, 218 (M + Na)+.<br>Anal. calcd for C11H17NO2: C, 67.66; H, 8.78; N, 7.17; Found C, C, 66.84; H, 8.78; N, 7.21. |
| 8(8-a) | 1H-NMR(400 MHz, CDCl3): δ ppm: 0.91 (3H, t, J = 7.5 Hz), 1.28 (3H, t, J = 7.2 Hz), 1.43-1.55 (2H, m). 1.98-2.28 (2H, m), 2.45-2.48 (2H, m), 2.88-2.93 (1H, m), 4.07-4.10 (1H, m), 4.10-4.20 (2H, m), 5.01-5.09 (2H, m), 5.75-5.86 (1H, m).<br>MS (FAB): m/z: 201 (M + H)+. |
| 8(8-b) | 1H-NMR(400 MHz, CDCl3): δ ppm: 0.91-0.96 (3H, m), 1.39-1.52 (3H, m), 2.01-2.28 (2H, m), 2.52-2.55 (2H, m), 4.05-4.15 (2H, m), 5.03-5.10 (2H, m), 5.74-5.86 (1H, m).<br>MS (FAB): m/z: 173 (M + H)+, 195 (M + Na)+. |

TABLE 4

| | |
|---|---|
| 8(8-c) | 1H-NMR(400 MHz, CDCl3): δ ppm:<br>Major isomer 1.06 (3H, t, J = 7.4 Hz), 1.45 (9H, s), 2.07-2.22 (3H, m), 2.59-2.70 (2H, m), 2.87-2.96 (1H, m), 3.30 (1H, ddt, J = 8.6, 18.4, 2.7 Hz), 3.86-3.88 (1H, m), 5.22-5.23 (1H, m), 5.45-5.47 (1H, m).<br>Minor isomer 1.08 (3H, t, J = 7.3 Hz), 1.49 (9H, s), 2.07-2.21 (3H, m), 2.43-2.47 (1H, m), 2.59-2.70 (1H, m), 2.75-2.85 (1H, m), 2.87-2.96 (1H, m), 4.28-4.31 (1H, m), 5.35-5.38 (1H, m), 5.45-5.47 (1H, m).<br>MS (FAB): m/z: 235 (M + H)+, 257 (M + Na)+. |
| 8(8-d) | 1H-NMR(400 MHz, CDCl3): δ ppm: 1.09 (3H, t, J = 7.4 Hz), 1.46 (9H, s), 1.52 (1H, dd, J = 7.6, 13.2 Hz), 2.06(1H, d, 16.6 Hz), 2.14 (2H, q, J = 7.4 Hz), 2.30 (1H, ddd, J = 2.4, 7.6, 13.2 Hz), 2.47 (2H, s), 2.49 (1H, dd, J = 7.6, 16.6 Hz), 2.86 (1H, quint, J = 7.6 Hz), 3.21-3.22 (1H, m), 4.75 (1H, d, J = 11.7 Hz), 4.84 (1H, d, J = 11.7 Hz), 5.27 (1H, s).<br>MS (FAB): m/z: 296 (M + H)+, 318 (M + Na)+. |
| 8(8-e) | Mp: 175-176° C.<br>1H-NMR(400 MHz, CD3OD): δ ppm: 1.10(3H, t, J = 7.4 Hz), 1.48(1H, dd, J = 7.5, 12.5 Hz), 2.03-2.08(2H, m), 2.14(2H, q, J = 7.4 Hz), 2.46(1H, d, J = 16.2 Hz), 2.46-2.53(1H, m), 2.51(1H, d, J = 16.2 Hz), 2.85(1H, quint, J = 7.5 Hz), 3.09-3.10(1H, m), 3.14(1H, d, J = 13.0 Hz), 3.18(1H, d, J = 13.0 Hz), 5.38(1H, dd, J = 1.7, 3.7 Hz).<br>IR (KBr): cm − 1: 2962, 2928, 2897, 2877, 1559, 1527, 1403.<br>MS (FAB): m/z: 210 (M + H)+, 232 (M + Na)+.<br>Anal. calcd for C12H19NO2: C, 68.87; H, 9.15; N, 6.69; Found C, 67.64; H, 9.18; N, 6.61. |
| 9(9-a) | 1H-NMR(400 MHz, CDCl3): δ ppm: 0.90 (3H, t, J = 7.5 Hz), 1.18-1.-1.55 (4H, m), 1.95-2.30 (2H, m). 2.42-2.53 (2H, m), 2.75-2.82 (1H, m), 3.72 (3H, s), 4.01-4.11 (1H, m), 5.01-5.09 (2H, m), 5.74-5.86 (1H, m). |
| 9(9-b) | 1H-NMR(400 MHz, CDCl3): δ ppm: 1.21 (3H, t, J = 7.5 Hz), 1.31-1.-1.43 (3H, m), 1.54-1.58 (1H, m). 2.00-2.29 (3H, m), 2.47-2.59 (2H, m), 4.04-4.11 (2H, m), 5.03-5.10 (2H, m), 5.77-5.89 (1H, m). |
| 9(9-c) | 1H-NMR(400 MHz, CDCl3): δ ppm:<br>Major isomer 0.91 (3H, t, J = 7.3 Hz), 1.45 (9H, s), 1.48-1.50 (3H, m), 2.06-2.19 (2H, m), 2.57-2.70 (2H, m), 2.87-2.96 (1H, m), 3.30 (1H, ddt, J = 8.6, 18.4, 2.7 Hz), 3.86 (1H, broad), 5.22-5.23 (1H, m), 5.45-5.46 (1H, m).<br>Minor isomer 0.91 (3H, t, J = 7.3 Hz), 1.49 (9H, s), 1.48-1.50 (3H, m), 2.06-2.47 (2H, m), 2.57-2.70 (2H, m), 2.87-2.96 (2H, m), 4.29 (1H, broad), 5.34-5.35 (1H, m), 5.45-5.46 (1H, m). |
| 9(9-d) | 1H-NMR(400 MHz, CDCl3): δ ppm: 0.91 (3H, t, J = 7.4 Hz), 1.27-1.32 (2H, m), 1.46 (9H, s), 1.45-1.58 (3H, m), 2.03-2.13 (2H, m), 2.27-2.29 (1H, m), 2.46-2.51 (2H, m), 2.84-2.92 (1H, m), 3.22 (1H, broad), 4.75 (1H, d, J = 11.7 Hz), 4.85 (1H, d, J = 11.7 Hz), 5.27 (1H, s). |
| 9(9-e) | Mp: 174-175° C.<br>1H-NMR(400 MHz, CD3OD): δ ppm: 0.94(3H, t, J = 7.4 Hz), 1.45-1.58(3H, m), 2.03-2.08(2H, m), 2.14(2H, t, J = 8.0 Hz), 2.46-2.50(1H, m), 2.48(1H, d, J = 12.0 Hz), 2.52(1H, d, J = 12.0 Hz), 2.85(1H, quint, J = 7.4 Hz), 3.10-3.12(1H, m), 3.14(1H, d, J = 13.1 Hz), 3.18(1H, d, J = 13.1 Hz), 5.38(1H, d, J = 1.7 Hz).<br>IR (KBr): cm − 1: 2957, 2928, 2905, 2834, 2629, 1540, 1397, 1380, 1285.<br>MS (FAB): m/z: 224 (M + H)+, 246 (M + Na)+.<br>Anal. calcd for C13H21NO2: C, 69.92; H, 9.48; N, 6.27; Found C, 69.13; H, 9.51; N, 6.21. |
| 10(10-a) | 1H-NMR(400 MHz, CDCl3): δ ppm: 0.90 (3H, t, J = 7 Hz), 1.20-1.40 (6H, m), 1.50-1.56 (1H, m), 1.95-2.27 (3H, m), 2.46-2.49 (2H, m), 2.74 (1H, d, J = 4 Hz), 3.72 (3H, s), 4.01-4.10 (1H, m), 5.00-5.10 (2H, m), 5.74-5.85 (1H, m). |
| 10(10-c) | 1H-NMR(400 MHz, CDCl3): δ ppm: 0.87-0.93 (3H, m), 1.25-1.45 (4H, m), 1.46 (1.49) (9H, s, 1.98-2.20 (3H, m), 2.40-2.95 (4H, m), 3.86-3.88 (4.29-4.40) (1H, br.s) 5.23 (5.05) (1H, m), 5.45 (5.35) (1H, br.s.). |
| 10(10d) | 1H-NMR(400 MHz, CDCl3): δ ppm: 0.92 (3H, t, J = 7 Hz), 1.25-1.38 (4H, m), 1.45 (9H, s), 1.96-2.15 (4H, m), 2.25-2.33 (1H, m), 2.45-2.55 (1H, m), 2.47 (2H, s), 2.81-2.88 (1H, m), 3.18-3.23 (1H, m), 4.75 (1H, d, J = 12 Hz), 4.84 (1H, d, J = 12 Hz), 5.26 (1H, s). |
| 10(10-e) | 1H-NMR(400 MHz, CDCl3): δ ppm: 0.91 (3H, t, J = 7), 1.25-1.49 (5H, m), 1.44 (18H, s), 1.95-2.15 (4H, m), 2.24 (2H, dd, J = 14, 21 Hz), 2.40-2.50 (1H, m), 2.75-2.90 (1H, m), 2.97-3.03 (1H, m), 3.30-3.45 (2H, m), 4.99 (1H, br. s), 5.33 (1H, br.s), |

TABLE 5

| | |
|---|---|
| 10(10-f) | 1H-NMR(400 MHz, CD3OD): δ ppm: 0.93 (3H, t, J = 7 Hz), 1.26-1.53 (5H, m), 1.97-2.17 (4H, m), 2.48-2.51 (1H, m), 2.46 (1H, d, J = 16 Hz), 2.50 (1H, d, J = 16 Hz), 2.82-2.91 (1H, m), 3.05-3.11 (1H, m), 3.14 (1H, d, J = 13 Hz), 3.18 (1H, d, J = 13 Hz), 5.38 (1H, br. s).<br>IR (KBr): cm − 1: 2957, 2926, 1564, 1525, 1397<br>MS (EI): m/z: 238 (M)+.<br>Anal. calcd for C14H23NO2; 0.2H2O: C, 69.79; H, 9.79; N, 5.81; Found C, 69.94; H, 9.74; N, 5.91.<br>Mp. 150° C.(decomp.) |
| 11(11-b) | 1H-NMR(400 MHz, CDCl3): δ ppm: 0.92 (isomerA3H, d, J = 7.0 Hz), 0.93 (isomerB3H, d, J = 7.0 Hz), 0.94 (isomerA3H, d, J = 7.0 Hz), 0.98 (isomerB3H,, d, J = 7.0 Hz), 1.28-1.33 (isomerA1H, m), 1.41-1.46 (isomerB1H, m), 1.84 (isomerA1H, d-sept, J = 4.7, 7.0 Hz), 1.95-2.07 (isomerB1H, m), 2.11-2.29 (2H, m), 2.44 (isomerB1H, dd, J = 3.1, 13.3 Hz), 2.48 (isomerA1H, dd, J = 3.1, 13.3 Hz), 2.51-2.62 (1H, m), 2.66 (isomerA1H, d, J = 3.9 Hz), 2.82 (isomerB1H,, d, J = 3.9 Hz), 3.72 (3H, s), 4.04-4.09 (isomerB1H, m), 4.18-4.22 (isomerA1H, m), 4.98-5.09 (2H, m), 5.81 (isomerB1H, ddt, J = 10.2, 17.2, 7.0 Hz), 5.89 (isomerA1H, ddt, J = 10.2, 17.2, 7.0 Hz). |
| 11(11-c) | 1H-NMR(400 MHz, CDCl3): δ ppm: 0.92 (isomerA3H, d, J = 7.0 Hz), 0.93 (isomerB3H, d, J = 7.0 Hz), 0.95 (isomerB3H, d, J = 7.0 Hz), 0.98 (isomerA3H, d, J = 7.0 Hz), 1.32-1.37 (isomerA1H, m), 1.43-1.49 (isomerB1H, m), 1.85 (isomerA1H, d-sept, J = 5.5, 7.0 Hz), 1.98 (isomerB1H, d-sept, J = 4.3, 7.0 Hz), 2.04-2.25 (2H, m), 2.49-2.68 (2H, m), 4.10 (isomerB1H, dt, J = 6.3, 3.1 Hz), 4.22 (isomerA1H, ddd, J = 2.7, 4.3, 9.4 Hz), 5.01 (1H, m), 5.08 (isomerB1H, ddd, J = 1.6, 3.2, 18.0 Hz), 5.10 (isomerA1H, ddd, J = 1.8, 3.3, 17.0 Hz), 5.81 (isomerB1H, m), 5.90 (isomerA1H, ddd, J = 7.0, 9.8, 17.0 Hz). |
| 11(11-d) | 1H-NMR(400 MHz, CDCl3): δ ppm: 1.07 (6H, d, J = 6.7 Hz), 2.35 (1H, m), 2.40 (1H, sept, J = 6.7 Hz), 2.75-2.85 (3H, m), 3.20 (1H, m), 4.19 (1H, br), 5.22 (1H, br). |

TABLE 5-continued

| | |
|---|---|
| 11(11-e) | 1H-NMR(400 MHz, CDCl3): δ ppm: E/Z mixture 1.05 (isomerA3H, d, J = 6.6 Hz), 1.06 (isomerB3H, d, J = 6.6 Hz), 1.06 (isomerA3H, d, J = 6.6 Hz), 1.06 (isomerB3H, d, J = 6.6 Hz), 1.46 (isomerA9H, s), 1.49 (isomerB9H, s), 2.18-2.25 (1H, m), 2.36 (1H, sept, J = 6.6 Hz), 2.41-2.68 (2H, m), 2.87-2.95 (isomerB1H + 1H, m), 3.29 (isomerA1H, ddt, J = 8.6, 18.0, 2.7 Hz), 3.83-3.88 (isomerA1H, m), 4.26-4.31 (isomerB1H, m), 5.21-5.23 (isomerA1H, m), 5.34-5.35 (isomerB1H, m), 5.43-5.45 (isomerB1H, m), 5.45-5.47 (isomerA1H, m). |
| 11(11-f) | 1H-NMR(400 MHz, CDCl3): δ ppm: 1.08 (3H, d, J = 6.8 Hz), 1.09 (3H, d, J = 6.8 Hz), 1.46 (9H, s), 1.45-1.52 (1H, m), 2.09 (1H, d, J = 16.4 Hz), 2.30 (1H, m), 2.41 (1H, sept, J = 6.8 Hz), 2.47 (2H, s), 2.52 (1H, dd, J = 7.8, 16.4 Hz), 2.86 (1H, quint, J = 7.8 Hz), 3.20 (1H, br), 4.75 (1H, d, J = 11.5 Hz), 4.85 (1H, d, J = 11.5 Hz), 5.26 (1H, s). |
| 11(11-g) | 1H-NMR(400 MHz, CDCl3): δ ppm: 1.07 (3H, d, J = 6.8 Hz), 1.09 (3H, d, J = 6.8 Hz), 1.40 (1H, m), 1.44 (9H, s), 1.95 (1H, ddd, J = 2.3, 8.6, 12.1 Hz), 2.04 (1H, m), 2.24 (1H, d, J = 13.7 Hz), 2.31 (1H, d, J = 13.7 Hz), 2.40 (1H, sept, J = 6.8 Hz), 2.48 (1H, m), 2.73 (1H, quint, J = 7.8 Hz), 2.85 (2H, s), 2.93 (1H, br), 5.37 (1H, s). |
| 11(11-h) | Mp 161-163° C. (decompose);<br>1H-NMR(400 MHz, CD3OD): δ ppm: 1.09 (3H, d, J = 6.7 Hz), 1.10 (3H, d, J = 6.7 Hz), 1.46 (1H, dd, J = 7.4, 12.1 Hz), 2.02-2.11 (2H, m), 2.42 (1H, sept, J = 6.7 Hz), 2.48 (2H, br), 2.52 (1H, d, J = 7.4 Hz), 2.85 (1H, quint, J = 7.4 Hz), 3.10 (1H, br), 3.15 (1H, d, J = 13.0 Hz), 3.20 (1H, d, J = 13.0 Hz), 5.37 (1H, s).<br>IR(KCl) vmax 1616.1, 1506.1, 1396.2 cm − 1<br>MS(ESI+) m/z: 278 (M + Na + MeOH)+, 268 (M + 2Na − H)+, 246 (M + Na)+, 224 (M + H)+<br>HRMS(ESI+) calcd for (M + Na)+: 246.14700. Found 246.14815 (1.15 mmu). |
| 12(12-a) | 1H-NMR(400 MHz, CDCl3): δ ppm: 0.89 (6H, d, J = 7 Hz), 1.1-1.3 (3H, m), 1.55-1.75 (2H, m), 2.10-2.14 (1H, m), 3.53(1H, dd, J = 6, 11 Hz), 3.57 (1H, dd, J = 6, 11 Hz), 5.01-5.11 (2H, m), 5.73-5.87 (1H, m). |
| 12(12-c) | 1H-NMR(400 MHz, CDCl3): δ ppm: 0.86-0.92 (6H, m), 1.16-1.24 (2H, m), 1.60-1.73 (2H, m), 1.96-2.29 (2H, m), 2.40-2.53 (2H, m), 2.73-2.78 (1H, m), 3.27 (3H, s), 4.0-4.15 (1H, m), 5.01-5.11 (1H, m), 5.77-5.85 (1H, m). |
| 12(12-e) | 1H-NMR(400 MHz, CDCl3): δ ppm: 0.86-0.89 (6H, m), 1.45 (1.49) (9H, m), 1.74-2.01 (4H, m), 2.50-2.95 (4H, m), 3.25-3.90 (1H, m), 5.20-5.24 (4.98-5.02) (1H, m), 5.43-5.48 (5.30-5.36) (1H, m). |
| 12(12-f) | 1H-NMR(400 MHz, CDCl3): δ ppm: 0.90 (3H, d, J = 6 Hz), 0.92 ((3H, d, J = 6 Hz), 1.46 (9H, s), 1.50-1.55 (1H, m), 1.76-1.83 (1H, m), 2.02-2.07 (4H, m), 2.25-2.34 (1H, m), 2.43-2.52 (1H, m), 2.49 (2H, br. s), 2.84-2.91 (1H, m), 3.21-3.74 (1H, m), 4.76 (1H, d J = 11 Hz), 4.85 (1H, d J = 11 Hz), 5.27 (1H, s). |
| 12(12-g) | 1H-NMR(400 MHz, CDCl3): δ ppm: 0.90 (3H, d, J = 6 Hz), 0.92 ((3H, d, J = 6 Hz), 1.40-1.50 (2H, m), 1.44 (18H, s), 1.75-1.81 (1H, m), 1.95-2.05 (5H, m), 2.25 (2H, dd, J = 14, 22 Hz), 2.35-2.46 (1H, m), 2.80-2.90 (1H, m), 3.30-3.41 (2H, m), 4.98-5.04 (1H, m), 5.33 (1H, s). |

TABLE 6

| | |
|---|---|
| 12(12-h) | 1H-NMR(400 MHz, CD3OD): δ ppm: 0.90 (3H, d, J = 6 Hz), 0.92 ((3H, d, J = 6 Hz), 1.48 (1H, dd, J = 7, 13 Hz), 1.81 (1H, sep, J = 6 Hz), 2.02-2.08 (4H, m), 2.43-2.51 (3H, m), 2.82-2.91 (1H, m), 3.09-3.14 (1H, m), 3.16 (2H, dd, J = 13, 23 Hz), 5.37 (1H, s).<br>Anal. calcd for C14H23NO2 0.25H2O: C, 69.58; H, 9.79; N, 5.80; Found C, 69.31; H, 10.01; N, 6.08.<br>IR (KBr): cm − 1: 2951, 2905, 1541, 1461, 1398<br>MS (EI): m/z: 237 (M)+.<br>Mp 171-174° C. |
| 13(13-b) | 1H-NMR(400 MHz, CDCl3): δ ppm: 0.85-0.92 (6H, m), 1.13-1.33 (2H, m), 1.37-1.65 (3H, m), 2.12-2.16 (1H, m), 3.63-3.69 (2H, m), 4.99-5.10 (2H, m), 5.90 (1H, m). |
| 13(13-d) | 1H-NMR(400 MHz, CDCl3): δ ppm: 0.86-0.96 (6H, m), 1.10-2.05 (4H, m), 2.07-2.31 (2H, m), 2.40-2.84 (3H, m), 3.72 (3H, s), 4.03-4.28 (1H, m), 4.97-5.09 (2H, m), 5.74-5.96 (1H, m). |
| 13(13-e) | 1H-NMR(400 MHz, CDCl3): δ ppm: 0.86-0.97 (6H, m), 1.13-1.79 (4H, m), 1.97-2.31 (2H, m), 2.47-2.69 (2H, m), 4.06-4.26 (1H, m), 4.99-5.12 (2H, m), 5.74-5.97 (1H, m). |
| 13(13-f) | 1H-NMR(400 MHz, CDCl3): δ ppm: 0.83 (isomerX3H, d, J = 7.0 Hz), 0.84 (isomerX3H, d, J = 7.0 Hz), 1.04 (isomerX3H, d, J = 7.0 Hz), 1.04 (isomerX3H, d, J = 7.0 Hz), 1.33-1.52 (2H, m), 2.22-2.37 (2H, m), 2.85-2.88 (3H, m), 3.16-3.24 (1H, m), 4.17-4.22 (1H, m), 5.24 (1H, br). |
| 13(13-g) | 1H-NMR(400 MHz, CDCl3): δ ppm: E/Z mixture 0.84 (3H, t, J = 7.0 Hz), 1.02-1.04 (3H, m), 1.29-1.48 (2H, m), 1.45 (isomerA9H, s), 1.49 (isomerB9H, s), 2.10-2.25 (2H, m), 2.40-2.68 (2H, m), 2.86-2.96 (isomerB1H + 1H, m), 3.29 (isomerA1H, m), 3.85 (isomerA1H, br), 4.29 (isomerB1H, br), 5.24 (isomerA1H, br), 5.34 (isomerB1H, m), 5.46 (isomerA1H + isomerB1H, m). |
| 13(13-h) | 1H-NMR(500 MHz, CDCl3): δ ppm: 0.86 (isomerX3H, t, J = 7.3 Hz), 0.87 (isomerX3H, t, J = 7.3 Hz), 1.05 (isomerX3H, d, J = 7.3 Hz), 1.06 (isomerX3H, d, J = 7.3 Hz), 1.46 (9H, s), 1.33-1.57 (3H, m), 2.03 (isomerX1H, d, J = 16.1 Hz), 2.08 (isomerX1H, d, J = 16.1 Hz), 2.24-2.32 (2H, m), 2.48 (2H, s), 2.43-2.52 (1H, m), 2.88 (1H, sep, J = 7.3 Hz), 3.21 (1H, br), 4.75 (1H, d, J = 11.7 Hz), 4.86 (1H, d, J = 11.7 Hz), 5.28 (1H, s). |
| 13(13-i) | 1H-NMR(400 MHz, CDCl3): δ ppm: 0.86 (isomerX3H, t, J = 7.4 Hz), 0.87 (isomerX3H, t, J = 7.4 Hz), 1.04 (isomerX3H, d, J = 7.0 Hz), 1.06 (isomerX3H, d, J = 7.0 Hz), 1.33-1.51 (3H, m), 1.44 (9H, s), 1.92-1.99 (1H, m), 1.99-2.06 (1H, m), 2.22-2.29 (1H, m), 2.25 (1H, dd, J = 2.7, 13.7 Hz), 2.32 (1H, dd, J = 2.0, 13.7 Hz), 2.38-2.48 (1H, m), 2.72 (1H, sep, J = 7.8 Hz), 2.85 (2H, s), 2.94 (1H, br), 5.38 (1H, m). |
| 13(13-j) | Mp 151-154° C.;<br>1H-NMR(400 MHz, CD3OD): δ ppm: 0.87 (isomerX3H, t, J = 7.4 Hz), 0.90 (isomerX3H, t, J = 7.4 Hz), 1.06 (isomerX3H, d, J = 7.0 Hz), 1.08 (isomerX3H, d, J = 7.0 Hz), 1.39 (1H, m), 1.44-1.53 (2H, m), 2.00-2.10 (2H, m), 2.28 (1H, sep, J = 6.6 Hz), 2.46 (2H, br), 2.49 (1H, d, J = 2.0 Hz), 2.85 (1H, sep, J = 7.4 Hz), 3.11 (1H, br), 3.14 (1H, d, J = 12.9 Hz), 3.20 (1H, d, J = 12.9 Hz), 5.40 (1H, d, J = 2.0 Hz).<br>MS(ESI+) m/z: 292 (M + Na + MeOH)+, 282 (M + 2Na − H)+, 260 (M + Na)+, 238 (M + H)+<br>HRMS(ESI+) calcd for (M + Na)+: 260.16265. Found 260.16353 (0.88 mmu). |
| 14(14-a) | 1H-NMR(400 MHz, CDCl3): δ ppm: 1.11-1.21 (2H, m), 1.25 (3H, t, J = 7.0 Hz), 1.48-1.73 (5H, m), 1.80-1.87 (1H, m), 1.94-2.05 (1H, m), 2.21-2.35 (2H, m), 4.13 (2H, q, J = 7.0 Hz), 4.98 (1H, ddd, J = 1.2, 2.0, 10.2 Hz), 5.05 (1H, dd, J = 1.2, 17.2 Hz), 5.75 (1H, ddt, J = 10.2, 17.2, 7.0 Hz). |

TABLE 6-continued

| | |
|---|---|
| 14(14-b) | 1H-NMR(400 MHz, CDCl3): δ ppm: 1.09-1.20 (2H, m), 1.30 (1H, dd, J = 5.9, 6.3 Hz), 1.40-1.67 (5H, m), 1.71-1.85 (3H, m), 2.13 (1H, ddt, J = 7.8, 14.1, 1.2 Hz), 2.30 (1H, dddt, J = 4.3, 6.6, 14.1, 1.6 Hz), 3.58 (1H, dt, J = 10.6, 5.9 Hz), 3.69 (1H, ddd, J = 4.3, 6.3, 10.6 Hz), 5.02 (1H, dtt, J = 10.2, 1.2, 1.6 Hz), 5.09 (1H, ddt, J = 1.2, 17.2, 1.6 Hz), 5.87 (1H, dddd, J = 6.6, 7.8, 10.2, 17.2 Hz). |
| 14(14-d) | 1H-NMR(400 MHz, CDCl3): δ ppm: 1.11-1.26 (2H, m), 1.33-1.68 (5H, m), 1.70-2.01 (3H, m), 2.41-2.73 (2H, m), 3.72 (3H, s), 4.11-4.24 (1h, m), 5.06 (isomerA1H, ddd, J = 1.6, 3.5, 15.6 Hz), 5.08 (isomerB1H, ddd, J = 1.6, 3.5, 15.6 Hz), 5.84-5.97 (1H, m). |
| 14(14-e) | 1H-NMR(400 MHz, CDCl3): δ ppm: 1.12-1.26 (2H, m), 1.40-1.67 (5H, m), 1.71-2.01 (3H, m), 2.19-2.27 (2H, m), 2.46-2.71 (2H, m), 4.18-4.25 (1H, m), 5.00-5.03 (1H, m), 5.06-5.10 (isomerA1H, m), 5.07-5.12 (isomerB1H, m), 5.84-5.97 (1H, m). |
| 14(14-f) | 1H-NMR(400 MHz, CDCl3): δ ppm: 1.36-1.45 (2H, m), 1.54-1.62 (2H, m), 1.62-1.69 (2H, m), 1.78-1.86 (2H, m), 2.30-2.38 (1H, m), 2.54 (1H, quint, J = 8.2 Hz), 2.76-2.83 (3H, m), 3.14-3.24 (1H, m), 4.16-4.21 (1H, m), 5.23 (1H, m). |
| 14(14-g) | 1H-NMR(500 MHz, CDCl3): δ ppm: E/Z mixture 1.39-1.59 (13H, m), 1.62-1.69 (2H, m), 1.78-1.83 (2H, m), 2.18-2.23 (1H, m), 2.51 (1H, quint, J = 7.8 Hz), 2.60-2.68 (2H, m), 2.85-2.94 (isomerB1H + 1H, m), 3.29 (isomerA1H, ddd, J = 2.9, 5.9, 12.5 Hz), 3.85 (isomerA1H, br), 4.28 (isomerB1H, br), 5.23 (isomerA1H, s), 5.34 (isomerB1H, m), 5.45 (1H, m). |
| 14(14-h) | 1H-NMR(400 MHz, CDCl3): δ ppm: 1.38-1.52 (12H, m), 1.56-1.72 (4H, m), 1.82 (2H, m), 2.08 (1H, d, J = 16.4 Hz), 2.29 (1H, ddd, J = 2.7, 9.0, 12.9 Hz), 2.46 (2H, s), 2.49-2.59 (2H, m), 2.86 (1H, quint, J = 7.8 Hz), 3.20 (1H, br), 4.74 (1H, d, J = 11.7 Hz), 4.85 (1H, d, J = 11.7 Hz), 5.26 (1H, s). |

TABLE 7

| | |
|---|---|
| 14 (14-i) | 1H-NMR (400 MHz, CDCl3): δ ppm: 1.37-1.49 (12H, m), 1.55-1.71 (4H, m), 1.82 (2H, m), 1.95 (1H, ddd, J = 2.7, 9.0, 12.5 Hz), 2.04 (1H, m), 2.23 (1H, d, J = 14.1 Hz), 2.31 (1H, d, J = 14.1 Hz), 2.48 (1H, m), 2.55 (1H, quint, J = 8.6 Hz), 2.73 (1H, quint, J = 7.4 Hz), 2.85 (2H, s), 2.94 (1H, br), 5.83 (1H, s). |
| 14 (14-j) | Mp 168° C. (decompse);<br>1H-NMR (500 MHz, CD3OD): δ ppm: 1.44-1.52 (3H, m), 1.56-1.73 (4H, m), 1.80-1.87 (2H, m), 2.05 (1H, ddd, J = 2.9, 8.8, 11.7 Hz), 2.07-2.10 (1H, m), 2.48-2.53 (3H, m), 2.58 (1H, quint, J = 8.3 Hz), 2.85 (1H, quint, J = 7.8 Hz), 3.09 (1H, m), 3.13 (1H, d, J = 13.2 Hz), 3.18 (1H, d, J = 13.2 Hz), 5.39 (1H, s);<br>IR (KCl) νmax 1616.1, 1505.2, 1395.2 cm−1;<br>MS (ESI+) m/z: 272 (M + Na)+, 250 (M + H)+;<br>HRMS (ESI+) calcd for (M + H)+: 250.18070. Found 250.18174 (1.04 mmu). |
| 15 (15-a) | 1H-NMR (400 MHz, CDCl3): δ ppm: 2.11-2.29 (4H, m), 2.35-2.44 (1H, m), 5.05 (4H, d, J = 12.9 Hz), 5.66-5.82 (3H, m), 6.93 (1H, ddd, J = 1.2, 8.6, 15.8 Hz). |
| 15 (15-b) | 1H-NMR (400 MHz, CDCl3): δ ppm:<br>Major isomer 1.45 (9H, s), 2.18-2.22 (1H, m), 2.58-2.71 (2H, m), 2.84-2.97 (3H, m), 3.26-3.34 (1H, m), 3.87-3.88 (1H, m), 5.02-5.09 (2H, m), 5.28-5.50 (2H, m), 5.80-5.90 (1H, m).<br>Minor isomer 1.47 (9H, s), 2.18-2.22 (1H, m), 2.58-2.71 (2H, m), 2.84-2.97 (3H, m), 3.26-3.34 (1H, m), 4.31-4.32 (1H, m), 5.02-5.09 (2H, m), 5.28-5.50 (2H, m), 5.80-5.90 (1H, m). |
| 15 (15-c) | 1H-NMR (400 MHz, CDCl3): δ ppm: 1.45 (9H, s), 1.52 (1H, dd, J = 7.6, 13.2 Hz), 2.05-2.10 (1H, m), 2.30 (1H, ddd, J = 2.4, 7.6, 13.2 Hz), 2.47 (2H, s), 2.51 (1H, dd, J = 8.6, 16.4 Hz), 2.86 (1H, quint, J = 7.6 Hz), 2.88 (2H, d, 6.7 Hz), 3.22-3.23 (1H, m), 4.75 (1H, d, J = 11.7 Hz), 4.84 (1H, d, J = 11.7 Hz), 5.05-5.11 (2H, m), 5.32 (1H, s), 5.81-5.91 (1H, m). |
| 15 (15-d) | Mp: 175-176° C.<br>1H-NMR (400 MHz, CD3OD): δ ppm: 1.49 (1H, dd, J = 7.5, 12.2 Hz), 2.03-2.09 (2H, m), 2.46 (1H, d, J = 16.2 Hz), 2.49 (1H, dd, J = 8.7, 15.5 Hz), 2.51 (1H, d, J = 16.2 Hz), 2.86 (1H, quint, J = 7.5 Hz), 2.89 (2H, d, J = 5.0 Hz), 3.10-3.12 (1H, m), 3.14 (1H, d, J = 13.1 Hz), 3.19 (1H, d, J = 13.1 Hz), 5.10-5.01 (2H, m), 5.42 (1H, d, J = 1.7 Hz), 5.94-5.84 (1H, m).<br>IR (KBr): cm−1: 2948, 2900, 2835, 1563, 1542, 1525, 1397, 1383, 910, 663.<br>MS (EI): m/z: 221 (M)+.<br>Anal. calcd for C13H19NO2: C, 70.56; H, 8.65; N, 6.33; Found C, C, 69.69; H, 8.73; N, 6.31. |
| 16 (16-a) | 1H-NMR (400 MHz, CDCl3): δ ppm: 1.27 (3H, t, J = 7.0 Hz), 1.34 (3H, d, J = 7.0 Hz), 2.31-2.38 (2H, m), 2.56-2.74 (2H, m), 3.52 (1H, q, J = 7.0 Hz), 4.19 (2H, q, J = 7.0 Hz), 4.98, 5.00, 5.02, and 5.05 (total 2H, each dd, J = 1.5, 3.1 Hz, 1.6, 3.1 Hz, 1.6, 3.2 Hz and 1.6, 3.2 Hz), 5.75-5.85 (1H, m). |
| 16 (16-b) | 1H-NMR (400 MHz, CDCl3): δ ppm: 1.20 and 1.23 (total 3H, each d, J = 7.0 and 7.4 Hz), 1.29 (3H, t, J = 7.0 Hz), 1.43-1.66 (2H, m), 2.09-2.34 (2H, m), 2.47-2.57 (1H, m), 3.63-3.73 and 3.88-3.95 (total 1H, each m), 4.18 (2H, q, J = 7.0 Hz), 4.97, 5.00, 5.04, and 5.08 (total 2H, each m), 5.77-5.89 (1H, m). |
| 16 (16-c) | 1H-NMR (400 MHz, CDCl3): δ ppm: 1.23 and 1.27 (total 3H, each d, J = 7.4 and 7.1 Hz), 1.47-1.73 (2H, m), 2.10-2.33 (2H, m), 2.53-2.67 (1H, m), 3.69-3.76 and 3.93-4.02 (total 1H, each m), 4.99, 5.02, 5.05, and 5.09 (total 2H, each m), 5.79-5.89 (1H, m). |
| 16 (16-d) | 1H-NMR (400 MHz, CDCl3): δ ppm: 1.29 (3H, s), 2.44 and 2.48 (1H, d, J = 18.0 Hz), 2.59-2.65 (1H, m), 2.75 (1H, dd, J = 5.9, 18.1 Hz), 2.90 (1H, dd, J = 7.8, 17.6 Hz), 3.18 (1H, dd, J = 8.8, 18.1 Hz), 5.45-5.48 (1H, m), 5.82-5.86 (1H, m). |
| 16 (16-e) | 1H-NMR (400 MHz, CDCl3): δ ppm: 1.26 (3H, s), 1.46 (9H, s), 2.30 (1H, d, J = 16.9 Hz), 2.47-2.60 (2H, m), 2.68-2.75 (1H, m), 3.30 (1H, ddd, J = 2.4, 9.7, 17.9 Hz), 5.44-5.47 (1H, m), 5.48-5.49 (1H, m), 5.71-5.74 (1H, m). |
| 16 (16-f) | 1H-NMR (400 MHz, CDCl3): δ ppm: 1.41 (3H, s), 1.48 (9H, s), 1.60 (1H, dd, J = 5.4, 11.2 Hz), 2.10-2.16 (1H, m), 2.55 (2H, s), 2.57-2.68 (3H, m), 5.52-5.55 (1H, m), 5.87-5.90 (1H, m).<br>by product: 1H-NMR (400 MHz, CDCl3): δ ppm: 1.10 (3H, s), 1.48 (9H, s), 2.09 (1H, d, J = 7.8, 12.7 Hz), 2.18-2.20 and 2.21-2.22 (total 1H, each m), 2.30 (1H, dd, J = 8.8, 12.7 Hz), 2.51 (1H, dd, J = 7.3, 7.9 Hz), 2.60-2.66 (1H, m), 2.72 (2H, dd, J = 16.1, 24.4 Hz), 5.82-5.86 (1H, m), 5.87-5.91 (1H, m). |
| 16 (16-g) | 1H-NMR (400 MHz, CDCl3): δ ppm: 1.45, 1.46 and 1.48 (total 18H, each s), 1.54-1.62 (4H, m), 2.00-2.20 (2H, m), 2.55 (2H, s), 2.55-2.69 (2H, m), 3.28 (1H, dd, J = 5.4, 13.7 Hz), 3.62 (1H, dd, J = 6.9, 13.2 Hz), 5.52-5.55 (1H, m), 5.88-5.91 (1H, m). |

TABLE 7-continued

| | |
|---|---|
| 16 (16-h) | 1H-NMR (400 MHz, CD3OD): δ ppm: 1.12 (3H, s), 1.37 (1H, dd, J = 7.3, 12.2 Hz), 2.02 (1H, dd, 8.8, 12.2 Hz), 2.08-2.10 and 2.11-2.13 (total 1H, each m), 2.44 (1H, dd, J = 7.3, 15.2 Hz), 2.52 (2H, s), 2.52-2.59 (1H, m), 3.19 (1H, d, J = 13.2 Hz), 3.32 (1H, d, J = 13.2 Hz), 5.74-5.80 (2H, m).<br>IR (KBr): cm−1: 2904, 1568, 1516, 1395, 1381<br>MS (FAB): m/z: 196 (M + H)+, 234 (M + K)+<br>Mp. 145-148° C. |

TABLE 8

| | |
|---|---|
| 17 (17-a) | 1H-NMR (400 MHz, CDCl3): δ ppm: 1.03 (1.04) (3H, d, J = 3 Hz), 1.31-1.40 (1H, m), 1.51-1.66 (1H, m), 2.34-2.54 (3H, m), 2.79 (2.86) (1H, d, J = 4 Hz), 3.71 (3.72) (3H, s), 4.01-4.11 (1H, m), 4.93-5.08 (2H, m), 5.60-5.80 (1H, m). |
| 17 (17-c) | 1H-NMR (400 MHz, CDCl3): δ ppm: major 0.95 (3H, d, J = 7 Hz), 1.45 (9H, s), 2.43-2.70 (2H, m), 2.85-23.20 (2H, m), 3.94 (1H, br. s), 5.49 (1H, br. s), 5.56-5.58 (1H, m), 5.77-5.79 (1H, m). |
| 17 (17-d) | 1H-NMR (400 MHz, CDCl3): δ ppm: 0.91 (3h, d, J = 7 Hz), 1.45 (9H, s), 1.45-1.50 (1H, m), 2.25-2.35 (1H, m), 2.45-2.55 (1H, m), 2.86-2.95 (1H, m), 3.30-3.35 (1H, m), 4.78 (1H, d, J = 12 Hz), 4.86 (1H, d, J = 12 Hz), 5.58-5.62 (1H, m), 5.70-5.77 (1H, m), 5.90-5.93 (1H, m). |
| 17 (17-e) | 1H-NMR (400 MHz, CDCl3): δ ppm: 0.89 (3h, d, J = 7 Hz), 1.53 (18H, s), 2.01 (1H, m), 2.19 (1H, d, J = 12 Hz), 2.25 (1H, d, J = 12 Hz), 2.42-2.46 (1H, m), 2.85-3.20 (2H, m), 3.30-3.50 (2H, m), 5.0 (1H, br.s), 5.65-5.70 (1H, m), 5.82-5.89 (1H, m). |
| 17 (17-f) | 1H-NMR (400 MHz, CD3OD): δ ppm: 0.92 (3H, t, J = 7 Hz), 1.47-1.53 (1H, m), 1.65-1.75 (1H, m), 2.02-2.10 (1H, m), 2.42-2.55 (3H, m), 3.15-3.30 (3H, m), 5.70-5.76 (1H, m), 5.90-5.93 (1H, m).<br>IR (KBr): cm−1: 2952, 1618, 1560, 1514, 1394<br>MS (EI): m/z: 196 (M)+.<br>Anal. calcd for C14H23NO2; 0.2H2O: C, 66.50; H, 8.82; N, 7.05; Found C, 66.55; H, 8.60; N, 7.17.<br>Mp. 148-152° C. |
| 18 (18-a) | 1H-NMR (CDCl3, 400 MHz): δ 1.27 (3H, t, J = 7.4 Hz), 1.74-1.87 (1H, m), 2.11-2.32 (2H, m), 2.43-2.58 (2H, m), 3.32 (1H of minor, d, J = 4.3 Hz), 3.40 (1H of major, d, J = 5.5 Hz), 3.49-3.64 (2H, m), 3.81 (3H, s), 4.10-4.26 (3H, m), 4.38-4.45 (2H, m), 5.00-5.09 (2H, m), 5.70-5.81 (1H, m), 6.88 (2H, d, J = 8.2 Hz), 7.23-7.26 (2H, m). |
| 18 (18-b) | 1H-NMR (CDCl3, 400 MHz): δ 1.77-1.84 (1H of major, m), 1.89-1.96 (1H of minor, m), 2.11-2.31 (2H, m), 2.46-2.60 (2H, m), 3.47-3.70 (2H, m), 3.82 (3H, s), 4.08-4.15 (1H of major, m), 4.21-4.25 (1H of minor, m), 4.39-4.48 (2H, m), 5.03-5.09 (2H, m), 5.68-5.79 (1H, m), 6.89 (2H, d, J = 8.6 Hz), 7.23 (2H, d, J = 8.6 Hz). |
| 18 (18-c) | 1H-NMR (CDCl3, 500 MHz):<br>Major isomer: δ 1.45 (9H, s), 2.27-2.31 (1H, m), 2.66-2.74 (2H, m), 2.92-3.01 (2H, m), 3.81 (3H, s), 3.93 (1H, br s), 4.06 (2H, s), 4.44 (2H, s), 5.47 (1H, br s), 5.56 (1H, br s), 6.87-6.90 (2H, m), 7.26-7.31 (2H, m).<br>Minor isomer (detectable peaks): δ 1.48 (9H, s), 2.45-2.52 (1H, m), 3.29-3.36 (2H, m), 4.08 (2H, s), 4.35 (1H, br s), 5.37 (1H, br s), 5.77 (1H, br s). |
| 18 (18-d) | 1H-NMR (CDCl3, 500 MHz): δ 1.45 (9H, s), 1.55-1.60 (1H, m), 2.16 (1H, br d, J = 16.6 Hz), 2.30-2.35 (1H, m), 2.49 (2H, s), 2.58 (1H, dd, J = 7.8, 16.6 Hz), 2.89-2.96 (1H, m), 3.29 (1H, br s), 3.81 (3H, s), 4.10 (2H, s), 4.46 (2H, s), 4.78 (1H, d, J = 11.2 Hz), 4.84 (1H, d, J = 11.2 Hz), 5.59 (1H, br s), 6.89 (2H, d, J = 9.8 Hz), 7.27 (2H, d, J = 9.8 Hz). |
| 18 (18-e) | 1H-NMR (CDCl3, 400 MHz): δ 1.42-1.46 (1H, m), 1.44 (9H, s), 1.45 (9H, s), 2.03-2.13 (2H, m), 2.23 (1H, d, J = 14.1 Hz), 2.29 (1H, d, J = 14.1 Hz), 2.50-2.57 (1H, m), 2.85-2.94 (1H, m), 3.06 (1H, br s), 3.35 (1H, dd, J = 6.3, 13.9 Hz), 3.43 (1H, dd, J = 6.7, 13.9 Hz), 3.81 (3H, s), 4.10 (2H, s), 4.45 (2H, s), 4.99 (1H, br s), 5.67 (1H, br s), 6.88 (2H, d, J = 8.6 Hz), 7.28 (2H, d, J = 8.6 Hz). |
| 18 (18-f) | 1H-NMR (CDCl3, 400 MHz): δ 1.43-1.47 (1H, m), 1.45 (18H, s), 2.04-2.13 (2H, m), 2.23 (1H, d, J = 14.1 Hz), 2.29 (1H, d, J = 14.1 Hz), 2.48-2.58 (1H, m), 2.82-2.96 (1H, m), 3.07 (1H, br s), 3.35 (1H, dd, J = 6.3, 14.1 Hz), 3.43 (1H, dd, J = 6.3, 14.1 Hz), 4.25 (2H, br s), 4.99 (1H, br s), 5.65 (1H, br s). |
| 18 (18-g) | 1H-NMR (CD3OD, 400 MHz): δ 1.54 (1H, dd, J = 7.8, 12.5 Hz), 2.06 (3H, s), 2.06-2.17 (2H, m), 2.48 (2H, s), 2.55 (1H, br dd, J = 7.8, 16.4 Hz), 2.88-2.96 (1H, m), 3.15 (1H, d, J = 12.9 Hz), 3.15-3.20 (1H, m), 3.22 (1H, d, J = 12.9 Hz), 4.69 (2H, s), 5.71 (1H, br s).<br>MS (FAB): m/z: 254 (M + 1)+.<br>Anal. Calcd for C13H19NO4: C 61.64; H 7.56; N 5.53; Found: C 60.66; H 7.32; N 5.62.<br>IR (KBr): cm−1: 2904, 1742, 1567, 1524, 1381, 1242.<br>Mp. 175-176° C. |
| 19 (19-a) | 1H-NMR (CDCl3, 400 MHz): δ 0.03 (6H, s), 0.88 (9H, s), 2.10-2.17 (1H, m), 2.29-2.36 (1H, m), 2.40-2.48 (1H, m), 3.59 (2H, d, J = 5.9 Hz), 3.73 (3H, s), 5.00-5.08 (2H, m), 5.67-5.78 (1H, m), 5.85 (1H, d, J = 16.3 Hz), 6.86 (1H, dd J = 8.2, 16.3 Hz). |
| 19 (19-b) | 1H-NMR (CDCl3, 400 MHz): δ 0.04 (6H, s), 0.88 (9H, s), 2.12-2.19 (1H, m), 2.28-2.36 (1H, m), 2.43-2.52 (1H, m), 3.59 (1H, dd, J = 5.9, 9.8 Hz), 3.63 (1H, dd, J = 5.9, 9.8 Hz), 5.02-5.09 (2H, m), 5.73 (1H, dddd, J = 7.0, 7.0, 10.2, 17.2 Hz), 5.86 (1H, dd, J = 1.2, 15.6 Hz), 6.97 (1H, dd, J = 8.2, 15.6 Hz). |

TABLE 9

| | |
|---|---|
| 19 (19-c) | 1H-NMR (CDCl3, 400 MHz):<br>Major isomer: δ 0.07 (6H, s), 0.91 (9H, s), 1.45 (9H, s), 2.18-2.25 (1H, m), 2.59-2.73 (2H, m), 2.92-3.01 (1H, m), 3.31 (1H, ddt, J = 2.7, 8.6, 18.4 Hz), 3.88-3.94 (1H, m), 4.21 (2H, br s), 5.46-5.50 (2H, m).<br>Minor isomer (detectable peaks): δ 1.48 (9H, s), 4.30-4.35 (1H, m), 4.23 (2H, br s), 5.35-5.36 (1H, m), 5.69-5.71 (1H, m). |
| 19 (19-d) | 1H-NMR (CDCl3, 400 MHz): Major isomer: δ 1.45 (9H, s), 2.28 (1H, br d, J = 16.4 Hz), 2.64-2.74 (2H, m), 2.93-3.04 (1H, m), 3.33 (1H, ddt, J = 2.7, 8.6, 18.4 Hz), 3.91-3.96 (1H, m), 4.23 (2H, br d, J = 4.3 Hz), 5.47-5.49 (1H, m), 5.52-5.55 (1H, m).<br>Minor isomer (detectable peaks): δ 1.49 (9H, s), 2.45-2.54 (1H, m), 4.33-4.38 (1H, m), 5.37-5.39 (1H, m), 5.74-5.77 (1H, m). |

TABLE 9-continued

| | |
|---|---|
| 19 (19-e) | 1H-NMR (CDCl3, 400 MHz): δ 1.45 (9H, s), 1.56-1.62 (1H, m), 2.12-2.19 (1H, m), 2.33 (1H, ddd, J = 2.7, 9.0, 12.9 Hz), 2.49 (2H, s), 2.51-2.59 (1H, m), 2.88-2.97 (1H, m), 3.27-3.31 (1H, m), 3.37 (3H, s), 4.03 (2H, s), 4.78 (1H, d, J = 11.7 Hz), 4.84 (1H, d, J = 11.7 Hz), 5.56-5.59 (1H, m). |
| 19 (19-f) | 1H-NMR (CDCl3, 400 MHz): δ 1.43-1.46 (1H, m), 1.44 (18H, s), 2.03-2.12 (2H, m), 2.23 (1H, d, J = 14.1 Hz), 2.29 (1H, d, J = 14.1 Hz), 2.47-2.55 (1H, m), 2.82-2.94 (1H, m), 3.04-3.09 (1H, m), 3.35 (3H, s), 3.35 (1H, dd, J = 6.3, 13.7 Hz), 3.42 (1H, dd, J = 6.3, 13.7 Hz), 4.02 (2H, s), 4.99 (1H, br s). |
| 19 (19-g) | 1H-NMR (CD3OD, 400 MHz): δ 1.53 (1H, dd, J = 7.4, 12.5 Hz), 2.09 (1H, ddd, J = 2.7, 8.6, 12.5 Hz), 2.10-2.16 (1H, m), 2.48-2.56 (1H, m), 2.50 (2H, s), 2.87-2.95 (1H, m), 3.16 (1H, d, J = 13.3 Hz), 3.16-3.20 (1H, m), 3.22 (1H, d, J = 13.3 Hz), 3.33 (3H, s), 4.04 (2H, s), 5.68 (1H, br s).<br>MS (FAB): m/z: 226 (M + 1)+.<br>Anal. Calcd for C12H19NO3: C 63.98; H 8.50; N 6.22; Found: C 62.83; H 8.37; N 6.21.<br>IR (KBr): cm−1: 2903, 1565, 1525, 1397, 1382, 1103.<br>Mp 160-162° C. |
| 20 (20-a) | 1H-NMR (400 MHz, CDCl3): δ ppm: 0.87 (1.5H, d, J = 7 Hz), 0.92 (1.5H, d, J = 1.5 Hz), 1.16 (1.5H, s), 1.20 (1.5H, s), 1.60-1.72 (2H, m), 2.38-2.60 (3H, m), 3.51 (0.5H, s), 3.54 (0.5H, s), 3.73 (3H, s), 4.98-5.05 (2H, m), 5.73-5.82 (1H, m). |
| 20 (20-c) | 1H-NMR (400 MHz, CDCl3): δ ppm: 1.46 (9H, s), 1.60 (3H, br. s), 1.64 (3H, br. s), 2.59-2.84 (4H, m), 3.25-3.33 (1H, m), 3.65-3.73 (1H, m), 5.38-5.40 (0.1H, m), 5.45-5.50 (0.9H, m). |
| 20 (20-d) | 1H-NMR (400 MHz, CDCl3): δ ppm:<br>1.44 (9H, s), 1.58 (3H, br. s), 1.54-1.60 (2H, m), 1.68 (3H, br. s), 2.05-2.21 (2H, m), 2.44 (1H, d, J = 17 Hz), 2.52 (1H, d, J = 17 Hz), 2.65-2.74 (1H, m), 3.16-3.23 (1H, m), 4.80 (1H, d, J = 12 Hz), 4.88 (1H, d, J = 12 Hz). |
| 20 (20-e) | 1H-NMR (400 MHz, CDCl3): δ ppm: 1.52-1.56 (1H, m), 1.53 (9H, s), 1.56 (9H, s), 1.61 (3H, br. s), 1.66 (3H, br. s), 2.15-2.30 (2H, m), 2.40-2.70 (2H, m), 2.90-2.98 (1H, m), 3.26-3.51 (2H, m), 4.94-5.05 81H, br. s). |
| 20 (20-f) | 1H-NMR (400 MHz, CD3OD): δ ppm: 1.45-1.55 (1H, m), 1.62 (3H, br. s), 1.70 (3H, br. s), 2.05-2.20 (2H, m), 2.35 (3H, br. s), 2.50-2.57 (3H, m), 2.68-2.74 (1H, m), 2.95-3.02 (1H, m), 3.32-3.36 (2H, m), 7.20-7.24 (2H, m), 7.68-7.72 (2H, m).<br>Anal. calcd for C19H27NO5S: C, 59.58; H, 7.19; N, 3.75; S, 8.59; Found C, 59.82; H, 7.13; N, 3.67; S, 8.41.<br>IR (KBr): cm−1: 1725, 1516, 1235, 1162, 1120.<br>MS (EI): m/z: 210 (M)+.<br>Mp. 186-189° C. |
| 21 (21-b) | 1H-NMR (400 MHz, CDCl3): δ ppm: 1.08 (3H, t, J = 7.6 Hz), 1.39 (1H, dd, J = 7.6, 12.1 Hz), 1.44 (18H, s), 1.98-2.02 (2H, m), 2.12 (2H, q, J = 7.6 Hz), 2.22 (1H, d, J = 14.5 Hz), 2.27 (1H, d, J = 14.5 Hz), 2.46-2.50 (1H, m), 2.80-2.88 (1H, m), 2.99-3.00 (1H, m), 3.33 (1H, dd, J = 6.2, 13.7 Hz), 3.41 (1H, dd, J = 6.2, 13.7 Hz), 5.00 (1H, broad), 5.33 (1H, d, J = 1.6 Hz).<br>[α]25D −90.6° (c = 1.37, CHCl3). |
| 21 (21-c) | Mp. 182-183° C.<br>[α]25D −110.3° (c = 0.85, MeOH).<br>1H-NMR (400 MHz, CD3OD): δ ppm: 1.10 (3H, t, J = 7.4 Hz), 1.48 (1H, dd, J = 7.5, 12.5 Hz), 2.03-2.08 (2H, m), 2.14 (2H, q, J = 7.4 Hz), 2.46 (1H, d, J = 16.2 Hz), 2.46-2.53 (1H, m), 2.51 (1H, d, J = 16.2 Hz), 2.85 (1H, quint, J = 7.5 Hz), 3.09-3.10 (1H, m), 3.14 (1H, d, J = 13.0 Hz), 3.18 (1H, d, J = 13.0 Hz), 5.38 (1H, dd, J = 1.7, 3.7 Hz).<br>IR (KBr): cm−1: 2962, 2928, 2897, 2877, 1559, 1527, 1403.<br>MS (FAB): m/z: 210 (M + H)+, 232 (M + Na)+.<br>Anal. calcd for C12H19NO2: C, 68.87; H, 9.15; N, 6.69; Found C, C, 65.55; H, 9.16; N, 6.45. |

TABLE 10

| | |
|---|---|
| 22 | Mp. 171-172° C.<br>[α]25D −59.6° (c = 1.02, MeOH)<br>1H-NMR (400 MHz, CD3OD): δ ppm: 1.11 (3H, t, J = 7.4 Hz), 1.51 (1H, dd, 7.4, 12.7 Hz), 2.06-2.20 (4H, m), 2.37 (3H, s), 2.49-2.56 (1H, m), 2.51 (2H, s), 2.87 (1H, quint, J = 7.4 Hz), 3.12-3.14 (1H, m), 3.28 (1H, d, J = 13.5 Hz), 3.33 (1H, d, J = 13.5 Hz), 5.31-5.32 (1H, m), 7.21-7.25 (2H, m), 7.69-7.72 (2H, m).<br>IR (KBr): cm−1: 3155, 2963, 1707, 1497, 1410, 1236, 1163, 1037, 812, 687, 567.<br>MS (FAB+): m/z: 210 (free + H)+; (FAB−): m/z: 208 (free − H)−, 171 (TsOH − H)−.<br>Anal. calcd for C19H27NO5S: C, 59.82; H, 7.21; N, 3.67; S, 8.41; Found C, 59.16; H, 7.21; N, 4.10; S, 8.53. |
| 23 (23-a) | 1H-NMR (400 MHz, CDCl3): δ ppm: 1.08 (3H, t, J = 7.6 Hz), 1.39 (1H, dd, J = 7.6, 12.1 Hz), 1.44 (18H, s), 1.98-2.02 (2H, m), 2.12 (2H, q, J = 7.6 Hz), 2.22 (1H, d, J = 14.5 Hz), 2.27 (1H, d, J = 14.5 Hz), 2.46-2.50 (1H, m), 2.80-2.88 (1H, m), 2.99-3.00 (1H, m), 3.33 (1H, dd, J = 6.2, 13.7 Hz), 3.41 (1H, dd, J = 6.2, 13.7 Hz), 5.00 (1H, broad), 5.33 (1H, d, J = 1.6 Hz).<br>[α]21D +68.1° (c = 1.37, CHCl3) |
| 23 (23-b) | 1H-NMR (400 MHz, CD3OD): δ ppm: 1.10 (3H, t, J = 7.4 Hz, Et), 1.48 (1H, dd, J = 7.5, 12.5 Hz), 2.03-2.08 (2H, m), 2.14 (2H, q, J = 7.4 Hz, Et), 2.46 (1H, d, J = 16.2 Hz), 2.46-2.53 (1H, m), 2.51 (1H, d, J = 16.2 Hz), 2.85 (1H, quint, J = 7.5 Hz), 3.09-3.10 (1H, m), 3.14 (1H, d, J = 13.0 Hz), 3.18 (1H, d, J = 13.0 Hz), 5.38 (1H, dd, J = 1.7, 3.7 Hz).<br>Mp. 163-166° C.<br>IR (KBr): cm−1: 2963, 2926, 2877, 1560, 1527, 1402<br>MS (FAB): m/z: 210 (M + H)+, 232 (M + Na)+.<br>Anal. calcd for C12H19NO2 0.7H2O: C, 64.95; H, 9.30; N, 6.30; Found C, 64.97; H, 9.08; N, 6.41.<br>[α]21D +96.2° (c = 1.0, MeOH) |
| 24 (24-a) | 1H-NMR (CDCl3, 400 MHz): δ 1.45 (9H, s), 1.56-1.61 (1H, m), 2.15 (1H, br d, J = 17.2 Hz), 2.34 (1H, ddd, J = 2.7, 8.6, 12.5 Hz), 2.49 (2H, s), 2.58 (1H, br dd, J = 7.8, 17.2 Hz), 2.90-2.99 (1H, m), 3.28 (1H, br s), 4.28 (2H, s), 4.78 (1H, d, J = 11.7 Hz), 4.84 (1H, d, J = 11.7 Hz), 5.58 (1H, br s). |

TABLE 10-continued

| | |
|---|---|
| 24 (24-b) | 1H-NMR (CDCl3, 400 MHz):<br>δ 1.45 (9H, s), 1.55-1.60 (1H, m), 2.04 (3H, s), 2.20 (1H, br d, J = 16.4 Hz), 2.34 (1H, ddd, J = 2.7, 9.0, 12.9 Hz), 2.49 (2H, s), 2.64 (1H, br dd, J = 7.8, 16.4 Hz), 2.89-2.98 (1H, m), 3.24 (2H, s), 3.28 (1H, br s), 4.77 (1H, d, J = 11.7 Hz), 4.84 (1H, d, J = 11.7 Hz), 5.48 (1H, br s). |
| 24 (24-c) | 1H-NMR (CDCl3, 500 MHz): δ 1.41-1.48 (1H, m), 1.44 (18H, s), 2.03 (3H, s), 2.05-2.09 (1H, m), 2.17 (1H, br d, J = 16.1 Hz), 2.24 (1H, d, J = 14.2 Hz), 2.28 (1H, d, J = 14.2 Hz), 2.57 (1H, br dd, J = 8.8, 16.1 Hz), 2.86-2.95 (1H, m), 3.07 (1H, br s), 3.22 (1H, d, J = 13.7 Hz), 3.26 (1H, d, J = 13.7 Hz), 3.34 (1H, dd, J = 5.9, 13.7 Hz), 3.42 (1H, dd, J = 5.9, 13.7 Hz), 5.00 (1H, br s), 5.55 (1H, br s). |
| 24 (24-d) | Mp: 165-167° C.<br>1H-NMR (CD3OD, 500 MHz): δ 1.51 (1H, dd, J = 7.3, 12.2 Hz), 2.02 (3H, s), 2.09 (1H, ddd, J = 2.4, 8.8, 12.2 Hz), 2.21 (1H, br d, J = 16.6 Hz), 2.51 (2H, s), 2.58 (1H, br dd, J = 7.8, 16.6 Hz), 2.87-2.94 (1H, m), 3.15 (1H, d, J = 13.2 Hz), 3.15-3.19 (1H, m), 3.21 (1H, d, J = 13.2 Hz), 3.23 (1H, d, J = 13.7 Hz), 3.27 (1H, d, J = 13.7 Hz), 5.58 (1H, br s).<br>MS (FAB): m/z: 242 (M + 1)+.<br>Anal. Calcd for C12H19NO2S: C 59.72; H 7.93; N 5.80; S 13.29; Found: C 58.72; H 8.03; N 5.71; S 13.12.<br>IR (KBr): cm−1: 2906, 2632, 1542, 1398, 1283. |
| 25 (25-b) | 1H-NMR (400 MHz, CDCl3): δ ppm:<br>1.40-1.50 (1H, m), 1.43 (9H, s), 1.51 (9H, s), 1.81 (3H, s), 1.96-2.08 (2H, m), 2.27 (2H, dd, J = 23 Hz, 14 Hz), 2.43-2.52 (1H, m), 2.81-2.91 (1H, m), 3.0 (1H, s), 3.31-3.46 (2H, m), 5.0 (1H, br.s), 5.34 (1H, m) |
| 25 (25-c) | 1H-NMR (400 MHz, CD3 OD): δ ppm:<br>1.46-1.53 (1H, m), 1.80 (3H, s), 2.1-2.17 (2H, m), 2.42-2.54 (3H, m), 2.78-2.90 (1H, m), 3.07-3.15 (1H, m), 5.25-5.30 (1H, m), 7.37-7.44 (3H, m), 7.78-7.84 (2H, m) |
| 25 (25-d) | 1H-NMR (400 MHz, CD3OD): δ ppm:<br>1.40 (1H, dd, J = 7.6, 12.3 Hz), 1.79 (3H, s), 2.02-2.08 (2H, m), 2.43-2.50 (1H, m), 2.45 (1H, d, J = 16.2 Hz), 2.51 (1H, d, J = 16.2 Hz), 2.85 (1H, quint, J = 7.6 Hz), 3.05-3.12 (1H, m), 3.13 (1H, d, J = 13.0 Hz), 3.17 (1H, d, J = 13.0 Hz), 5.36 (1H, t, J = 1.6 Hz).<br>IR (KBr): cm−1: 2946, 2927, 2905, 2832, 1564, 1525, 1396, 1384.<br>MS (FAB): m/z: 196 (M + H)+, 218 (M + Na)+.<br>Anal. calcd for C11H17NO2: C, 67.66; H, 8.78; N, 7.17; Found: C, 67.53; H, 8.90; N, 7.28.<br>[α]21D −140.4° (c = 1.23, MeOH) |

TABLE 11

| | |
|---|---|
| 26 (26-a) | 1H-NMR (400 MHz, CDCl3): δ ppm:<br>1.40-1.50 (1H, m), 1.43 (9H, s), 1.51 (9H, s), 1.81 (3H, s), 1.96-2.08 (2H, m), 2.27 (2H, dd, J = 23 Hz, 14 Hz), 2.43-2.52 (1H, m), 2.81-2.91 (1H, m), 3.0 (1H, s), 3.31-3.46 (2H, m), 5.0 (1H, br.s), 5.34 (1H, m) |
| 26 (26-b) | 1H-NMR (400 MHz, CD3 OD): δ ppm:<br>1.46-1.53 (1H, m), 1.80 (3H, s), 2.1-2.17 (2H, m), 2.42-2.54 (3H, m), 2.78-2.90 (1H, m), 3.07-3.15 (1H, m), 5.25-5.30 (1H, m), 7.37-7.44 (3H, m), 7.78-7.84 (2H, m) |
| 26 (26-c) | 1H-NMR (400 MHz, CD3OD): δ ppm:<br>1.40 (1H, dd, J = 7.6, 12.3 Hz), 1.79 (3H, s), 2.02-2.08 (2H, m), 2.43-2.50 (1H, m), 2.45 (1H, d, J = 16.2 Hz), 2.51 (1H, d, J = 16.2 Hz), 2.85 (1H, quint, J = 7.6 Hz), 3.05-3.12 (1H, m), 3.13 (1H, d, J = 13.0 Hz), 3.17 (1H, d, J = 13.0 Hz), 5.36 (1H, t, J = 1.6 Hz).<br>IR (KBr): cm−1: 2946, 2927, 2905, 2832, 1564, 1525, 1396, 1384.<br>MS (FAB): m/z: 196 (M + H)+, 218 (M + Na)+.<br>Anal. calcd for C11H17NO2: C, 67.66; H, 8.78; N, 7.17; Found: C, 67.46; H, 8.89; N, 7.25.<br>[α]21D +130.71° (c = 1.41, MeOH) |
| 27 (27-a) | 1H-NMR (400 MHz, CDCl3): δ ppm:<br>0.90 (1.5H, d, J = 6.4 Hz), 0.95 (1.5H, d, J = 6.4 Hz), 1.18 (1.5H, s), 1.23 (1.5H, s), 1.63-1.78 (1H, m), 2.39-2.64 (4H, m), 4.98-5.08 (2H, m), 5.72-5.86 (1H, m) |
| 27 (27-b) | 1H-NMR (400 MHz, CDCl3): δ ppm:<br>Major isomer<br>1.42 (9H, s), 1.56 (3H, s), 1.60 (3H, s), 2.07-2.20 (1H, m), 2.51-2.67 (2H, m), 2.69-2.83 (1H, m), 3.17-3.31 (1H, m), 3.59-3.70 (1H, m) |
| 27 (27-d) | 1H-NMR (400 MHz, CDCl3): δ ppm:<br>1.47 (9H, s), 1.61 (3H, s), 1.71 (3H, s), 2.04-2.27 (2H, m), 2.51-2.78 (2H, m), 2.51 (2H, dd, J = 16.6, 43.5 Hz), 2.65-2.79 (2H, m), 4.87 (2H, dd, J = 11.7, 39.6 Hz) |
| 27 (27-e) | 1H-NMR (400 MHz, CDCl3): δ ppm:<br>1.46 (9H, s), 1.56 (9H, s), 1.58 (3H, s), 1.68 (3H, s), 2.00-2.35 (3H, m), 2.46-2.56 (1H, m), 2.62-2.78 (1H, m), 2.95-3.02 (1H, m), 3.25-3.35 (1H, m), 3.46-3.57 (1H, m), 4.96-5.08 (1H, m) |
| 27 (27-f) | 1H-NMR (400 MHz, CD3OD): δ ppm:<br>1.47 (1H, dd, J = 7.2, 12.3 hz), 1.64 (3H, s), 1.68 (3H, s), 2.06-2.1 (1H, m), 2.1-2.18 (1, m), 2.46-2.55 (1H, m), 2.48 (2H, dd, J = 16.3, 39.5 Hz), 2.66-2.77 (1H, m), 2.87-2.93 (1H, m), 3.18 (2H, dd, 12.7, 32.9 Hz)<br>MS (FAB): m/z: 210 (M + H)+. |
| 28 (28-a) | 1H-NMR (400 MHz, CDCl3): δ ppm:<br>1.28 (3H, t, J = 7.1 Hz), 1.50-1.63 (1H, m), 1.72-1.83 (1H, m), 2.11-2.25 (2H, m), 2.42-2.51 (1H, m), 3.54-3.73 (2H, m), 4.17 (2H, q, J = 7.2 Hz), 4.99-5.07 (2H, m), 5.64-5.77 (1H, m), 5.81 (1H, d, J = 15.6 Hz), 6.77 (1H, dd, J = 6.77, 15.6 Hz). |
| 28 (28-b) | 1H-NMR (400 MHz, CDCl3): δ ppm:<br>1.30 (3H, t, J = 7.2 Hz), 1.58-1.76 (1H, m), 1.86-2.03 (1H, m), 2.15-2.30 (2H, m), 2.44-2.57 (1H, m), 4.19 (2H, q, J = 7.1 Hz), 5.00-5.11 (2H, m), 5.64-5.77 (1H, m), 5.85 (1H, d, J = 15.6 Hz), 6.77 (1H, dd, J = 6.77, 15.6 Hz). |
| 28 (28-c) | 1H-NMR (400 MHz, CDCl3): δ ppm:<br>1.45 (9H, s), 2.08-2.17 (1H, m), 2.26-2.37 (1H, m), 2.42-2.63 (4H, m), 2.83-2.95 (1H, m), 3.17-3.29 (1H, m), 4.52 (1H, t, J = 6.3 Hz), 4.64 (1H, t, J = 6.1 Hz), 4.76 (1H, d, J = 11.7 Hz), 4.84 (1H, d, J = 11.7 Hz), 5.4-5.44 (1H, m). |

TABLE 11-continued

| | |
|---|---|
| 28 (28-d) | 1H-NMR (400 MHz, CDCl3): δ ppm:<br>1.44 (18H, s), 1.50-1.60 (2H, m), 2.01-2.10 (2H, m), 2.21 (1H, d, J = 14.1 Hz), 2.27 (1H, d, J = 14.7 Hz), 2.45-2.60 (3H, m), 2.78-2.92 (1H, m), 3.00-3.07 (1H, m), 3.33 (1H, dd, J = 6.1, 13.9 Hz), 3.41 (1H, dd, J = 6.4, 13.9 Hz), 4.52 (1H, t, J = 6.3 Hz), 4.63 (1H, t, J = 6.3 Hz), 4.92-5.03 (1H, m). |
| 28 (28-e) | 1H-NMR (400 MHz, CD3OD): δ ppm:<br>1.50 (1H, dd, J = 7.4, 12.1 Hz), 2.03-2.16 (2H, m), 2.44-2.61 (5H, m), 2.81-2.92 (1H, m), 3.15 (1H, d, J = 12.9 Hz), 3.20 (1H, d, J = 12.9 Hz), 3.10-3.17 (1H, m), 4.50 (1H, t, J = 6.3 Hz), 4.64 (1H, t, J = 6.3 Hz), 5.46-5.53 (1H, m).<br>IR (KBr): cm−1: 1627, 1564, 1524, 1398, 1382.<br>MS (FAB): m/z: 228 (M + H)+.<br>Anal. calcd for C12H18NFO2: C, 63.42; H, 7.98; N, 6.16; F, 8.36; Found: C, 62.85; H, 8.04; N, 6.22; F, 8.39. |

TABLE 12

| | |
|---|---|
| 29 (29-a) | 1H-NMR (400 MHz, CDCl3): δ ppm: 1.30 (3H, s), 1.63-1.71 (1H, m), 2.06-2.20 (2H, m), 2.52 (1H, d, J = 15.9 Hz), 2.59 (1H, d, J = 15.9 Hz), 3.50 (1H, q, J = 7.4 Hz), 4.97 (1H, d, J = 10.3 Hz), 5.50 (1H, d, J = 17.1 Hz), 5.79-5.87 (1H, m). |
| 29 (29-b) | MS (FAB): m/z: 155 (M + H)+.<br>1H-NMR (400 MHz, CDCl3): δ ppm: 1.76 (3H, s), 2.35-2.41 (2H, m), 2.76-2.84 (3H, m), 4.02 (1H, s), 5.46 (1H, s). |
| 29 (29-c) | 1H-NMR (400 MHz, CDCl3): δ ppm: Major isomer 1.46 (9H, s), 1.71 (3H, s), 2.22-2.27 (1H, m), 2.59-2.72 (2H, m), 2.88-2.97 (1H, m), 3.27-3.35 (1H, m), 3.65-3.68 (1H, m), 5.39 (1H, s), 5.49-5.50 (1H, m):<br>Minor isomer 1.49 (9H, s), 1.77 (3H, s), 2.18-2.27 (1H, m), 2.47-2.97 (2H, m), 2.78-2.85 (1H, m), 2.88-2.97 (1H, m), 4.31-4.32 (1H, m), 5.41-5.42 (1H, m), 5.49-5.50 (1H, m). |
| 29 (29-d) | 1H-NMR (400 MHz, CDCl3): δ ppm: 1.44 (9H, s), 1.65 (1H, dd, J = 7.4, 12.9 Hz), 1.70 (3H, s), 2.12 (1H, dd, J = 1.6, 17.2 Hz), 2.20-2.25 (1H, m), 2.45-2.55 (1H, m), 2.49 (1H, d, J = 17.2 Hz), 2.55 (1H, d, J = 17.2 Hz), 2.85 (1H, quint, J = 7.8 Hz), 3.15-3.17 (1H, m), 4.82 (1H, d, J = 12.1 Hz), 4.90 (1H, d, J = 12.1 Hz), 5.56 (1H, s). |
| 29 (29-e) | Mp. 160° C. (decompose).<br>1H-NMR (400 MHz, CD3OD): δ ppm: 1.53 (1H, dd, J = 6.9, 12.9 Hz), 1.75 (3H, d, J = 1.8 Hz), 2.08-2.17 (2H, m), 2.46 (1H, d, J = 16.2 Hz), 2.47-2.54 (1H, m), 2.56 (1H, d, J = 16.2 Hz), 2.84 (1H, quint, J = 6.9 Hz), 2.86-2.88 (1H, m), 3.16 (1H, dd, J = 1.2, 13.2 Hz), 3.23 (1H, dd, J = 1.2, 13.2 Hz), 5.54 (1H, s).<br>IR (KBr): cm−1: 3029, 2950, 2937, 2910, 1889, 2842, 1631, 1589, 1500, 1396, 1188, 1024, 680, 603.<br>MS (FAB): m/z: 196 (M + H)+, 218 (M + Na)+.<br>Anal. calcd for C11H17NO2: C, 67.66; H, 8.78; N, 7.17; Found C, 66.43; H, 8.77; N, 7.11. |
| 30 | 1H-NMR (400 MHz, CDCl3): δ ppm: 1.09 (3H, t, J = 7.8 Hz), 1.44 (9H, s), 1.44-1.46 (1H, m), 1.97-2.05 (2H, m), 2.13 (2H, q, J = 7.8 Hz), 2.28 (1H, d, J = 14.1 Hz), 2.35 (1H, d, J = 14.1 Hz), 2.43-2.51 (1H, m), 2.76 (1H, quint. J = 7.6 Hz), 2.92 (2H, s), 2.98-2.99 (1H, m), 5.35-5.35 (1H, m).<br>MS (FAB+): m/z: 296 (M + H)+, 334 (M + K)+. |
| 31 | Mp. 172-173° C.<br>[α]20D −68.1° (c 0.98, MeOH).<br>1H-NMR (400 MHz, CD3OD): δ ppm: 1.11 (3H, t, J = 7.4 Hz), 1.50 (1H, dd, J = 7.5, 12.6 Hz), 2.08 (1H, d, 16.5 Hz), 2.10-2.20 (3H, m), 2.46-2.56 (3H, m), 2.87 (1H, quint. J = 7.5 Hz), 3.12-3.13 (1H, m), 3.28 (1H, d, J = 13.4 Hz), 3.33 (1H, d, J = 13.4 Hz), 5.31 (1H, d, J = 1.8 Hz), 7.39-7.45 (3H, m), 7.80-7.85 (2H, m).<br>IR (KBr): cm−1: 3197, 3149, 3054, 2964, 2927, 2878, 2831, 1714, 1495, 1445, 1410, 1220, 1164, 1123, 1019, 730.<br>MS (FAB+): m/z: 210 (free + H)+, (FAB−): m/z: 157 (bensensulfonic acid-H)−.<br>Anal. calcd for C18H25NO5S: C, 58.83; H, 6.86; N, 3.81; S, 8.73; Found C, 58.69; H, 6.94; N, 3.99; S, 8.73. |
| 32 (32-a) | 1H-NMR (400 MHz, CDCl3): δ ppm: 2.06-2.31 (2H, m), 2.82-2.87 (2H, m), 3.11-3.15 (2H, m), 3.68 (3H, s), 5.59-5.61 (1H, m). |
| 32 (32-b) | 1H-NMR (400 MHz, CDCl3): δ ppm: 1.94-2.03 (2H, m), 2.65-2.75 (4H, m), 4.00-4.02 (2H, m), 5.31-5.35 (1H, m). |
| 32 (32-c) | 1H-NMR (400 MHz, CDCl3): δ ppm: 1.81-2.05 (6H, m), 3.59 (2H, t, J = 7.1 Hz), 3.73-3.77 (3H, m), 5.03-5.07 (2H, m), 5.88-5.95 (1H, m). |
| 32 (32-d) | 1H-NMR (400 MHz, CDCl3): δ ppm: 1.66 (1H, dd, J = 4.2, 14.0 Hz), 1.82-1.88 (4H, m), 1.94-2.08 (3H, m), 2.42-2.44 (2H, m), 2.67 (1H, d, J = 3.9 Hz), 3.70 (3H, s), 4.02-4.07 (1H, m), 5.11-5.14 (2H, m), 5.94 (1H, dd, J = 10.3, 17.6 Hz).<br>MS (FAB): m/z: 199 (M + H) +. |
| 32 (32-e) | 1H-NMR (400 MHz, CDCl3): δ ppm: 1.70 (1H, dd, J = 3.9, 14.8 Hz), 1.83-2.11 (7H, m), 2.48-2.50 (2H, m), 4.04-4.10 (1H, m), 5.13-5.17 (2H, m), 5.95 (1H, dd, J = 10.2, 17.6 Hz).<br>MS (FAB): m/z: 185 (M + H)+, 207 (M + Na) +. |
| 32 (32-f) | 1H-NMR (400 MHz, CDCl3): δ ppm: Major isomer 1.45 (9H, s), 1.79-2.19 (7H, m), 2.68-2.76 (1H, m), 2.78-2.89 (1H, m), 3.10-3.18 (1H, m), 3.85-3.87 (1H, m), 5.36-5.91 (3H, m):<br>Minor isomer 1.47 (9H, s), 1.79-2.19 (7H, m), 2.49-2.54 (1H, m), 2.68-2.76 (2H, m), 4.28-4.10 (1H, m), 5.36-5.91 (3H, m).<br>MS (FAB): m/z: 247 (M + H) +, 285 (M + K) +. |
| 32 (32-g) | 1H-NMR (400 MHz, CDCl3): δ ppm: 1.45 (9H, s), 1.57 (1H, dd, J = 7.6, 12.9 Hz), 1.76-2.05 (6H, m), 2.15 (1H, ddd, J = 2.7, 9.0, 12.9 Hz), 2.42 (2H, s), 2.80 (1H, q, J = 7.8 Hz), 3.25 (1H, d, 7.8 Hz), 4.75 (1H, d, J = 11.5 Hz), 4.85 (1H, d, J = 11.5 Hz), 5.52 (1H, dd, J = 2.4, 5.5 Hz), 6.01 (1H, d, J = 5.5 Hz).<br>MS (FAB): m/z: 308 (M + H) +, 346 (M + K) +. |

TABLE 13

| | | |
|---|---|---|
| 32 (32-h) | | Mp.: 180-190° C.<br>1H-NMR (400 MHz, CD3OD): δ ppm: 1.53 (1H, dd, J = 7.7, 12.4 Hz), 1.75-2.07 (7H, m), 2.40 (1H, d, J = 16.1 Hz), 2.45 (1H, d, J = 16.1 Hz), 2.80 (1H, quint. J = 7.5 Hz), 3.12-3.14 (1H, m), 3.14 (1H, d, J = 13.2 Hz), 3.19 (1H, d, J = 13.2 Hz), 5.63 (1H, dd, J = 2.3, 5.7 Hz), 6.00 (1H, dd, J = 0.6, 5.7 Hz).<br>IR (KBr): cm−1: 3029, 2969, 2943, 2925, 1740, 1617, 1510, 1394, 748.<br>MS (FAB): m/z: 222 (M + H)+.<br>Anal. calcd for C13H19NO2: C, 70.56; H, 8.65; N, 6.33; Found C, 69.82; H, 8.80; N, 6.34. |
| 33 (33-a) | | 1H-NMR (400 MHz, CDCl3): δ ppm: 1.63-1.70 (2H, m), 1.72-1.79 (2H, m), 2.42-2.46 (2H, m), 2.76-2.79 (2H, m), 3.69 (3H, s), 5.80-5.82 (1H, m). |
| 33 (33-b) | | 1H-NMR (400 MHz, CDCl3): δ ppm: 1.59-1.72 (4H, m), 2.24-2.32 (4H, m), 4.11-4.15 (2H, m), 5.49-5.54 (1H, m). |
| 33 (33-c) | | 1H-NMR (400 MHz, CDCl3): δ ppm: 1.40-1.45 (2H, m), 1.59-1.74 (8H, m), 3.65 (2H, t, J = 7.2 Hz), 4.96-5.02 (2H, m), 5.10 (1H, s), 5.10 (1H, dd, J = 10.6, 17.2 Hz). |
| 33 (33-d) | | 1H-NMR (400 MHz, CDCl3): δ ppm: 1.40-1.74 (10H, m), 2.44-2.26 (2H, m), 2.71 (1H, d, J = 7.5 Hz), 3.70 (3H, s), 4.10-4.15 (1H, m), 5.03 (1H, d, J = 17.2 Hz), 5.07 (1H, d, J = 10.7 Hz), 5.86 (1H, dd, J = 10.7, 17.2 Hz).<br>MS (FAB): m/z: 212 (M + H) +. |
| 33 (33-e) | | 1H-NMR (400 MHz, CDCl3): δ ppm: 1.40-1.79 (10H, m), 2.49-2.51 (2H, m), 4.11-4.17 (1H, m), 5.06 (1H, d, J = 17.6 Hz), 5.10 (1H, d, J = 10.8 Hz), 5.88 (1H, dd, J = 10.8, 17.6 Hz).<br>MS (FAB): m/z: 199 (M + H)+, 221 (M + Na) +. |
| 33 (33-f) | | 1H-NMR (400 MHz, CDCl3): δ ppm: Major isomer: 1.46 (9H, s), 1.43-1.76 (7H, m), 2.70-2.58 (2H, m), 2.90-2.93 (1H, m), 3.04-3.08 (1H, m), 3.87-3.88 (1H, m), 5.49-5.52 (2H, m), 5.62-5.52 (1H, m): Minor isomer: 1.48 (9H, s), 1.43-1.76 (7H, m), 2.70-2.58 (2H, m), 2.85-2.88 (1H, m), 3.09-3.12 (1H, m), 5.37-5.38 (1H, m), 5.62-5.65 (1H, m), 5.69-5.71 (1H, m).<br>MS (FAB): m/z: 261 (M + H) +. |
| 33 (33-g) | | 1H-NMR (400 MHz, CDCl3): δ ppm: 1.37-1.66 (8H, m), 1.45 (9H, s), 1.75 (1H, dd, J = 8.0, 12.9 Hz), 2.07 (1H, ddd, J = 3.1, 8.6, 12.5 Hz), 2.46 (2H, s), 2.54-2.60 (1H, m), 3.27-3.28 (1H, m), 4.75 (1H, d, J = 11.3 Hz), 4.85 (1H, d, J = 11.3 Hz), 5.52 (1H, dd, J = 2.4, 5.5 Hz), 5.75 (1H, d, J = 5.5 Hz). |
| 33 (33-h) | | Mp. 178-180° C.<br>1H-NMR (400 MHz, CD3OD): δ ppm: 1.37-1.46 (2H, m), 1.53-1.87 (9H, m), 2.44 (1H, d, J = 16.3 Hz), 2.49 (1H, d, J = 16.3 Hz), 2.57 (1H, dd, J = 8.1, 14.5 Hz), 2.85 (1H, quint. J = 7.5 Hz), 3.14 (1H, d, J = 13.1 Hz), 3.20 (1H, d, J = 13.1 Hz), 5.62-5.64 (1H, m), 5.72-5.74 (1H, m).<br>IR (KBr): cm−1: 3504, 3448, 3020, 2940, 2864, 1557, 1511, 1405, 1291, 1260, 757.<br>MS (FAB): m/z: 236 (M + H)+.<br>Anal. calcd for C14H21NO2: C, 71.46; H, 8.99; N, 5.95; Found C, 68.84; H, 9.81; N, 5.80. |
| 34 (34-a) | | 1H-NMR (400 MHz, CDCl3): δ ppm: 1.26 (3H, t, J = 7.3 Hz), 1.68-1.92 (4H, m), 1.97-2.13 (2H, m), 2.17-2.29 (2H, m), 2.43 (1H, ddd, J = 4.9, 6.8, 11.7 Hz), 2.47-2.54 (1H, m), 4.14 (2H, dq, J = 2.9, 7.3 Hz), 5.01 (1H, d-quint, J = 9.8, 1.0 Hz), 5.07 (1H, dt, J = 17.1, 1.5 Hz), 5.76 (1H, ddt, J = 9.8, 17.1, 7.3 Hz). |
| 34 (34-d) | | 1H-NMR (500 MHz, CDCl3): δ ppm: E/Z mixture 1.48 (isomerA9H, s), 1.52 (isomerB9H, s), 1.77-1.83 (1H, m), 1.90-2.23 (6H, m), 2.45-2.72 (2H, m), 2.91-2.99 (isomerB1H + 1H, m), 3.00-3.06 (1H, m), 3.33 (isomerA1H, ddt, J = 8.8, 19.0, 2.9 Hz), 3.90 (isomerA1H, br), 4.33 (isomerB1H, br), 5.24 (isomerA1H, br), 5.38 (isomerB1H, br), 5.45-5.48 (isomerB1H, m), 5.48-5.51 (isomerA1H, m). |
| 34 (34-e) | | 1H-NMR (500 MHz, CDCl3): δ ppm: 1.49 (9H, s), 1.79-1.89 (1H, m), 1.92-2.23 (6H, m), 2.33 (1H, ddd, J = 2.9, 8.8, 12.7 Hz), 2.46-2.54 (3H, m), 2.90 (1H, quint, J = 7.3 Hz), 3.01-3.09 (1H, m), 3.25 (1H, br), 4.78 (1H, d, J = 12.2 Hz), 4.88 (1H, d, J = 12.2 Hz), 5.28 (1H, br). |
| 34 (34-f) | | 1H-NMR (400 MHz, CDCl3): δ ppm: 1.33-1.42 (10H, m), 1.73-1.80 (1H, m), 1.85-1.99 (5H, m), 2.04-2.15 (2H, m), 2.21 (1H, d, J = 13.7 Hz), 2.28 (1H, d, J = 13.7 Hz), 2.40 (1H, ddd, J = 1.2, 7.8, 16.4 Hz), 2.70 (1H, quint, J = 7.8 Hz), 2.81 (2H, s), 2.91 (1H, br), 2.95-3.03 (1H, m), 5.32 (1H, br). |
| 34 (34-g) | | Mp. 157-159° C.;<br>1H-NMR (500 MHz, CD3OD): δ ppm: 1.50 (1H, dd, J = 7.8, 12.2 Hz), 1.83-2.20 (8H, m), 2.45-2.50 (1H, m), 2.52 (2H, d, J = 4.9 Hz), 2.89 (1H, quint, J = 7.8 Hz), 3.08 (1H, quint, J = 8.3 Hz), 3.14 (1H, br), 3.17 (1H, d, J = 12.7 Hz), 3.21 (1H, d, J = 12.7 Hz), 5.40 (1H, br).<br>IR (KCl): cm−1: 1616, 1503, 1395.<br>MS (ESI+): m/z: 274 (M + K)+, 258 (M + Na)+, 236 (M + H)+.<br>HRMS (ESI+) calcd for (M +H)+: 258.14700. Found 258.14669 (−0.31 mmu). |
| 35 (35-a) | | 1H-NMR (400 MHz, CDCl3): δ ppm: E/Z mixture 1.02-1.09 (3H, m), 2.14-2.26 (4H, m), 2.61 (isomerA2H, q, J = 7.4 Hz), 2.68 (isomerB2H, dd, J = 7.4, 8.2 Hz), 3.67 (3H, s), 4.92-5.07 (2H, m), 5.61 (isomerA1H, s), 5.64 (isomerB1H, s), 5.73-5.89 (1H, m). |

TABLE 14

| | | |
|---|---|---|
| 35 (35-b) | | 1H-NMR (500 MHz, CDCl3): δ ppm: E/Z mixture 1.11 (3H, t, J = 7.8 Hz), 2.22-2.33 (4H, m), 2.66 (isomerA2H, q, J = 7.8 Hz), 2.74 (isomerB2H, t, J = 7.8 Hz), 4.98-5.13 (2H, m), 5.67 (isomerA1H, s), 5.71 (isomerB1H, s), 5.79-5.91 (1H, m). |
| 35 (35-c) | | 1H-NMR (500 MHz, CDCl3): δ ppm: E/Z mixture 1.09 (3H, t, J = 7.3 Hz), 1.48 (9H, s), 1.95-2.03 (1H, m), 2.13-2.21 (1H, m), 2.26-2.33 (1H, m), 3.63-2.73 (2H, m), 2.96 (1H, quint, J = 7.3 Hz), 3.34 (1H, ddt, J = 8.3, 18.1, 2.4 Hz), 3.78 (1H, br), 5.42 (1H, br), 5.51 (1H, ddd, J = 1.5, 2.0, 3.4 Hz). |
| 35 (35-d) | | 1H-NMR (500 MHz, CDCl3): δ ppm: 1.08 (3H, t, J = 7.3 Hz), 1.46 (9H, s), 1.68 (1H, dd, J = 7.3, 12.7 Hz), 1.87-1.96 (1H, m), 2.10-2.20 (2H, m), 2.24 (1H, ddd, J = 2.4, 8.8, 12.7 Hz), 2.50 (1H, d, J = 17.1 Hz), 2.53-2.60 (1H, m), 2.87 (1H, quint, J = 7.8 Hz), 3.28-3.32 (1H, m), 4.83 (1H, d, J = 12.2 Hz), 4.95 (1H, d, J = 12.2 Hz), 5.60 (1H, br). |
| 35 (35-e) | | 1H-NMR (500 MHz, CDCl3): δ ppm: 1.09 (3H, t, J = 7.3 Hz), 1.45 (9H, s), 1.70 (1H, dd, J = 6.8, 12.2 Hz), 1.87-1.95 (1H, m), 1.96 (1H, ddd, J = 2.4, 9.3, 12.2 Hz), 2.09-2.19 (2H, m), 2.29 (1H, d, J = 13.7 Hz), 2.35 (1H, d, J = 13.7 Hz), 2.49-2.58 (1H, m), 2.75 (1H, quint, J-7.8 Hz), 2.90 (2H, s), 2.93-2.97 (1H, br), 5.54 (1H, s). |

TABLE 14-continued

| | |
|---|---|
| 35 (35-f) | Mp. 152-155° C.;<br>1H-NMR (500 MHz, CD3OD): δ ppm: 1.10 (3H, t, J = 7.3 Hz), 1.54 (1H, dd, J = 7.3, 12.7 Hz), 1.68 (1H, m), 2.15-2.28 (3H, m), 2.47 (1H, d, J = 16.1 Hz), 2.54 (1H, ddt, J = 2.0, 2.9, 8.3 Hz), 2.57 (1H, d, J = 16.1 Hz), 2.86 (1H, quint, J = 7.8 Hz), 2.97-3.01 (1H, m), 3.19 (1H, d, J = 13.2 Hz), 3.26 (1H, d, J = 13.2 Hz), 5.61 (1H, s).<br>IR (KCl): cm−1: 1624, 1499, 1394, 1296, 1197, 1025.<br>MS (ESI+): m/z: 254 (M + 2Na − H)+, 232 (M + Na)+, 210 (M + H)+.<br>HRMS (ESI+) calcd for (M + H)+: 210.14940. Found 210.14898 (−0.42 mmu).<br>Anal. calcd for C12H19NO2: C, 68.87; H, 9.15; N, 6.69; O, 15.29. Found C, 68.22; H, 9.04; N, 6.88; O, 16.05. |
| 36 | Mp. 98-99° C.;<br>1H-NMR (500 MHz, CDCl3): δ ppm:<br>1.13 (3H, t, J = 7.3 Hz), 1.55 (1H, dd, J = 7.8, 12.7 Hz), 2.12 (1H, d, J = 16.6 Hz), 2.20 (2H, q, J = 7.3 Hz), 2.26 (1H, ddd, J = 3.4, 7.8, 12.7 Hz), 2.55 (1H, dd, J = 7.8, 16.6 Hz), 2.60 (2H, d, J = 3.4 Hz), 2.94 (1H, quint, J = 7.8 Hz), 3.24 (1H, br), 3.63 (1H, d, J = 13.2 Hz), 3.68 (1H, d, J = 13.2 Hz), 5.32 (1H, s).<br>IR (KCl): cm−1: 1700, 1443, 1246.<br>MS (ESI+): m/z: 226 (M + H)+.<br>HRMS (ESI+): calcd for (M + H)+: 226.14432. Found 226.14259 (−1.72 mmu).<br>Anal. calcd for C12H2ONO3Cl: C, 55.06; H, 7.70; N, 5.35; O, 18.34; Cl, 13.54. Found C, 53.67; H, 7.71; N, 5.36; O, 18.09; Cl, 13.50. |
| 37 | Mp. 167-169° C.;<br>1H-NMR (500 MHz, CDCl3): δ ppm: 1.14 (3H, t, J = 7.3 Hz), 1.54 (1H, dd, J = 7.3, 11.7 Hz), 2.06-2.14 (2H, m), 2.20 (1H, q, J = 7.3 Hz), 2.54 (1H, dd, J = 7.3, 17.1 Hz), 2.71 (1H, d, J = 15.6 Hz), 2.81 (1H, d, J = 15.6 Hz), 2.95 (2H, s), 2.96 (1H, m), 3.04 (1H, br), 5.42 (1H, s).<br>MS (ESI+): m/z: 254 (M + 2Na − H)+, 232 (M + Na)+, 210 (M + H)+.<br>HRMS (ESI+) calcd for (M + H)+: 210.14940. Found 210.14842 (−0.98 mmu).<br>Anal. calcd for C12H19NO2: C, 68.87; H, 9.15; N, 6.69; O, 15.29. Found C, 67.32; H, 9.05; N, 6.53; O, 16.30. |
| 38 (38-a) | 1H-NMR (400 MHz, CDCl3): δ ppm: E/Z mixture 1.31 (isomerB3H, s), 1.31 (isomerA3H, s), 1.46 (isomerA9H, d, J = 1.2 Hz), 1.49 (isomerB9H, d, J = 0.8 Hz), 2.34-2.50 (2H, m), 2.54 (isomerB1H, dt, J = 17.6, 2.7 Hz), 2.67 (isomerB1H, dt, J = 17.6, 2.7 Hz), 2.91 (isomerA1H, dt, J = 18.0, 2.3 Hz), 2.93 (isomerA1H, dt, J = 18.0, 2.3 Hz), 3.45 (isomerA1H, br), 3.87 (ismerB1H, br), 5.53-5.55 (isomerB1H, m), 5.57-5.61 (isomerA1H, m), 5.57-5.60 (isomerB2H, m), 5.74-5.82 (isomerA2H, m). |
| 38 (38-b) | 1H-NMR (500 MHz, CDCl3): δ ppm: 1.31 (isomerB3H, s), 1.35 (isomerA3H, s), 1.45 (isomerA9H, s), 1.46 (isomerB9H, s), 1.73 (isomerB1H, d, J = 13.2 Hz), 1.86 (isomerA1H, d, J = 13.2 Hz), 1.94 (isomerA1H, dd, J = 2.0, 13.2 Hz), 2.10 (isomerB1H, dd, J = 2.4, 13.2 Hz), 2.24-2.38 (2H, m), 2.47 (isomerA2H, s), 2.75 (isomerB2H, s), 2.86 (isomerB1H, br), 2.89 (isomerA1H, br), 4.55 (isomerA1H, d, J = 12.7 Hz), 4.62 (isomerA1H, d, J = 12.7 Hz), 4.81 (isomerB1H, d, J = 11.7 Hz), 4.94 (isomerB1H, d, J = 11.7 Hz), 5.06 (isomerA1H, dt, J = 7.8, 2.4 Hz), 5.72 (isomerB1H, dt, J = 7.8, 2.4 Hz), 5.90 (isomerA1H, dq, J = 7.8, 2.0 Hz), 5.92 (isomerB1H, dq, J = 7.8, 2.0 Hz). |
| 38 (38-c) | 1H-NMR (500 MHz, CDCl3): δ ppm: 1.29 (isomerA3H, s), 1.31 (isomerB3H, s), 1.44 (isomerA9H, s), 1.46 (isomerB9H, s), 1.57 (isomerB1H, d, J = 12.2 Hz), 1.67 (isomerA1H, d, J = 12.2 Hz), 1.76 (isomerA1H, d, J = 12.2 Hz), 1.90 (isomerB1H, d, J = 12.2 Hz), 2.19-2.35 (2H + isomerA2H, m), 2.55-2.77 (1H + isomerB4H, m), 2.92 (isomerA1H, d, J = 13.2 Hz), 2.94 (isomerA1H, d, J = 13.2 Hz), 5.70 (1H, br), 5.82-5.83 (1H, m). |

TABLE 15

| | |
|---|---|
| 38 (38-d) | Mp. 177-178° C.;<br>1H-NMR (400 MHz, CD3OD): δ ppm: 1.33 (isomerA3H, s), 1.36 (isomerB3H, s), 1.71 (isomerA1H, d, J = 12.5 Hz), 1.76 (isomerB1H, d, J = 12.5 Hz), 1.89 (isomerA1H, d, J = 12.5 Hz), 2.21-2.23 (isomerB1H, m), 2.25-2.28 (isomerA1H, m), 2.33-2.37 (isomerA1H, m), 2.38-2.41 (isomerB1H, m), 2.48 (isomerB2H, s), 2.70 (isomerB1H, br), 2.76 (isomerB1H, d, J = 15.6 Hz), 2.79 (isomerB1H, br), 2.85 (isomerA1H, d, J = 15.6 Hz), 2.92 (isomerB2H, s), 3.18 (isomerA1H, d, J = 12.9 Hz), 3.27 (isomerA1H, d, J = 12.9 Hz), 5.68-5.74 (1H, m), 5.88 (isomerA1H, ddd, J = 2.0, 3.5, 5.9 Hz), 5.93 (isomerB1H, ddd, J = 2.0, 3.5, 5.9 Hz).<br>IR (KCl): cm−1: 1632, 1508, 1397, 711.<br>MS (ESI+): m/z: 250 (M + Na + MeOH)+, 240 (M + 2Na − H)+, 218 (M + Na)+, 196 (M + H)+.<br>HRMS (ESI+) calcd for (M + H)+: 196.13375. Found 196.13106 (−2.69 mmu).<br>Anal. calcd for C11H17NO2: C, 67.66; H, 8.78; N, 7.17. Found C, 67.31; H, 8.97; N, 7.16. |
| 39 (39-a) | 1H NMR (CDCl3, 400 MHz): Two isomers:<br>δ 1.16 (1.5H, d, J = 7.4 Hz) and 1.34 (1.5H, d, J = 7.0 Hz), 1.46 (4.5H, s) and 1.49 (4.5H, s), 1.61-1.72 (1H, m), 2.30-2.38 (1H, m), 2.43-2.51 (1H, m), 2.62-2.73 (1H, m), 3.85-3.93 (0.5H, m) and 4.30-4.34 (0.5H, m), 5.38-5.39 (0.5H, m) and 5.44-5.46 (0.5H, m), 5.59-5.65 (0.5H, m) and 5.77-5.89 (1.5H, m). |
| 39 (39-b) | 1H NMR (CDCl3, 400 MHz): Three isomers:<br>δ 0.93 (0.9H, d, J = 7.8 Hz) and 0.97 (1.2H, d, J = 7.0 Hz) and 1.04 (0.9H, d, J = 7.4 Hz), 1.44 (2.7H, s) and 1.46 (2.7H, s) and 1.47 (3.6H, s), 2.02-2.22 (1H, m), 2.35-2.42 (1H, m), 2.44-2.49 (2H, m), 2.52-2.59 (1H, m), 2.65-2.67 (1H, m), 3.05-3.12 (0.3H, m) and 3.18-3.22 (0.4H, m) and 3.33-3.37 (0.3H, m), 4.61 (0.4H, d, J = 12.1 Hz) and 4.71 (0.3H, d, J = 12.1 Hz) and 4.81 (0.3H, d, J = 11.7 Hz), 4.76 (0.4H, d, J = 12.1 Hz) and 4.92 (0.3H, d, J = 11.7 Hz) and 4.98 (0.3H, d, J = 12.1 Hz), 5.65-5.69 (0.6H) and 5.71-5.74 (0.4H), 5.90-5.96 (1H, m). |
| 39 (39-c) | 1H NMR (CDCl3, 400 MHz): Two major isomers:<br>δ 0.89 (1.8H, d, J = 7.8 Hz) and 0.99 (1.2H, d, J = 7.4 Hz), 1.42-1.47 (19H, m), 2.04-2.17 (1H, m), 2.26-2.36 (2H, m), 2.40-2.47 (2H, m), 2.97-3.03 (1H, m), 3.18-3.22 (0.4H, m) and 3.31 (0.6H, dt, J = 11.3, 13.7 Hz), 3.40-3.54 (1H, m), 4.89 (0.4H, br s) and 5.01 (0.6H, br s), 5.71-5.86 (2H, m). |

TABLE 15-continued

| | |
|---|---|
| 39 (39-d) | 1H NMR (CD3OD, 400 MHz): Two major isomers:<br>δ 0.99 (1.5H, d, J = 7.8 Hz) and 1.03 (1.5H, d, J = 7.0 Hz), 1.81-1.92 (0.5H, m) and 2.13-2.20 (0.5H, m), 2.26-2.51 (4H, m), 2.64-2.75 (1H, m), 2.94-2.99 (1H, m), 3.08-3.24 (2H, m), 5.77-5.81 (1H, m), 5.88-5.95 (1H, m).<br>MS (EI): m/z: 195 (M+).<br>Anal. Calcd for C11H17NO2: C 67.66; H 8.78; N 7.17; Found: C 67.00; H 8.83; N 7.18.<br>IR (KBr): cm−1: 2951, 2651, 1628, 1540, 1399, 652. |
| 40 (40-a) | 1H NMR (CDCl3, 400 MHz):<br>δ 1.08 (3H, t, J = 7.4 Hz), 1.46 (9H, s), 1.51-1.58 (1H, m), 1.92-2.04 (2H, m), 2.13 (2H, q, J = 7.4 Hz), 2.31 (1H, d, J = 14.1 Hz), 2.39 (1H, d, J = 14.1 Hz), 2.47 (1H, dd, J = 7.8, 16.4 Hz), 2.76-2.84 (1H, m), 2.98-3.03 (1H, m), 3.32 (1H, dd, J = 6.3, 14.5 Hz), 3.47 (1H, dd, J = 6.3, 14.5 Hz), 2.72 (1H, br s), 5.31-5.33 (1H, m). |
| 40 (40-b) | 1H NMR (CDCl3, 400 MHz):<br>δ 1.08 (3H, t, J = 7.4 Hz), 1.46-1.47 (1H, m), 1.47 (9H, s), 1.98-2.00 (1H, m), 2.02-2.04 (1H, m), 2.09-2.16 (2H, m), 2.32-2.38 (1H, m), 2.43-2.49 (2H, m), 2.79-2.83 (1H, m), 3.02 (3H, s), 3.18-3.20 (1H, m), 3.35-3.44 (1H, m), 3.64-3.72 (1H, m), 5.32-5.34 (1H, m). |
| 40 (40-c) | Mp. 177-179° C.<br>1H NMR (CD3OD, 400 MHz):<br>δ 1.11 (3H, t, J = 7.4 Hz), 1.51 (1H, dd, J = 7.4, 12.5 Hz), 2.08-2.12 (1H, m), 2.15-2.21 (3H, m), 2.50-2.56 (1H, m), 2.54 (2H, s), 2.77 (3H, s), 2.87-2.95 (1H, m), 3.14-3.19 (1H, m), 3.35 (1H, d, J = 12.9 Hz), 3.40 (1H, d, J = 12.9 Hz), 5.30-5.33 (1H, m).<br>MS (FAB): m/z: 224 (M (free) + H)+.<br>Anal. Calcd for C13H22NO2Cl: C 60.11; H 8.54; N 5.39; Cl 13.65; Found: C 58.70; H 8.43; N 5.32; Cl 15.67.<br>IR (KBr): cm−1: 2965, 1714, 1467, 1208, 1020, 788. |
| 41 (41-a) | 1H NMR (CDCl3, 400 MHz):<br>δ 0.04 (6H, s), 0.87 (3H, t, J = 7.4 Hz), 0.89 (9H, s), 1.17-1.30 (1H, m), 1.51-1.60 (1H, m), 2.03-2.11 (1H, m), 3.49 (1H, dd, J = 6.3, 9.8 Hz), 3.53 (1H, dd, J = 6.3, 9.8 Hz), 5.00-5.03 (1H, m), 5.05-5.06 (1H, m), 5.57-5.66 (1H, m). |

TABLE 16

| | |
|---|---|
| 41 (41-b) | 1H NMR (CDCl3, 400 MHz):<br>δ 0.87 (3H, t, J = 7.4 Hz), 1.29 (3H, t, J = 7.4 Hz), 1.29-1.36 (1H, m), 1.41-1.51 (1H, m), 2.03-2.12 (1H, m), 2.17-2.31 (2H, m), 4.18 (2H, q, J = 7.4 Hz), 4.97-5.05 (2H, m), 5.53-5.62 (1H, m), 5.81 (1H, d, J = 15.6 Hz), 6.91 (1H, dt, J = 7.4, 15.6 Hz). |
| 41 (41-c) | 1H NMR (CDCl3, 500 MHz):<br>δ 0.88 (3H, t, J = 7.3 Hz), 1.25-1.35 (1H, m), 1.42-1.50 (1H, m), 2.05-2.12 (1H, m), 2.20-2.27 (1H, m), 2.29-2.35 (1H, m), 4.98-5.06 (2H, m), 5.53-5.60 (1H, m), 5.82 (1H, d, J = 15.6 Hz), 7.03 (1H, dt, J = 7.8, 15.6 Hz). |
| 41 (41-d) | 1H NMR (CDCl3, 400 MHz):<br>Major isomer:<br>δ 0.86 (3H, t, J = 7.4 Hz), 1.23-1.38 (2H, m), 1.45 (9H, s), 2.45-2.51 (1H, m), 2.54-2.62 (1H, m), 2.97-3.07 (1H, m), 3.25-3.33 (1H, m), 3.86-3.90 (1H, m), 5.48-5.50 (1H, m), 5.57-5.63 (1H, m), 5.79-5.84 (1H, m).<br>Minor isomer:<br>δ 0.93 (3H, t, J = 7.4 Hz), 1.23-1.38 (2H, m), 1.49 (9H, s), 2.40-2.43 (1H, m), 2.65-2.68 (1H, m), 2.78-2.86 (1H, m), 2.88-2.96 (1H, m), 4.30-4.33 (1H, m), 5.36-5.38 (1H, m), 5.65-5.68 (1H, m), 5.79-5.84 (1H, m). |
| 41 (41-e) | 1H NMR (CDCl3, 400 MHz):<br>Major isomer:<br>δ 0.83 (3H, t, J = 7.4 Hz), 1.18-1.34 (2H, m), 1.45 (9H, s), 1.50-1.54 (1H, m), 2.29 (1H, ddd, J = 2.7, 8.9, 12.9 Hz), 2.33-2.38 (1H, m), 2.46 (2H, s), 2.50-2.56 (1H, m), 3.22-3.28 (1H, m), 4.78 (1H, d, J = 11.7 Hz), 4.85 (1H, d, J = 11.7 Hz), 5.65-5.67 (1H, m), 5.92-5.95 (1H, m).<br>Minor isomer:<br>δ 0.88 (3H, t, J = 7.4 Hz), 1.33-1.39 (1H, m), 1.45 (9H, s), 1.85 (1H, dd, J = 8.2, 12.9 Hz), 1.97 (1H, ddd, J = 3.1, 8.6, 12.9 Hz), 2.46 (2H, s), 2.69-2.70 (1H, m), 2.71-2.77 (1H, m), 2.95-3.03 (1H, m), 3.17-3.21 (1H, m), 4.54 (1H, d, J = 12.5 Hz), 4.60 (1H, d, J = 12.5 Hz), 5.59-5.62 (1H, m), 5.76-5.82 (1H, m). |
| 41 (41-f) | 1H NMR (CDCl3, 500 MHz):<br>Major isomer:<br>δ 0.83 (3H, t, J = 7.3 Hz), 1.17-1.22 (1H, m), 1.24-1.31 (1H, m), 1.43 (9H, s), 1.44-1.48 (1H, m), 1.95 (1H, ddd, J = 2.9, 8.8, 12.2 Hz), 2.22 (1H, d, J = 13.7 Hz), 2.29 (1H, d, J = 13.7 Hz), 2.29-2.32 (1H, m), 2.37-2.42 (1H, m), 2.87 (2H, s), 2.95-2.99 (1H, m), 5.77-5.79 (1H, m), 5.85-5.86 (1H, m).<br>Minor isomer:<br>δ 0.87 (3H, t, J = 7.3 Hz), 1.24-1.31 (1H, m), 1.43 (9H, s), 1.48-1.54 (1H, m), 1.61 (1H, ddd, J = 2.9, 8.3, 12.2 Hz), 1.75 (1H, dd, J = 7.8, 12.2 Hz), 2.22 (1H, d, J = 13.7 Hz), 2.29 (1H, d, J = 13.7 Hz), 2.29-2.32 (1H, m), 2.53-2.59 (1H, m), 2.67-2.71 (1H, m), 2.88 (2H, s), 5.69-5.74 (2H, m). |
| 41 (41-g) | 1H NMR (CD3OD, 400 MHz):<br>Major isomer:<br>δ 0.85 (3H, t, J = 7.4 Hz), 1.17-1.28 (1H, m), 1.28-1.36 (1H, m), 1.50 (1H, dd, J = 7.4, 12.5 Hz), 2.15 (1H, ddd, J = 2.7, 9.0, 12.5 Hz), 2.33-2.37 (1H, m), 2.37 (3H, s), 2.50 (2H, s), 2.53-2.59 (1H, m), 3.14-3.18 (1H, m), 3.32 (1H, d, J = 13.3 Hz), 3.36 (1H, d, J = 13.3 Hz), 5.70-5.72 (1H, m), 5.97-5.98 (1H, m), 7.23 (2H, d, J = 7.8 Hz), 7.70 (2H, d, J = 7.8 Hz).<br>Minor isomer:<br>δ 0.91 (3H, t, J = 7.4 Hz), 1.36-1.42 (1H, m), 1.56 (1H, dd, J = 6.7, 13.7 Hz), 1.81-1.88 (2H, m), 2.37 (3H, s), 2.49 (2H, s), 2.70-2.77 (1H, m), 2.97-3.04 (1H, m), 3.12-3.19 (2H, m), 3.32-3.35 (1H, m), 5.64-5.66 (1H, m), 5.81-5.84 (1H, m), 7.23 (2H, d, J = 7.8 Hz), 7.70 (2H, d, J = 7.8 Hz). |

TABLE 16-continued

| | |
|---|---|
| 41 (41-h) | 1H NMR (CD3OD, 400 MHz): |
| | Major isomer: |
| | δ 0.85 (3H, t, J = 7.4 Hz), 1.19-1.27 (1H, m), 1.27-1.35 (1H, m), 1.48 (1H, dd, J = 7.4, 12.5 Hz), 2.05 (1H, ddd, J = 2.7, 9.0, 12.5 Hz), 2.31-2.37 (1H, m), 2.47 (2H, s), 2.51-2.57 (1H, m), 3.12-3.24 (3H, m), 5.76-5.78 (1H, m), 5.92-5.93 (1H, m). |
| | Minor isomer: |
| | δ 0.90 (3H, t, J = 7.4 Hz), 1.35-1.42 (1H, m), 1.55 (1H, dd, J = 6.7, 13.7 Hz), 1.72 (1H, ddd, J = 2.7, 8.2, 12.1 Hz), 1.83 (1H, dd, J = 7.8, 12.1 Hz), 2.46 (2H, s), 2.67-2.75 (1H, m), 2.95-3.02 (1H, m), 3.12-3.25 (3H, m), 5.70-5.72 (1H, m), 5.76-5.78 (1H, m). |
| | MS (EI): m/z: 209 (M+). |
| | Anal. Calcd for C12H19NO2: C 68.87; H 9.15; N 6.69; Found: C 68.52; H 9.24; N 6.68. |
| | IR (KBr): cm−1: 2958, 2641, 1621, 1511, 723. |

TABLE 17

| | |
|---|---|
| 42 (42-a) | 1H NMR (CDCl3, 400 MHz): |
| | δ 2.05 (1H, dd, J = 4.7, 12.5 Hz), 2.18-2.23 (1H, m), 2.32 (1H, ddd, J = 2.0, 10.2, 19.6 Hz), 2.44-2.55 (2H, m), 2.68-2.82 (2H, m), 3.17-3.22 (1H, m), 3.80-3.95 (4H, m). |
| 42 (42-b) | 1H NMR (CDCl3, 400 MHz): |
| | δ 2.25-2.33 (1H, m), 2.42 (1H, ddd, J = 1.6, 3.9, 16.8 Hz), 2.59-2.68 (2H, m), 2.82-2.89 (1H, m), 3.46-3.51 (1H, m), 3.81-3.99 (4H, m), 5.66-5.68. |
| 42 (42-c) | 1H NMR (CDCl3, 400 MHz): |
| | δ 2.09 (1H, ddd, J = 1.6, 6.7, 12.9 Hz), 2.31-2.38 (1H, m), 2.50-2.56 (1H, m), 2.62-2.70 (2H, m), 3.53-3.56 (1H, m), 3.84-3.89 (2H, m), 3.93-3.97 (2H, m), 5.10-5.14 (2H, m), 5.68 (1H, br s), 6.63 (1H, dd, J = 10.2, 18.0 Hz). |
| 42 (42-d) | 1H NMR (CDCl3, 400 MHz): |
| | Major isomer: |
| | δ 1.45 (9H, s), 2.40-2.46 (1H, m), 2.70-2.79 (2H, m), 2.96-3.05 (1H, m), 3.33 (1H, ddt, J = 2.7, 8.6, 18.4 Hz), 3.95-3.99 (1H, m), 5.11-5.17 (2H, m), 5.48-5.49 (1H, m), 5.60 (1H, br s), 6.56-6.66 (1H, m). |
| | Minor isomer: |
| | δ 1.49 (9H, s), 2.40-2.51 (2H, m), 2.65-2.68 (1H, m), 2.96-3.05 (2H, m), 4.38-4.42 (1H, m), 5.11-5.17 (2H, m), 5.38-5.39 (1H, m), 5.83 (1H, br s), 6.56-6.66 (1H, m). |
| 42 (42-e) | 1H NMR (CDCl3, 500 MHz): |
| | δ 1.45 (9H, s), 1.45-1.47 (1H, m), 2.29-2.32 (1H, m), 2.34 (1H, ddd, J = 2.9, 8.8, 12.7 Hz), 2.48 (2H, s), 2.63 (1H, dd, J = 7.3, 16.1 Hz), 2.92-2.98 (1H, m), 3.32-3.35 (1H, m), 4.78 (1H, d, J = 11.7 Hz), 4.84 (1H, d, J = 11.7 Hz), 5.15-5.19 (2H, m), 5.64 (1H, br s), 6.64 (1H, dd, J = 10.7, 17.6 Hz). |
| 42 (42-f) | 1H NMR (CDCl3, 400 MHz): |
| | δ 1.44 (9H, s), 1.44-1.48 (1H, m), 2.01 (1H, ddd, J = 2.4, 8.6, 12.1 Hz), 2.24 (1H, d, J = 14.1 Hz), 2.24-2.29 (1H, m), 2.31 (1H, d, J = 14.1 Hz), 2.56-2.63 (1H, m), 2.78-2.86 (1H, m), 2.88 (2H, s), 3.04-3.08 (1H, m), 5.10-5.14 (2H, m), 5.77-5.78 (1H, m), 6.66 (1H, dd, J = 10.2, 17.6 Hz). |
| 42 (42-g) | 1H NMR (CD3OD, 400 MHz): |
| | δ 1.51 (1H, dd, J = 7.4, 12.5 Hz), 2.20 (1H, ddd, J = 2.7, 8.6, 12.5 Hz), 2.30-2.34 (1H, m), 2.37 (3H, s), 2.51 (2H, s), 2.63 (1H, dd, J = 7.8, 16.4 Hz), 2.91-2.99 (1H, m), 3.22-3.26 (1H, m), 3.31 (1H, d, J = 13.3 Hz), 3.36 (1H, d, J = 13.3 Hz), 5.16-5.21 (2H, m), 5.68 (1H, br s), 6.68 (1H, dd, J = 11.0, 17.6 Hz), 7.23 (2H, d, J = 8.2 Hz), 7.71 (2H, d, J = 8.2 Hz). |
| 42 (42-h) | Mp. 183-185° C. |
| | 1H NMR (CD3OD, 400 MHz): |
| | δ 1.48 (1H, dd, J = 7.4, 12.1 Hz), 2.11 (1H, ddd, J = 2.7, 8.6, 12.1 Hz), 2.27-2.32 (1H, m), 2.49 (2H, s), 2.60 (1H, dd, J = 7.4, 16.0 Hz), 2.90-2.97 (1H, m), 3.17 (1H, d, J = 12.9 Hz), 3.19-3.24 (1H, m), 3.22 (1H, d, J = 12.9 Hz), 5.12-5.17 (2H, m), 5.75 (1H, br s), 6.67 (1H, dd, J = 11.0, 17.6 Hz). |
| | MS (FAB): m/z: 208 (M + H)+. |
| | Anal. Calcd for C12H17NO2: C 69.54; H 8.27; N 6.76; Found: C 68.74; H 8.10; N 6.76. |
| | IR (KBr): cm−1: 2905, 2648, 1634, 1525, 1397, 896. |
| 43 (43-a) | 1H NMR (CDCl3, 400 MHz): |
| | δ 0.19 (9H, s), 2.17 (1H, ddd, J = 1.2, 6.7, 12.9 Hz), 2.30-2.36 (1H, m), 2.49-2.55 (1H, m), 2.56-2.63 (1H, m), 2.72 (1H, ddt, J = 2.4, 7.8, 16.4 Hz), 3.52-3.57 (1H, m), 3.81-3.96 (4H, m), 6.02 (1H, ddd, J = 2.4, 2.4, 2.4 Hz). |
| 43 (43-b) | 1H NMR (CDCl3, 400 MHz): |
| | Major isomer: |
| | δ 0.20 (9H, s), 1.45 (9H, s), 2.39-2.45 (1H, m), 2.76-2.79 (1H, m), 2.80-2.86 (1H, m), 2.91-3.00 (1H, m), 3.31 (1H, ddt, J = 2.7, 8.6, 18.4 Hz), 3.96-4.01 (1H, m), 5.46-5.48 (1H, m), 5.94-5.96 (1H, m). |
| | Minor isomer: |
| | δ 0.20 (9H, s), 1.48 (9H, s), 2.38-2.45 (1H, m), 2.51-2.57 (1H, m), 2.71-2.75 (1H, m), 2.91-3.00 (2H, m), 4.37-4.42 (1H, m), 5.37-5.39 (1H, m), 6.16-6.18 (1H, m). |
| 43 (43-c) | 1H NMR (CDCl3, 500 MHz): |
| | δ 1.45 (9H, s), 1.64 (1H, dd, J = 7.3, 13.2 Hz), 2.29-2.34 (1H, m), 2.36 (1H, ddd, J = 2.9, 8.8, 13.2 Hz), 2.49 (2H, s), 2.72 (1H, ddt, J = 2.4, 8.3, 16.6 Hz), 2.90-2.96 (1H, m), 3.08 (1H, s), 3.37-3.38 (1H, m), 4.77 (1H, d, J = 11.7 Hz), 4.82 (1H, d, J = 11.7 Hz), 6.04-6.05 (1H, m). |

TABLE 18

| | |
|---|---|
| 43 (43-d) | 1H NMR (CDCl3, 400 MHz):<br>δ 1.44 (9H, s), 1.49-1.54 (1H, m), 2.02 (1H, ddd, J = 2.4, 8.6, 12.5 Hz), 2.25 (1H, d, J = 14.1 Hz),<br>2.25-2.31 (1H, m), 2.32 (1H, d, J = 14.1 Hz), 2.69 (1H, ddt, J = 2.4, 7.8, 16.0 Hz), 2.76-2.82 (1H, m), 2.86 (2H,<br>s), 3.03 (1H, s), 3.06-3.11 (1H, m), 6.19-6.21 (1H, m). |
| 43 (43-e) | 1H NMR (CD3OD, 400 MHz):<br>δ 1.58 (1H, dd, J = 7.8, 12.9 Hz), 2.20 (1H, ddd, J = 2.4, 8.6, 12.9 Hz), 2.26-2.31 (1H, m), 2.37 (3H, s),<br>2.51 (2H, s), 2.69 (1H, ddt, J = 2.4, 7.8, 16.4 Hz), 2.89-2.97 (1H, m), 3.23-3.28 (1H, m), 3.31 (1H, d, J = 13.3 Hz),<br>3.35 (1H, d, J = 13.3 Hz), 3.48 (1H, s), 6.00-6.02 (1H, m), 7.23 (2H, d, J = 8.2 Hz), 7.70 (2H, d,<br>J = 8.2 Hz). |
| 43 (43-f) | Mp. 184-186° C.<br>1H NMR (CD3OD, 500 MHz):<br>δ 1.56 (1H, dd, J = 7.8, 12.2 Hz), 2.11 (1H, ddd, J = 2.9, 8.8, 12.2 Hz), 2.23-2.28 (1H, m), 2.49 (2H, s),<br>2.66 (1H, ddt, J = 2.4, 7.8, 16.1 Hz), 2.88-2.94 (1H, m), 3.16 (1H, d, J = 12.7 Hz), 3.22 (1H, d, J = 12.7 Hz),<br>3.22-3.26 (1H, m), 3.42 (1H, s), 6.08-6.10 (1H, m).<br>MS (FAB): m/z: 206 (M + H)+.<br>Anal. Calcd for C12H15NO2: C 70.22; H 7.37; N 6.82; Found: C 69.00; H 7.49; N 6.77.<br>IR (KBr): cm−1: 3288, 2908, 1525, 1397, 1063, 665. |

Preparation Example 5 g of the compound of Example 21, 90 g of lactose, 34 g of corn starch, 20 g of crystalline cellulose, and 1 g of magnesium stearate are mixed using a blender and then compressed using a tableting machine to obtain a tablet.

Test Example 1

Construction of Human Calcium Channel Subunit $\alpha_2\delta_1$ (Hereinafter, Referred to Human Cacna2d-1) Gene Expression Plasmid, and Preparation of Human Cacna2d-1-Expressing Cell Membrane Fraction a) Construction of Human Cacna2d1 Expression Plasmid pRK/hCacna2d1
a-1) Preparation of DNA Fragment The human Cacna2d1 gene was obtained as two fragments, the first half and second half fragments. PCR was performed using a cDNA library (QUICK-Clone cDNA Human Brain (Clontech Laboratories, Inc.)) as a template and an enzyme KOD polymerase (TOYOBO CO., LTD.) according to the protocol provided for this enzyme. PCR primers used were, for the first half fragment, primers having the following sequences:
Primer 1: 5'-agctgcggcc gctagcgcca ccatggctgg ctgcctgctg gc-3' (SEQ ID NO: 1), and
Primer 2: 5'-attaggatcg attgcaaagt aatacccc-3' (SEQ ID NO: 2); and for the second half fragment, primers having the following sequences:
Primer 3: 5'-aatgggtatt actttgcaat cgatcc-3' (SEQ ID NO: 3), and
Primer 4: 5'-agtcggatcc tcataacagc cggtgtgtgc tg-3' (SEQ ID NO: 4)
purchased from SIGMA GENOSYS. The PCR reaction was performed for both the first half and second half fragments using a thermal cycler (GeneAmp PCR System 9700 (Applied Biosystems, Inc.)) through a process involving heating at 94° C. for 1 minute, then 35 thermal cycles (94° C. for 15 sec., 60° C. for 30 sec., and 68° C. for 2 min.), placing at 68° C. for 5 minutes, and cooling to 4° C.

These two reaction products were purified using a PCR product purification kit (MiniElute PCR Purification Kit (QIAGEN)) according to the protocol included in this kit. The obtained first half fragment was digested with a restriction enzyme Not1 (TOYOBO CO., LTD.). The second half fragment was digested with restriction enzymes Cla1 (TOYOBO CO., LTD.) and BamHI (TOYOBO CO., LTD.). Subsequently, these fragments were purified using a reaction product purification kit (MiniElute Reaction Cleanup Kit (QIAGEN)) according to the protocol included in this kit.

a-2) Preparation of Vector

The multicloning site (hereinafter, referred to as MCS) of an expression vector pRK5 for animal cells (BD Pharmingen) was changed to the MCS of a vector pBluescript 2 (STRATAGENE) to prepare a vector. Specifically, pRK5 was treated with restriction enzymes Cla1 (TOYOBO CO., LTD.) and Hind3 (TOYOBO CO., LTD.), and both the ends of this DNA were then blunt-ended using Klenow fragment (TAKARA BIO INC.). Both of these ends were further dephosphorylated using calf intestine alkaline phosphatase (hereinafter, referred to as CIAP; TAKARA BIO INC.), and the fragment was then purified using MiniElute Reaction Cleanup Kit (QIAGEN). Then, this enzyme-treated DNA was electrophoresed on 1.0% agarose gel. After the electrophoresis, the gel was stained with ethidium bromide. Then, a band portion corresponding to approximately 4.7 kbp was separated under UV irradiation using a razor blade. DNA was extracted therefrom using a gel extraction/purification kit (MiniElute Gel Extraction Kit (QIAGEN)) according to the protocol included in this kit.

To obtain a DNA fragment corresponding to the MCS of pBluescript 2, pBluescript 2 was treated with restriction enzymes Sac1 (TOYOBO CO., LTD.) and Kpn1 (TOYOBO CO., LTD.), and both the ends of this DNA were then blunt-ended using Klenow fragment (TAKARA BIO INC.). Then, this enzyme-treated DNA was electrophoresed on 2.0% agarose gel. After the electrophoresis, the gel was stained with ethidium bromide. Then, a band portion corresponding to approximately 100 bp was separated under UV irradiation using a razor blade. DNA was extracted therefrom using a gel extraction/purification kit (MiniElute Gel Extraction Kit (QIAGEN)) according to the protocol included in this kit.

The obtained DNA fragment and the already-cleaved pRK5 were ligated using a DNA ligation kit (TAKARA BIO INC.) according to the protocol included in the kit. With this reaction product, E. Coli DH5α competent cells (TOYOBO CO., LTD.) were transformed to obtain ampicillin-resistant colonies. Some of the colonies were collected, and the collected colonies were then cultured. From the obtained bacterial cells, a plasmid was extracted and analyzed for its nucleotide sequence using a DNA sequencer (Model 3700 (Applied Biosystems, Inc.)) to confirm the introduction of the MCS sequence in the pRK5. In this context, a vector in which, when the CMV promoter is viewed as being located upstream, the MCS sequence was incorporated such that it was oriented in a downstream direction as follows: 5'-ccac-cgcggtggeggccgctctagaactagtg-gatccccgggctgcaggaattcgatat-caagcttatcgataccgtcgacctcgaggg ggggcccg-3' (SEQ ID NO: 5) was designated as pRK-SK, and a vector in which the MCS sequence was incorporated in an orientation opposite thereto was designated as pRK-KS.

a-3) Construction of Plasmid

The pRK-SK obtained in paragraph a-2) was treated with a restriction enzyme XbaI (TOYOBO CO., LTD.), and both the ends of the DNA were blunt-ended using Klenow fragment (TAKARA BIO INC.). The blunt-ended DNA was further digested with a restriction enzyme Not1 (TOYOBO CO., LTD.) and purified in the same way as in paragraph a-2). This pRK-SK thus made linear and the first half DNA fragment of the human Cacna2d1 gene obtained in paragraph a-1) were electrophoresed on 1.0% agarose gel, and DNAs of approximately 4.7 kbp and approximately 1.5 kbp were extracted from the gel and purified in the same way as in paragraph a-2). The obtained two DNAs were ligated in the same way as in paragraph a-2), and E. coli was transformed with the ligation product. From the obtained E. coli clones, a plasmid was extracted and analyzed for its nucleotide sequence using a DNA sequencer (Model 3700 (Applied Biosystems, Inc.)) to confirm the introduction of the sequence represented by SEQ ID NO: 6 therein. Next, the obtained plasmid was treated with restriction enzymes Cla1 (TOYOBO CO., LTD.) and BamH1 (TOYOBO CO., LTD.), and CIAP treatment and purification were performed in the same way as in paragraph a-2). This plasmid DNA thus made linear and the second half DNA fragment of the human Cacna2d1 gene obtained in paragraph a-1) were electrophoresed on 1.0% agarose gel, and DNAs of approximately 6.2 kbp and approximately 1.8 kbp were extracted from the gel and purified in the same way as in paragraph a-2). The obtained two DNAs were ligated in the same way as in paragraph a-2), and E. coli was transformed with the ligation product. From the obtained E. coli clones, a plasmid was extracted and analyzed for its nucleotide sequence using a DNA sequencer (Model 3700 (Applied Biosystems, Inc.)) to confirm the introduction of the sequence represented by SEQ ID NO: 7 in the vector pRK-SK. The obtained plasmid was designated as pRK/hCacna2d1.

b) Obtainment of Human Cacna2d1-expressing 293 Cell Line 293 cells were transfected with the human Cacna2d1 expression plasmid pRK/hCacna2d1 constructed in paragraph a), and a cell line stably expressing human Cacna2d1 was obtained with human Cacna2d1 protein expression as an index. Specifically, $2 \times 10^6$ 293 cells were inoculated onto a φ6 cm dish and cultured for 12 hours. Then, the cells were cotransfected with 5 µg of pRK/hCacna2d1 and 0.5 µg of a neomycin-resistant gene expression plasmid pSV2neo (Clontech) using a transfection reagent Lipofectamine Plus (Invitrogen Corp.) according to the protocol provided for the reagent.

The cells thus transfected were collected, then inoculated onto a φ15 cm dish after dilution, and cultured for 2 weeks in DMEM (Invitrogen Corp.) supplemented with 10% fetal bovine serum (Cansera International, Inc.) and 500 µg/ml G418 (Invitrogen Corp.). The neomycin-resistant cells that successfully formed colonies were isolated. After expansion culture, the cells were collected, and the cell lysate was evaluated by Western assay to obtain a human Cacna2d1-expressing 293 cell line. In the Western assay, anti-hCacna2d1 antibodies (Chemicon Inc.) were used as primary antibodies.

c) Preparation of Cell Membrane Fraction of Human Cacna2d1-Expressing 293 cell

The human Cacna2d1-expressing 293 cells obtained in paragraph b) were cultured in large scale in DMEM (Invitrogen Corp.) supplemented with 10% fetal bovine serum (Cansera International, Inc.) and 500 µg/ml G418 (Invitrogen Corp.), and the cells were collected. A protease inhibitor (Complete EDTA free (Roche Applied Science)) was added in an amount recommended for the reagent to a binding assay buffer (10 mM MOPS (pH 7.4), 10 mM HEPES (pH 7.4), 100 mM NaCl) to prepare a membrane fraction preparation buffer. The collected cells were washed with the membrane fraction preparation buffer and then homogenized using an ultrasonicator. Then, the homogenate was centrifuged at 12,000 rpm at 4° C. for 1 hour using a centrifuge. The supernatant was discarded, and the precipitate was suspended in the membrane fraction preparation buffer. The procedure from the ultrasonication using a ultrasonicator to the suspension of the precipitate after centrifugation was further repeated three times, and the obtained suspension was used as a human Cacna2d1-expressing cell membrane fraction. The total level of proteins contained in the membrane fraction was calculated from UV absorbance at a wavelength of 280 nm.

Test Example 2

Construction of Detection System for Binding Reaction between Cacna2d1 and Gabapentin (Hereinafter, Referred to as GBP), and Detection of Cacna2d1/GBP Binding Reaction Inhibitory Activities of Compounds of Examples a) Construction of Detection System for Binding Reaction between Cacna2d1 and GBP The human Cacna2d1-expressing cell membrane fraction and GBP labeled with a radioisotope $^3$H (hereinafter, referred to as $^3$H-GBP; Tocris Cookson Ltd.) were diluted with a binding assay buffer (10 mM MOPS (pH 7.4), 10 mM HEPES (pH 7.4), 100 mM NaCl) at a final concentration of 2.5 mg/ml in terms of the total protein level and a final $^3$H-GBP concentration of 4.5 nM, respectively, to prepare 120 µl of a reaction solution, which was in turn left standing at 4° C. for 3 hours. This reaction product was added to wells of a filter plate (UniFilter 350 GF/B (Whatman)) and filtered through the filter. Then, a washing procedure involving the addition of 350 µl of a binding assay buffer (10 mM MOPS (pH 7.4), 10 mM HEPES (pH 7.4), 100 mM NaCl) and filtration through the filter was repeated three times. The filter plate was thoroughly dried, and the underside was sealed. After addition of 50 µl of Microscint 20 (PerkinElmer Inc.), the upper surface was also sealed, and radiation derived from the radioisotope $^3$H remaining on the filter was counted using TopCount (PerkinElmer Inc.). From the obtained value, a value obtained by adding unlabeled GBP (SIGMA-ALDRICH INC.) at a final concentration of 20 µM to the present assay was subtracted as that derived from nonspecific adsorption, and the obtained value was used as the specific binding level of $^3$H-GBP to Cacna2d1 (unit: "count").

b) Detection of Cacna2d1/GBP Binding Reaction Inhibitory Activities of Test Compounds Each test compound was added at various concentrations to the Cacna2d1/GBP binding reaction detection assay constructed in paragraph a), and the binding level was measured by the method described in paragraph a). Then, with the Cacna2d1/GBP specific binding level obtained by the addition of the compound at a concentration of x nM defined as "binding level [x]" and the Cacna2d1/GBP binding inhibitory rate thereagainst defined as "inhibitory rate [x]", the inhibitory rate (%) was determined based on the following equation:

Inhibitory rate [x](%)=(1−(binding level [x]/binding level [0]))×100, wherein the binding level [0] refers to the binding level of $^3$H-GBP obtained without the addition of the compound.

The inhibitory rate was plotted against the concentration. From this result, an "$IC_{50}$ value" was calculated, which is the concentration of the test compound necessary for inhibiting 50% of Cacna2d1/GBP binding. The test results of the test compounds are shown in Table 19.

TABLE 19

| Example | $IC_{50}$ (nM) |
|---|---|
| 1 | 51 |
| 2 | 27 |
| 5 | 24 |
| 6 | 26 |
| 7 | 36 |
| 8 | 28 |
| 9 | 32 |
| 10 | 28 |
| 11 | 89 |
| 12 | 32 |
| 13 | 200 |
| 14 | 55 |
| 15 | 73 |
| 16 | 65 |
| 17 | 120 |
| 18 | 670 |
| 20 | 100 |
| 21 | 14 |
| 22 | 10 |
| 23 | 41 |
| 24 | 85 |
| 31 | 14 |

Test Example 3

Mechanical Hyperalgesia Assay

It has been reported that animals with peripheral nerve injury and diabetic model animals exhibit hyperalgesia and allodynia symptoms to mechanical or thermal stimulation. In the present invention, mice suffering from mechanical hyperalgesia were used in evaluation.

The mice were acclimatized for 30 minutes in a plastic cage for measurement. Then, the test compound was orally administered to the mice, which were in turn evaluated for mechanical hyperalgesia at a measurement time predetermined by a person in charge of the test. The evaluation of mechanical hyperalgesia was conducted by a partial modification of the method of Takasaki et al. (Pain 86 95-101, 2000) to confirm the effect of the test compound on mechanical hyperalgesia. Specifically, mechanical hyperalgesia was evaluated by assessing, based on scores according to the following criteria, behavior induced by pressing 1.4 g of von Frey filament onto the sole of the animal:
0: no response, 1: withdrawal from von Frey filament, and 2: shaking or licking of the hind paw immediately after the stimulation.

In one measurement, 6 stimulations were given to the mice, and the total score was used as a pain score.

The test compound was evaluated by calculating $ID_{50}$, which is the dose of the compound that offers 50% improvement relative to the pain score of a vehicle-administered group. In these models, for example, the compound described in Example 2 exhibited $ID_{50}$ of 10.4 mg/kg.

Test Example 4

Thermal Hyperalgesia Assay

In the present invention, mice and rats suffering from thermal hyperalgesia are used in evaluation.

The test compound is orally administered to the animals, which are in turn evaluated for thermal hyperalgesia at a measurement time predetermined by a person in charge of the test. Specifically, the sole of the hind paw of the animal is thermally stimulated, and the latent time to withdrawal behavior such as licking or shaking of the paw is measured.

Test Example 5

Cold Plate Test

In the present invention, mice and rats suffering from cold allodynia are used in evaluation.

The evaluation of cold allodynia is conducted according to the method of Tanimoto-Mori et al. (Behavioural Pharmacology 19, 85-90, 2008). Specifically, the animal is placed on a metal plate at a low temperature, and the latent time to observable hind paw-lifting behavior and the duration of the paw-lifting behavior are measured.

Test Example 6

Acetic Acid-Induced Writhing Test in Mice

The test compound is orally administered to mice, to which 0.6% acetic acid is in turn administered intraperitoneally at a measurement time predetermined by a person in charge of the test. The total number of writhing behaviors is counted for 10 minutes (from 5 minutes after the intraperitoneal administration to 15 minutes thereafter).

Test Example 7

Adjuvant-Induced Arthritis Pain Test in Rats

An adjuvant is prepared by pulverizing heat-killed bacterial cells of *Mycobacterium butyricum* using an agate mortar and then suspending the powder in dry heat-sterilized liquid paraffin, followed by ultrasonication.

This adjuvant (100 μg/0.05 mL/paw in terms of the amount of the heat-killed bacterial cells) is intradermally injected into the right hind paws of rats to induce arthritis. On day 18 after the adjuvant treatment, the pain test is conducted. Specifically, the test compound is orally administered to the animals. Their tarsotibial joints are flexed five times at a measurement time predetermined by a person in charge of the test, and the number of vocalizations (0-5) is recorded as a pain score.

Test Example 8

Electrically Induced Convulsion Test

The test compound is orally administered to mice. Their corneas in both the eyes are electrically stimulated (60 Hz, 50 mA, 0.2 sec.) using an electric stimulation apparatus and a bipolar electrode at a measurement time predetermined by a person in charge of the test, and the presence or absence of tonic extension of the hind paw is observed and recorded.

Test Example 9

Pentylenetetrazol-Induced Convulsion Test

The test compound is orally administered to mice, to which a pentylenetetrazol solution (85 mg/10 ml/kg, dissolved in saline) is in turn administered hypodermically at a measurement time predetermined by a person in charge of the test. The presence or absence of clonic convulsion is observed and recorded over 30 minutes.

Test Example 10

In addition, the effect of the present invention can be confirmed by evaluation according to methods described in the following homepage of National Institutes of Health (NIH), US: NIH HP: Antiepileptic Drug Development (ADD) Program (http://www.ninds.nih.gov./funding/research/asp/add-add_review.pdf)

INDUSTRIAL APPLICABILITY

A compound of the present invention or a pharmacologically acceptable salt thereof can be used as an active ingredient in a pharmaceutical composition for treating and/or preventing pain or disorders such as those involving the central nervous system.

FREE TEXT FOR SEQUENCE LISTING

SEQ ID NO: 1: PCR sense primer for the first half fragment of human Cacna2d1.

SEQ ID NO: 2: PCR antisense primer for the first half fragment of human Cacna2d1.

SEQ ID NO: 3: PCR sense primer for the second half fragment of human Cacna2d1.

SEQ ID NO: 4: PCR antisense primer for the second half fragment of human Cacna2d1.

SEQ ID NO: 5: multicloning site of a vector pBluescript 2.

The invention claimed is:

1. A compound according to formula (I) or a pharmacologically acceptable salt thereof, wherein formula (I) is selected from the group consisting of:

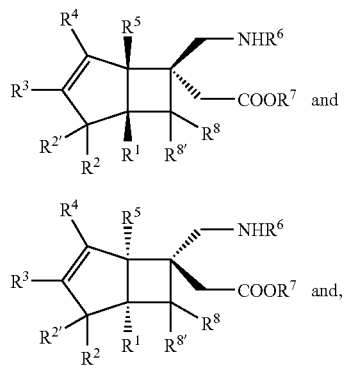

wherein
$R^1, R^2, R^{2'}, R^4, R^5, R^6, R^7, R^8$, and $R^{8'}$ are a hydrogen atom; and
$R^3$ is a hydrogen atom, a methyl group or an ethyl group.

2. A pharmacologically acceptable salt of a compound according claim 1, wherein the pharmacologically acceptable salt is hydrochloride, benzenesulfonate, or p-toluenesulfonate.

3. A compound selected from the group consisting of:
[(1R,5S,6S)-6-(aminomethyl)bicyclo[3.2.0]hept-3-en-6-yl]acetic acid;
[(1R,5S,6S)-6-(aminomethyl)bicyclo[3.2.0]hept-3-en-6-yl]acetic acid hydrochloride;
[(1R,5S,6S)-6-aminomethyl-3-ethylbicyclo[3.2.0]hept-3-en-6-yl]acetic acid;
[(1R,5S,6S)-6-aminomethyl-3-ethylbicyclo[3.2.0]hept-3-en-6-yl]acetic acid p-toluenesulfonate; and
[(1R,5S,6S)-6-aminomethyl-3-ethylbicyclo[3.2.0]hept-3-en-6-yl]acetic acid benzenesulfonate.

4. [(1R,5S,6S)-6-(aminomethyl)bicyclo [3.2.0]hept-3-en-6-yl]acetic acid.

5. [(1R,5S,6S)-6-(aminomethyl)bicyclo[3.2.0]hept-3-en-6-yl]acetic acid hydrochloride.

6. [(1R,5S,6S)-6-aminomethyl-3-ethylbicyclo[3.2.0]hept-3-en-6-yl]acetic acid p-toluenesulfonate.

7. [(1R,5S,6S)-6-aminomethyl-3-ethylbicyclo[3.2.0]hept-3-en-6-yl]acetic acid benzenesulfonate.

8. A pharmaceutical composition comprising [(1R,5S,6S)-6-(aminomethyl)bicyclo[3.2.0]hept-3-en-6-yl]acetic acid as an active ingredient and a pharmaceutically acceptable additive.

9. A pharmaceutical composition comprising [(1R,5S,6S)-6-(aminomethyl)bicyclo[3.2.0]hept-3-en-6-yl]acetic acid hydrochloride as an active ingredient and a pharmaceutically acceptable additive.

10. A pharmaceutical composition comprising [(1R,5S,6S)-6-aminomethyl-3-ethylbicyclo[3.2.0]hept-3-en-6-yl]acetic acid p-toluenesulfonate as an active ingredient and a pharmaceutically acceptable additive.

11. A pharmaceutical composition comprising [(1R,5S,6S)-6-aminomethyl-3-ethylbicyclo[3.2.0]hept-3-en-6-yl]acetic acid benzenesulfonate as an active ingredient and a pharmaceutically acceptable additive.

12. A method of treating a disease or disorder selected from the group consisting of postherpetic neuralgia, neuropathic pain, diabetic neuropathic pain, and fibromyalgia comprising administering a compound or a pharmacologically acceptable salt thereof selected from the group consisting of [(1R,5S,6S)-6-(aminomethyl)bicyclo[3.2.0]hept-3-en-6-yl]acetic acid; [(1R,5S,6S)-6-(aminomethyl)bicyclo[3.2.0]hept-3-en-6-yl]acetic acid hydrochloride; [(1R,5S,6S)-6-aminomethyl-3-ethylbicyclo[3.2.0]hept-3-en-6-yl]acetic acid p-toluenesulfonate; and [(1R,5S,6S)-6-aminomethyl-3-ethylbicyclo[3.2.0]hept-3-en-6-yl]acetic acid benzenesulfonate.

13. The method according to claim 12, wherein the disease or disorder is postherpetic neuralgia.

14. The method according to claim 12, wherein the disease or disorder is neuropathic pain.

15. The method according to claim 12, wherein the disease or disorder is diabetic neuropathic pain.

16. The method according to claim 12, wherein the disease or disorder is fibromyalgia.

17. The method according to claim 12, wherein the compound or the pharmacologically acceptable salt thereof is [(1R,5S,6S)-6-(aminomethyl)bicyclo [3.2.0]hept-3-en-6-yl] acetic acid.

18. The method according to claim 12, wherein the compound or the pharmacologically acceptable salt thereof is [(1R,5S,6S)-6-(aminomethyl)bicyclo [3.2.0]hept-3-en-6-yl] acetic acid hydrochloride.

19. The method according to claim 12, wherein the compound or the pharmacologically acceptable salt thereof is [(1R,5S,6S)-6-aminomethyl-3-ethylbicyclo[3.2.0]hept-3-en-6-yl]acetic acid p-toluenesulfonate.

20. The method according to claim 12, wherein the compound or the pharmacologically acceptable salt thereof is [(1R,5S,6S)-6-aminomethyl-3-ethylbicyclo[3.2.0]hept-3-en-6-yl]acetic acid benzenesulfonate.

* * * * *